United States Patent
Huang et al.

(10) Patent No.: US 11,603,352 B2
(45) Date of Patent: Mar. 14, 2023

(54) MASS SPECTROMEIRY-CLEAVABLE CROSS-LINKER

(71) Applicant: The Regents of The University of California, Oakland, CA (US)

(72) Inventors: Lan Huang, Irvine, CA (US); Scott D. Rychnovsky, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 111 days.

(21) Appl. No.: 16/870,431

(22) Filed: May 8, 2020

(65) Prior Publication Data

US 2021/0253524 A1 Aug. 19, 2021

Related U.S. Application Data

(60) Provisional application No. 62/845,240, filed on May 8, 2019.

(51) Int. Cl.
| | |
|---|---|
| *G01N 33/68* | (2006.01) |
| *C07D 207/452* | (2006.01) |

(52) U.S. Cl.
CPC ..... *C07D 207/452* (2013.01); *G01N 33/6845* (2013.01); *G01N 33/6848* (2013.01); *G01N 2560/00* (2013.01)

(58) Field of Classification Search
None
See application file for complete search history.

(56) References Cited

U.S. PATENT DOCUMENTS

| | | |
|---|---|---|
| 9,222,943 B2 | 12/2015 | Rychnovsky et al. |
| 2016/0245822 A1 | 8/2016 | Rychnovsky et al. |
| 2017/0082635 A1 | 3/2017 | Rychnovsky et al. |
| 2017/0350901 A1 | 12/2017 | Huang et al. |
| 2020/0002375 A1* | 1/2020 | Chowdhury ......... C07K 5/1008 |

OTHER PUBLICATIONS

Pan et al., "Targeting Jab1/CSN5 in nasopharyngeal carcinoma." Cancer Lett. 326(2): 155-160 (2012).
Peth et al., "Downregulation of COP9 signalosome subunits differentially affects the CSN complex and target protein stability." BMC Biochemistry 8(27):1-14 (2007).
Petroski et al., "Function and Regulation of Cullin_RING Ubiquitin Ligases." Nature Reviews Molecular Cell Biology 6(1):9-20 (2005).
Petrotchenko et al., "An Isotopically Coded CID-cleavable Biotinylated Cross-linker for Structural Proteomics." Molecular Cell Proteomics 10(2):M110.001420 (2011).
(Continued)

*Primary Examiner* — Xiaoyun R Xu
(74) *Attorney, Agent, or Firm* — Gavrilovich, Dodd & Lindsey LLP

(57) ABSTRACT

Synthesis of a sulfoxide-containing homobifunctional cysteine-reactive mass spectrometry-cleavable cross-linker for mapping intra-protein interactions in a protein and inter-protein interactions in a protein complex is provided. Methods for mapping intra-protein interactions in a protein and inter-protein interactions in a protein complex and cross-linking mass spectrometry for identifying one or more cross-linked peptides using the cross-linker are provided.

13 Claims, 59 Drawing Sheets

Specification includes a Sequence Listing.

(56) References Cited

OTHER PUBLICATIONS

Richardson et al., "The Emerging Role of the COP9 Signalosome in Cancer." Mol Cancer Res 3(12):645-653 (2005).
Rieping et al., "Inferential Structure Determination." Science 309:303-306 (2005).
Robinson et al., "Molecular architecture of the yeast Mediator complex," eLife:08719 (2015).
Rout et al., "Principles for Integrative Structural Biology Studies." Cell 177:1384-1403 (May 30, 2019).
Rozen et al., "CSNAP Is a Stoichiometric Subunit of the COP9 Signalosome." Cell Reports 13, 585-598 (2015).
Russel et al., "Putting the Pieces Together: Integrative Modeling Platform Software for Structure Determination of Macromolecular Assemblies." PLoS Biology 10(1):e1001244 (2012).
Sali et al., "Comparative Protein Modelling by Satisfaction of Spatial Restraints." Journal of Molecular Biology 234:779-815 (1993).
Sali et al., "Outcome of the First wwPDB Hybrid/Integrative Methods Task Force Workshop." Structure 23:1157-1167 (2015).
Schilling et al., "MS2Assign, Automated Assignment and Nomenclature of Tandem Mass Spectra of Chemically Crosslinked Peptides." J Am Soc Mass Spectrom 4:834 850 (2003).
Schneidman-Duhovny et al., "Uncertainty in Integrative Structural Modeling." Curr Opin Struct Biol. 0: 96-104 (2014).
Scott et al., "Spatial organization and molecular interactions of the Schizosaccharomyces pombe Ccq1-Tpz1-Poz1 shelterin complex." J Mol Biol. 429(19):2863-2872 (2017).
Seeger et al., "A novel protein complex involved in signal transduction possessing similarities to 26S proteasome subunits." The FASEB Journal 12:469-478 (1998).
Sharon et al., "Structural Organization of the 19S Proteasome Lid: Insights from MS of Intact Complexes." PLoS Biology 4(8):e267 (2006).
Sharon et al., "Symmetrical Modularity of the COP9 Signalosome Complex Suggests its Multifunctionality." Structure 17, 31-40 (2009).
Shen et al., "Statistical potential for assessment and prediction of protein structures." Protein Science 15:2507-2524 (2006).
Shi et al., "Structural Characterization by Cross-linking Reveals the Detailed Architecture of a Coatomer-related Heptameric Module from the Nuclear Pore Complex." Molecular & Cellular Proteomics 13(11):2927-2943 (2014).
Sinz, A., "Investigation of protein-protein interactions in living cells by chemical crosslinking and mass spectrometry." Anal Bioanal Chem 397:3433-3440 (2010).
Sinz et al., "Chemical cross-linking and native mass spectrometry: A fruitful combination for structural biology." Protein Science 24:1193-1209 (2015).
Skaar et al., "Mechanisms and function of substrate recruitment by F-box proteins." Nat Rev Mol Cell Biol. 14(6):1-28 2013.
Tacke et al., "An update on the recent advances in antifibrotic therapy." Expert Review of Gastroenterology & Hepatology 12(11):1143-1152 (Nov. 2018).
Tang et al., "Mass Spectrometry Identifiable Cross-Linking Strategy for Studying Protein-Protein Interactions." Anal. Chem. 77:311-318 (2005).
Tang et al., "One-pot N-glycosylation remodeling of IgG with non-natural sialylglycopeptides enables glycosite-specific and dual-payload antibody-drug conjugates." Org. Biomol. Chem. 14:9501 (2016).
Upla et al., "Molecular Architecture of the Major Membrane Ring Component of the Nuclear Pore Complex." Structure 25:434-445 (2017).
Viswanath et al., "Assessing Exhaustiveness of Stochastic Sampling for Integrative Modeling of Macromolecular Structures." Biophysical Journal 113:2344-2353 (2017).
Wang et al., "The proteasome-interacting Ecm29 protein disassembles the 26S proteasome in response to oxidative stress." J. Biol. Chem. 292(39):16310-16320 (2017).
Wang et al., "Molecular Details Underlying Dynamic Structures and Regulation of the Human 26S Proteasome." Molecular & Cellular Proteomics 16(5):840-854 (2017).
Wei et al., "Making Sense of the COP9 Signalosome, a regulatory protein complex conserved from *Arabidopsis* to humans." Trends Genet 15(3):98-103 (1999).
Wei et al., "The COP9 Signalosome." Annu. Rev. Cell Dev. Biol. 19:261-86 (2003).
Wei et al., "The COP9 signalosome: more than a protease." Trends in Biochemical Sciences 33(12):592-600 (2008).
Wells et al., "Reaching for high-hanging fruit in drug discovery at protein-protein interfaces." Nature 450(13):1001-1009 (2007).
Wolf et al., "The COP9/Signalosome: An Assembly and Maintenance Platform for Cullin Ubiquitin Ligases?" Nature Cell Biology 5:1029-1033 (2003).
Wu et al., "Porous molybdenum carbide nano-octahedrons synthesized via confined carburization in metal-organic frameworks for efficient hydrogen production." Nature Communications 6:6512 (2015).
Yu et al., "Developing New Isotope-Coded Mass Spectrometry-Cleavable Cross-Linkers for Elucidating Protein Structures." Anal. Chem. 86:2099-2106 (2014).
Yu et al., "Gln40 deamidation blocks structural reconfiguration and activation of SCF ubiquitin ligase complex by Nedd8." Nature Communications 6:10053 (2015).
Yu et al., "Characterization of Dynamic UbR-Proteasome Subcomplexes by In vivo Cross-linking (X) Assisted Bimolecular Tandem Affinity Purification (XBAP) and Label-free Quantitation." Molecular & Cellular Proteomics 15(7):2279-2292 (2016).
Yu et al., "Developing a Multiplexed Quantitative Cross-linking Mass Spectrometry Platform for Comparative Structural Analysis of Protein Complexes" Anal Chem. 88(20): 10301-10308 (2016).
Yu et al., "Cross-Linking Mass Spectrometry (XL-MS): an Emerging Technology for Interactomics and Structural Biology." Anal Chem. 90(1): 144-165 (Jan. 2, 2018).
Zang et al., "Carboxylate-Selective Chemical Cross-Linkers for Mass Spectrometric Analysis of Protein Structures." Anal. Chem. 90:1195-1201 (2017).
Zhong et al., "CSN5 silencing inhibits invasion and arrests cell cycle progression in human colorectal cancer SW480 and LS174T cells in vitro." Int J Clin Exp Pathol 8(3):2809-2815 (2015).
Alber et al., "The molecular architecture of the nuclear pore complex." Nature 450(7170):695-701 (2007).
Algret et al., "Molecular architecture and function of the SEA complex, a modulator of the TORC1 pathway." Mol. Cell Proteomics 13(11):2855-2870 (2014).
Arkin et al., "Small-Molecule Inhibitors of Protein-Protein Interactions: Progressing toward the Reality." Chem Biol 21:1102-1114 (2014).
Bai et al., "In-depth Analysis of the Lid Subunits Assembly Mechanism in Mammals." Biomolecules 9(213):1-15 (May 31, 2019).
Birol et al., "Structural and biochemical characterization of the Cop9 signalosome CSN5/CSN6 heterodimer." PLoS One 9(8):e105688 (2014).
Bruce, J., "In vivo protein complex topologies: Sights through a crosslinking lens." Proteomics 12:1565-1575 (2012).
Buchan et al., "Scalable web services for the PSIPRED Protein Analysis Workbench." Nucleic Acids Res 41: W349-357 (2013).
Burke et al., "Synthesis of Two New Enrichable and MS-Cleavable Cross-linkers to Define Protein-Protein Interactions by Mass Spectrometry." Org Biomol Chem 13:5030-5037 (2015).
Chakrabarty et al., "Differential Tandem Mass Spectrometry-Based Cross-Linker: A New Approach for High Confidence in Identifying Protein Cross-Linking." Anal Chem 88:10215-10222 (2016).
Chavez et al., "A General Method for Targeted Quantitative Cross-Linking Mass Spectrometry." PLoS One 11(12):e0167547 (2016).
Cope et al., "Role of Predicted Metalloprotease Motif of Jab1/Csn5 in Cleavage of Nedd8 from Cul1." Science 298(5593):608-611 (2002).
Cope et al., "COP9 signalosome: a multifunctional regulator of SCF and other cullin-based ubiquitin ligases." Cell 114(6):663-671 (2003).

(56) References Cited

OTHER PUBLICATIONS

Cope et al., "Targeted silencing of Jab1/Csn5 in human cells downregulates SCF activity through reduction of F-box protein levels." BMC Biochemistry 7:1 (2006).
Deshaies et al., "RING Domain E3 Ubiquitin Ligases." Annu. Rev. Biochem. 78:399-434 (2009).
Dubiel et al., "Diversity of COP9 signalosome structures and functional consequences." FEBS Letters 589:2507-2513 (2015).
Emberley et al., "Deconjugation of Nedd8 from Cul1 Is Directly Regulated by Skp1-F-box and Substrate, and the COP9 Signalosome Inhibits Deneddylated SCF by a Noncatalytic Mechanism." The Journal of Biological Chemistry 287(35):29679-29689 (2012).
Enchev et al., "Structural Basis for a Reciprocal Regulation between SCF and CSN." Cell Reports 2:616-627 (2012).
Ezberger et al., "Molecular Architecture of the 40S,eIF1,eIF3 Translation Initiation Complex." Cell 158:1123-1135 (2014).
Faull et al., "Structural basis of Cullin 2 RING E3 ligase regulation by the COP9 signalosome." Nature Communications 10:3814 (Aug. 23, 2019).
Fernandez-Martinez et al., "Structure and Function of the Nuclear Pore Complex Cytoplasmic mRNA Export Platform." Cell 167(5):1215-1228 (2016).
Fischer et al., "The Molecular Basis of CRL4DDB2/CSA Ubiquitin Ligase Architecture, Targeting, and Activation." Cell 147:1024-1039 (2011).
Fischer et al., "Structure of the DDB1-CRBN E3 ubiquitin ligase in complex with thalidomide." Nature 512(7512):49-53 (2014).
Fuzesi-Levi et al., "CSNAP, the smallest CSN subunit, modulates proteostasis through cullin-RING ubiquitin ligases." bioRxv preprint (Oct. 2, 2018).
Guela et al., "Structure-based Analysis of VDAC1 Protein Defining Oligomer Contact Sites." The Journal of Biological Chemistry 287(3):2179-2190 (2012).
Gunnoo et al., "Chemical Protein Modification through Cysteine." Chembiochem 17:529-553 (2016).
Gutierrez et al., "Developing an Acidic Residue Reactive and Sulfoxide-Containing MS-Cleavable Homobifunctional Cross-Linker for Probing Protein-Protein Interactions." Anal. Chem. 88:8315-8322 (2016).
Gutierrez et al., "Developing a Novel Sulfoxide-containing MS-cleavable Homobifunctional Cysteine Reactive Cross-linker for Studying Protein-Protein Interactions." Anal Chem. 2018 90(12):7600-7607 (Jun. 19, 2018).
Herzog et al., "Structural Probing of a Protein Phosphatase 2A Network by Chemical Cross-Linking and Mass Spectrometry." Science 337:1348-1352 (2012).
Heusel et al., "Complex-centric proteome profiling by SEC-SWATH-MS." Molecular Systems Biology 15: e8438 | (Jan. 14, 2019).
Jia et al., "SCF E3 Ubiquitin Ligases as Anticancer Targets." Curr Cancer Drug Targets 11(3): 347-356 (2011).
Kaake et al., "A New in Vivo Cross-linking Mass Spectrometry Platform to Define Protein-Protein Interactions in Living Cells." Molecular & Cellular Proteomics 13(12):3533-3543 (2014).
Kao et al., "Development of a Novel Cross-linking Strategy for Fast and Accurate Identification of Cross-linked Peptides of Protein Complexes." Molecular & Cellular Proteomics 10(1):M110.002212 (2011).
Kao et al., "Development of a Novel Cross-linking Strategy for Fast and Accurate Identification of Cross-linked Peptides of Protein Complexes." Molecular & Cellular Proteomics 11(12):1566-1577 (2012).
Kim et al., "Integrative Structure and Functional Anatomy of a Nuclear Pore Complex." Nature 555(7697):475-482 (Mar. 22, 2018).
Knepp et al., "Rhodopsin forms a dimer with cytoplasmic helix 8 contacts in native membranes." Biochemistry 51(9):1819-1821 (2012).
Lee et al., "Roles of COP9 signalosome in cancer." Cell Cycle 10(18):3057-3066 (2011).
Lee et al., "The Steady-State Repertoire of Human SCF Ubiquitin Ligase Complexes Does Not Require Ongoing Nedd8 Conjugation." Molecular & Cellular Proteomics 10(5):M110.006460-1 (2011).
Lee et al., "Molecular targeting of CSN5 in human hepatocellular carcinoma: a mechanism of therapeutic response." Oncogene 30(40):4175-4184 (2011).
Leitner et al., "Lysine-specific chemical cross-linking of protein complexes and identification of cross-linking sites using LC-MS/MS and the xQuest/xProphet software pipeline." Nature Protocols 9(1):120-137 (2013).
Leitner et al., "Chemical cross-linking/mass spectrometry targeting acidic residues in proteins and protein complexes." PNAS 111(26):9455-9460 (2014).
Leitner et al., "Cross-linking and other structural proteomics techniques: how chemistry is enabling mass spectrometry applications in structural biology." Chem. Sci. 7:4792-4803 (2016).
Liu et al., "Dissecting Fission Yeast Shelterin Interactions via MICro-MS Links Disruption of Shelterin Bridge to Tumorigenesis." Cell Reports 12, 2169-2180 (2015).
Liu et al., "The interactome of intact mitochondria by cross-linking mass spectrometry provides evidence for coexisting respiratory supercomplexes." Molecular & Cellular Proteomics 17(2):15473 (2017).
Liu et al., "Optimized fragmentation schemes and data analysis strategies for proteome-wide cross-link identification." Nature Communications 8:15473 (2017).
Lopiccolo et al., "Assembly and Molecular Architecture of the Phosphoinositide 3-Kinase p85a Homodimer." The Journal of Biological Chemistry 290(51):30390-30405 (2015).
Lu et al., "Ionic Reagent for Controlling the Gas-Phase Fragmentation Reactions of Cross-Linked Peptides." Anal. Chem. 80:9279-9287 (2008).
Luo et al., "An Integrated Chemical Cross-linking and Mass Spectrometry Approach to Study Protein Complex Architecture and Function." Molecular & Cellular Proteomics 11(2):M111.008318 (2012).
Luo et al., "Architecture of the human and yeast general transcription and DNA repair factor TFIIH." Mol Cell. 59(5):794-806 (2015).
Mosadeghi et al., "Structural and kinetic analysis of the COP9-Signalosome activation and the cullin-RING ubiquitin ligase deneddylation cycle." eLife 5:e12102 (2016).
Muller et al., "Cleavable Cross-Linker for Protein Structure Analysis: Reliable Identification of Cross-Linking Products by Tandem MS." Anal Chem 82:6958-6968 (2010).
Aguirre, Amanda L., Non-Final Office Action for U.S. Appl. No. 15/275,001, dated May 1, 2018.
Aguirre, Amanda L., Final Office Action for U.S. Appl. No. 15/275,001, dated Dec. 14, 2018.
Aguirre, Amanda L., Notice of Allowance for U.S. Appl. No. 15/275,001, dated Apr. 3, 2019.
Cavadini et al., "Cullin-RING ubiquitin E3 ligase regulation by the COP9 signalosome." Nature 531:598-603 + Suppl (31 Mar. 31, 2016).
Lingaraju et al., "Crystal structure of the human COP9 signalosome." Nature 512:161-165 + Suppl (Aug. 14, 2014).
Liu et al., "Proteome-wide profiling of protein assemblies by cross-linking mass spectrometry." Nature Methods 12:1179-1184 (2015).
Negin, Russel Scott, Non-Final Office Action for U.S. Appl. No. 13/471,365, dated Feb. 24, 2015.
Negin, Russel Scott, Notice of Allowance for U.S. Appl. No. 13/471,365, dated Aug. 3, 2015.
Negin, Russel Scott, Non-Final Office Action for U.S. Appl. No. 14/927,332, dated Oct. 29, 2015.
Rockel et al., "Electron microscopy and in vitro deneddylation reveal similar architectures and biochemistry of isolated human and Flag-mouse COP9 signalosome complexes." Biochemical and Biophysical Research Communications 450:991-997 (2014).
Sawyer Jennifer C., Non-Final Office Action for U.S. Appl. No. 15/613,065, dated Nov. 19, 2018.
Sawyer Jennifer C., Final Office Action for U.S. Appl. No. 15/613,065, dated Jul. 8, 2019.
Sawyer Jennifer C., Notice of Allowance for U.S. Appl. No. 15/613,065, dated Feb. 27, 2020.

(56) References Cited

OTHER PUBLICATIONS

Zhang et al., "COPS5 inhibition arrests the proliferation and growth of serous ovarian cancer cells via the elevation of p27 level." Biochemical and Biophysical Research Communications 493:85e93 (2017).

* cited by examiner

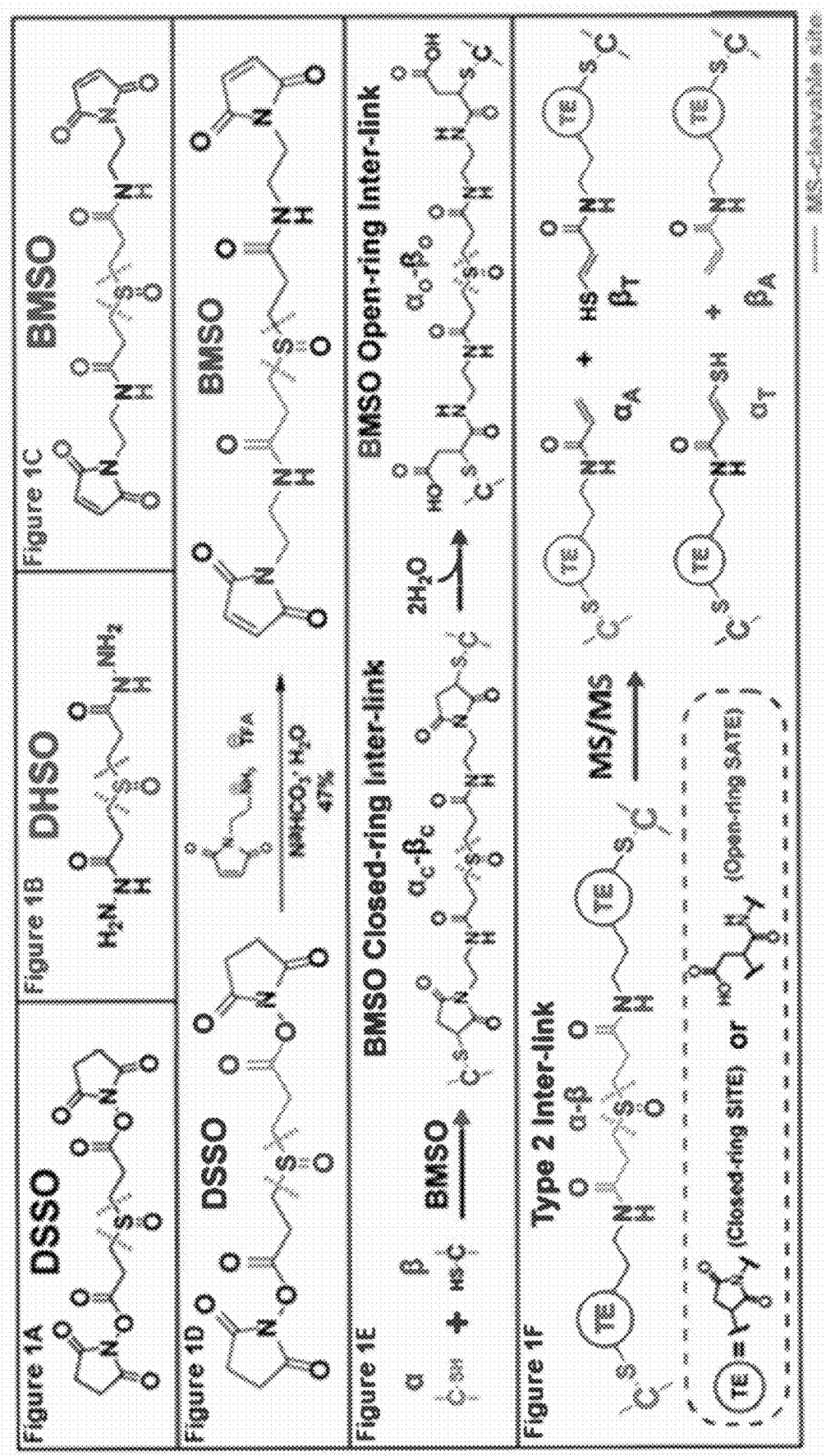

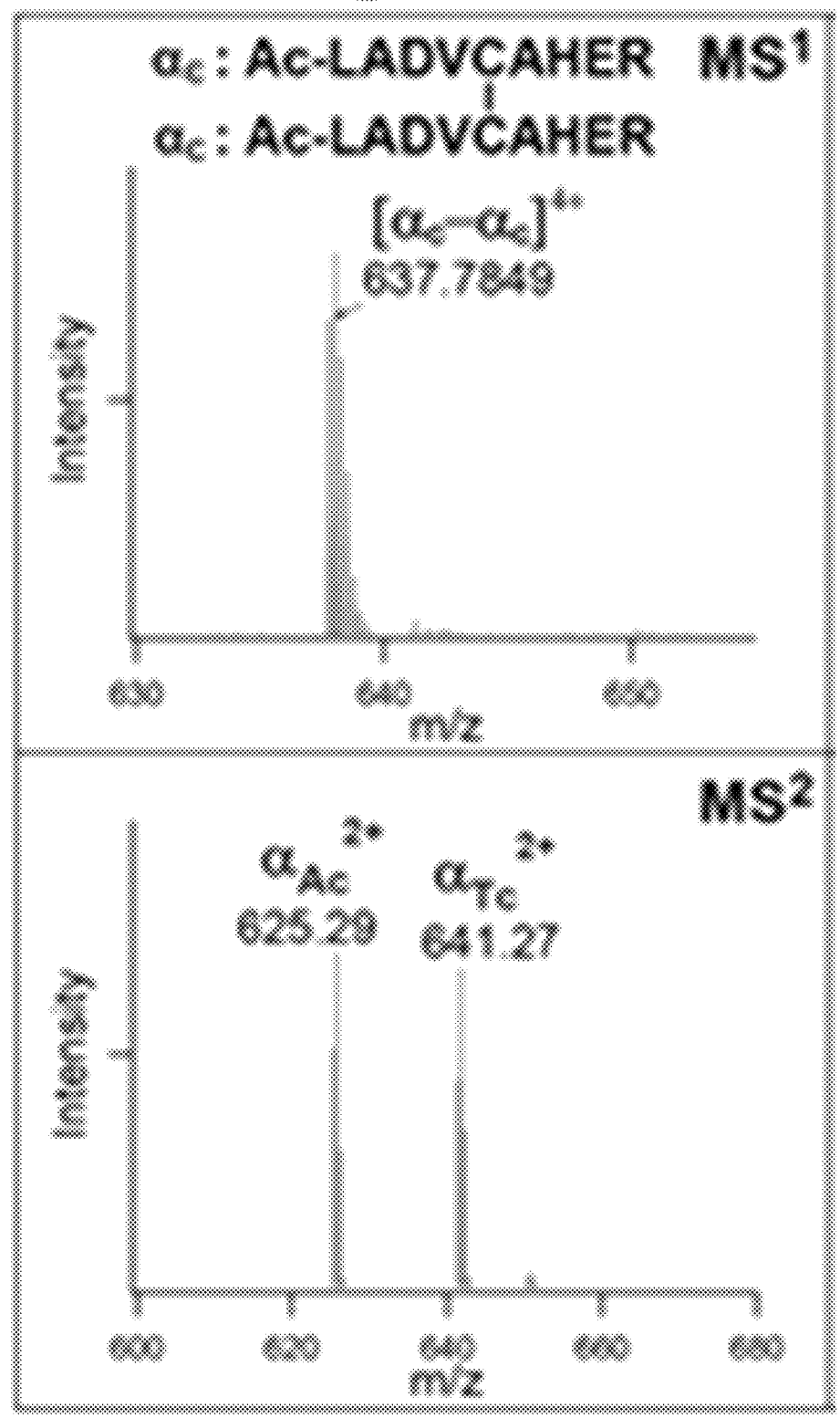

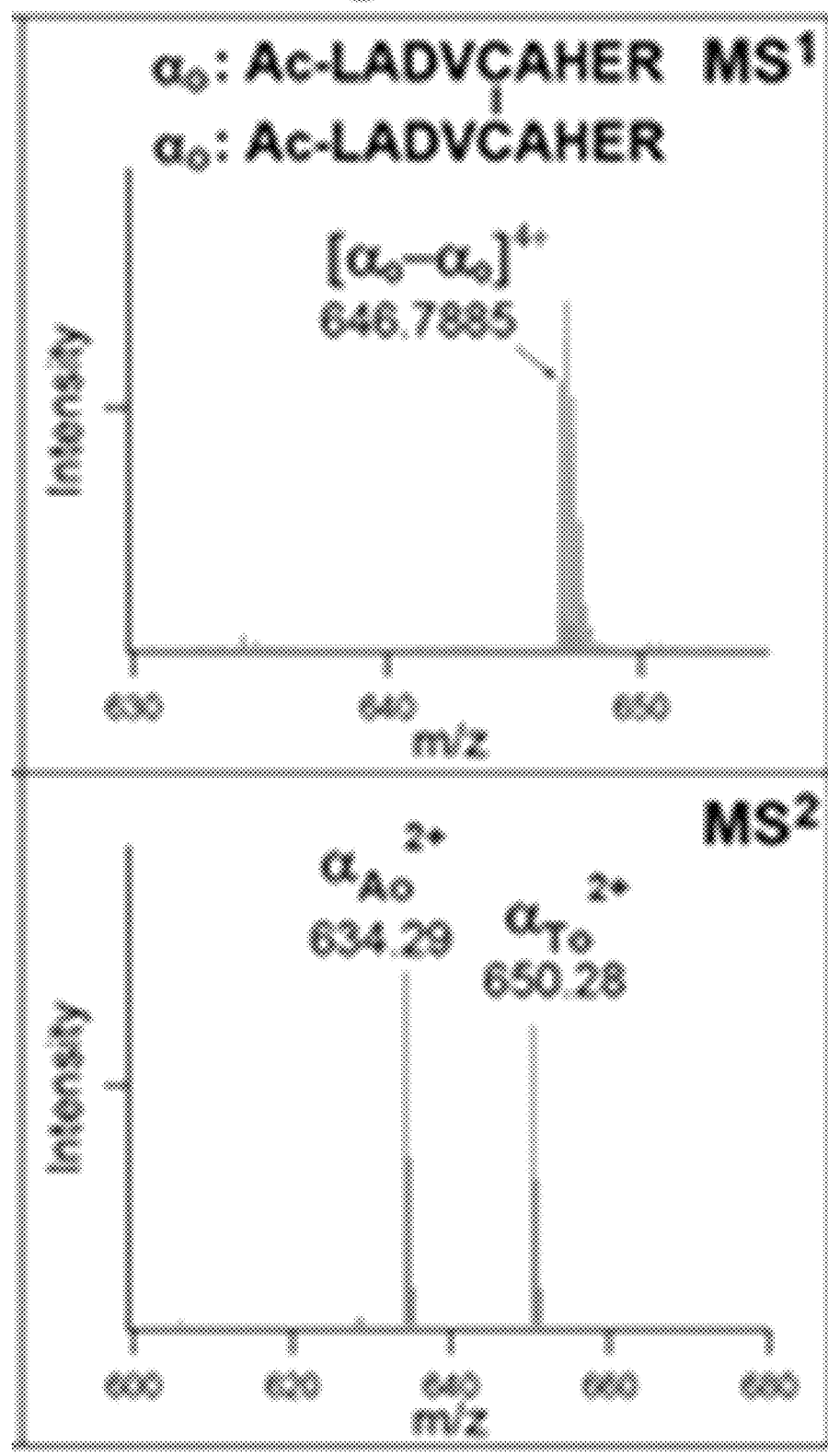

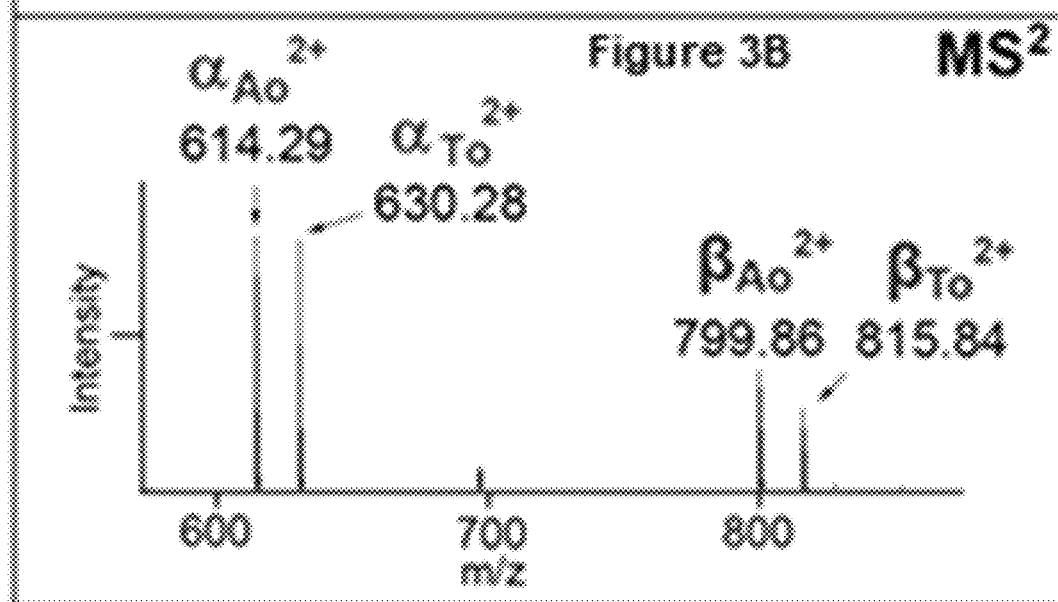

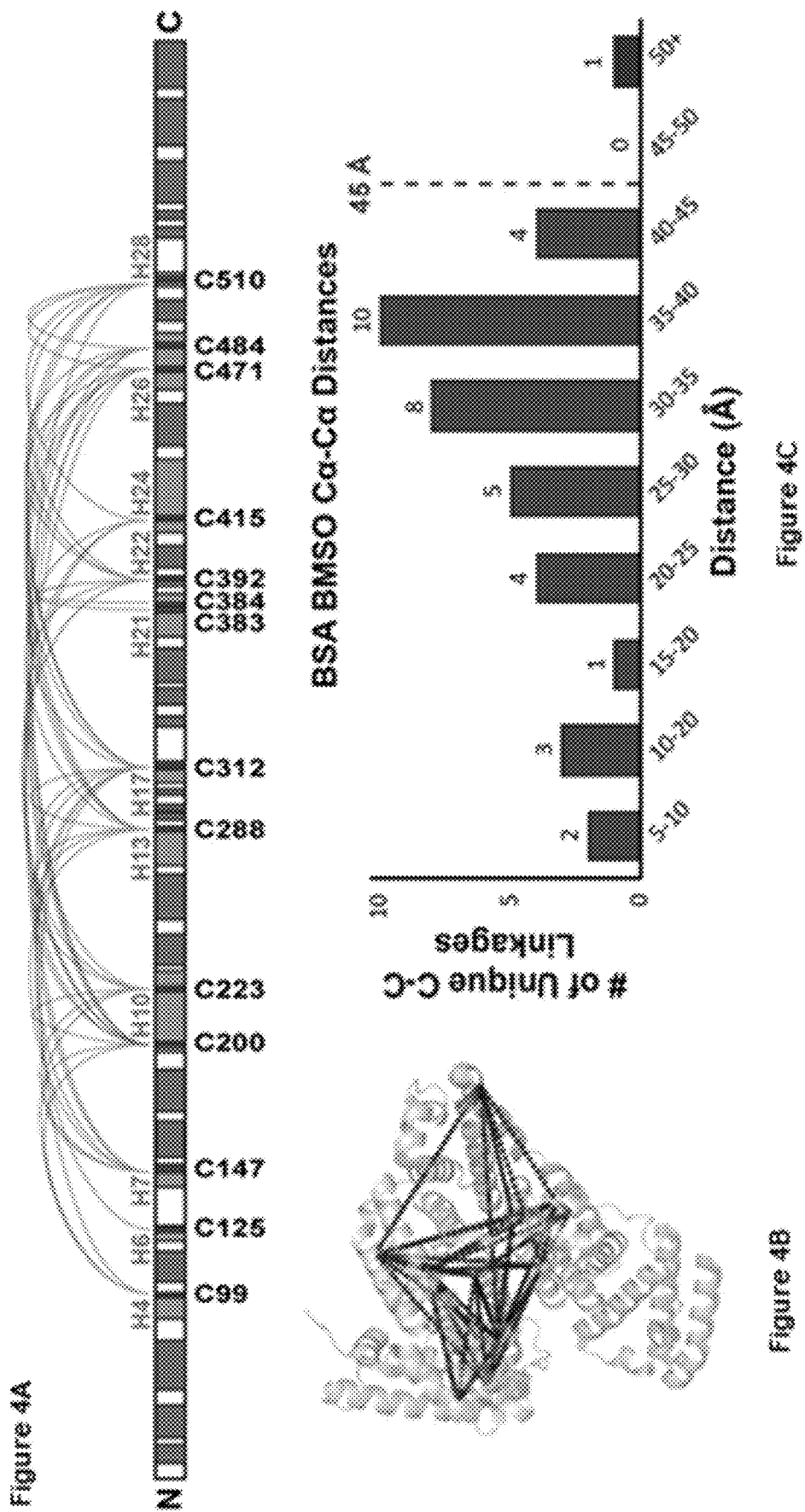

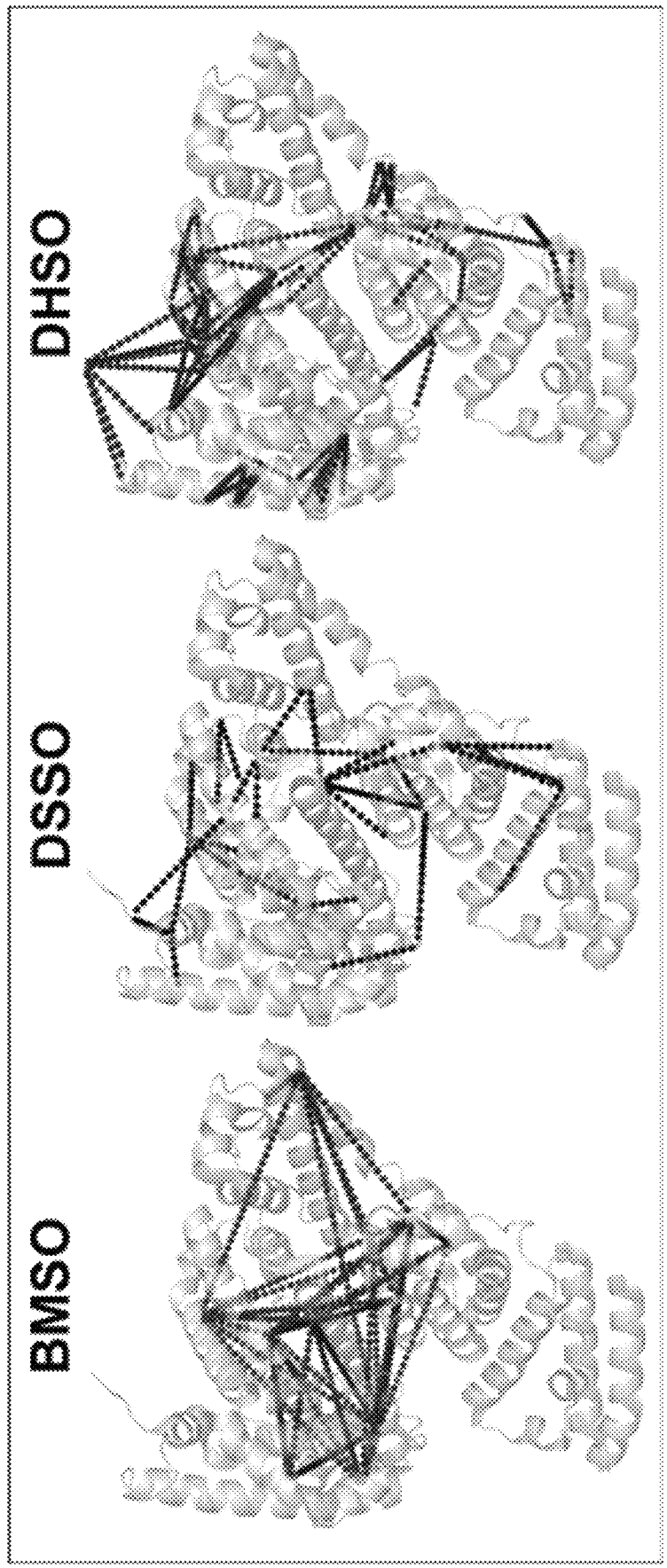

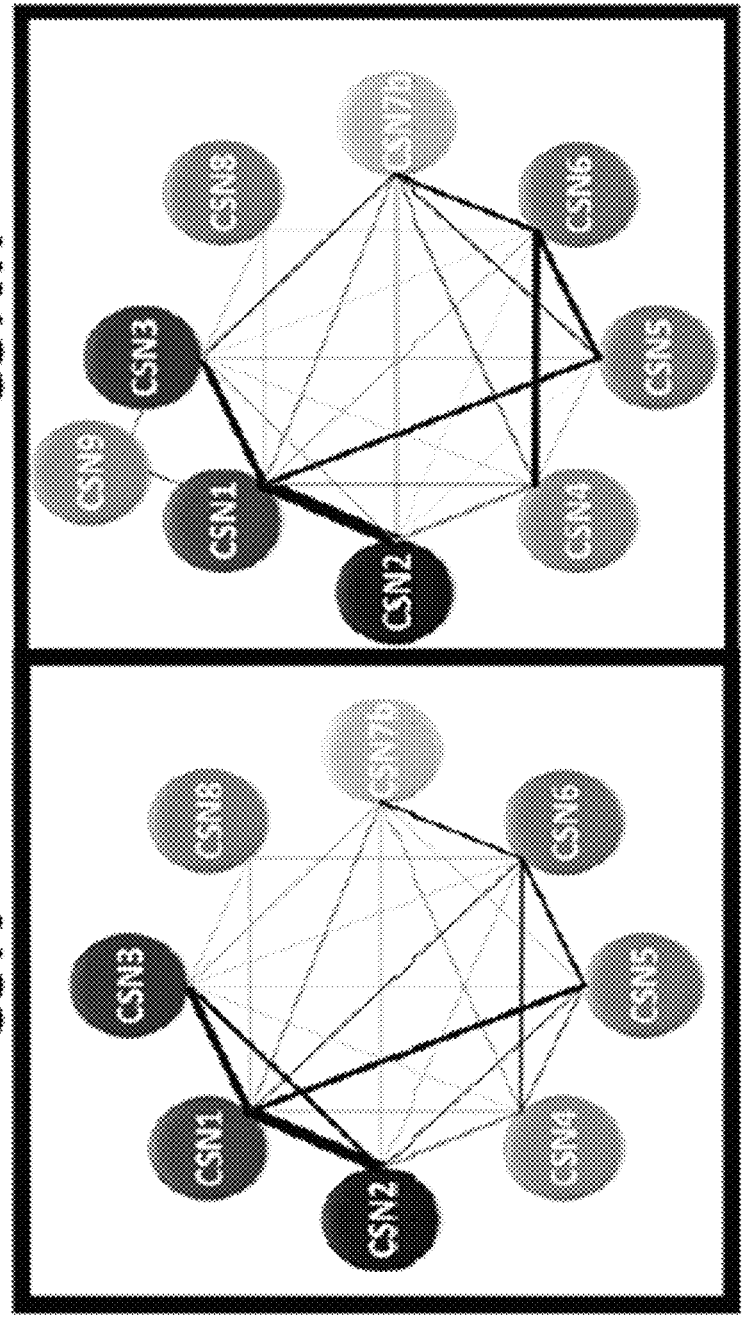

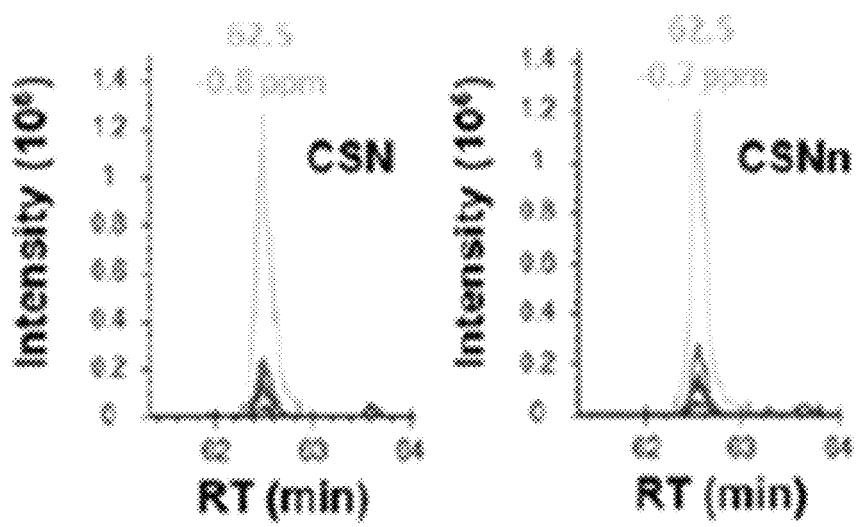
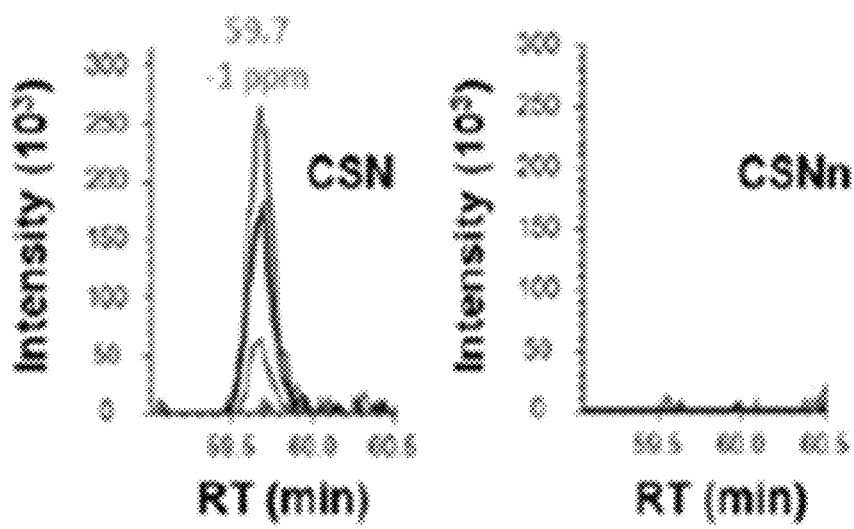
Figure 16A

Figure 16B
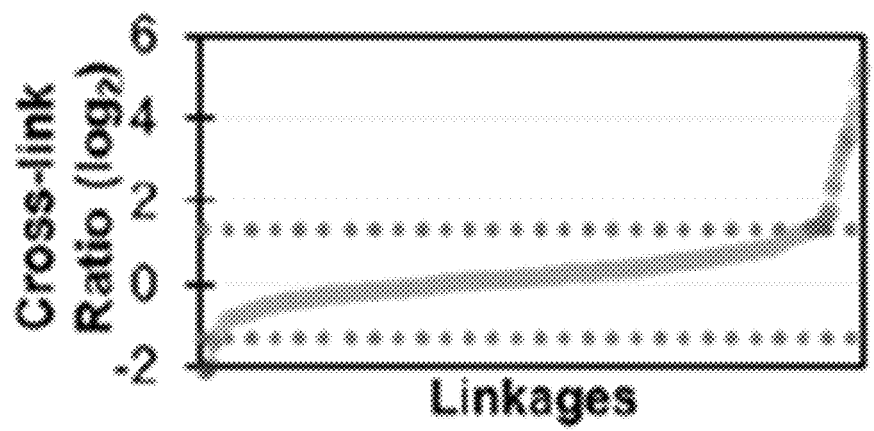
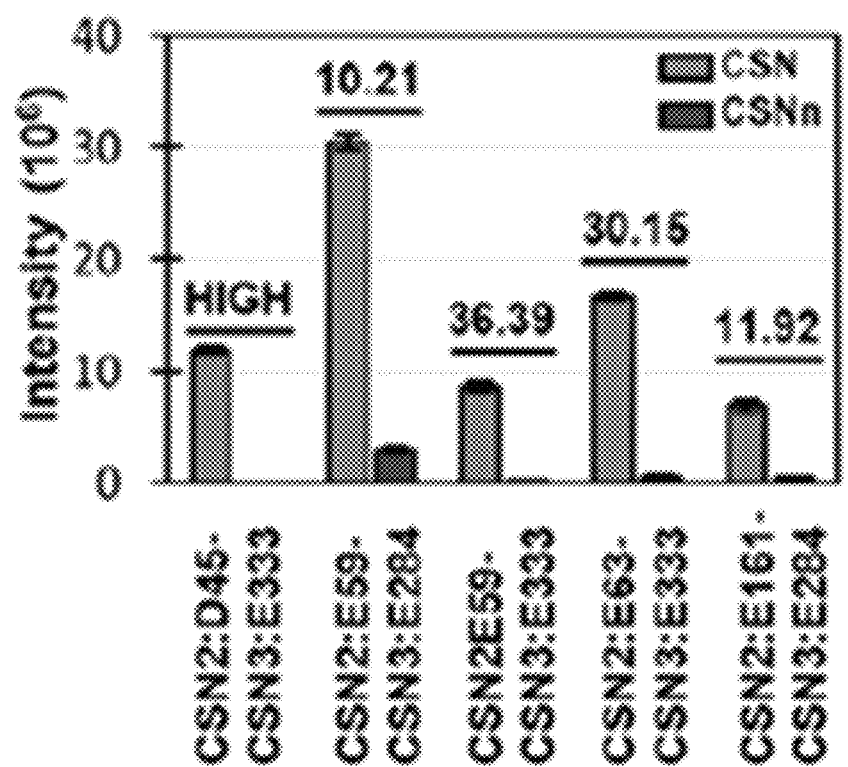
Figure 16C

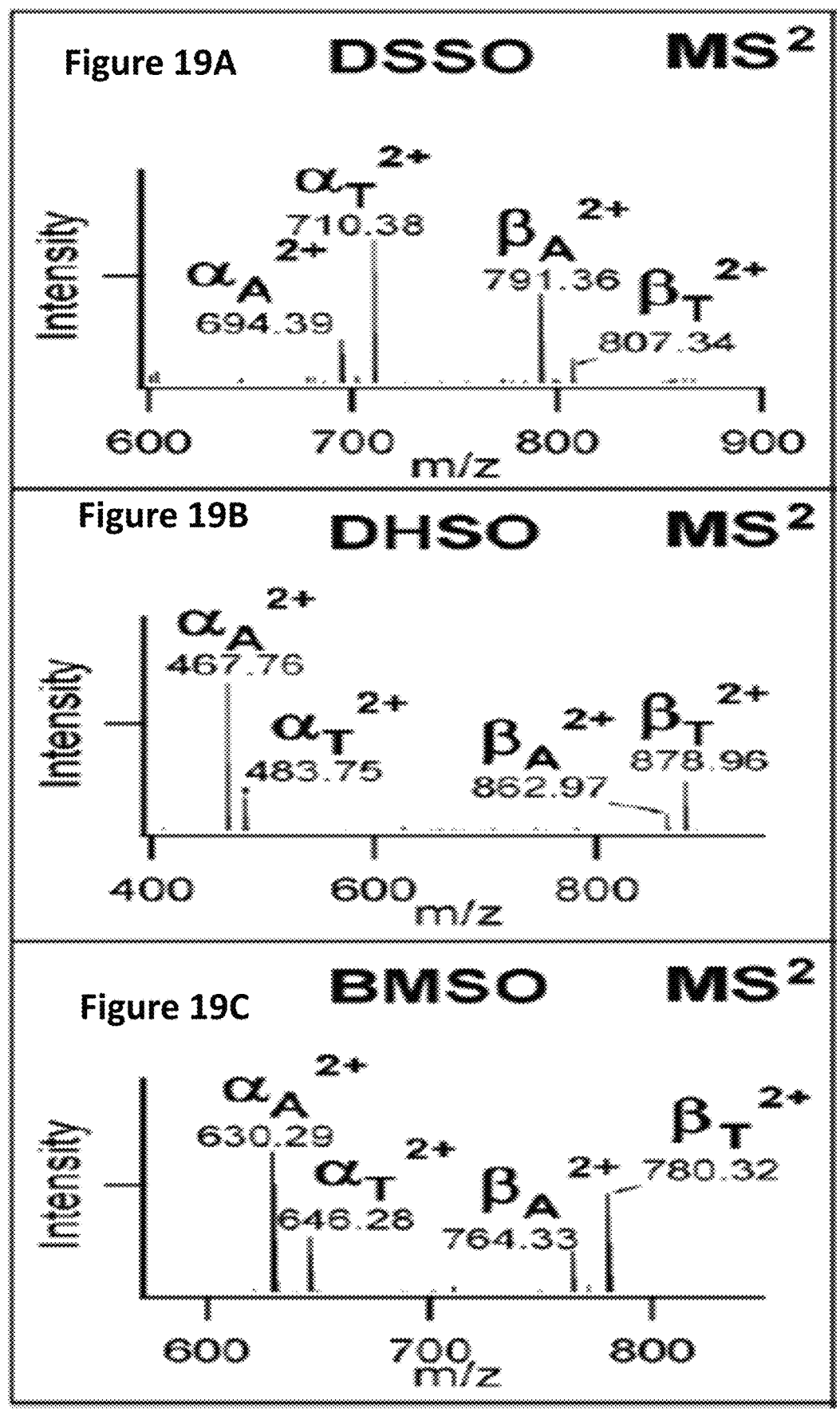

Figure 19D
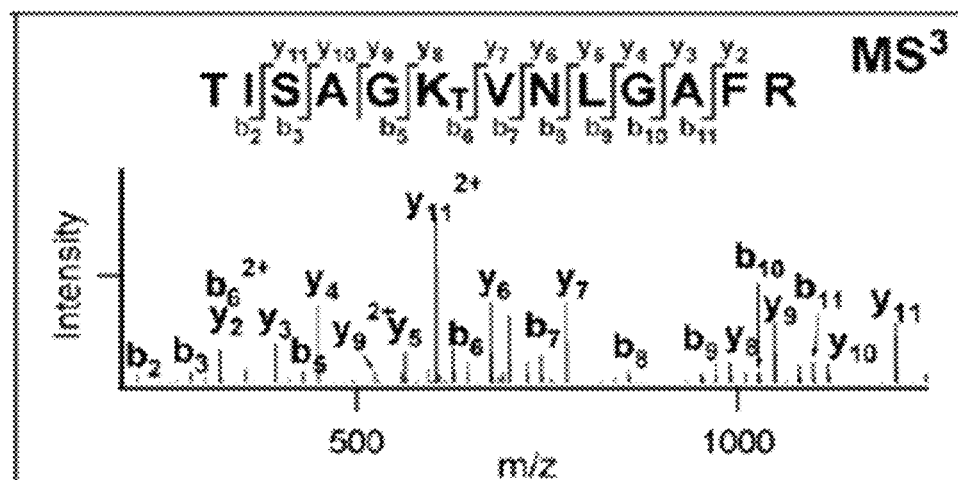
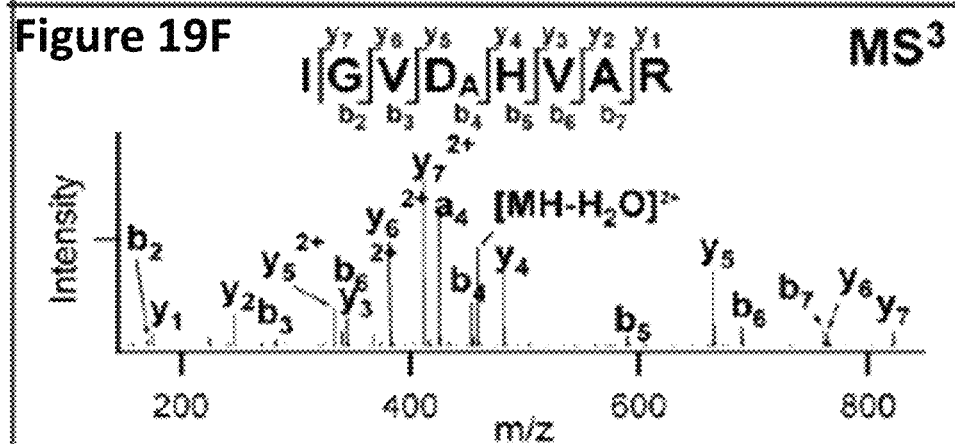
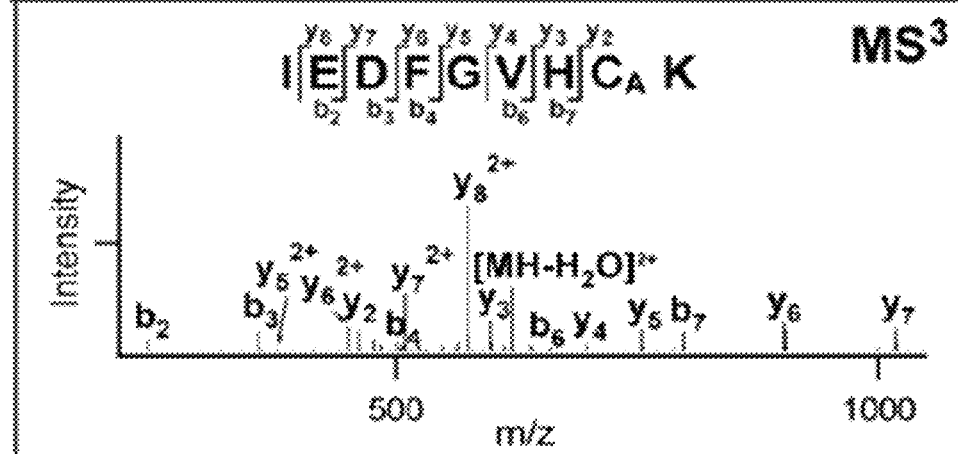
Figure 19H

Figure 19E
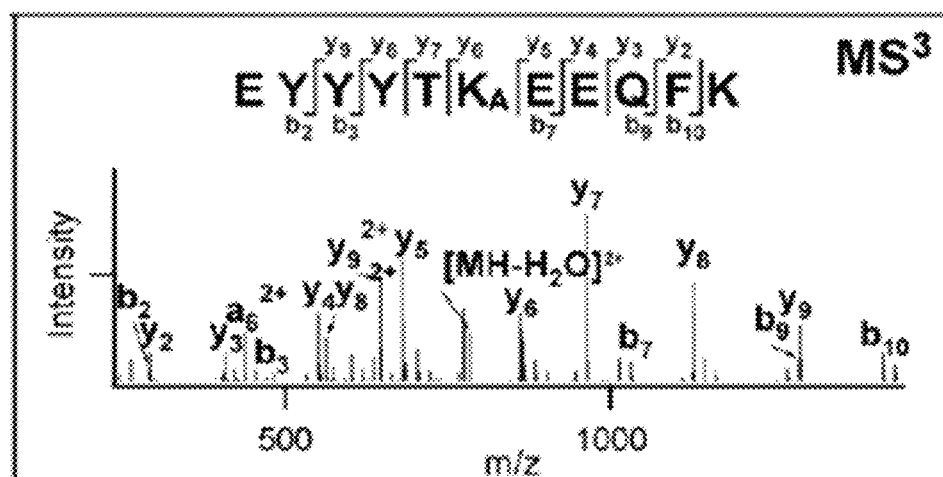
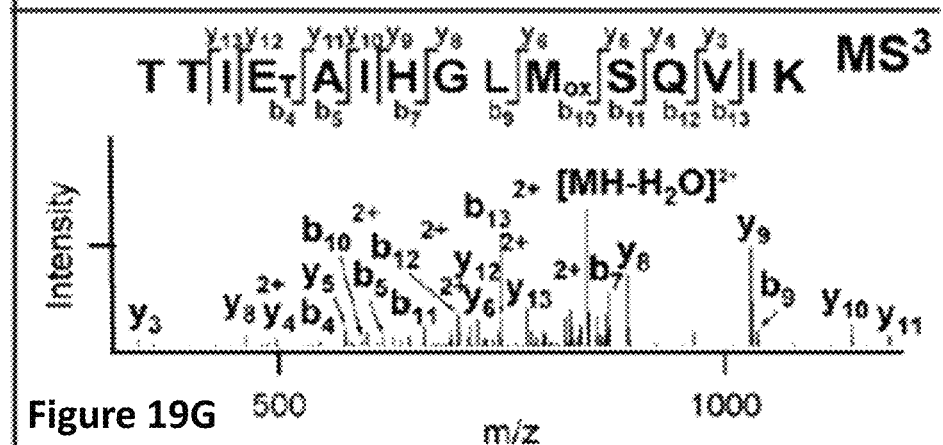
Figure 19G
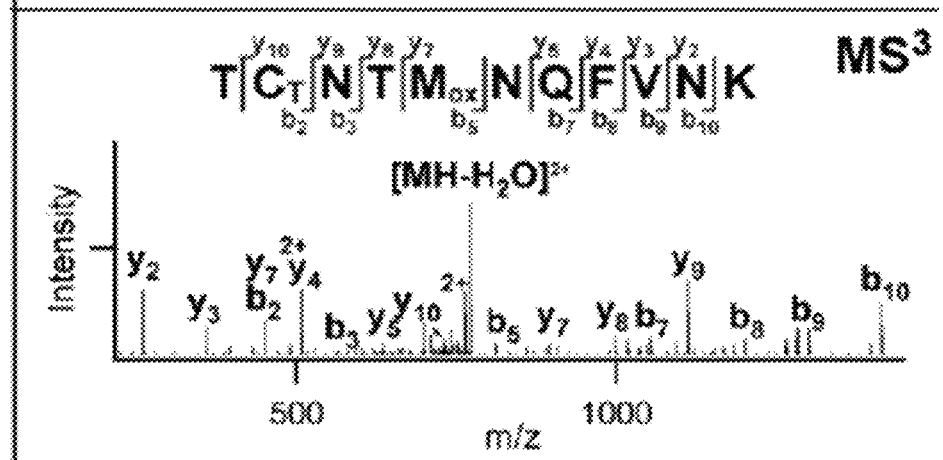
Figure 19I

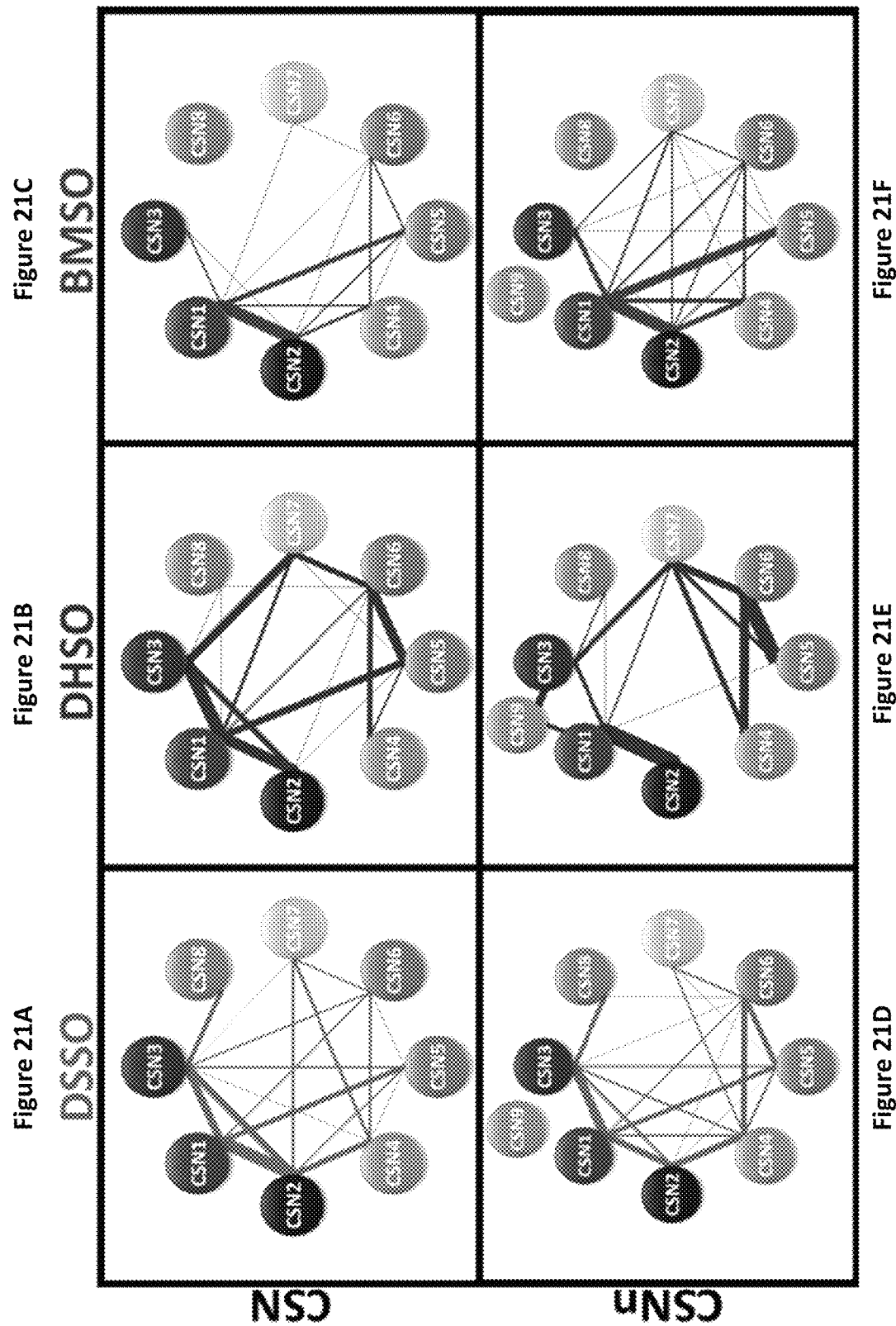

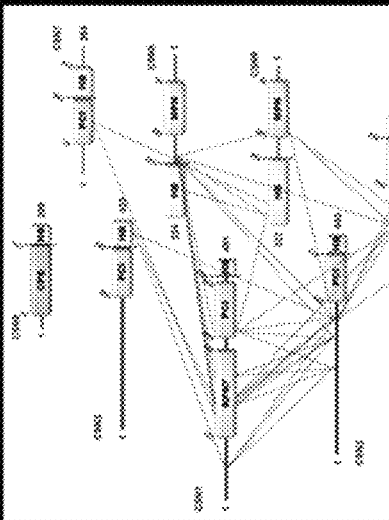
Figure 21I BMSO
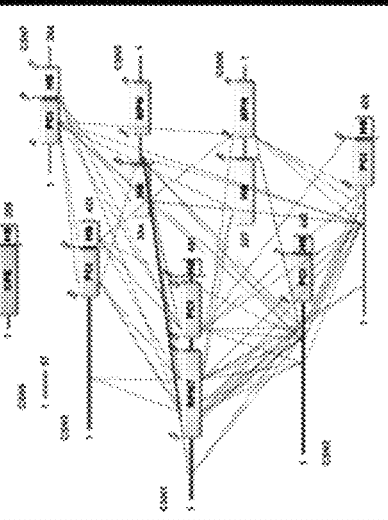
Figure 21L
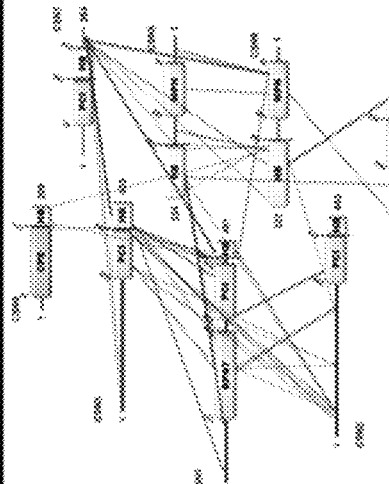
Figure 21H DHSO
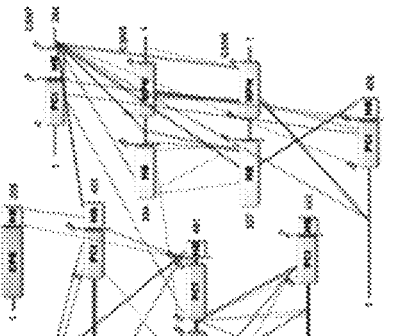
Figure 21K
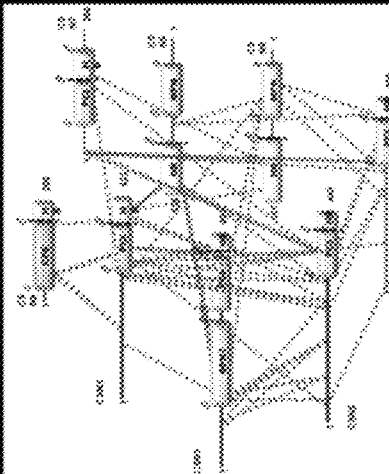
Figure 21G DSSO
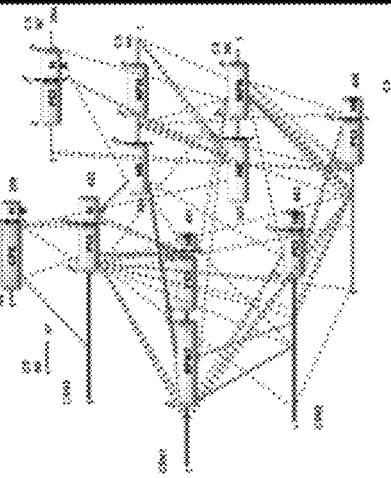
Figure 21J

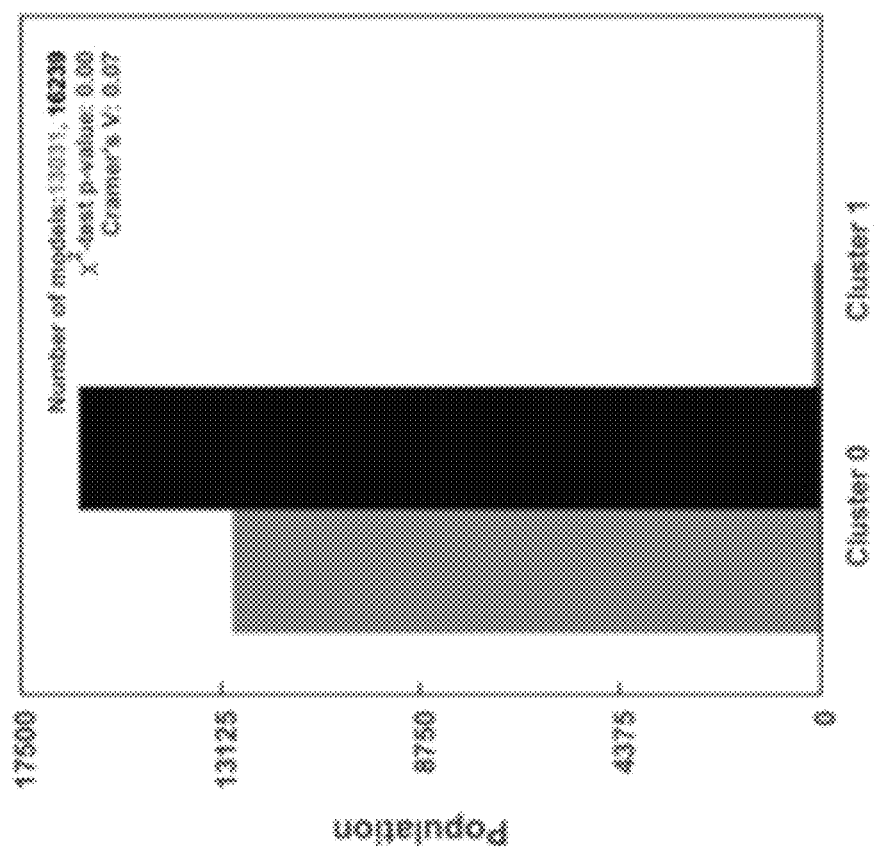
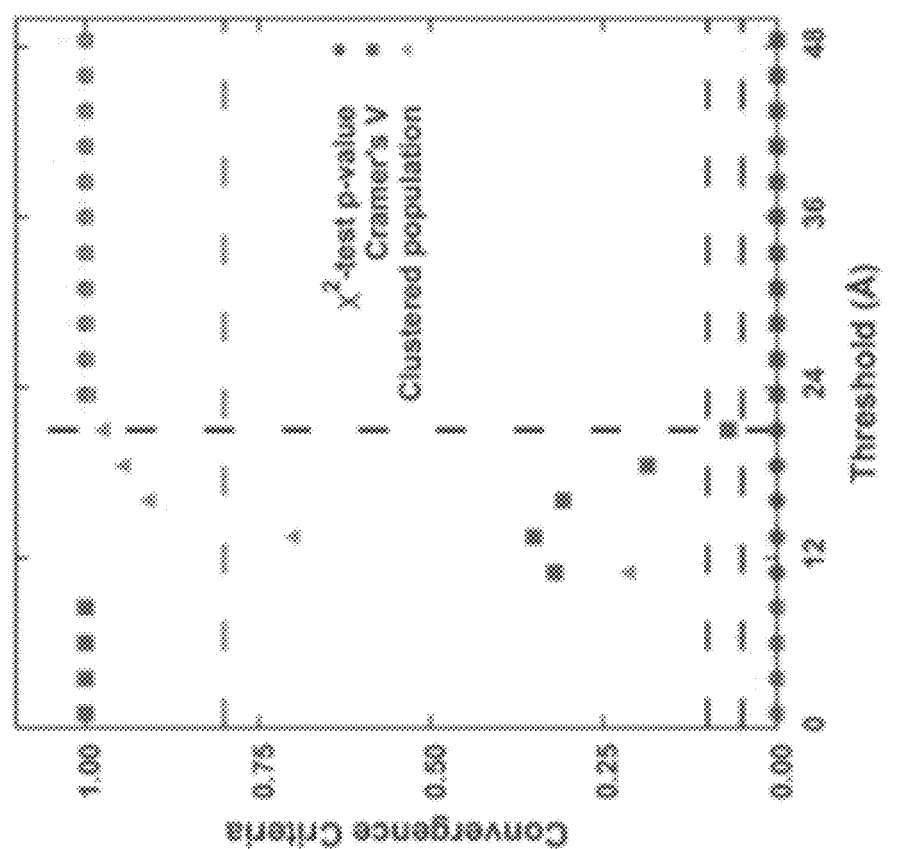
Figure 24D
Figure 24C

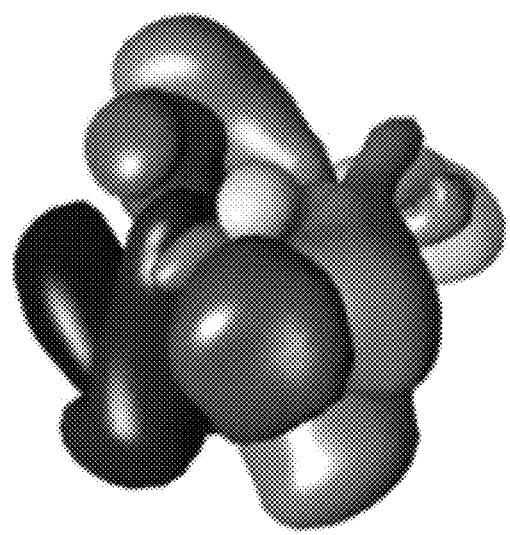
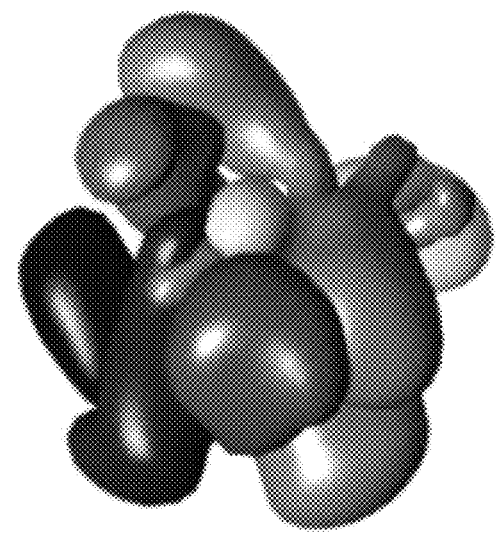
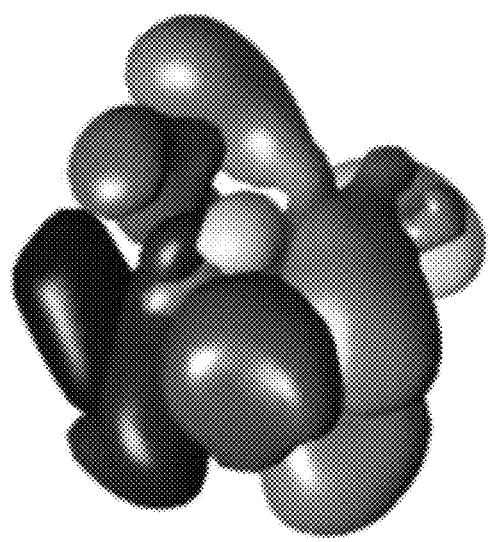
Figure 24E

  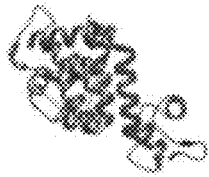 
CSN1:44-107   CSN1:128-227   CSN1:246-426   CSN2:30-179
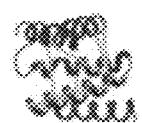   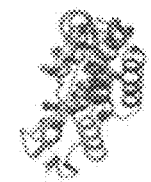
CSN2:192-289   CSN2:308-397   CSN3:3-163   CSN3:177-361
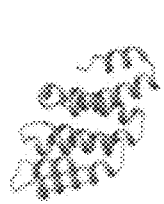 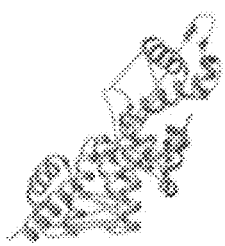  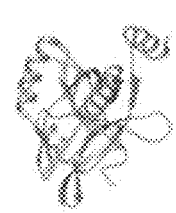
CSN4:3-131   CSN4:139-361   CSN5:25-283   CSN6:29-207
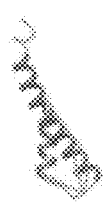 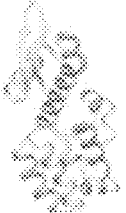 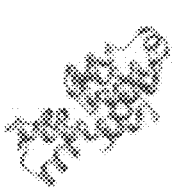 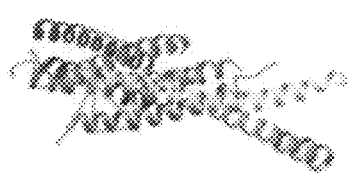
CSN6:215-267   CSN7B:8-158   CSN8:11-164   Helical core bundle
Figure 24H

  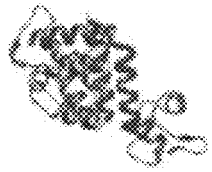 
CSN1:44-107  CSN1:128-227  CSN1:246-426  CSN2:30-179
  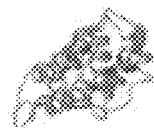 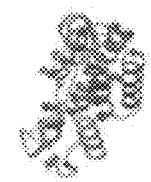
CSN2:192-289  CSN2:308-397  CSN3:3-163  CSN3:177-361
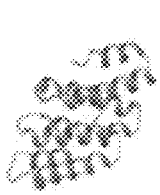 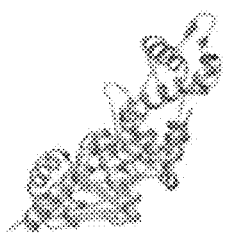  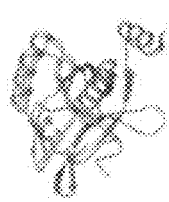
CSN4:3-131  CSN4:139-361  CSN5:25-283  CSN6:29-207
  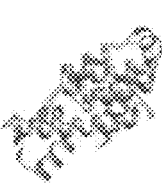 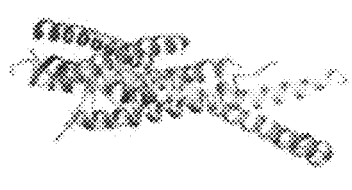
CSN6:215-267  CSN7B:3-158  CSN8:11-164 Helical core bundle
Figure 27H

MASS SPECTROMETRY-CLEAVABLE CROSS-LINKER

PRIORITY AND CROSS REFERENCE TO RELATED APPLICATIONS

This application claims the benefit of U.S. Provisional Application 62/845,240 filed on May 8, 2019, which is hereby incorporated by reference in its entirety.

STATEMENT REGARDING FEDERALLY SPONSORED R&D

This invention was made with Government support under Grant Nos. NIH: R01GM074830; R01GM074830-1251; R01GM106003 awarded by the National Institutes of Health. The Government has certain rights in the invention.

SEQUENCE LISTING IN ELECTRONIC FORMAT

The present application is being filed along with a Sequence Listing as an ASCII text file via EFS-Web. The Sequence Listing is provided as a file entitled UCI012005ASEQLIST.txt, created and last saved on Sep. 8, 2020, which is 19,314 bytes in size. The information in the electronic format of the Sequence Listing is incorporated herein by reference in its entirety in accordance with 35 U.S.C. § 1.52(e).

BACKGROUND

Field

The present disclosure is related to MS-cleavable cross-linkers for Studying Protein-Protein Interactions. Some embodiments of the present disclosure are related to a sulfoxide-containing MS-cleavable for studying protein-protein interactions

Description of the Related Art

Cross-linking mass spectrometry (XL-MS) has become an emerging technology for defining protein-protein interactions (PPIs) and elucidating architectures of large protein complexes. Up to now, the most widely used cross-linking reagents target lysines. While such reagents have been successfully applied to map PPIs at the proteome-wide scale, comprehensive PPI profiling would require additional cross-linking chemistries.

SUMMARY

In some embodiments, an MS-cleavable cross-linker for mapping intra-protein interactions in a protein, inter-protein interactions in a protein complex or a combination thereof is provided.

In some embodiments, the MS-cleavable cross-linker comprises two maleimide functional groups, a spacer arm with at least one central sulfoxide group, wherein the at least one central sulfoxide group is linked to each of the two maleimide functional groups, and two symmetric collision-induced dissociation (CID) cleavable bonds on the spacer arm, wherein each of the two CID cleavable bond is a C—S bond adjacent to the at least one central sulfoxide.

In some embodiments of the MS-cleavable cross-linker, each maleimide functional group is designed to react with a cysteine in a peptide or a protein.

In some embodiments, the MS-cleavable cross-linker is homobifunctional.

In some embodiments of the MS-cleavable cross-linker, the two maleimide functional groups are separated by a 24.2 Å long spacer arm comprising the two symmetric CID cleavable C—S bonds flanking the at least one central sulfoxide group.

In some embodiments, the MS-cleavable cross-linker is BMSO, comprising the structure:

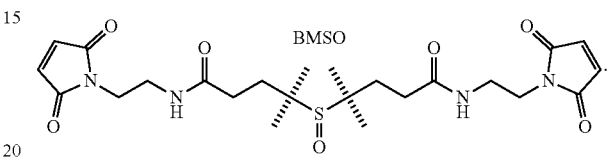

In some embodiments, a method for synthesis of an MS-cleavable cross-linker for mapping intra-protein interactions in a protein, inter-protein interactions in a protein complex or a combination thereof, the method comprises the steps of:

(i) providing a solution comprising DSSO and a trifluoroacetate salt of 1-(2-aminoethyl) maleimide;

(ii) adding $NaHCO_3$ to the solution of step (i) to obtain a mixture;

(iii) concentrating the mixture of step (ii) in vacuo to obtain a crude material; and (iv) purifying the MS-cleavable cross-linker from the crude material of step (iii) using column chromatography.

In some embodiments of the method for synthesis of an MS-cleavable cross-linker, step (ii) is performed at room temperature.

In some embodiments of the method for synthesis of an MS-cleavable cross-linker, step (ii) is performed for about 12 h.

In some embodiments of the method for synthesis of an MS-cleavable cross-linker, the MS-cleavable cross-linking agent is BMSO, comprising the structure:

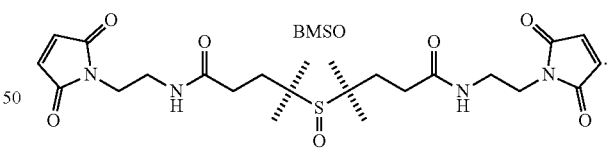

In some embodiments, a method for mapping intra-protein interactions in a protein, inter-protein interactions in a protein complex or a combination thereof is provided.

In some embodiments of method for mapping intra-protein interactions in a protein, inter-protein interactions in a protein complex or a combination thereof, the method comprises providing the MS-cleavable cross-linker BMSO, forming a cross-linked protein or protein complex by cross-linking the protein or the protein complex with the MS-cleavable cross-linker, forming one or more peptide fragments that are chemically bound to the MS-cleavable cross-linker by digesting the cross-linked protein or protein complex with an enzyme, and identifying the one or more peptide fragments using tandem mass spectrometry ($MS^n$), thereby mapping intra-protein interactions in a protein and inter-protein interactions in a protein complex.

In some embodiments of method for mapping intra-protein interactions in a protein, inter-protein interactions in a protein complex or a combination thereof, the cross-linking the protein or the protein complex with the MS-cleavable cross-linker occurs by conjugation of cysteines.

In some embodiments of method for mapping intra-protein interactions in a protein, inter-protein interactions in a protein complex or a combination thereof, the conjugation of cysteines occurs via maleimide chemistry.

In some embodiments of method for mapping intra-protein interactions in a protein, inter-protein interactions in a protein complex or a combination thereof, wherein the maleimide chemistry yields two different forms of cross-linked cysteines.

In some embodiments of method for mapping intra-protein interactions in a protein, inter-protein interactions in a protein complex or a combination thereof, the two different forms of cross-linked cysteines comprise a closed-ring structure and a hydrolyzed open-ring structure.

In some embodiments of method for mapping intra-protein interactions in a protein, inter-protein interactions in a protein complex or a combination thereof, the MS-cleavable cross-linking agent is BMSO, comprising the structure:

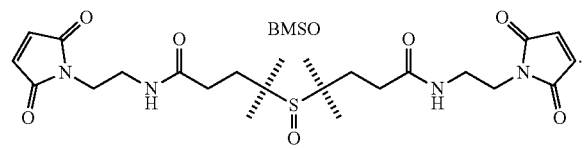

In some embodiments, a method for cross-linking mass spectrometry (XL-MS) for identifying one or more cross-linked peptides is provided.

In some embodiments, the method for cross-linking mass spectrometry (XL-MS) for identifying one or more cross-linked peptides comprises performing cross-linking with the MS-cleavable cross-linker BMSO to obtain one or more cross-linked proteins, digesting the one or more cross-linked proteins with trypsin to obtain one or more cross-linked peptides, performing a liquid chromatography-tandem mass spectrometry (LC-MS$^n$) analysis on the one or more cross-linked peptides, wherein the LC-MS$^n$ analysis comprises detecting the one or more cross-linked peptides by MS$^1$ analysis, selecting the one or more cross-linked peptides detected by MS$^1$ for MS$^2$ analysis, selectively fragmenting the at least one CID cleavable bond and separating the one or more cross-linked peptides during MS$^2$ analysis, sequencing the one or more cross-linked peptides separated during MS$^2$ analysis by MS$^3$ analysis, and integrating data obtained during MS$^1$, MS$^2$ and MS$^3$ analyses to identify the one or more cross-linked peptides.

In some embodiments of the method for cross-linking mass spectrometry (XL-MS) for identifying one or more cross-linked peptides, the cross-linking with the MS-cleavable cross-linker occurs by conjugation of cysteines.

In some embodiments of the method for cross-linking mass spectrometry (XL-MS) for identifying one or more cross-linked peptides, the conjugation of cysteines occurs via maleimide chemistry.

In some embodiments of the method for cross-linking mass spectrometry (XL-MS) for identifying one or more cross-linked peptides, the maleimide chemistry yields two different forms of cross-linked cysteines, wherein the two different forms of cross-linked cysteines comprise a closed-ring structure and a hydrolyzed open-ring structure.

In some embodiments of a method for XL-MS, the MS-cleavable cross-linking agent is BMSO, consisting of the structure:

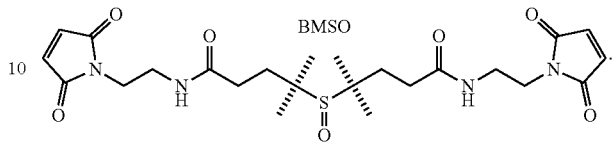

BRIEF DESCRIPTION OF THE DRAWINGS

FIGS. 1A-1F show design, synthesis and characteristics of the Sulfoxide-containing MS-cleavable Cysteine Reactive Cross-linker, BMSO.

FIG. 1A shows molecular structure of DSSO[17].

(FIG. 1B) shows molecular structure of DHSO[9].

FIG. 1C shows molecular structure of BMSO.

FIG. 1D shows an embodiment of a synthesis scheme of BMSO.

FIG. 1E shows an embodiment of data related to BMSO cross-linking results in the formation of an inter-linked heterodimer (α-β), in which the closed-ring SITE structure on cross-linked cysteines can be converted to open-ring SATE structures upon hydrolysis.

FIG. 1F shows an embodiment of predicted characteristic MS$^2$ fragmentation of a BMSO inter-linked heterodimer α-β, in which thioester (TE) structures on cross-linked cysteines can be in the form of either closed-ring SITE or open-ring SATE. Note: c: closed-ring; o: open-ring.

FIGS. 2A-2D show data related to an embodiment MS analysis of the BMSO inter-linked Ac-LR9 homodimer (α-α).

FIG. 2A shows MS$^1$ spectrum of the inter-link with closed-ring form, $(\alpha_c\text{-}\alpha_c)^{4+}$ (m/z 637.7849$^{4+}$).

FIG. 2B shows MS$^2$ spectrum of the $(\alpha_c\text{-}\alpha_c)^{4+}$ detected in (FIG. 2A), in which two dominant fragment ions, i.e. $\alpha_{Ac}$ (m/z 625.29$^{2+}$) and $\alpha_{Tc}$ (m/z 641.27$^{2+}$), were detected as predicted for homodimer inter-links.

FIG. 2C shows MS$^1$ spectrum of the inter-link with open-ring form, $(\alpha_o\text{-}\alpha_o)^{4+}$ (m/z 646.7885$^{4+}$).

FIG. 2D shows MS$^2$ spectrum of the $(\alpha_o\text{-}\alpha_o)^{4+}$ detected in (FIG. 2C), in which two dominant fragment ions, i.e. $\alpha_{Ao}$ (m/z 634.29$^{2+}$) and $\alpha_{To}$ (m/z 650.28$^{2+}$) were detected as expected. Note: c: closed-ring; o: open-ring; Ac/Tc: alkene/unsaturated thiol moieties with closed-ring SITE; Ao/To: alkene/unsaturated thiol moieties with open-ring SATE.

FIGS. 3A-3D show data related to an embodiment of MS$^n$ analysis of a representative BMSO inter-linked peptide of BSA.

FIG. 3A shows the BMSO inter-linked peptide with open-ring SATE structures, $(\alpha_o\text{-}\beta_o)$ (m/z 719.5689$^{4+}$).

FIG. 3B shows MS$^2$ spectrum of the $(\alpha_o\text{-}\beta_o)$, in which two characteristic fragment ion pairs were detected, i.e. $\alpha_{Ao}/\beta_{To}$ (m/z 614.29$^{2+}$/815.84$^{2+}$) and $\alpha_{To}/\beta_{Ao}$ (m/z 630.28$^{2+}$/799.86$^{2+}$).

FIG. 3C shows MS$^3$ analysis of $\alpha_{Ao}$ (m/z 614.29$^{2+}$) identified the sequence as SHC$_{Ao}$IAEVEK (SEQ ID NO: 83), in which the cysteine residue was modified with alkene moiety carrying an open-ring SATE.

FIG. 3D shows MS$^3$ analysis of $\beta_{To}$ (m/z 815.84$^{2+}$) identified the sequence as YIC$_{To}$DNQDTISSK (SEQ ID NO:

84), in which the cysteine residue was modified with unsaturated thiol moiety carrying an open-ring SATE.

FIGS. 4A-4C show BMSO XL-MAP of BSA.

FIG. 4A shows 2-D BMSO XL-map on BSA linear sequence. Helical secondary structures are designated by gray regions, green if containing cross-linked cysteines.

FIG. 4B shows 3-D BMSO cross-link map on BSA crystal structure (PDB: 4F5S). Helices containing cross-linked cysteines are shown in green.

FIG. 4C shows the distribution plot of identified C-C linkages vs. their spatial distances showing the number of linkages within (purple) and greater than (red) the expected distance constraint (<45 Å).

Figure 5:
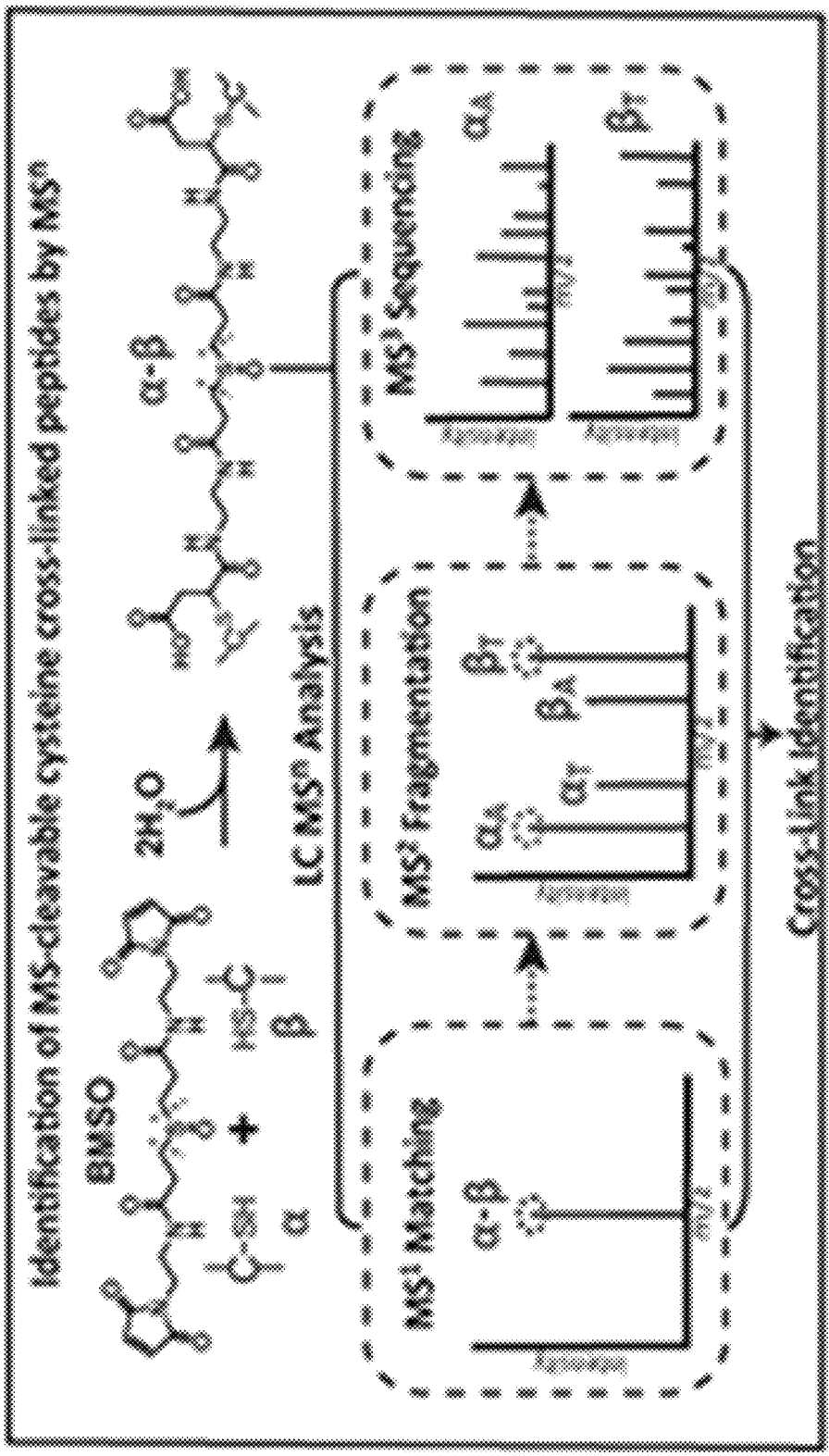

FIG. 5 shows an embodiment of a general scheme for the identification of MS-cleavable cysteine cross-linked peptides by MS$^n$ using BMSO.

Figure 6:
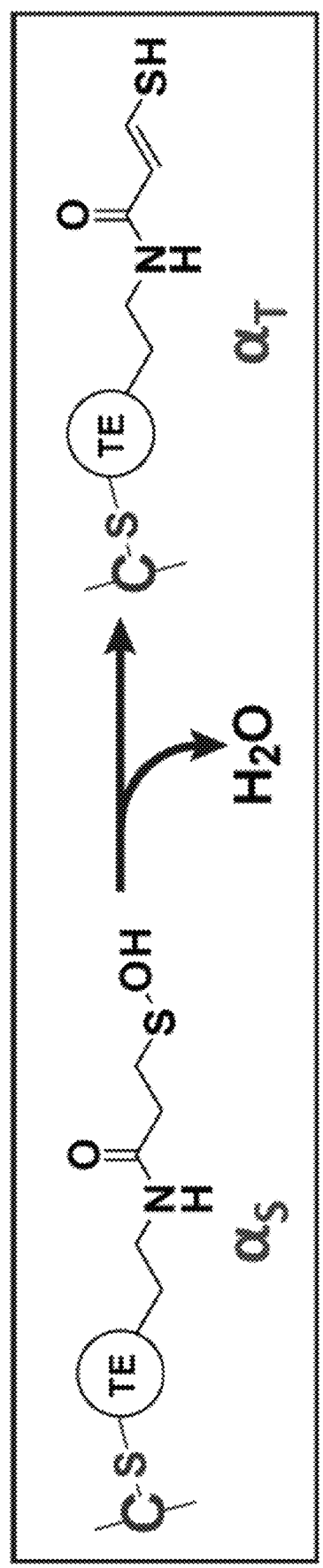

FIG. 6 shows an embodiment of the conversion scheme of αS to αT, in which the sulfenic acid moiety (S) became the more stable unsaturated thiol moiety (T) via water loss.

Figure 7A:
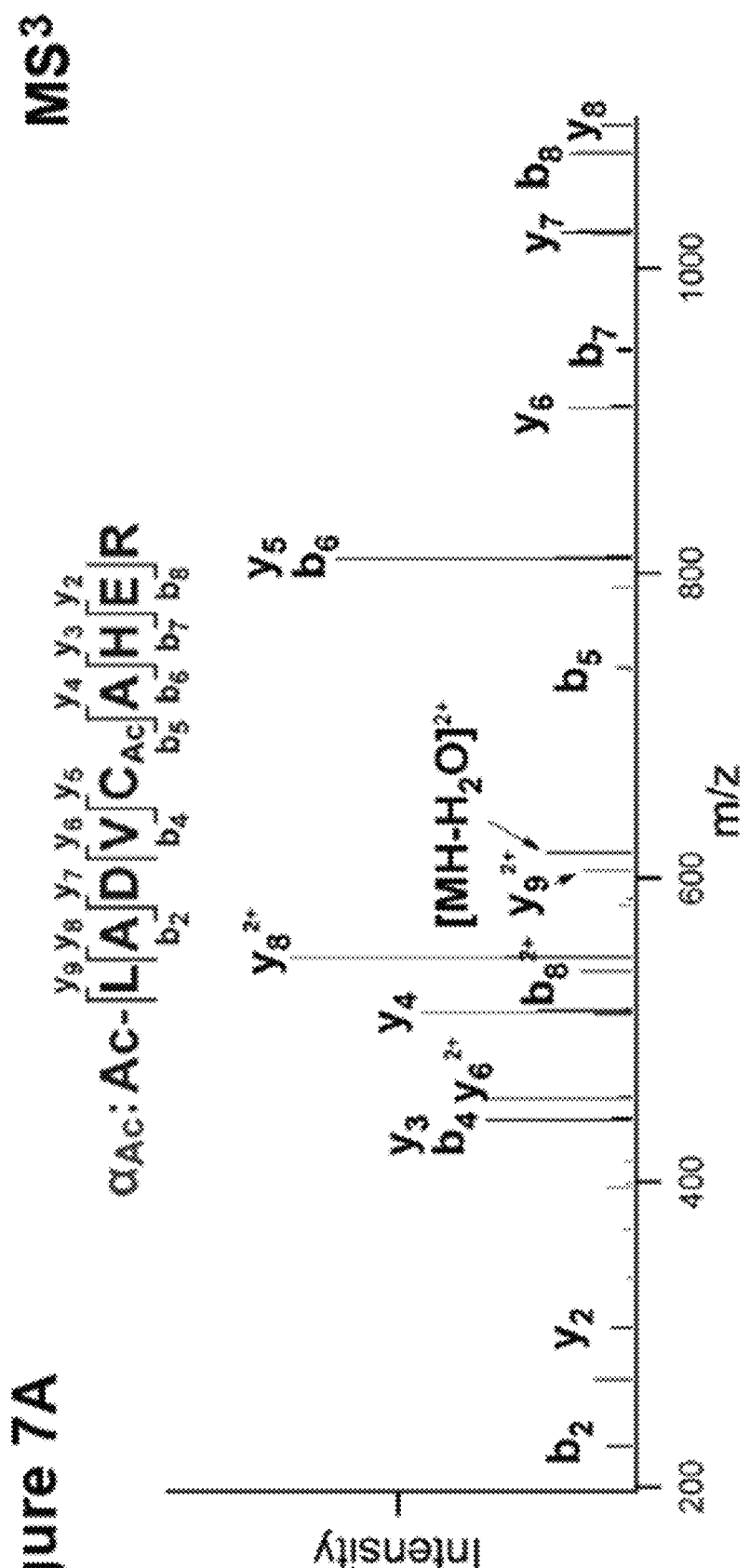
Figure 7B:
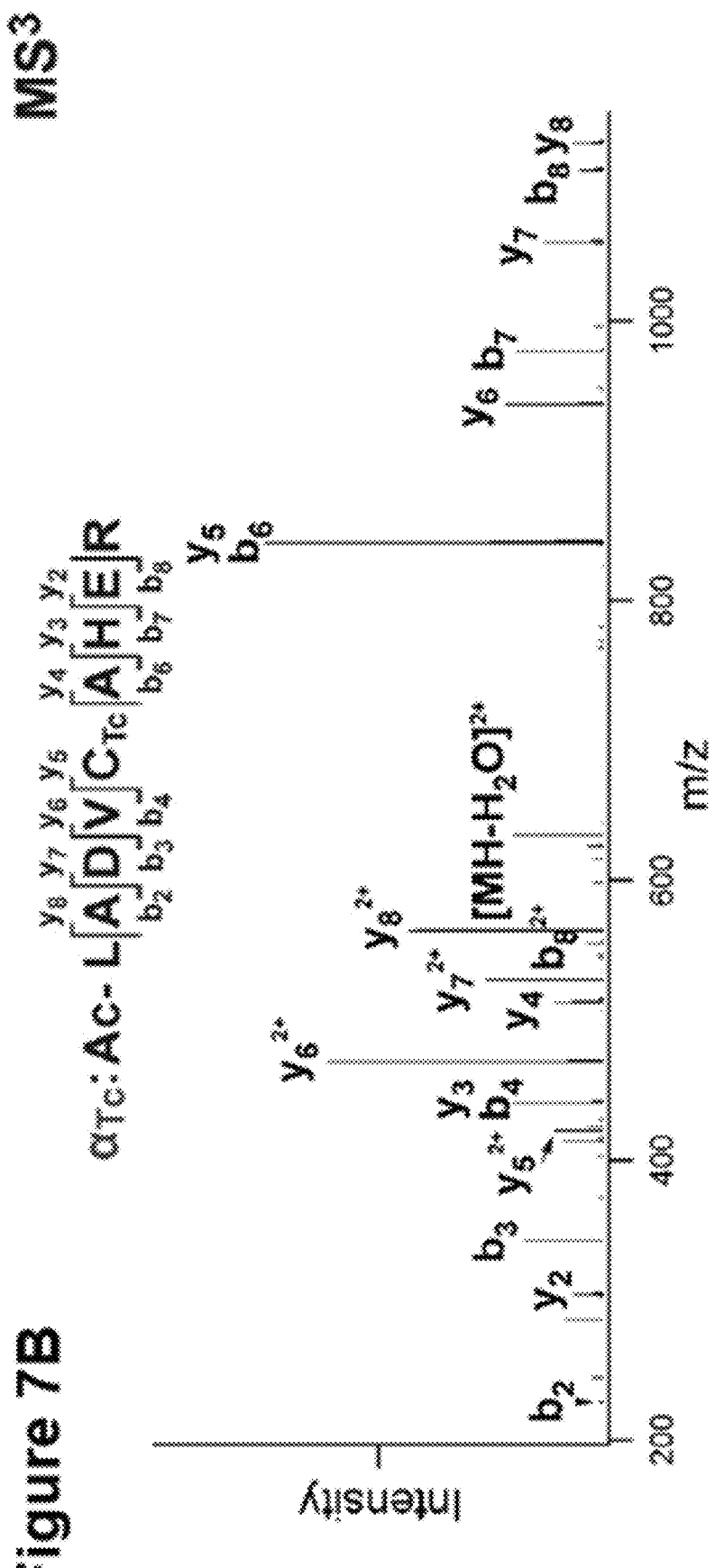

FIGS. 7A-7B show embodiments of MS$^3$ analysis of the BMSO inter-linked Ac-LR9 homodimer with closed-ring as shown in FIG. 2A, and MS$^3$ spectra of MS$^2$ fragment ions detected in FIG. 2B.

FIG. 7A shows $\alpha_{Ac}$ (m/z 625.29$^{2+}$).

FIG. 7B shows $\alpha_{Tc}$ (m/z 641.27$^{2+}$).

Figure 8A:
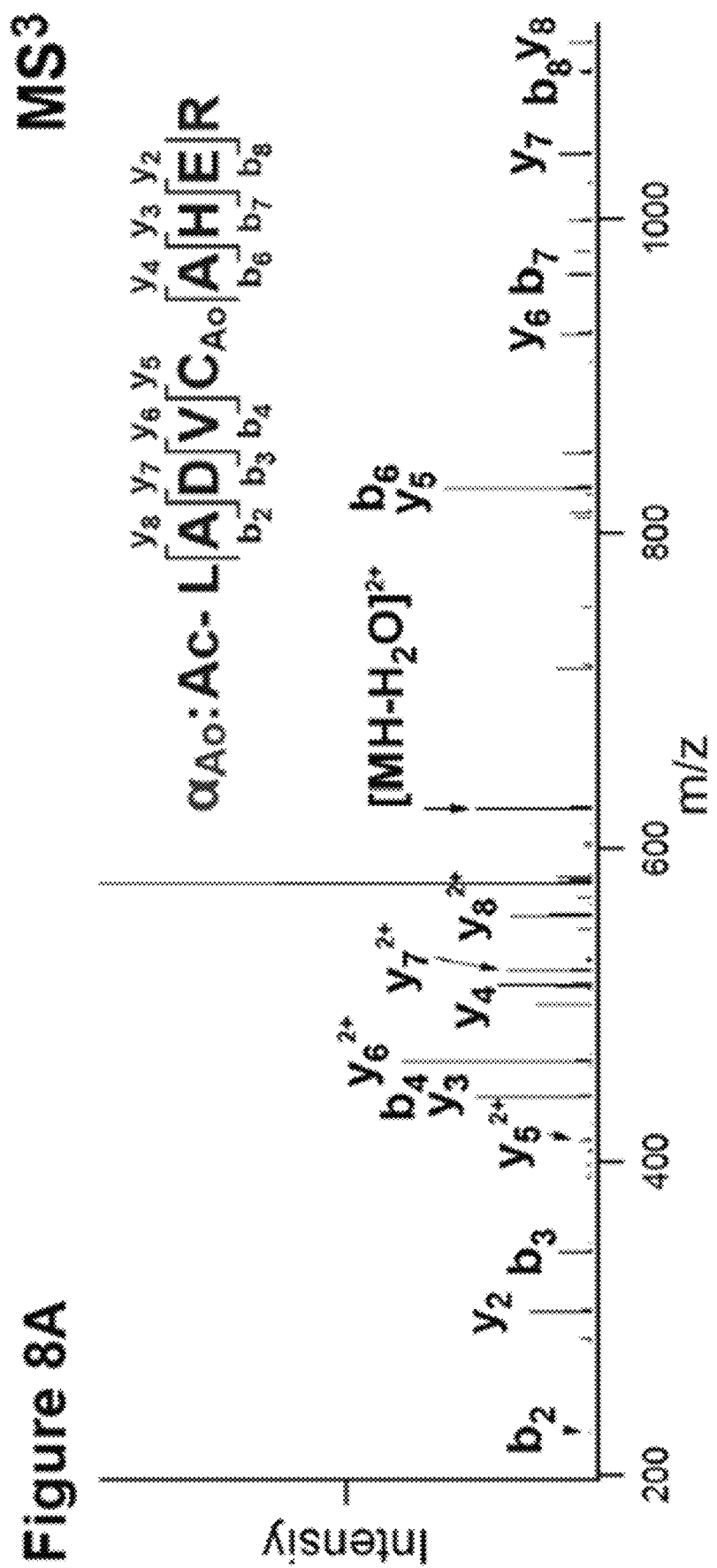
Figure 8B:
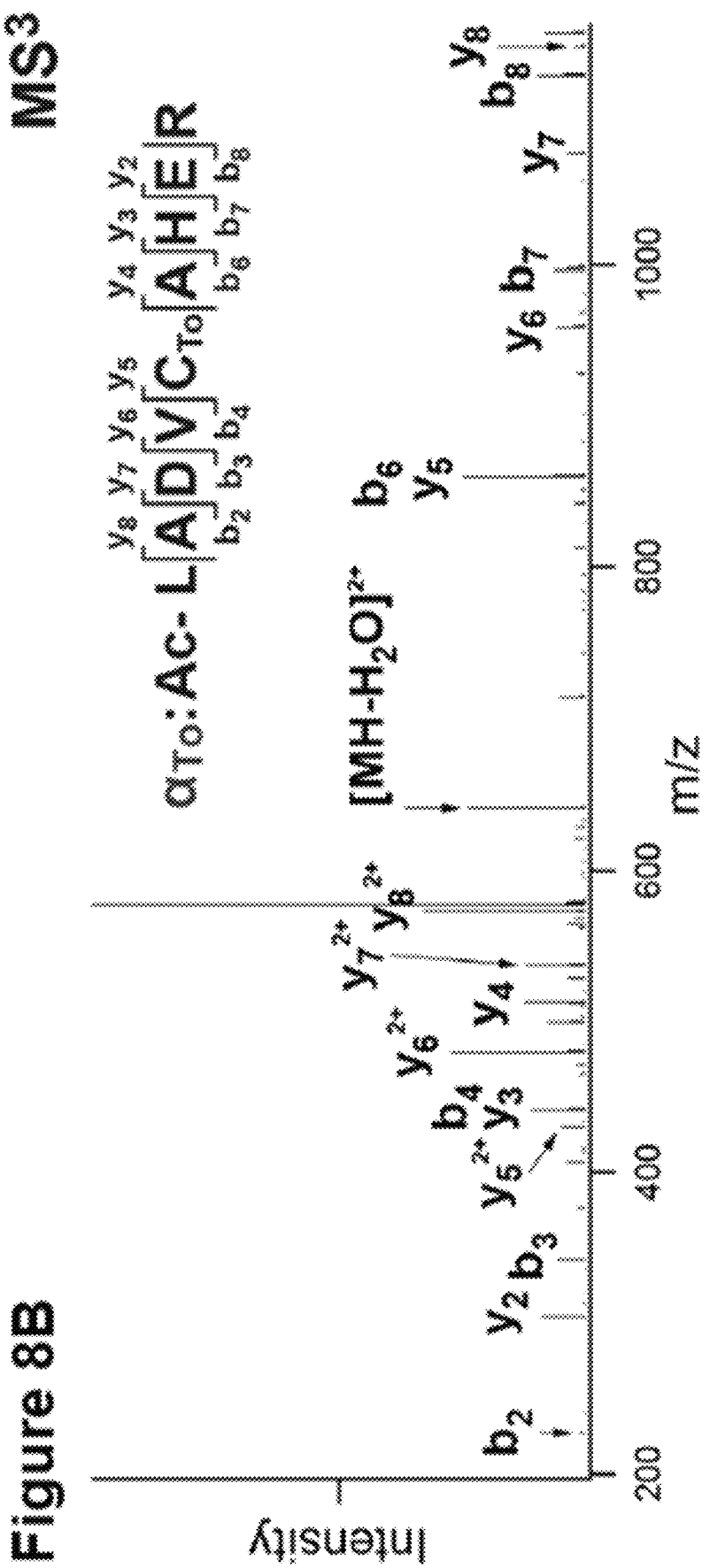

FIGS. 8A-8B show embodiments of MS$^3$ analysis of the BMSO inter-linked Ac-LR9 homodimer with open-ring as shown in FIG. 2C, and MS$^3$ spectra of MS$^2$ fragment ions detected in FIG. 2D.

FIG. 8A shows $\alpha_{Ao}$ (m/z 634.29$^{2+}$).

FIG. 8B shows $\alpha_{To}$ (m/z 650.28$^{2+}$).

FIGS. 9A-9D shows an embodiment of MSn analysis of the BMSO inter-linked Ac-LR9 homodimer with one closed-ring and one open-ring structures (αc-αo).

Figure 9A:
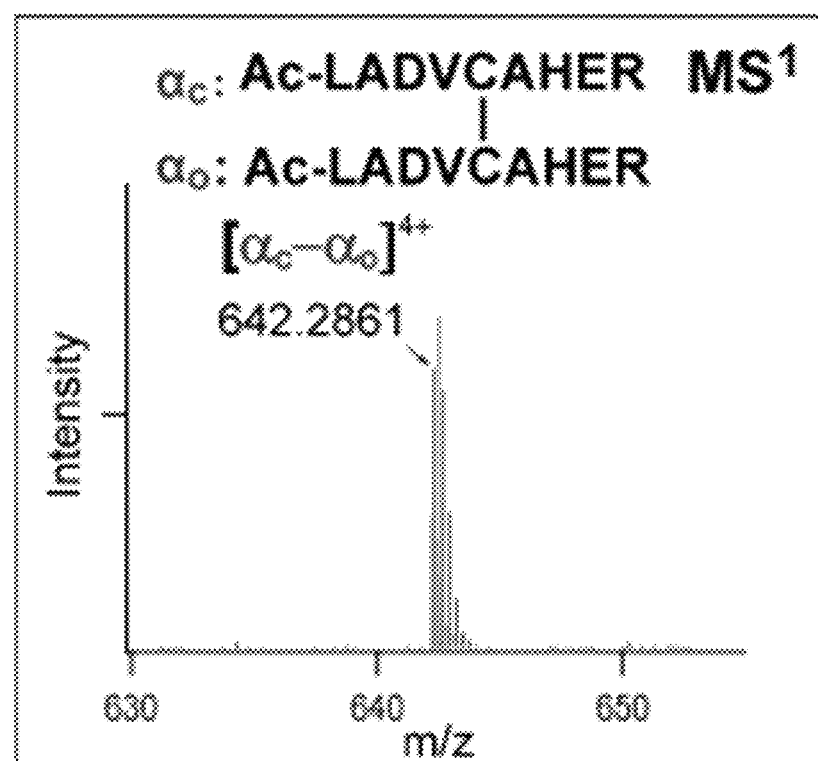

FIG. 9A shows an embodiment of MS$^1$ spectrum of the BMSO mixed-ring Ac-LR9 homodimer: $(\alpha_c-\alpha_o)^{4+}$ (m/z 642.2861$^{4+}$).

Figure 9B:
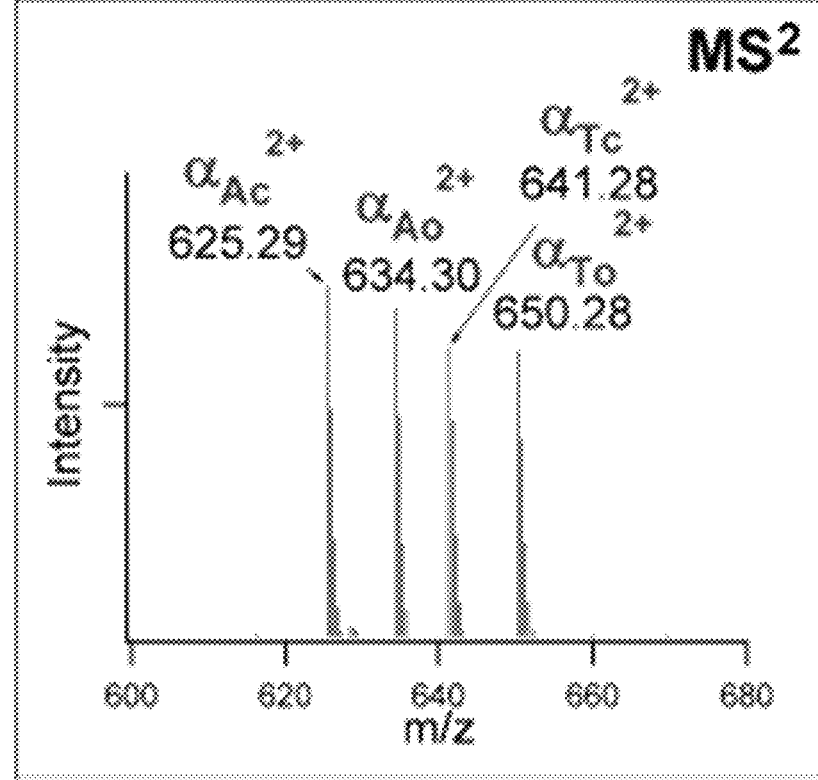

FIG. 9B shows an embodiment of MS$^2$ analysis of $(\alpha_c-\alpha_o)^{4+}$ detected in (FIG. 9A) resulted in two fragment ion pairs: $\alpha_{Ac}/\alpha_{To}$ (m/z 625.29$^{2+}$/650.28$^{2+}$) and $\alpha_{Tc}/\alpha_{Ao}$ (m/z 641.28$^{2+}$/634.30$^{2+}$). This is expected as the ring states made the two identical sequences different, by modifying them with alkene and unsaturated moieties carrying either closed-ring or open-ring structures. Therefore, this makes the peptide $(\alpha_c-\alpha_o)$ behave like heterodimer instead of homodimer.

Figure 9C:
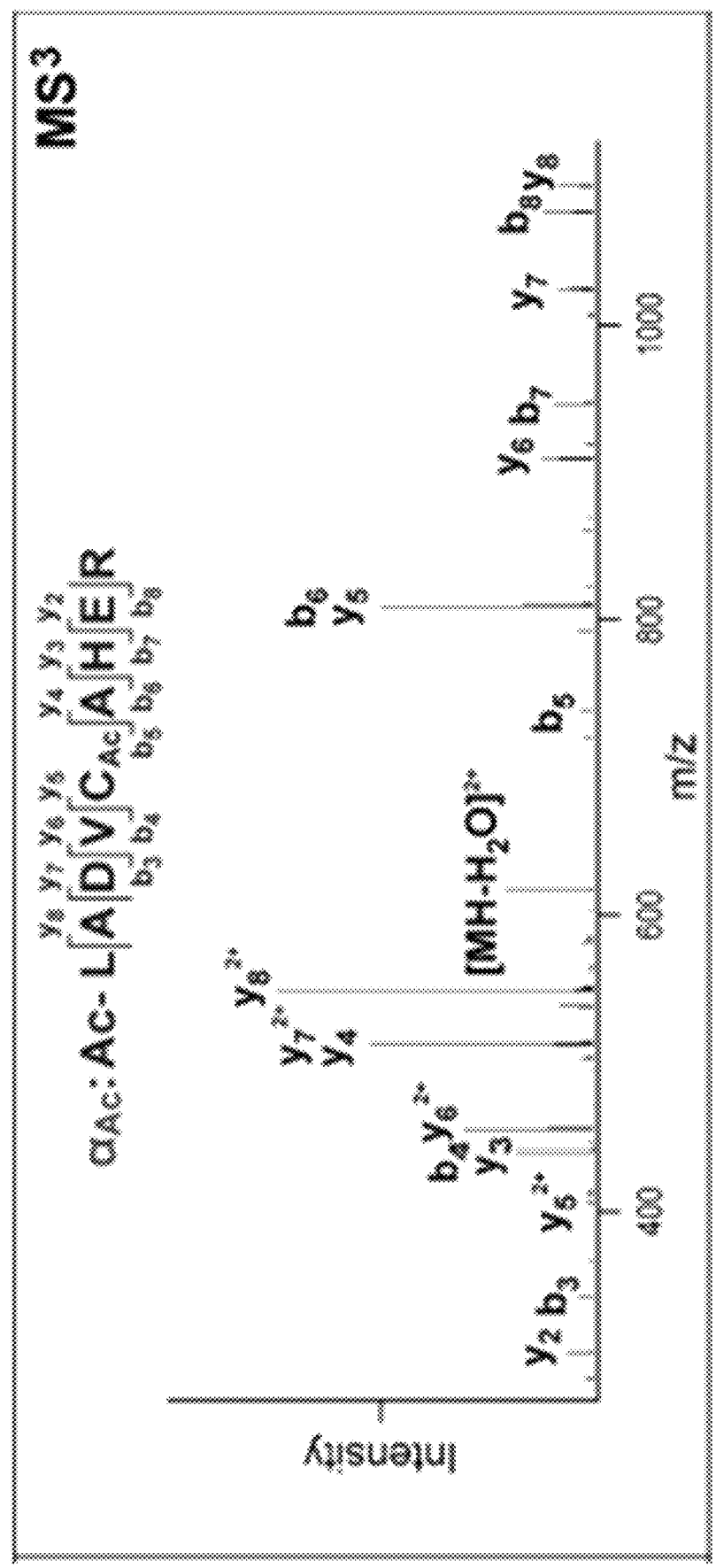

FIG. 9C shows an embodiment of MS$^3$ analyses of $\alpha_{Ac}$ (m/z 625.29$^{2+}$), which identified the sequence as Ac-LAD-VC$_{Ac}$AHER (SEQ ID NO: 85). Note: c: closed-ring; o: open-ring; Ac/Tc: alkene/unsaturated thiol moieties with closed-ring SITE; Ao/To: alkene/unsaturated thiol moieties with open-ring SATE.

Figure 9D:
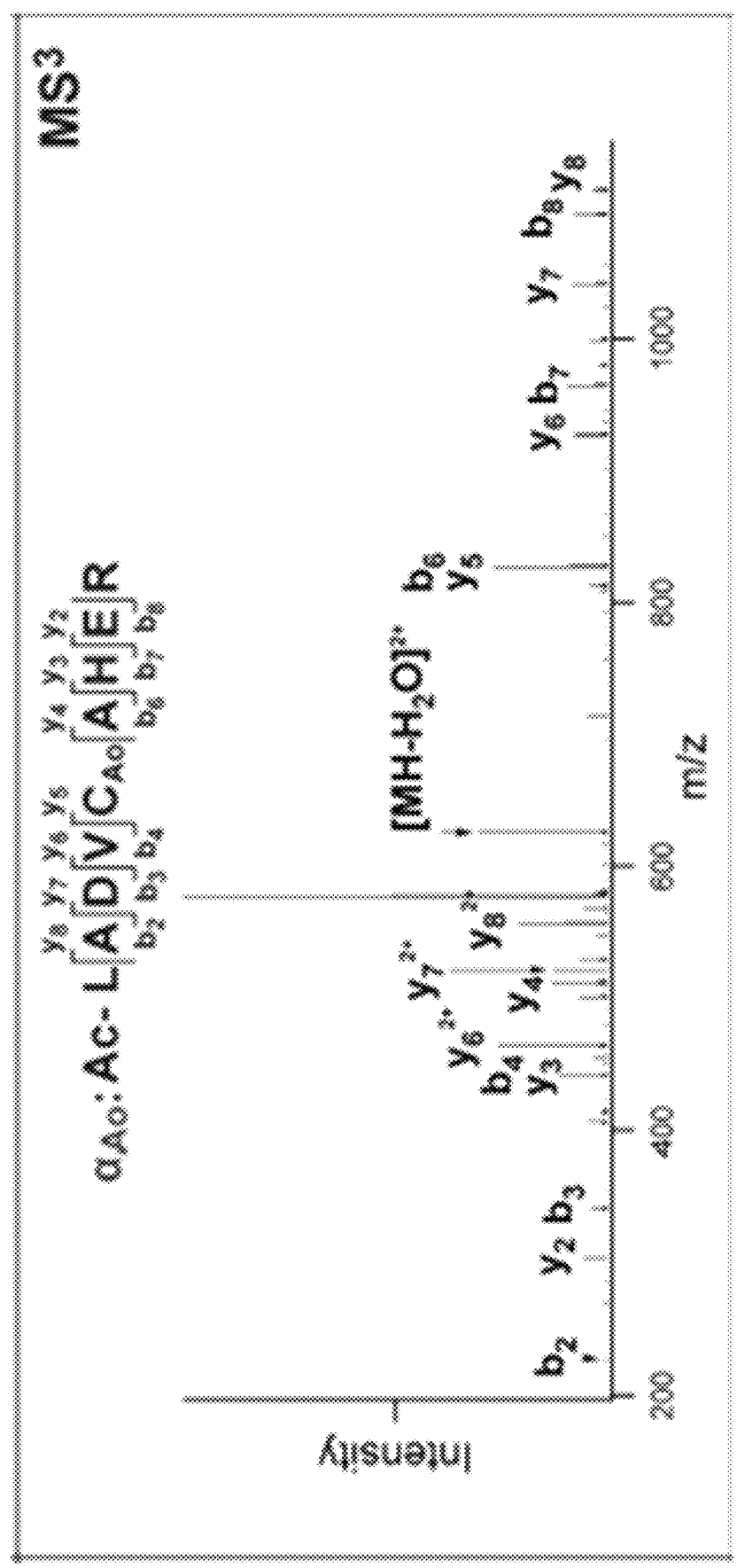

FIG. 9D shows an embodiment of MS$^3$ analyses of $\alpha_{To}$ (m/z 650.28$^{2+}$), which identified the sequence as Ac-LAD-VC$_{Ac}$AHER (SEQ ID NO: 85) and Ac-LADVC$_{To}$AHER (SEQ ID NO: 86), respectively. Note: c: closed-ring; o: open-ring; Ac/Tc: alkene/unsaturated thiol moieties with closed-ring SITE; Ao/To: alkene/unsaturated thiol moieties with open-ring SATE.

Figure 10A:
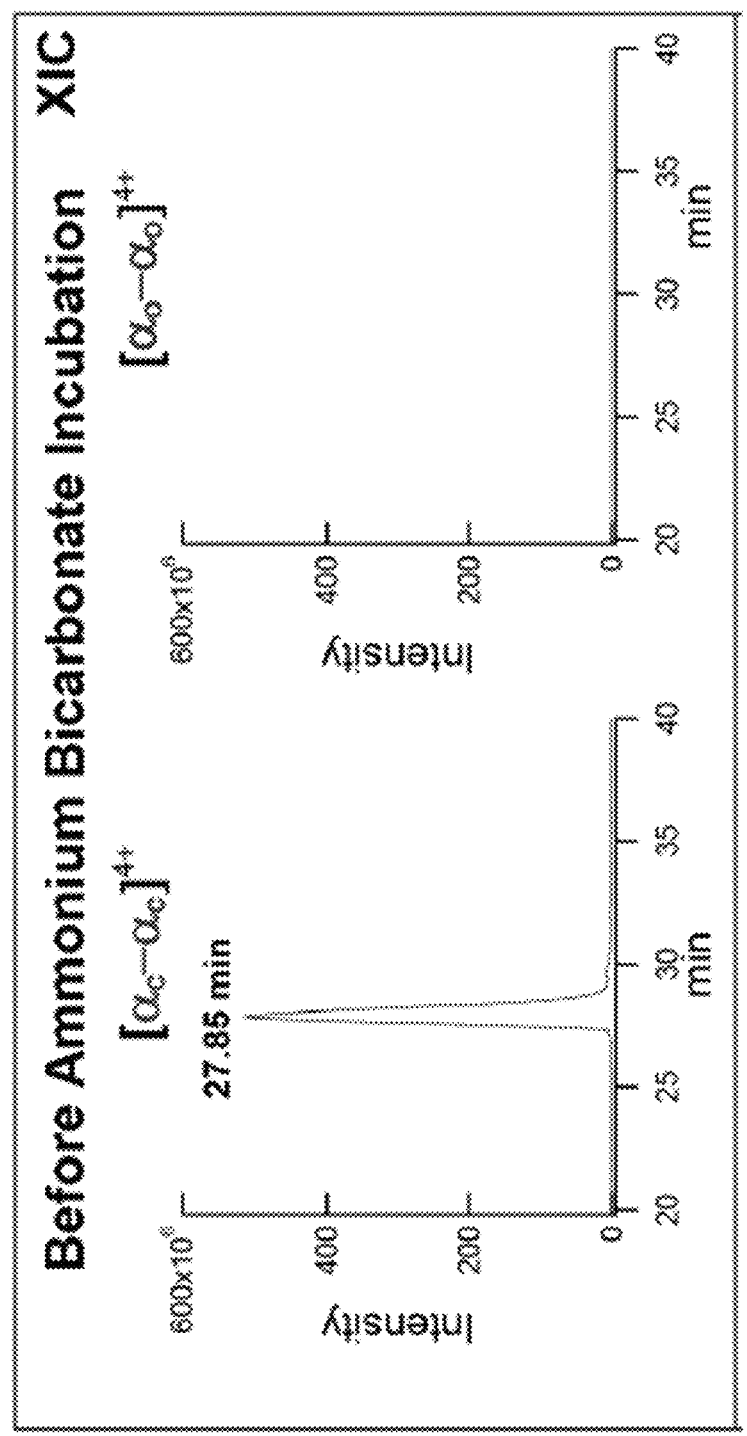
Figure 10B:
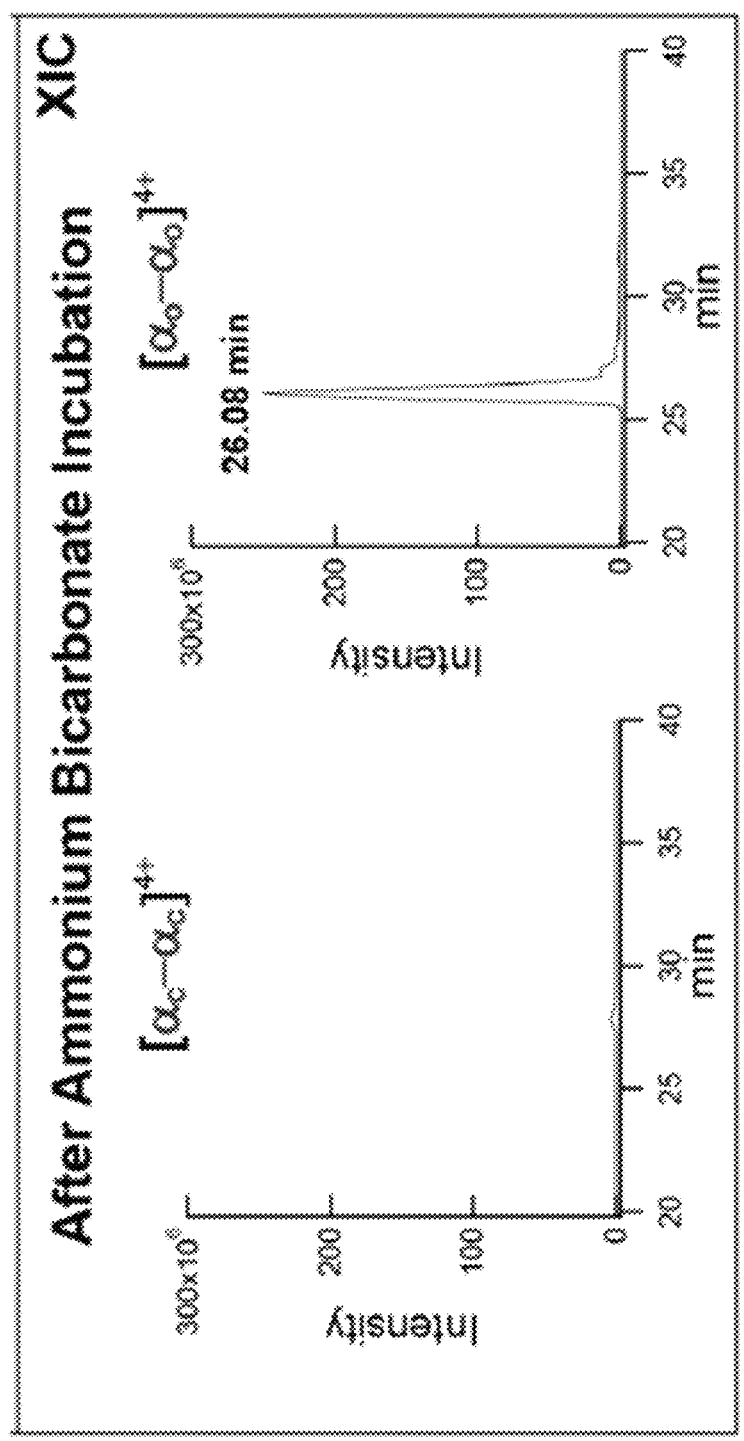

FIGS. 10A-10B show embodiments of MS analysis of BMSO inter-linked Ac-LR9 homodimer before and after ammonium bicarbonate treatment.

FIG. 10A shows an embodiment of extracted Ion Chromatograms display ion intensities of the two forms: $(\alpha_c-\alpha_c)$ with closed-ring and $(\alpha_o-\alpha_o)$ with open-ring before incubation with Ammonium Bicarbonate at 37° C. overnight.

FIG. 10B shows an embodiment of extracted Ion Chromatograms display ion intensities of the two forms: $(\alpha_c-\alpha_c)$ with closed-ring and $(\alpha_o-\alpha_o)$ with open-ring after incubation with Ammonium Bicarbonate at 37° C. overnight.

FIGS. 11A-11C show embodiments of comparison of XL-MS maps on BSA crystal structure (PDB: 4F5S) using BMSO (purple), DSSO (blue), and DHSO (red).

FIG. 11A shows an embodiment of comparison of XL-MS maps on BSA crystal structure (PDB: 4F5S) using BMSO (purple).

FIG. 11B shows an embodiment of comparison of XL-MS maps on BSA crystal structure (PDB: 4F5S) using DSSO (blue).

FIG. 11C shows and embodiment of comparison of XL-MS maps on BSA crystal structure (PDB: 4F5S) using DHSO (red).

FIGS. 12A-12B show embodiments of PPI maps of the CSN complexes based on cross-link data from all three linkers (DSSO, DHSO, BMSO).

FIG. 12A shows an embodiment of CSN (CSN1-8). Each CSN subunit was represented by colored nodes. The edges between two connected nodes were color-coded to describe PPIs resulted from individual or combinations of cross-linkers, i.e. blue-DSSO, red-DHSO, purple-BMSO, Lime-DSSO+BMSO, magenta-DHSO+BMSO, gold-DSSO+DHSO, black-DSSO+DHSO+BMSO. Edge thickness was determined by the total number of unique cross-links identified between the interactors.

FIG. 12B shows an embodiment of CSNn (CSN1-9). Each CSN subunit was represented by colored nodes. The edges between two connected nodes were color-coded to describe PPIs resulted from individual or combinations of cross-linkers, i.e. blue-DSSO, red-DHSO, purple-BMSO, Lime-DSSO+BMSO, magenta-DHSO+BMSO, gold-DSSO+DHSO, black-DSSO+DHSO+BMSO. Edge thickness was determined by the total number of unique cross-links identified between the interactors.

Figure 13A:
Figure 13B:
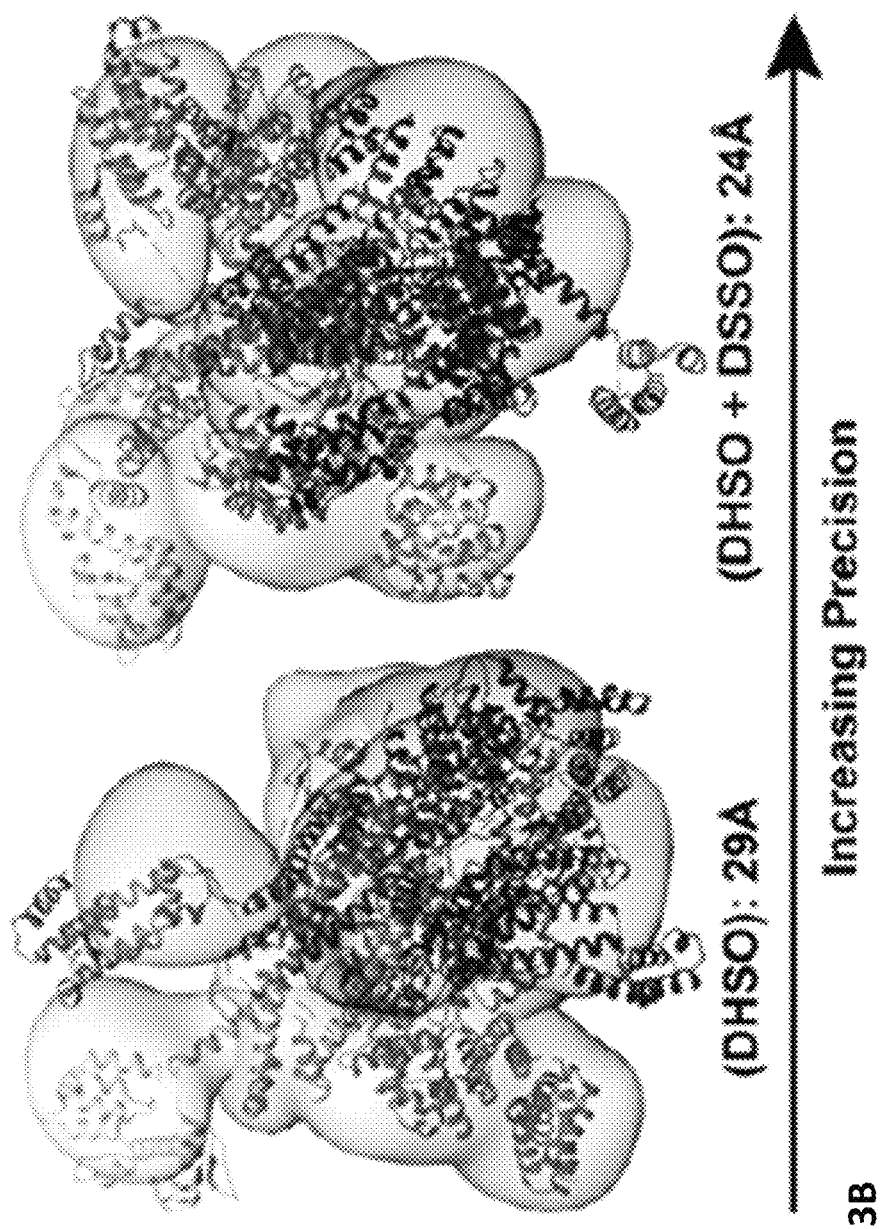
Figure 13C:
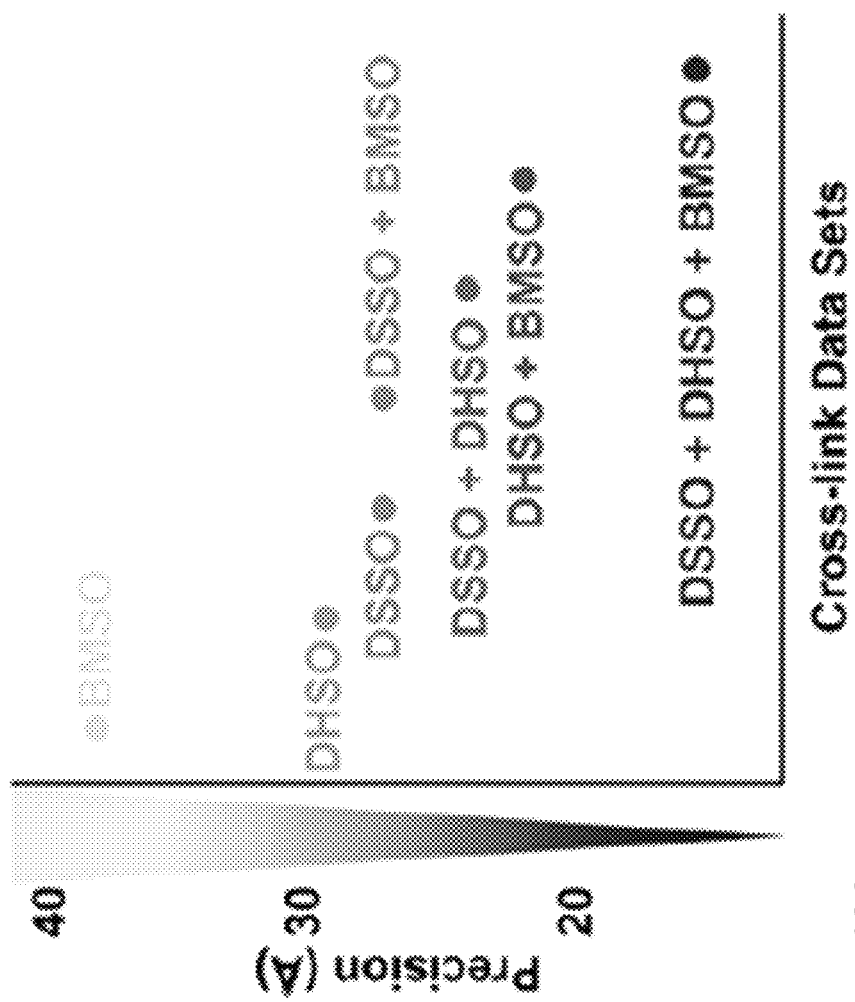

FIGS. 13A-13C show embodiments of integrative structures of CSN.

FIG. 13A shows an embodiment of the integrative structure of CSN determined at 16 Å precision when all three cross-link datasets (DSSO+DHSO+BMSO) were used for modeling. For each subunit, the localization probability density of the ensemble of models is shown with a representative structure (the centroid) from the ensemble embedded within it.

FIG. 13B shows an embodiment of Integrative modeling of CSN determined using DHSO or DHSO+DSSO datasets yielded models determined at 29 Å and 24 Å precision respectively.

FIG. 13C shows an embodiment of graphical representation of determined model precisions with 7 combinations of the three cross-link datasets, illustrating that increasing the number of cross-linking chemistries (abscissa axis) for integrative structure modeling leads to increased model precision (ordinate axis). CSN subunit was color-coded as illustrated.

FIGS. 14A-14D show embodiments of comparison of integrative and X-ray structures of the CSN complexes.

Figures 14A, 14B, 14C, 14D:
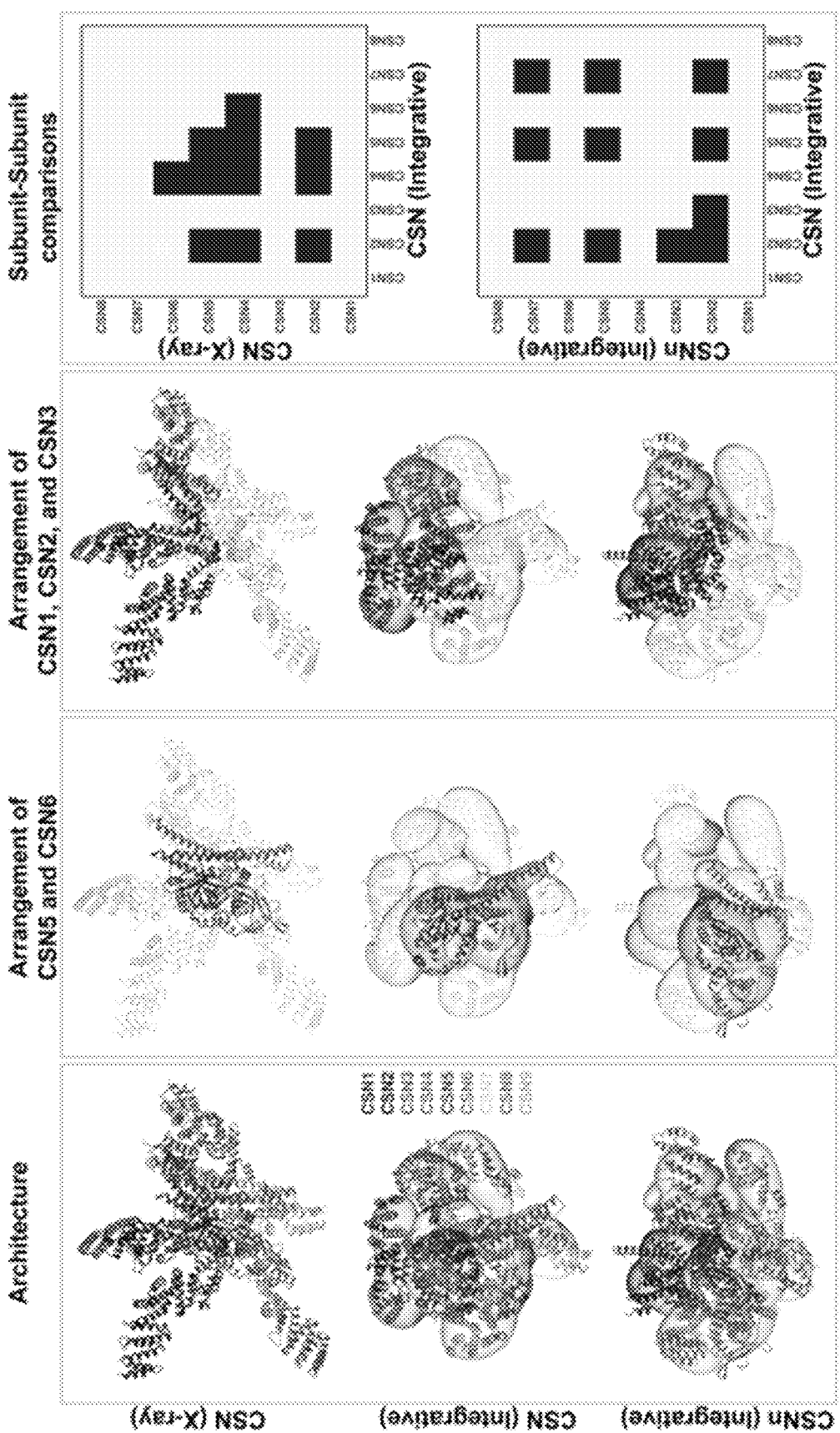

FIG. 14A shows an embodiment of overall architectures of CSN: X-ray structure (PBD 4D10) (top row), CSN integrative structure (middle row) and CSNn integrative structure (bottom row). For each subunit in the integrative structures, the localization probability density of the ensemble of models is shown with a representative structure (the centroid) from the ensemble embedded within it. The CSN and CSNn structures show that the models adopt a more condensed state as compared to the X-ray structure, but they generally retain the overall architecture with only the helical bundle being constrained during modeling.

FIG. 14B shows an embodiment of the arrangement of CSN5-CSN6 (MPN domain containing subunits) dimer was an emerging feature in integrative structures, however, a slight shift in the interface was observed in the CSNn model.

FIG. 14C shows an embodiment of models indicate that the arrangement of CSN1, CSN2 and CSN3 was altered in the presence of CSN9; CSN2 moved from a state interacting with CSN3 in CSN to an opened state in the CSNn model, resembling the overall architecture of the CSN X-ray structure.

FIG. 14D shows an embodiment of respective binary subunit-subunit comparison of the CSN integrative structure with the CSN X-ray structure (top) and the CSNn integrative structure (bottom row) respectively. The structures were compared by calculating their ensemble overlap; the overlap was quantified by the ratio of the distance between ensemble centroids to three times the sum of the ensemble precisions. Differences are shown in red. CSN subunit was color-coded as illustrated.

Figures 15A, 15B:
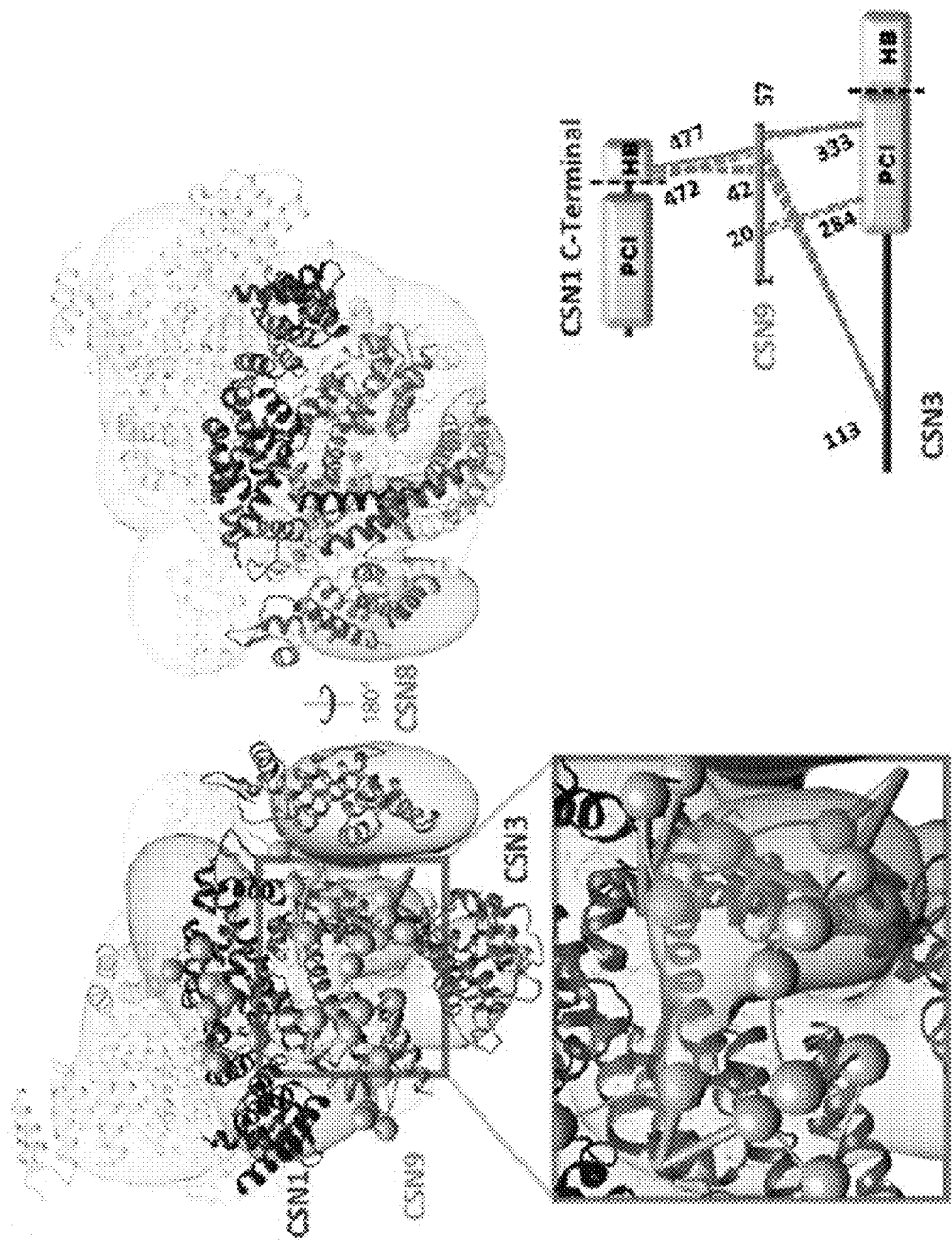

FIGS. 15A-15B shows embodiments of binding of CSN9 in the CSNn integrative structure.

FIG. 15A shows an embodiment of the integrative structure of CSNn determined at 22 Å precision using all three cross-link datasets (DSSO+DHSO+BMSO). For each subunit, the localization probability density of the ensemble of models is shown with a representative structure (the centroid) from the ensemble embedded within it. The higher probable localization of CSN9, corresponding to its C-terminal, on the CSNn model is represented by the orange localization probability density, and a representative structure from the ensemble is show with spheres corresponding to 2-residue per beads connected by an extrapolated trace of the backbone. CSN9 primarily interacts with the main body of CSN3 (red) while its C-terminal tail also falls into the cavity between CSN1 (purple), CSN3 (red), and CSN8 (green). The inset displays a closer view of CSN9 interaction. Green lines represent CSN9-containing DHS 0 cross-links.

FIG. 15B shows an embodiment of 2-D DHSO XL-map linking CSN9 to CSN1 and CSN3 at specific residues.

FIGS. 16A-16D show embodiments of PRM-based targeted quantitation of DHSO cross-linked peptides to validate CSN9-induced structural changes in CSN.

FIG. 16A shows an embodiment of skyline outputs for PRM quantitation of a representative DHSO intra-subunit (CSN4:E306-CSN4:E345) (top) and an inter-subunit (CSN2:E63-CSN3:E333) (bottom) cross-linked peptides to compare their relative abundance in the CSN and CSNn complexes. Based on peak areas, the relative abundance ratio (CSN/CSNn) of the intra-subunit cross-link was determined as 1.11 (top), indicating no significant change. In contrast, the relative abundance of the inter-subunit cross-link (CSN/CSNn) was determined as 30.15 (bottom), suggesting a significant change.

FIG. 16B shows an embodiment of the distribution of cross-link ratios (CSN/CSNn) of 229 DHSO cross-linked peptides (represented as log 2 values) determined by PRM quantitation, in which only 22 cross-linked peptides displayed significant changes (>2.5-fold, greater than 3σ), including 4 with decreased ratios (red dots) and 18 with increased ratios (blue dots). The cross-link ratios (CSN/CSNn) describe the relative abundance of cross-linked peptides in the two compared complexes.

FIG. 16C shows an embodiment of abundance of five quantifiable CSN2-CSN3 cross-links (CSN2:D45-CSN3:E333, CSN2:E59-CSN3:E284, CSN2:E59-CSN3:E333, CSN2:E63-CSN3:E333, and CSN2:E161-CSN3:E284) detected in the CSN and CSNn complexes. The underlined numbers shown represent relative abundance ratios (CSN/CSNn) of the selected cross-linked peptides between the two complexes, indicating that these interactions are favored in CSN.

Figure 16D:
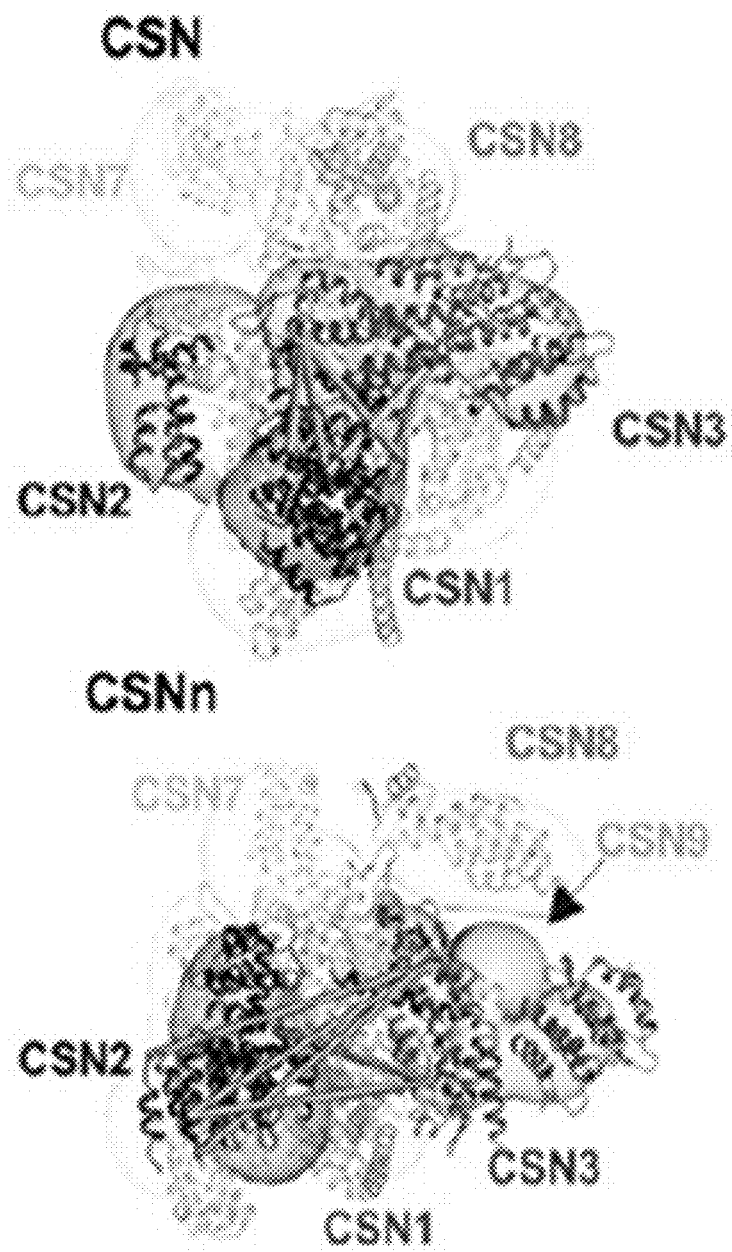

FIG. 16D shows an embodiment of the five cross-links shown in FIG. 16C were mapped on CSN and CSNn integrative structures. The linkages in CSN model (green) are satisfied within the expected distance (<30 Å), which are not satisfied in the CSNn model (magenta). Details on PRM quantitation of the cross-linked peptides as an embodiment of the identified DHSO cross-linked peptides of CSNn (Chymotrypsin Digest) are available as Dataset S8 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety. Embodiments of the Detailed Summary of the Identified DHSO Cross-linked Peptides of CSNn are available as Dataset S7 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety.

Figure 17:
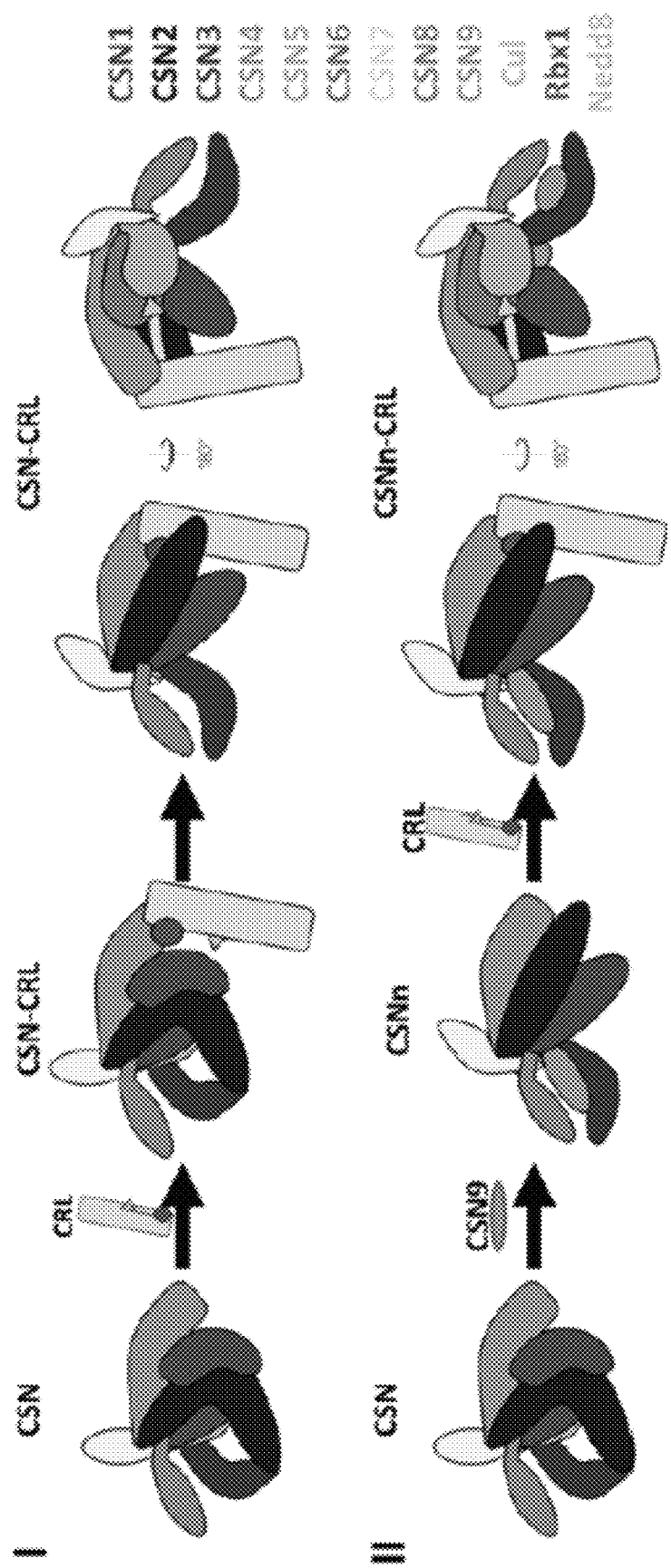

FIG. 17 shows an embodiment of the proposed structural model of CSN9 binding to facilitate CSN interaction with neddylated CRLs. CSN and neddylated CRL subunits were color-coded as illustrated (I) CSN9-free CSN needs to undergo substantial conformational changes upon binding to a neddylated CRL. In comparison, (II) CSN9-bound CSN adopts a configuration better suited for CRL binding.

Figure 18:
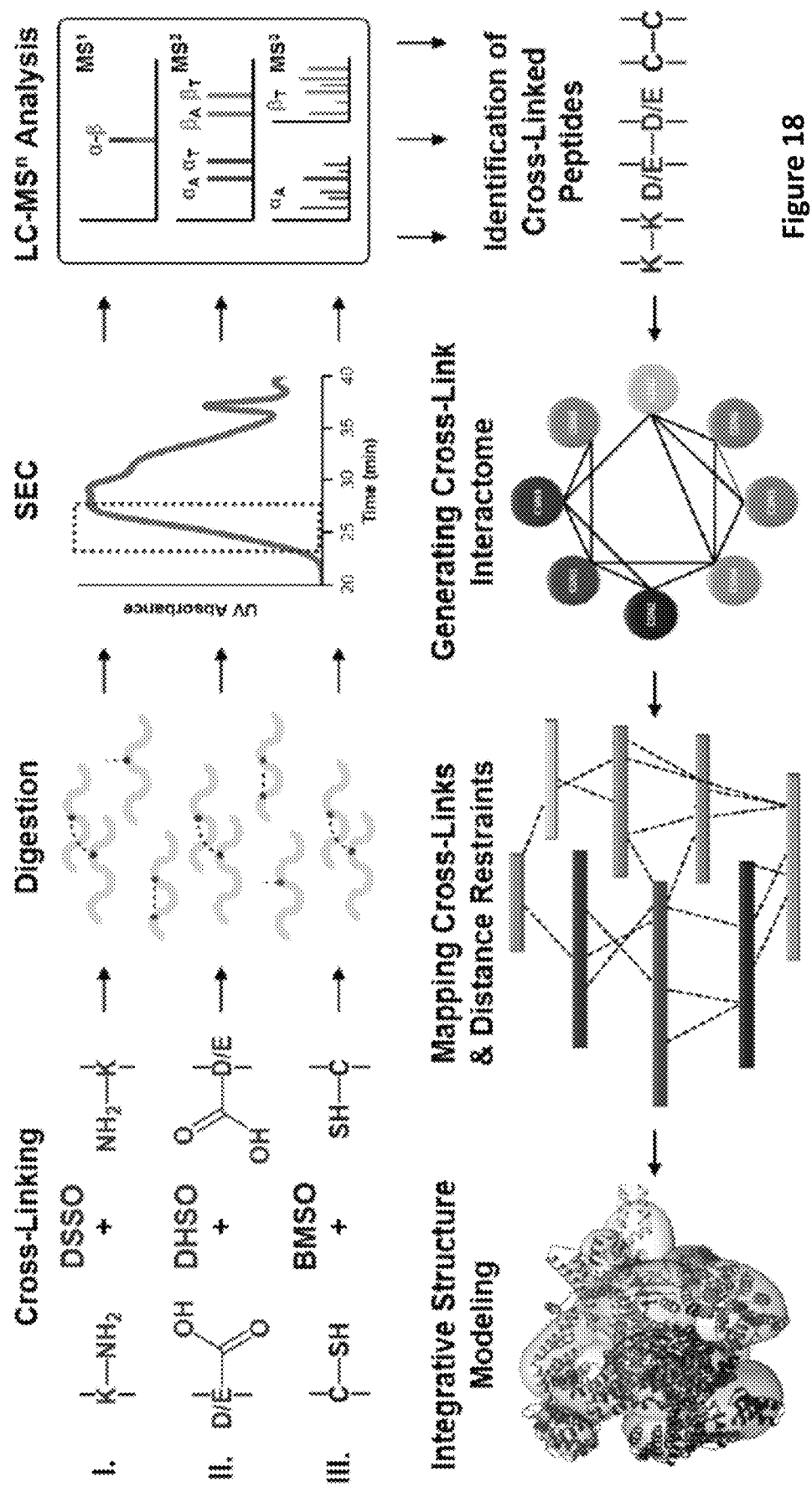

FIG. 18 shows an embodiment of the multi-chemistry XL-MS workflow based on DSSO, DHSO and BMSO cross-linking. The two CSN complexes were independently cross-linked by each linker (path I (DSSO), II (DHSO), and III (BMSO)) and subsequently digested. Then cross-linked peptides were enriched from peptide mixtures by SEC, analyzed by LC-MS$^n$, and identified through database searching and result integration. The identified cross-linked peptides were then used for generating PPI networks, distance mapping and integrative structure modeling.

FIGS. 19A-19I show embodiments of representative MS$^n$ analysis of a DSSO, DHSO and BMSO inter-linked peptide from CSN describing interactions between CSN5 and CSN6. MS$^2$ spectra of DSSO (m/z 755.3713$^{4+}$) (FIG. 19A), DHSO (m/z 678.1147$^{4+}$) (FIG. 19B), and BMSO (m/z 710.0565$^{4+}$) (FIG. 19C) cross-linked peptides ($\alpha$-$\beta$), which fragmented similarly to yield two characteristic fragment ion pairs detected as $\alpha_A/\beta_T$ and $\alpha_T/\beta_A$, respectively. This feature is unique to sulfoxide-containing MS-cleavable cross-linked peptides. MS$^3$ analyses of $\alpha_T$ (m/z 710.38$^{2+}$) (FIG. 19C) and $\beta_A$ (m/z 791.36$^{2+}$) (FIG. 19D) fragment ions of the DSSO cross-link in FIG. 19A resulted in unambiguous identification of $\alpha_T$ as TISAGK$_T$VNLGAFR (SEQ ID NO: 87) and of $\beta$A as EYYYTK$_A$EEQFK (SEQ ID NO: 88), signifying a cross-link between CSN5:K180 and CSN6:K108. MS$^3$ analyses of $\alpha_A$ (m/z 467.76$^{2+}$) (FIG. 19F) and $\beta_T$ (m/z 878.96$^{2+}$) (FIG. 19G) of the DHSO cross-link in FIG. 19B resulted in unambiguous identification of $\alpha_A$ as IGVD$_A$H-VAR (SEQ ID NO: 97) and of $\beta_T$ as TTIE$_T$AIHGLM$_{ox}$SQ-VIK (SEQ ID NO: 89), signifying a cross-link between CSN5:E313 and CSN6:D201. MS$^3$ analyses of $\alpha_A$ (m/z 630.29$^{2+}$) (FIG. 19H) and $\beta_T$ (m/z 780.32$^{2+}$) (FIG. 19I) of the BMSO cross-link in FIG. 19C resulted in unambiguous identification of $\alpha_A$ as IEDFGVHC$_A$K (SEQ ID NO: 90) and of $\beta_T$ as TC$_T$NTM$_{ox}$NQFVNK (SEQ ID NO: 91), signifying a cross-link between CSN5:C218 and CSN6:C299. K$_T$, E$_T$ and C$_T$ represent unsaturated thiol modified cross-link residue; whereas K$_A$, D$_A$ and C$_A$ represent alkene modified residues.

Figure 20:
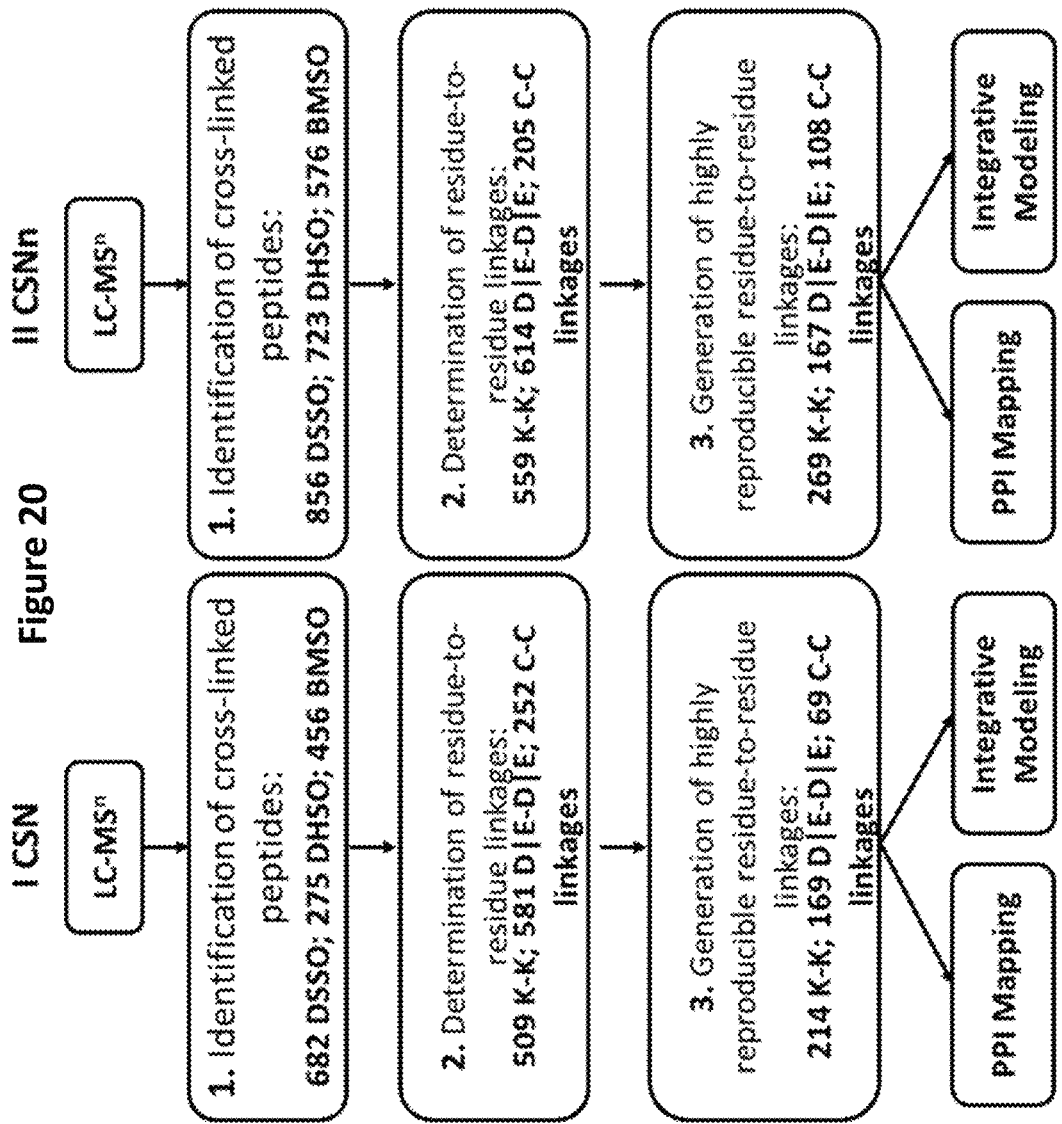

FIG. 20 shows an embodiment of the highly reproducible residue-to-residue linkages were determined based on three steps: 1) identification of cross-linked peptides using LC MS$^n$ (embodiments of the identified DSSO cross-linked peptides of CSN, identified DHSO cross-linked peptides of CSN, and identified BMSO cross-linked peptides of CSN are available as Datasets S3-S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety); 2) determination of residue-to-residue linkages (K—K for DSSO, DIE-DIE for DHSO, C-C for BMSO) based on the identified cross-linked peptides; 3) generation of highly reproducible residue-to-residue linkages that occur in ≥60% biological replicates (e.g. 3 out of 5 biological replicates) for each set of XL-MS experiments (embodiments of the Highly Reproducible DSSO Cross-links of CSN and Their Distance Mapping to the Known CSN Crystal Structure (PDB 4D10), Highly Reproducible DHSO Cross-links of CSN and Their Distance Mapping to the Known CSN Crystal Structure (PDB 4D10), and Highly Reproducible BMSO Cross-links of CSN and Their Distance Mapping to the Known CSN Crystal Structure (PDB 4D10) are available as Datasets S10-S12, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), based on which PPI interaction topologies and integrative modeling were determined. XL-MS Data for CSN (path I) and CSNn (path II) were presented. It is noted that while the number of targetable residues in protein sequences attributes to the number of possible cross-links, the actual number of cross-linked peptides identified for each linker in XL-MS experiments mainly depends on: 1) the number of cross-linkable residues within the maximum distance range spanned by each linker; 2) the number of tryptic cross-linked peptides that can be detected and sequenced by mass spec analysis. Among the three selected linker, BMSO has the longest spacer arm (24.2 Å) compared to DSSO (10.1 Å) and DHSO (12.4 Å). Thus, BMSO can bridge a significantly longer distance between targetable residues, which could contribute to increased number of cross-linkable residues in the structure and of cross-linked peptides identified.

FIGS. 21A-21L show embodiments of PPI maps of the CSN (FIGS. 21A-21C) and CSNn (FIGS. 21D-21F) complexes based on the selected cross-link data: DSSO only (FIGS. 21A, 21D); DHSO only (FIGS. 21B, 21E); BMSO only (FIGS. 21C, 21F). Each CSN subunit was represented by colored nodes as illustrated. Edges between two connected nodes were color-coded to describe PPIs determined by a specific cross-linker (blue-DSSO, red-DHSO, purple-BMSO). Edge thickness was determined based on the total number of linkages identified for each PPI. Respective 2-D XL-maps for CSN (FIGS. 21G-21I) and CSNn (FIGS. 21Js-21L), illustrating residue-to-residue connectivity of inter-subunit interactions for the three linkers: DSSO (FIGS. 21G, 21J), DHSO (FIGS. 21H, 21K) and BMSO (FIGS. 21H, 21K). Each subunit was displayed as a linear sequence containing their respective conserved domains.

FIGS. 22A-22F show embodiments of respective cross-link distance distribution plots for DSSO, DHSO or BMSO cross-link data on the known CSN X-ray structure (PDB 4D10), displaying the number of linkages identified from both the CSN (FIGS. 22A-22C) and CSNn (FIGS. 22D-22F) complexes within and over the expected distance thresholds (30 Å for DSSO and DHSO, and 45 Å for BMSO). The greyed bars represent intra-subunit linkages, and the solid bars represent inter-subunit linkages. Cross-linkers were color coded: DSSO-blue, DHSO-red, and BMSO-purple. The % listed at the top left corners indicates % of cross-links (upper, intra-subunit; lower, inter-subunit) that were satisfied within the expected distances, whereas the % listed at the top right corners indicates % of cross-links (upper, intra-subunit; lower, inter-subunit) that were unsatisfied and outside the expected distances.

Figure 23:
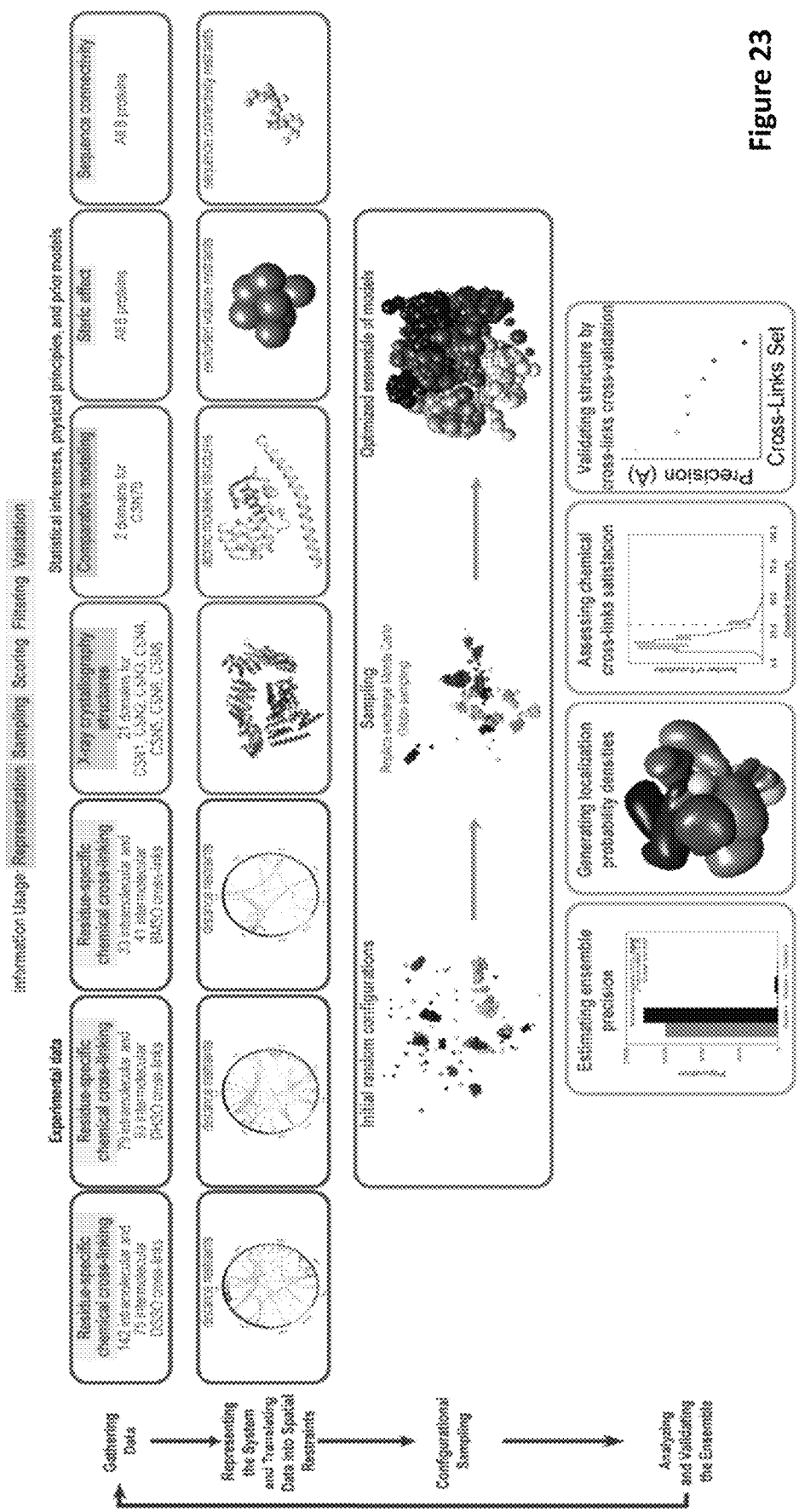

FIG. 23 shows the general scheme of integrative structure modeling. Integrative structure determination of the human CSN complex, preceded through four stages: (1) gathering data, (2) representing subunits and translations data into spatial restraints, (3) configurational sampling to produce an ensemble of structures that satisfies the restraints, and (4) analyzing and validating the ensemble structures and data. The integrative structure modeling protocol (stages 2, 3, and 4) was scripted using the Python modeling interface package, which is a library for modeling macromolecular complexes based on the open-source Integrative Modeling Platform (IMP) package version 2.9 (integrativemodeling.org). Files containing the input data, scripts, and output results are available at salilab.org/CSN2019.

FIGS. 24A-24H show embodiments of validation of the canonical CSN structure. FIGS. 24A-24E show thoroughness of configurational sampling and model precision.

Figure 24B:
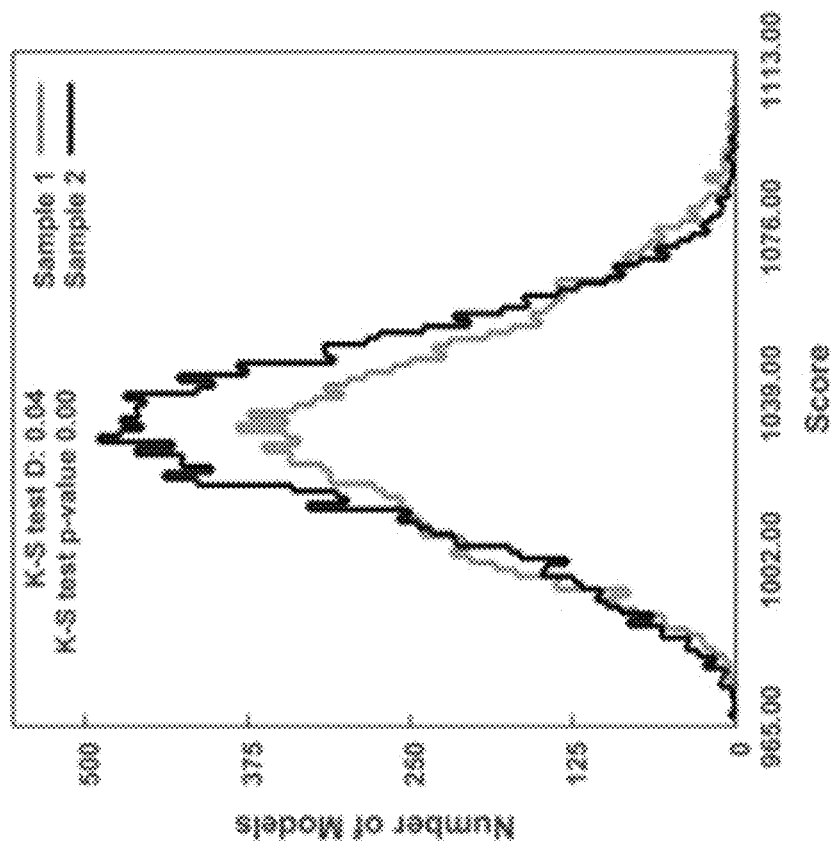
Figure 24A:
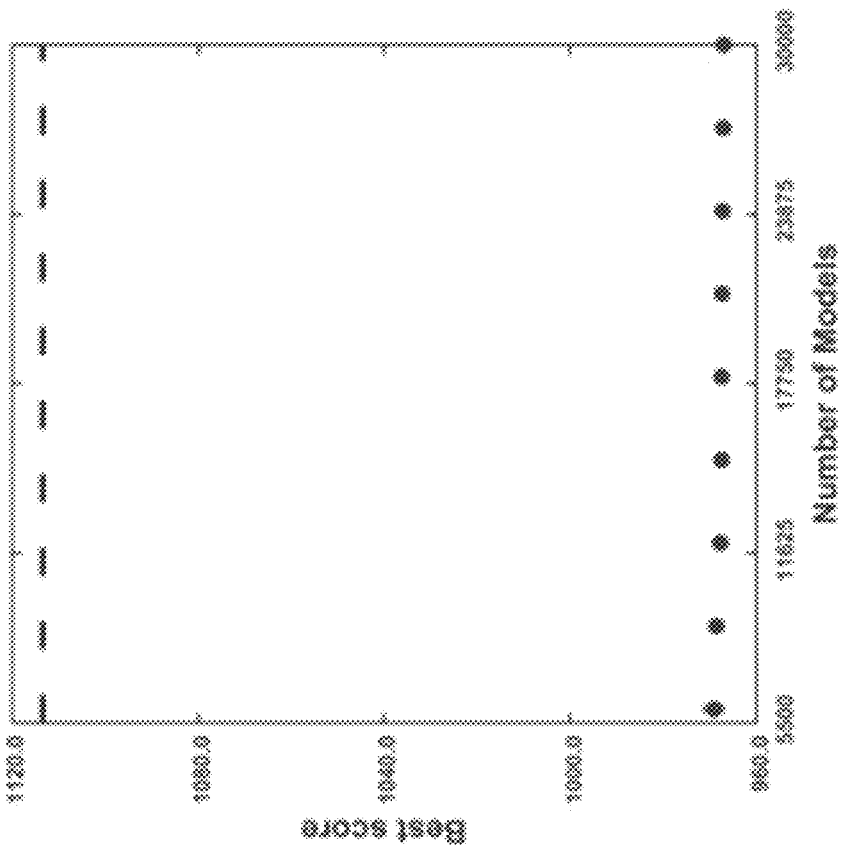

FIG. 24A shows an embodiment of convergence of the structure score for 30,000 randomly selected models of the canonical CSN complex out of the 54,702 clustered models; the scores do not continue to improve as more structures are computed, essentially independently of each other.

FIG. 24B shows an embodiment of distribution of scores for model samples 1 (red) and 2 (blue), comprising the 30,000 models (nsample1=13,123 and nsample2=16,876 structures). The non-parametric Kolmogorov-Smirnov two-sample test (two-sided) indicates that the difference between the two score distributions is insignificant, the magnitude of the difference is small, as demonstrated by the Kolmogorov-Smirnov two-sample test statistic, D, of 0.04. Thus, the two score distributions are effectively equal.

FIG. 24C shows an embodiment of three criteria for determining the sampling precision (y axis), evaluated as a function of the RMSD. clustering threshold (x axis) (n=30,000 models). First, the P value is computed using the $\chi$2-test (one-sided) for homogeneity of proportions (red dots). Second, an effect size for the $\chi$2-test is quantified by the Cramer's V value (blue squares). Third, the population of structures in sufficiently large clusters (containing at least ten structures from each sample) is shown as green triangles. The vertical dotted grey line indicates the RMSD. clustering threshold at which two conditions are satisfied (Cramer's V (0.07)<0.10 (blue, horizontal dotted line) and the population of clustered structures (0.98)>0.80 (green, horizontal dotted line)), thus defining the sampling precision of 21 Å. The three solid curves (in red, blue and green) were drawn through the points to help visualize the results.

FIG. 24D shows an embodiment of population of sample 1 and 2 structures in the two clusters obtained by threshold-based clustering using an RMSD. threshold of 21 Å. The dominant cluster (cluster 1) contains 97% of the models. The precision of the dominant cluster defines the model precision, 16.4 Å.

FIG. 24E shows an embodiment of comparison of localization probability densities of models from sample 1 (red) and sample 2 (blue) in the main cluster. The cross-correlation coefficient of 0.98 between the two samples localization probability densities suggests that the two samples are structurally identical.

Figure 24F:
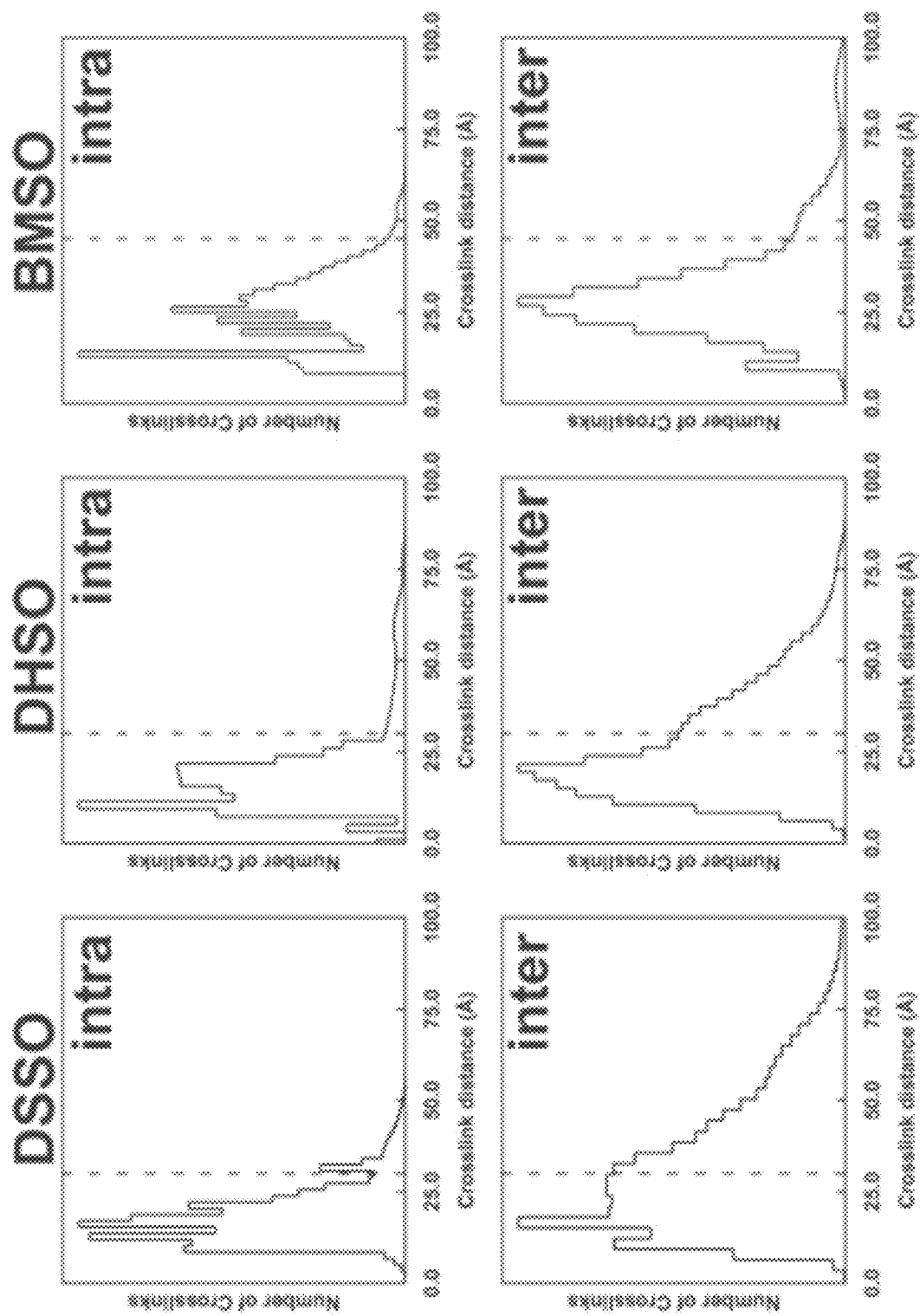

FIG. 24F shows an embodiment of Euclidean Cα-Cα distance distributions of all measured cross-links in the ensemble of solutions for each cluster. The y axis provides the normalized number of cross-links that were mapped onto the model. The dashed redline denotes the expected maximum reach of a cross-link.

Figure 24G:
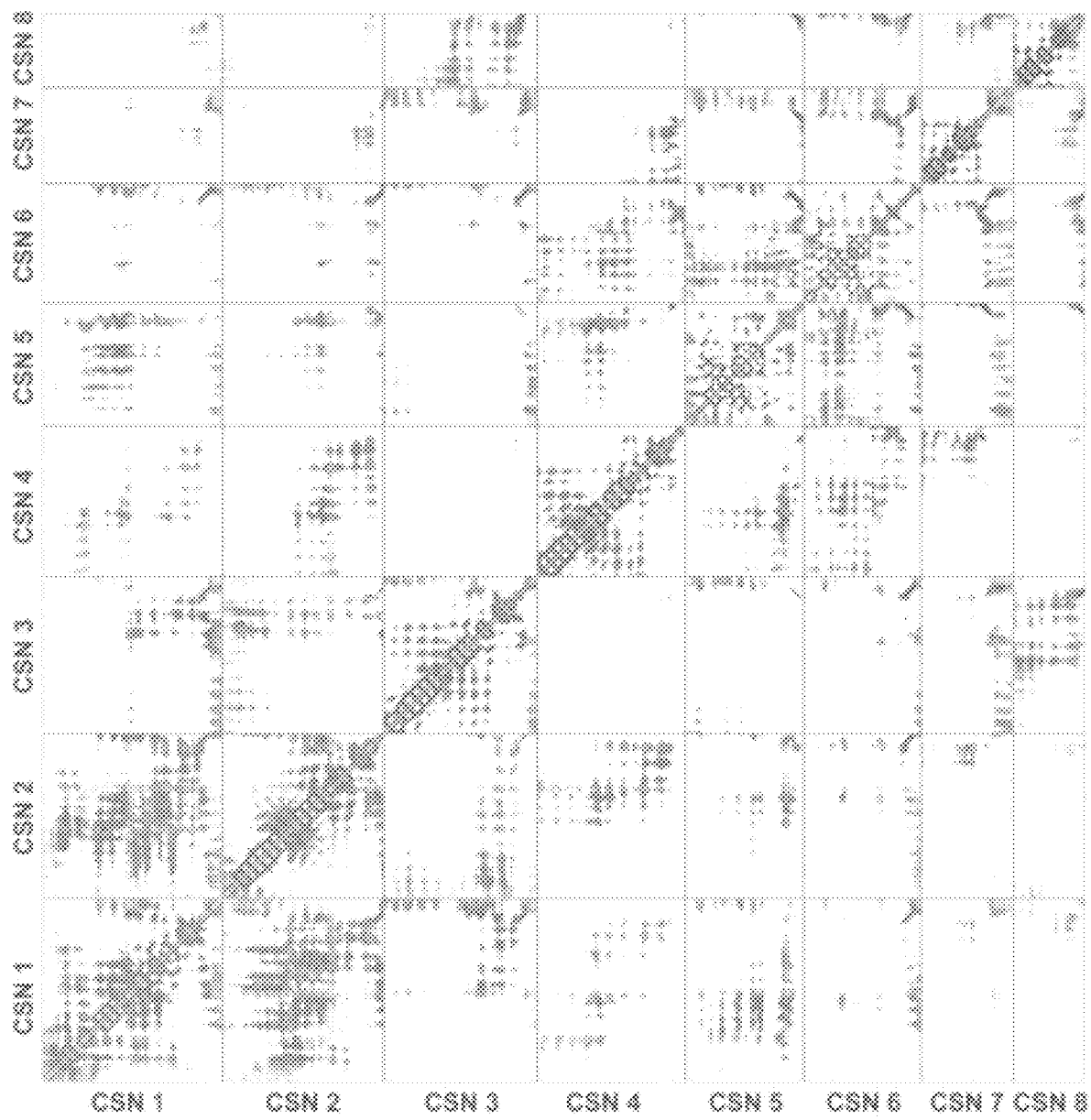

FIG. 24G shows an embodiment of average contact maps calculated for the main cluster. Each square is a contact map calculated between a given pair of subunit of the CSN complex module proteins with border length proportional to the length of corresponding subunit sequences. The grey-shaded areas indicate observed interactions, with the grey-scale proportional to the fraction of models observing the corresponding interaction.

FIG. 24H shows an embodiment of an illustration of the rigid bodies defined for modeling of the canonical CSN complex. The 16 rigid bodies used for modeling are shown in ribbon representation. The cross-links that map within each rigid body are visualized and are colored based on whether they were satisfied (green) or violated (gold) by the rigid body definition. 97% of these cross-links observed in the absence of CSN9 are satisfied by the rigid body definition.

Figure 25B:
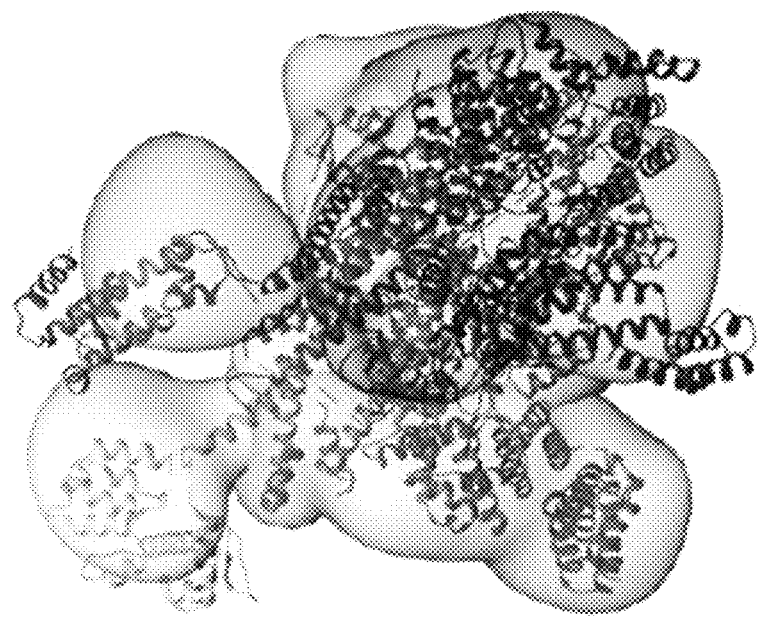
Figure 25A:
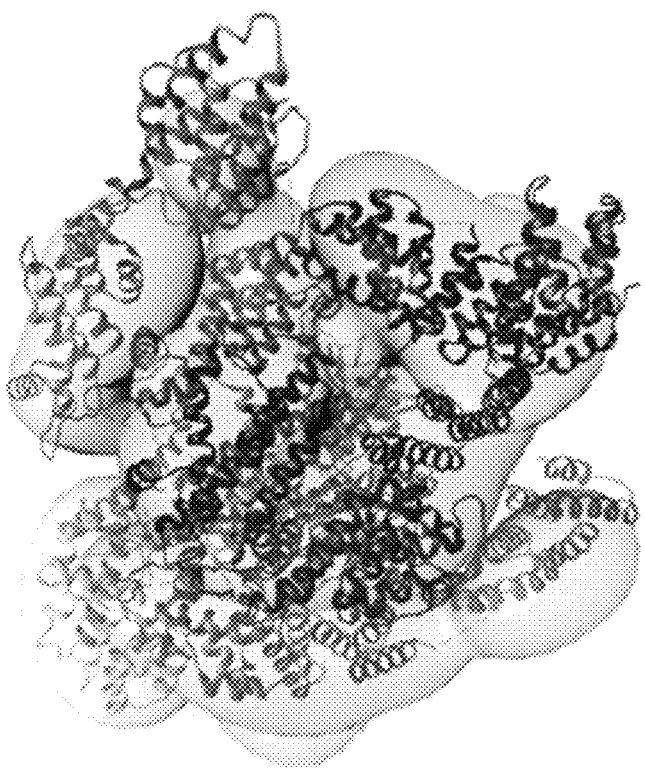
Figure 25D:
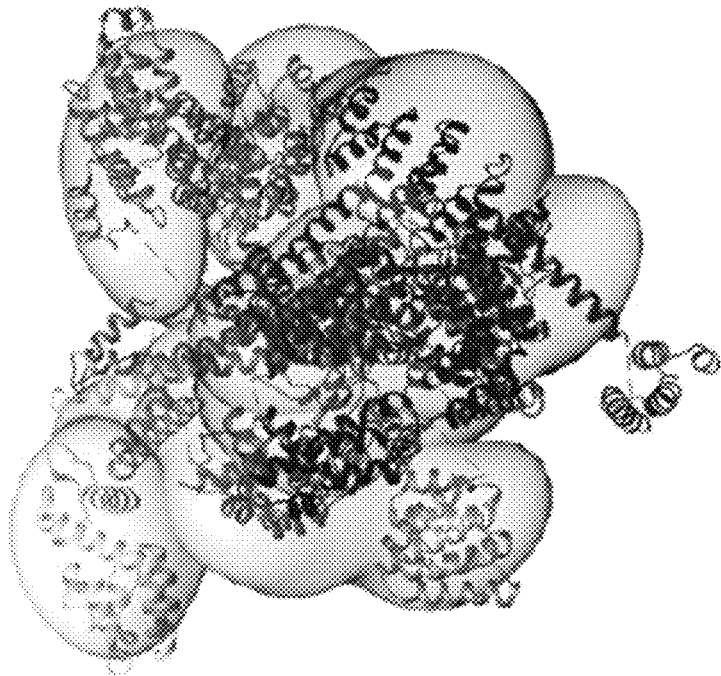
Figure 25C:
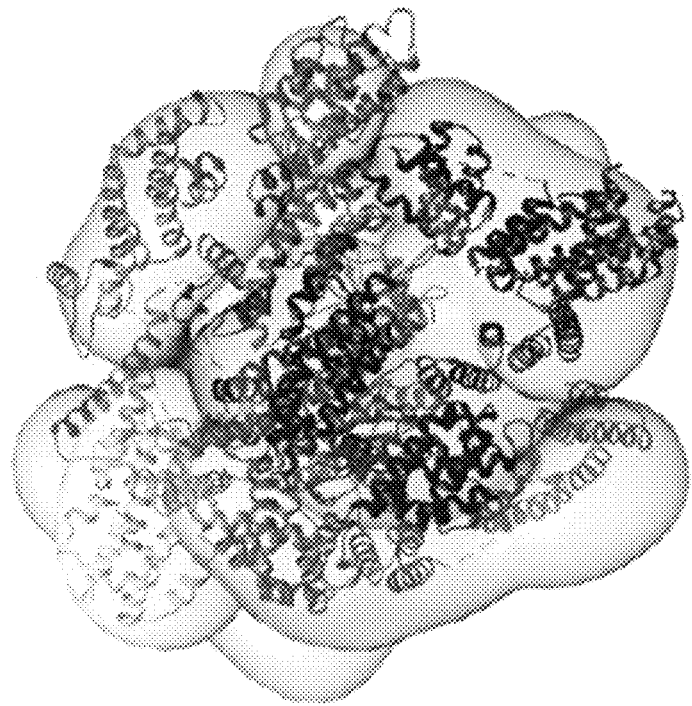
Figure 25F:
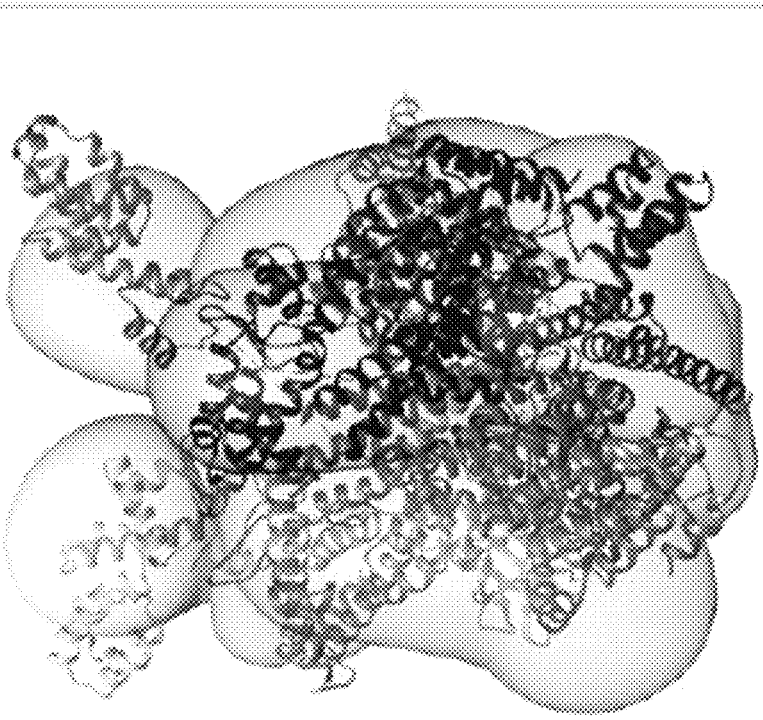
Figure 25E:
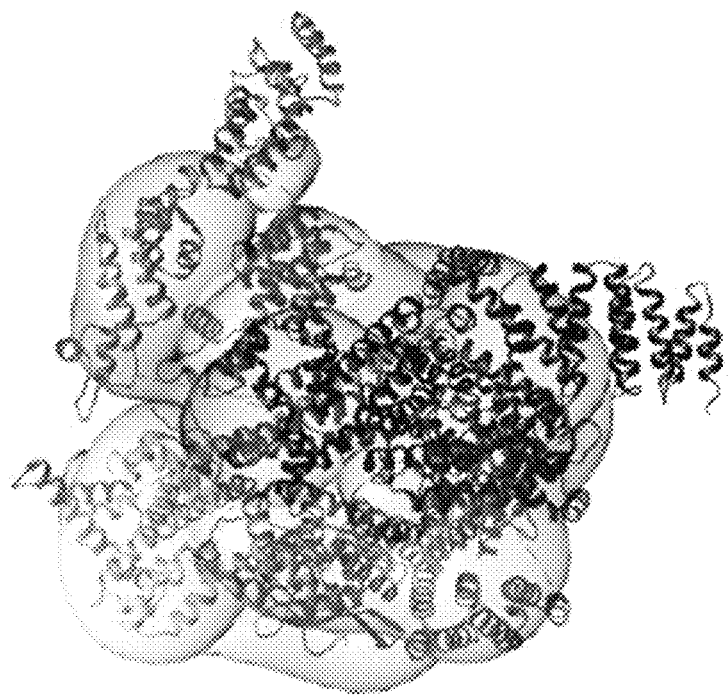

FIGS. 25A-25F show embodiments of cross-validation of the canonical CSN complex integrative structure determination. Integrative structures of CSN obtained using different cross-links subset (i.e. DSSO (FIG. 25A), DHSO (FIG. 25B), BMSO (FIG. 25C), DSSO+DHSO (FIG. 25D), DSSO+BMSO (FIG. 25E), DHSO+BMSO (FIG. 25F). The localization probability densities and the centroid of each ensemble of structures are shown, with the value of their respective precision.

Figure 26A:
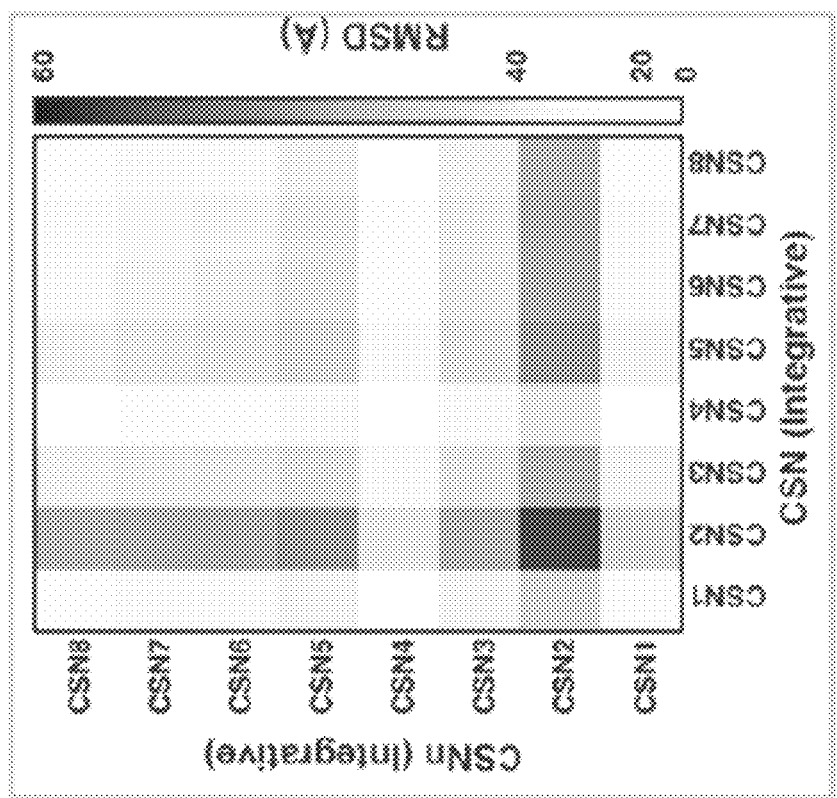
Figure 26B:
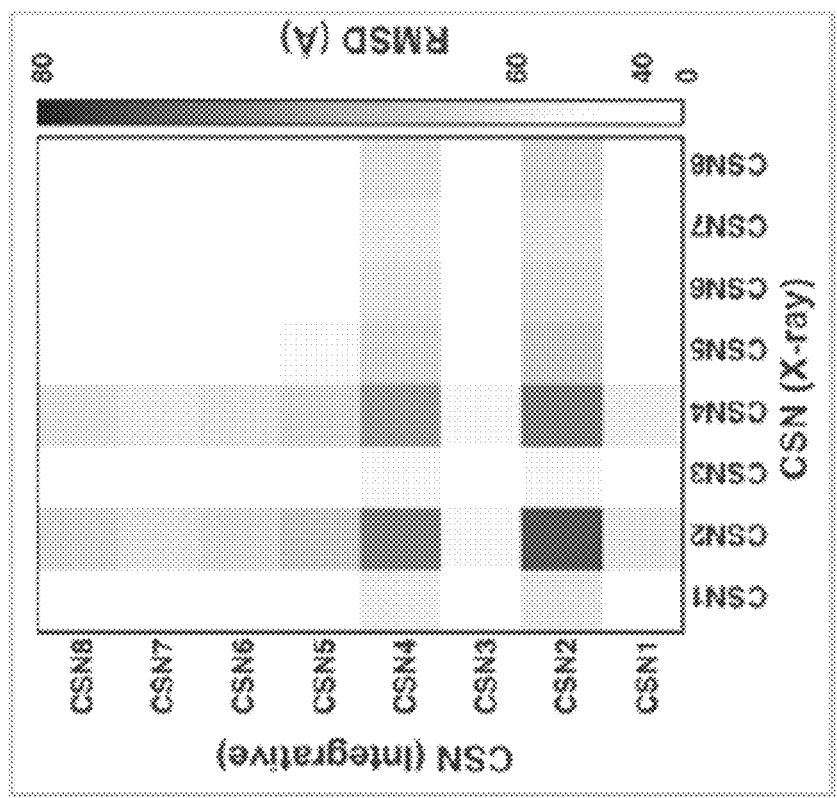
Figure 26E:
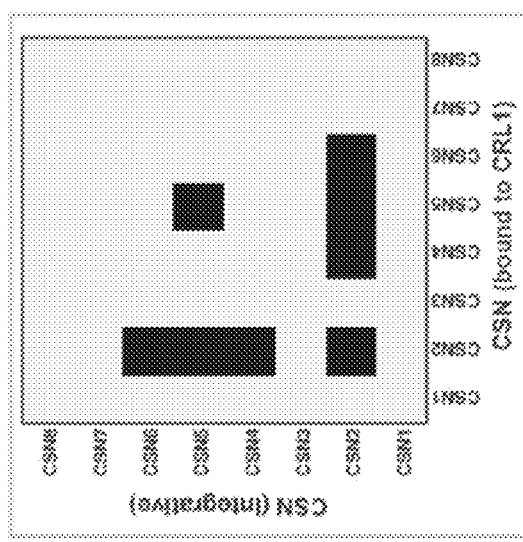
Figure 26D:
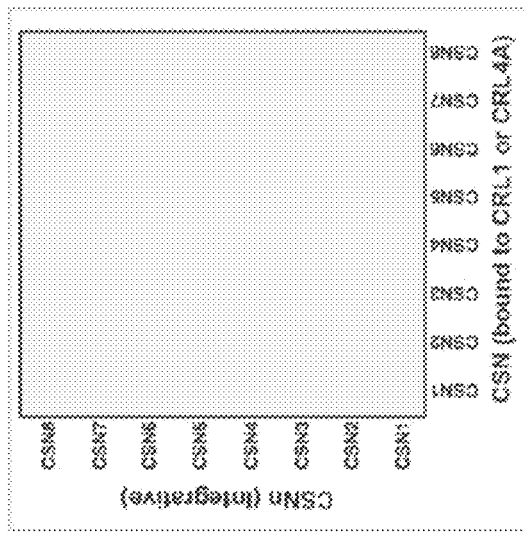
Figure 26C:
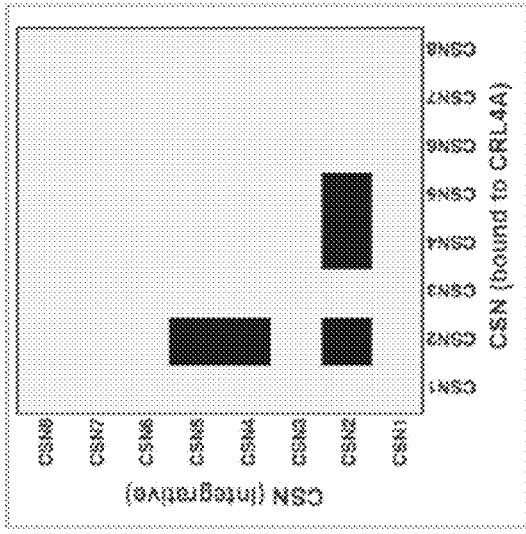

FIGS. 26A-26E show embodiments of subunit-subunit comparison among different CSN structures, using RMSD between the centroid of each ensemble (FIGS. 26A-26B) and the overlap between structure ensembles (FIGS. 26C-26E). Subunit-subunit comparison between the integrative and X-ray structures of CSN (FIG. 26A), the integrative structures of CSN and CSNn (FIG. 26B), the integrative structure of CSN and the cryo-EM Structure of CSN bound to neddylated CRL4 Å(27) (FIG. 26C), the integrative structure of CSNn and the cryo-EM structures of CSN bound to neddylated CRL4A or CRL1(27, 28) (FIG. 26D), the integrative structure of CSN and the cryo-EM structure of CSN bound to neddylated CRL1(28) (FIG. 26E). When there was no overlap between the two structures, the differences were larger than three times precision of the respective structures as shown in red.

FIGS. 27A-27H show embodiments of validation of the non-canonical CSN structure. FIGS. 27A-27E show thoroughness of configurational sampling and model precision.

Figure 27B:
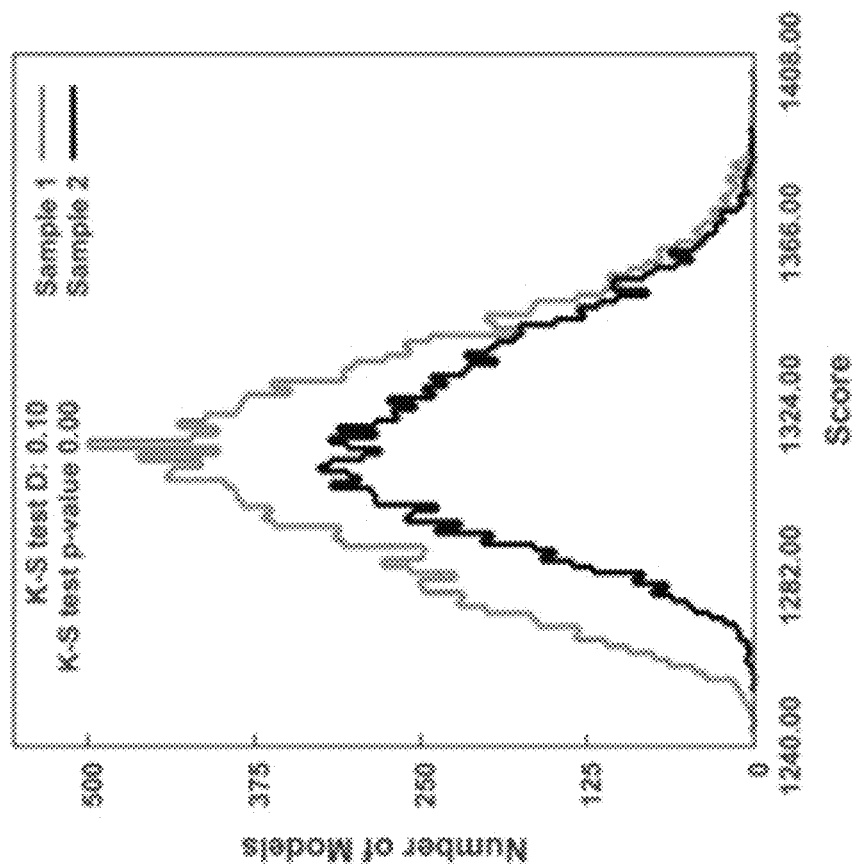
Figure 27A:
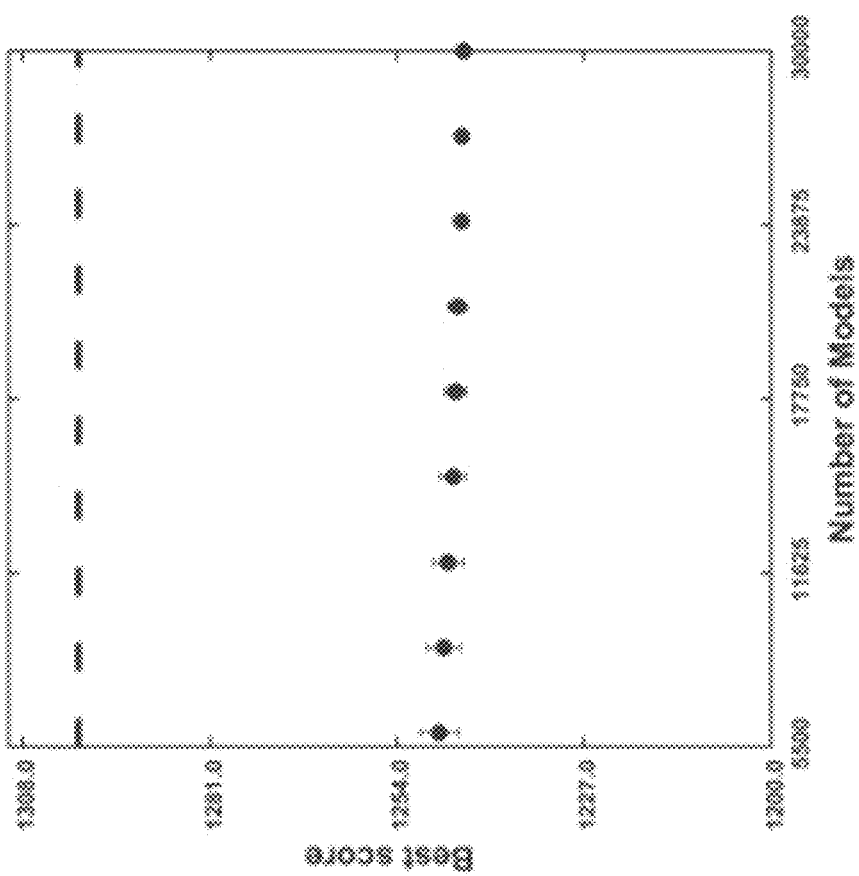

FIG. 27A shows an embodiment of convergence of the structure score for 30,000 randomly selected models of the non-canonical CSN complex out of the 99,902 clustered models; the scores do not continue to improve as more structures are computed, essentially independently of each other.

FIG. 27B shows an embodiment of distribution of scores for model samples 1 (red) and 2 (blue), comprising the 30,000 models (nsample1=17,252 and nsample2=12,747 structures). The non-parametric Kolmogorov-Smirnov two-sample test (two-sided) indicates that the difference between the two score distributions is insignificant, the magnitude of the difference is small, as demonstrated by the Kolmogorov-Smirnov two-sample test statistic, D, of 0.10. Thus, the two score distributions are effectively equal.

Figure 27D:
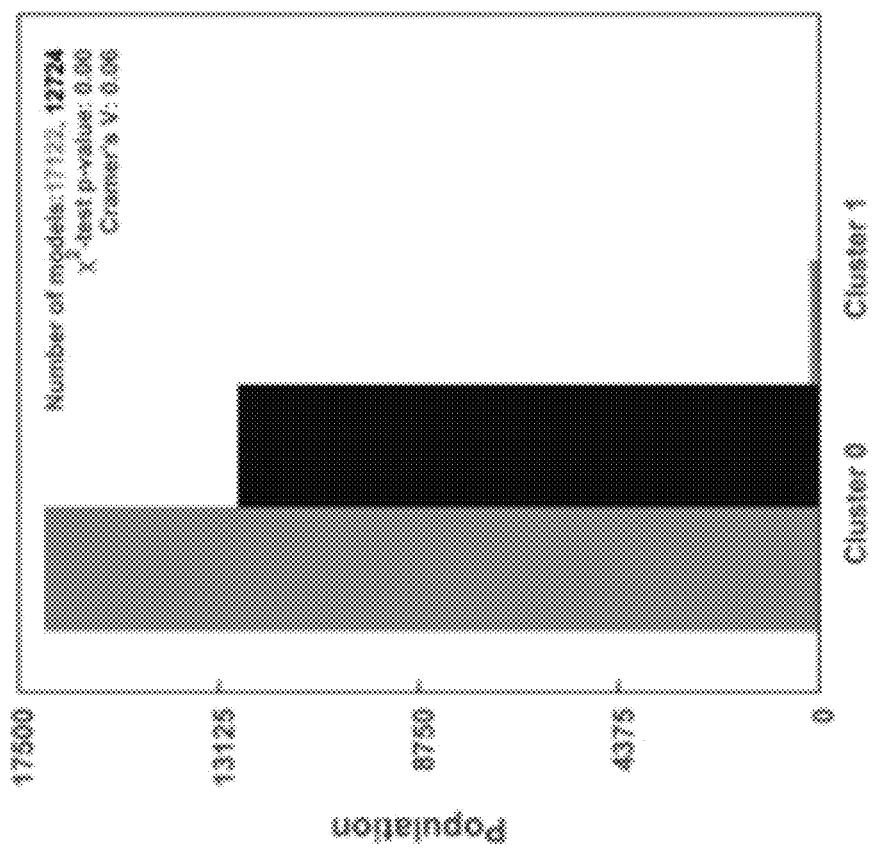
Figure 27C:
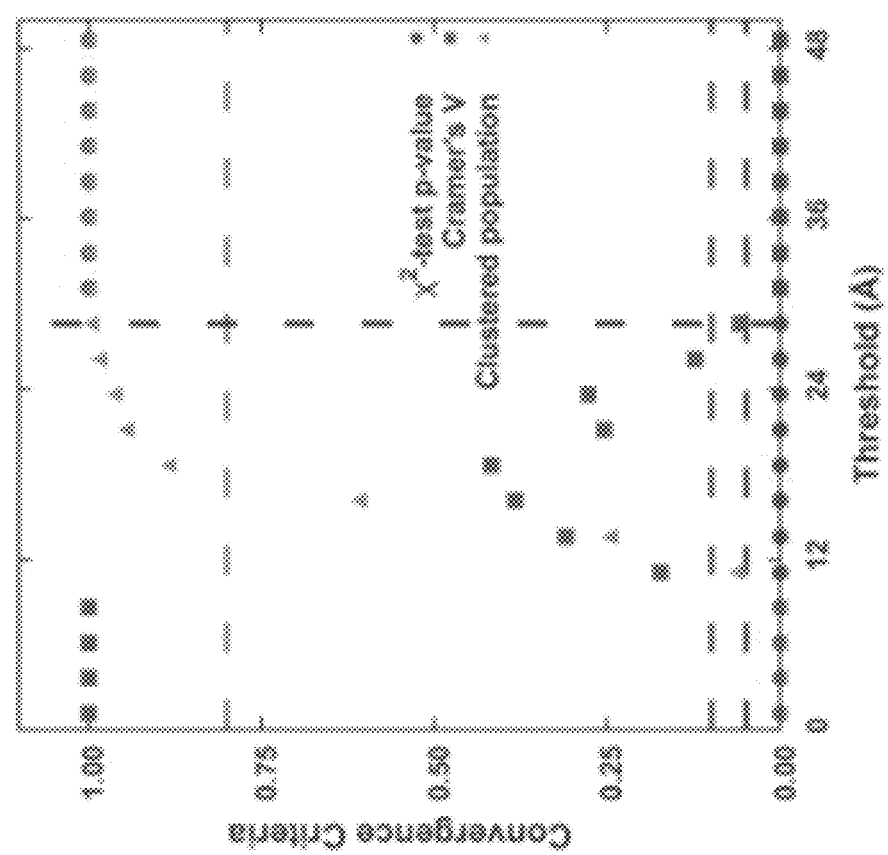

FIG. 27C shows an embodiment of three criteria for determining the sampling precision (y axis), evaluated as a function of the RMSD. clustering threshold (x axis) (n=30, 000 models). First, the P value is computed using the $\chi 2$-test (one-sided) for homogeneity of proportions (red dots). Second, an effect size for the $\chi 2$-test is quantified by the Cramer's V value (blue squares). Third, the population of structures in sufficiently large clusters (containing at least ten structures from each sample) is shown as green triangles. The vertical dotted grey line indicates the RMSD. clustering threshold at which two conditions are satisfied (Cramer's V (0.06)<0.10 (blue, horizontal dotted line) and the population of clustered structures (0.99)>0.80 (green, horizontal dotted line)), thus defining the sampling precision of 29 Å. The three solid curves (in red, blue and green) were drawn through the points to help visualize the results.

FIG. 27D shows an embodiment of population of sample 1 and 2 structures in the two clusters obtained by threshold-based clustering using an RMSD. threshold of 29 Å. The dominant cluster (cluster 1) contains 99% of the models. The precision of the dominant cluster defines the model precision, 21 Å.

Figure 27E:
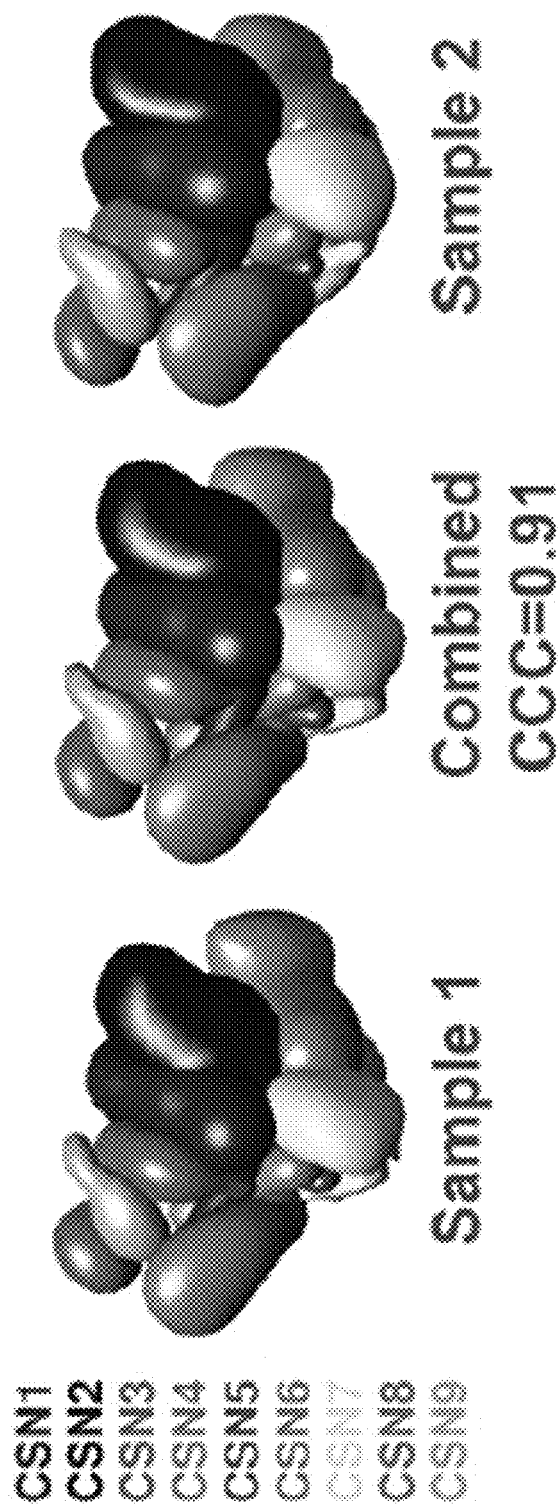
Figure 24F:
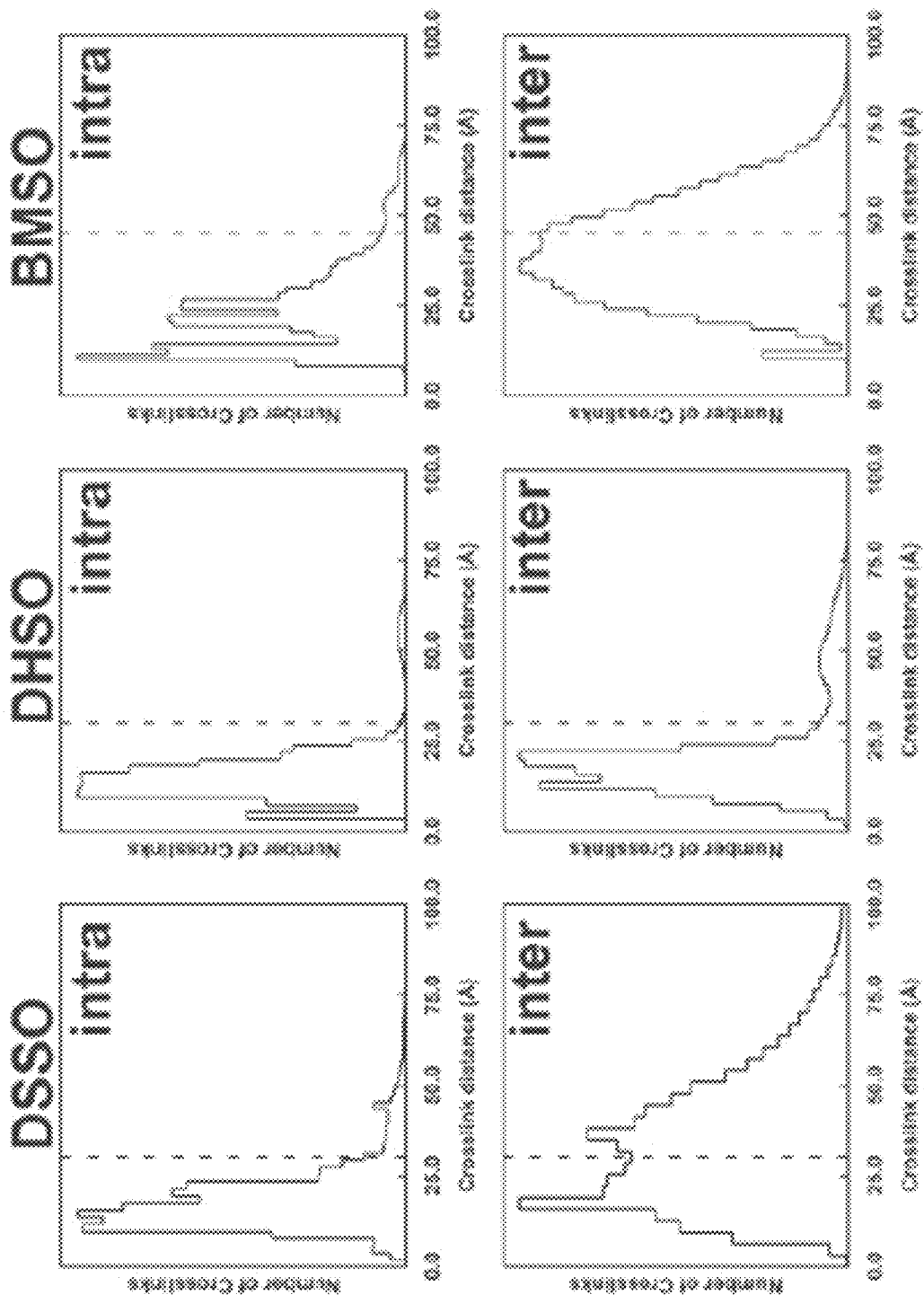

FIG. 27E shows an embodiment of comparison of localization probability densities of models from sample 1 (red) and sample 2 (blue) in the main cluster. The cross-correlation coefficient of 0.91 between the two samples localization probability densities suggests that the two samples are structurally identical.

FIG. 27F shows an embodiment of Euclidean Cα-Cα distance distributions of all measured cross-links in the ensemble of solutions for each cluster. The y axis provides the normalized number of cross-links that were mapped onto the model. The dashed redline denotes the expected maximum reach of a cross-link.

Figure 27G:
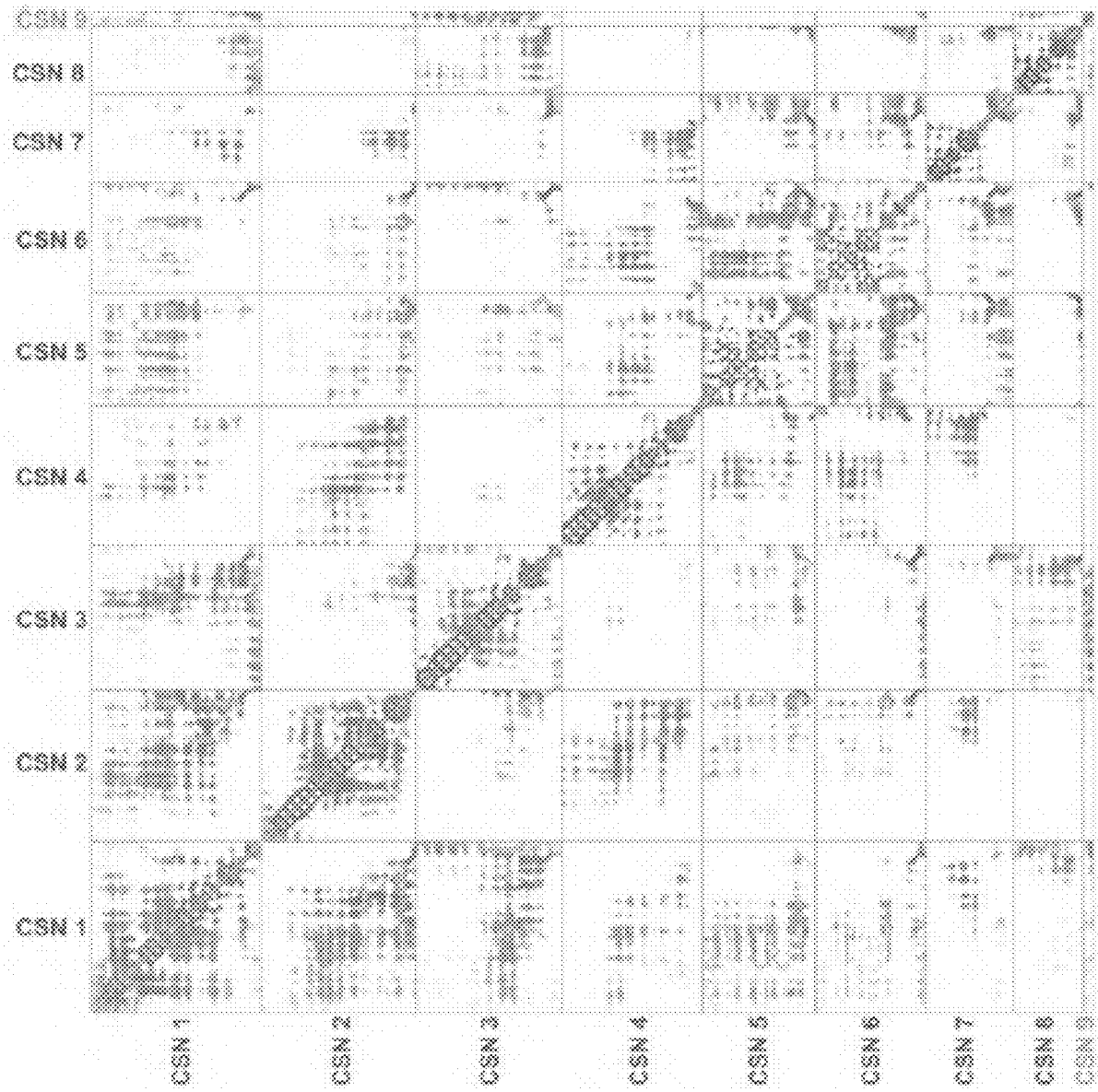

FIG. 27G shows an embodiment of average contact maps calculated for the main cluster. Each square is a contact map calculated between a given pair of subunits of the CSNn complex module proteins with border length proportional to the length of corresponding subunit sequences. The grey-shaded areas indicate observed interactions, with the grey-scale proportional to the fraction of models observing the corresponding interaction.

FIG. 27H shows an embodiment of an illustration of the rigid bodies defined for modeling of the non-canonical CSN complex. The 16 rigid bodies used for modeling are shown in ribbon representation. The cross-links that map within each rigid body are visualized and are colored based on whether they were satisfied (green) or violated (gold) by the rigid body definition. 99% of these cross-links observed in the presence of CSN9 are satisfied by the rigid body definition.

Figure 28:
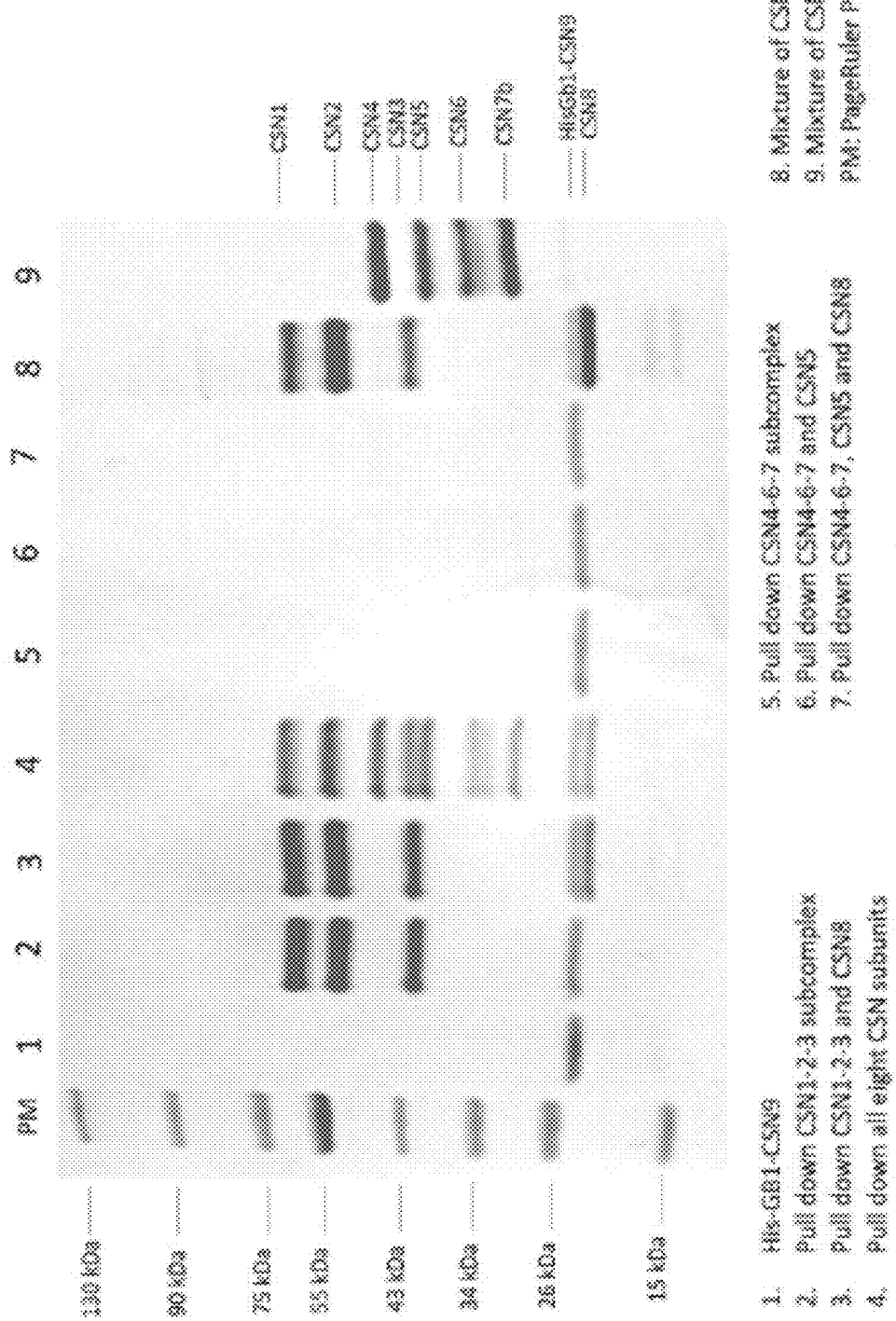

FIG. 28 shows an embodiment of in vitro pulldown assays to confirm the interactions of CSN9 with CSN1 and CSN3. Six different CSN subcomplexes were used for CSN9 pulldown assay (Lane 2-7), in which His-GB1 fused CSN9 served as the bait protein to identify its binding partners. Lane 1, 8 and 9 display protein bands corresponding to CSN subunits (CSN1-9). The description of each lane is included.

FIGS. 29A-29D show embodiments of CSN deneddylation activity in the presence or absence of CSN9.

Figure 29A:
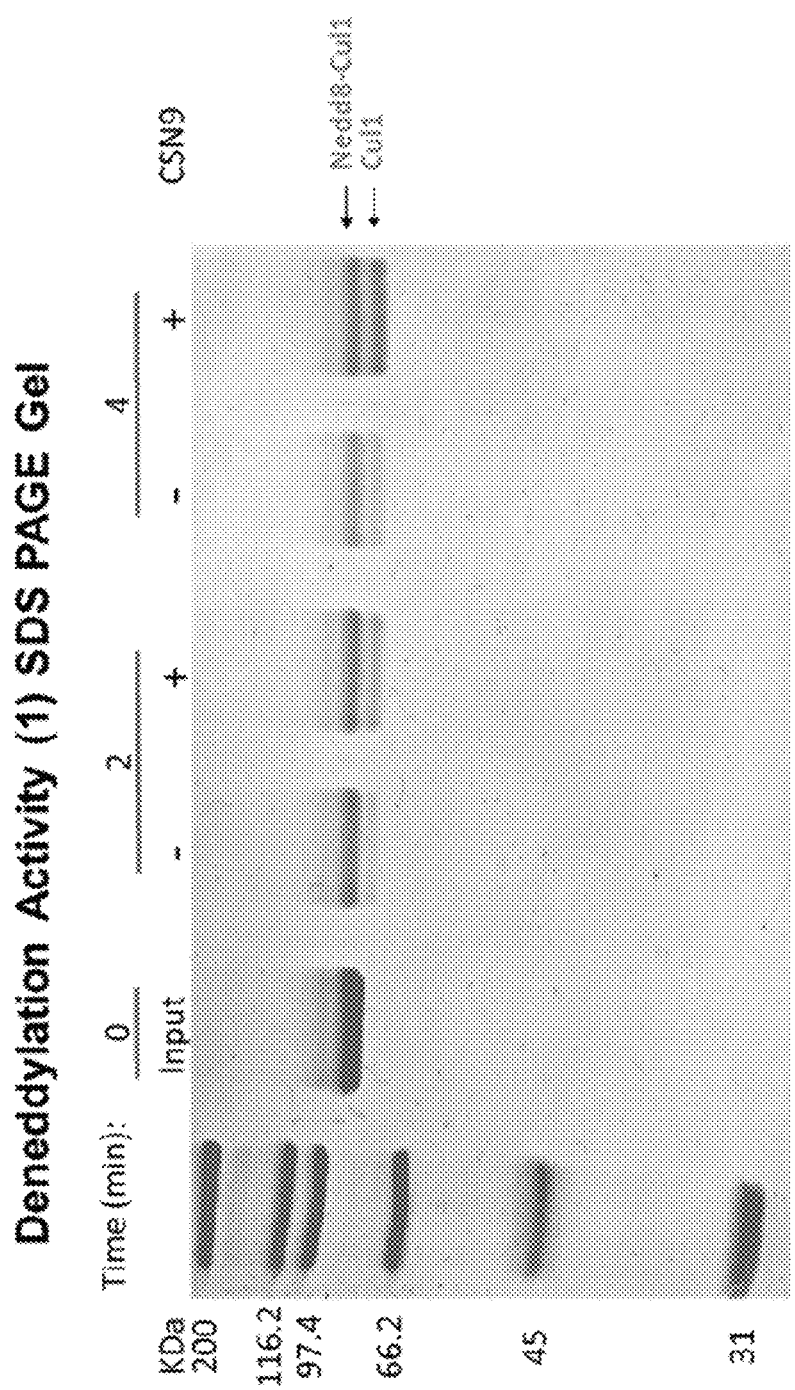

FIG. 29A shows an embodiment of purified CSN or CSNn was incubated with Nedd8-Cull over a 4 min period. Time points were collected at 2, and 4 minutes. SDS-PAGE analysis shows an increased rate of deneddylation for CSNn complex as compared to the CSN (CSN1-8) complex.

Figures 29B, 29C, 29D:
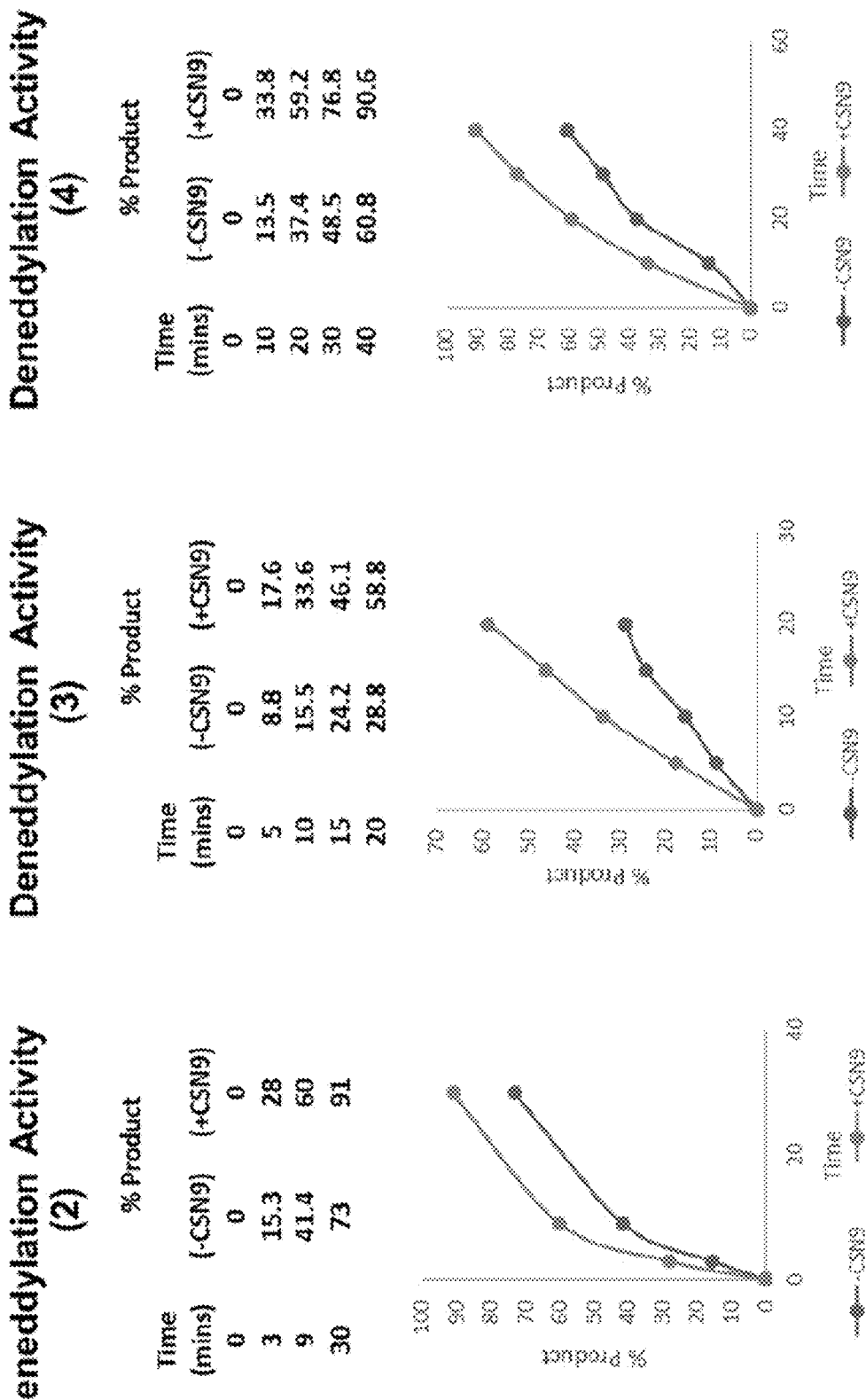

FIGS. 29B-29D show embodiments of the same assay in FIG. 29A performed three additional times with different time intervals to further demonstrate CSN9-induced activation of CSN deneddylase activity using neddylated Cull as the substrate. To illustrate the differences in the deneddylase activities of CSN in the absence and presence of CSN9, the percentage of un-neddylated Cull (the product) to total Cull at each time point was estimated based on protein band intensities on SDS-PAGE. Roughly, CSN9 can enhance CSN activity about 2-3 folds. Note: All assays were performed at room temperature with 5 μM Nedd8-Cull and 10 nM CSN in Buffer containing 20 mM HEPES (pH 7.5), 150 mM NaCl, and 1 mM TCEP.

DETAILED DESCRIPTION

In some embodiments, the present disclosure is related to developing a novel sulfoxide-containing MS-cleavable homobifunctional cysteine-reactive cross-linker for studying protein-protein interactions.

In some embodiments, a novel sulfoxide-containing MS-cleavable homobifunctional cysteine-reactive cross-linker is provided.

In some embodiments, a novel sulfoxide-containing MS-cleavable homobifunctional cysteine-reactive cross-linker is utilized for studying protein-protein interactions.

Proteins rarely act alone in cells, instead, often functioning in the context of multi-subunit protein complexes. These macromolecular entities participate in complex protein-protein interaction (PPI) networks essential for controlling a diverse range of biological processes. Dysregulation of endogenous PPI networks can be detrimental to cell homeostasis and viability, which has been linked to multiple human diseases. Thus, protein interaction interfaces have become attractive targets for drug discovery[1,2]. Therefore, full characterization of PPIs can help not only understand the assembly, structure and function of protein complexes, but also identify PPIs critical in human pathologies, diagnostics and therapeutics.

Owing to recent technological innovations, cross-linking mass spectrometry (XL-MS) has become a powerful and effective method for studying PPIs in vitro and in vivo[3-7]. In comparison to other structural tools, XL-MS is unique due to its capability to simultaneously capture PPIs from their native environment and uncover their physical interaction contacts, thus permitting the determination of both identity and connectivity of PPIs in cells[3,6,7]. In addition, identified cross-links provide distance constraints to facilitate three-dimensional modeling of protein complexes by refining existing high-resolution protein structures and/or complementing low-resolution structures to elucidate architectures of large protein complexes[4,5,7] that have remained recalcitrant to traditional methodologies alone.

To date, amine-reactive reagents targeting lysine residues are still the most commonly used cross-linkers in XL-MS studies. This is due to the relatively high occurrence of lysines in protein sequences (~6% of all residues) and at surfaces of protein structures, as well as the specificity and efficiency of amine-reactive chemistries. However, it is clear that lysine-reactive reagents alone cannot provide a full picture of PPI maps as some protein interaction interfaces do not contain proximal lysines for cross-linking. Therefore, exploring additional cross-linking chemistries would be important for generating comprehensive PPI network topologies. Recently, acidic residue targeting reagents, i.e. non-cleavable[8] and MS-cleavable[9] dihydrazides have been developed and proven successful in yielding complementary information to lysine cross-linkers, thus expanding the coverage of PPI regions and aiding in protein structure characterization. Apart from lysines and acidic residues, cysteines are useful alternatives for protein cross-linking due to several factors. First, the high specificity and efficiency of sulfhydryl chemistry has permitted its widespread adoption in a gamut of proteomics studies. Secondly, cysteine cross-linking can be more selective and informative due to the lower prevalence of cysteines compared to lysine and acidic residues. Therefore, developing new cysteine-targeting cross-linkers would be advantageous for profiling PPIs, and can further complement existing reagents.

Cross-linking mass spectrometry (XL-MS) has become an emerging technology for defining protein-protein interactions (PPIs) and elucidating architectures of large protein complexes. Up to now, the most widely used cross-linking reagents target lysines. While such reagents have been successfully applied to map PPIs at the proteome-wide scale, comprehensive PPI profiling would require additional cross-linking chemistries. Cysteine is one of the most reactive amino acids and an attractive target for cross-linking owing to its unique role in protein structures. Although sulfhydryl-reactive cross-linkers are commercially available, their applications in XL-MS studies remain sparse—likely due to the difficulty in identifying cysteine cross-linked peptides. Previously, the inventors developed a new class of sulfoxide-containing MS-cleavable cross-linkers to enable fast and accurate identification of cross-linked peptides using multistage tandem mass spectrometry (MS$^n$).

Among various types of cysteine-reactive reagents, maleimides are most widely utilized due to the specificity and efficiency of thiol-maleimide coupling[10]. In addition, maleimide moieties are also easily functionalized and reactions can occur at physiological pH in the absence of catalysts or heating, making these reagents well-suited for a variety of experimental uses. Such chemistry has been successfully employed in cross-linking studies to probe protein structures and identify interaction domains[10-12]. While homobifunctional maleimide cross-linkers are commercially available, their uses in XL-MS studies remain sparse. This is more likely due to difficulty in MS identification of cross-linked peptides. During the development of lysine and acidic residue-targeting reagents, it has been demonstrated that MS-cleavable cross-linkers are powerful and effective in facilitating accurate identification of cross-linked peptides[3,9,13-22]. In recent years, the inventors have successfully developed a suite of sulfoxide-containing, MS-cleavable cross-linkers (i.e. DSSO (FIG. 1A)[17], DMDSSO[19], Azide/Alkyne-A-DSBSO[20,23] and DHSO (FIG. 1B)[9]) that permit simplified and accurate identification of cross-linked peptides. The MS-labile C—S bonds adjacent to the sulfoxide can be selectively and preferentially fragmented prior to peptide backbone cleavage upon collision-induced dissociation (CID), physically separating the peptides for individual sequencing[9,17,19,20]. Notably, this robust and predictable fragmentation occurs independent of cross-linking chemistry, peptide charge and peptide sequence. These unique characteristics enable straightforward and unambiguous identification of cross-linked peptides by MS$^n$ analysis coupled with conventional database searching tools[9,17,19,20]. Sulfoxide-containing MS-cleavable cross-linkers have been successfully applied to not only study PPIs in vitro[17,24-30] and in vivo[20,27], but also to quantify structural dynamics of protein complexes[19,31].

Bis-Maleimide Sulfoxide (BMSO)

Given the robustness of sulfoxide-based cleavability, in some embodiments, the present disclosure is related to the design, synthesis and characterization of a novel sulfoxide-containing MS-cleavable homobifunctional cysteine linker, namely, BMSO (Bis-maleimide sulfoxide) to facilitate the identification of cysteine cross-linked peptides. The structure of BMSO is shown below:

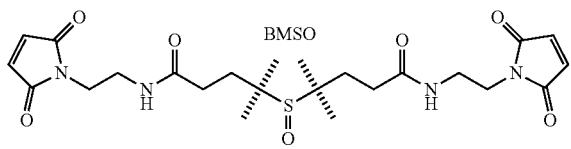

It is believed that BMSO represents the first generation of cysteine-reactive cross-linking reagents with MS cleavability, which, according to several embodiments, enhances the capability of mapping PPIs.

In some embodiments, the present disclosure is relate to the development of a new sulfoxide-containing MS-cleavable homobifunctional cysteine reactive cross-linker, Bis-maleimide Sulfoxide (BMSO). An embodiment of a general scheme for the identification of MS-cleavable cysteine cross-linked peptides by MS$^n$ using BMSO is shown in FIG. 5. In some embodiments, BMSO cross-linked peptides display the same characteristic fragmentation pattern during collision induced dissociation (CID) as other sulfoxide-containing MS-cleavable cross-linked peptides, thus permitting their simplified analysis and unambiguous identification by MS$^n$. In some embodiments, BMSO can complement amine- and acidic residue-reactive reagents for mapping protein interaction regions. Without being limited by any particular theory, the present disclosure not only enlarges the toolbox of MS-cleavable cross-linkers with diverse chemistries, but more importantly, expands the capacity and capability of studying PPIs in general.

Cross-linking mass spectrometry (XL-MS) has become an emergent technology for studying protein-protein interactions and characterizing architectures of protein complexes. Currently, amine-reactive reagents targeting lysine residues are the most commonly used cross-linkers in XL-MS studies. However, it is clear that lysine-reactive reagents alone cannot provide a full picture of PPI maps as some protein interaction interfaces do not contain proximal lysines for cross-linking. Therefore, exploring additional cross-linking chemistries would be important for generating comprehensive PPI network topologies. Thus, in some embodiments, a new sulfoxide-containing MS-cleavable cross-linker, BMSO, targeting cysteine residues is provided. In some embodiments, a sulfoxide-containing MS-cleavable cysteine reactive cross-linking reagent for studying protein-protein interactions and elucidating architectures of protein complexes is provided.

Apart from lysines, cysteines are useful alternatives for protein cross-linking due to several factors. First, the high specificity and efficiency of sulfhydryl chemistry has permitted its widespread adoption in a gamut of proteomics studies. Secondly, cysteine cross-linking can be more selective and informative due to the lower prevalence of cysteines compared to lysine and acidic residues. Therefore, developing new cysteine-targeting cross-linkers would be advantageous for profiling PPIs, and can further complement existing reagents.

Among various types of cysteine-reactive reagents, maleimides are most widely utilized due to the specificity and efficiency of thiol-maleimide coupling. In addition, maleimide moieties are also easily functionalized and reactions can occur at physiological pH in the absence of catalysts or heating, making these reagents well-suited for a variety of experimental uses. Such chemistry has been successfully employed in cross-linking studies to probe protein structures and identify interaction domains. While homobifunctional maleimide cross-linkers are commercially available, their uses in XL-MS studies remain sparse. This is more likely due to difficulty in MS identification of cross-linked peptides. In order to facilitate the identification of cysteine cross-linked peptides, a sulfoxide-containing MS-cleavable cysteine reactive cross-linker based on maleimide chemistry was synthesized.

To expand the coverage of protein-protein interactions, the inventors have developed a novel sulfoxide-containing MS-cleavable homobifunctional cysteine linker, namely, BMSO (Bis-maleimide sulfoxide) to facilitate the identification of cysteine cross-linked peptides. It is believed that BMSO represents the first generation of cysteine-reactive cross-linking reagents with MS cleavability, which undoubtedly enhances the capability of mapping PPIs in the future.

BMSO (bismaleimide sulfoxide or 3,3'-sulfinylbis(N-(2-(2,5-dioxo-2,5-dihydro-1H-pyrrol-1-yl)ethyl)propanamide)), consists of two maleimide functional groups for cross-linking cysteines connected by a spacer arm containing a central sulfoxide group with two symmetric MS-cleavable C—S bonds. The MS-labile C—S bonds adjacent to the sulfoxide can be selectively and preferentially fragmented prior to peptide backbone cleavage upon collision-induced dissociation (CID), physically separating the peptides for individual sequencing. These unique characteristics enable straightforward and unambiguous identification of cross-linked peptides by MS$^n$ analysis coupled with conventional database searching tools. BMSO is established based on the Inventors' previous work on the development of other sulfoxide-containing cross-linkers targeting lysines (i.e. DSSO, Azide/Alkyne-A-DSBSO) and acidic residues (DHSO) to enable simplified and accurate identification of cross-linked peptides. BMSO represents the first MS-cleavable cysteine reactive cross-linker that can be effectively used for probing protein-protein interactions. It can be used to study protein-protein interactions of protein complexes and decipher interaction landscapes at the proteome-wide scale.

During the analysis, it was found that conjugation of cysteines via maleimide chemistry can yield two different forms of cross-linked cysteines, either containing the SITE (closed-ring) or hydrolyzed SATE (open-ring) structures. While this occurrence potentially decreases cross-link spectral abundance, in some embodiments, it was shown that SATE formation can be pushed near completion during the experimental process—minimizing cross-linked peptide ion heterogeneity during MS$^n$ analysis. More importantly, the ring states of BMSO cross-linked cysteines do not interfere with their identification by MS$^n$ analysis, permitting the identification of cross-links in regions not covered by and complementing the structural data afforded by lysine- and acidic residue-targeting cross-linkers.

In some embodiments, synthesis of BMSO only requires one additional amide bond forming step using DSSO as the starting material. The core of DSSO is elaborated through the addition of the trifluoroacetate salt of 1-(2-aminoethyl) maleimide to install the cysteine-reactive moiety. BMSO has a spacer arm of 24.2 Å, well within the distance range among cross-linking reagents that have been successfully applied for studying PPIs. The scheme for its synthesis is shown below:

herein further illustrate that the same MS$^n$ workflow can be applied for simplified and accurate identification of all sulfoxide-containing MS-cleavable cross-linked peptides regardless of cross-linking chemistries, thus facilitating rapid and simplified identification for BMSO cross-linked cysteine residues. However, unlike DSSO (NHS, amine-reactive) and DHSO (hydrazide, acidic residue-reactive) cross-linking chemistries, conjugation of cysteines via maleimide chemistry can yield two different forms of cross-

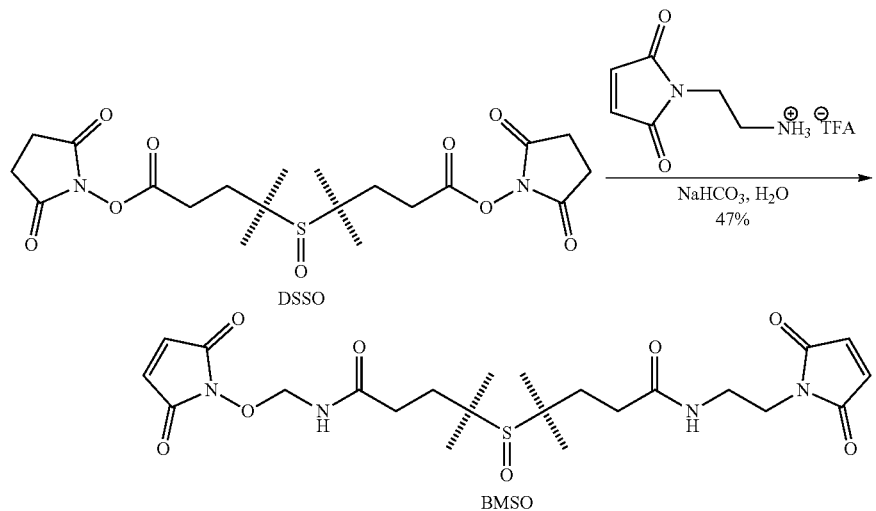

In some embodiments, the new sulfoxide-containing MS-cleavable cysteine reactive cross-linker, BMSO, fills a gap in XL-MS analysis. Although maleimide based non-cleavable cross-linkers have been used for studying protein-protein interactions, they have not been widely used in the field. The development of BMSO will undoubtedly facilitate protein interaction studies by targeting cysteine residues. Given the importance of cysteines in protein structure and function, BMSO will provide additional new insights on protein structures and functions that cannot be assessed by existing reagents. BMSO represents the first generation of cysteine-reactive cross-linking reagents with MS cleavability, which, according to several embodiments disclosed herein, enhances the capability of mapping PPIs. The identification of BMSO cross-linked peptides is much more robust, fast and accurate than the identification of non-cleavable cysteine cross-linked peptides. The MS-cleavability allows the application of BMSO cross-linking to very complex biological samples.

In some embodiments, BMSO was synthesized and characterized with synthetic peptides and simple model proteins to confirm the features of its design. The cysteine reactivity, MS cleavability, and MS identification were validated in these characterization steps. In some embodiments, BMSO based cross-linking mass spectrometry workflow was established and employed to define protein-protein interactions of protein complexes and of cell lysates.

In some embodiments, the development and characterization of a novel sulfoxide-containing MS-cleavable cysteine reactive cross-linker, BMSO, derived from DSSO[17]. In some embodiments, using both a standard peptide and protein, it was demonstrated that BMSO cross-linking is efficient and that BMSO cross-linked peptides display the same characteristic MS-cleavability unique to other sulfoxide-containing cross-linked peptides[9,17,19,20]. The results linked cysteines, either containing the SITE (closed-ring) or hydrolyzed SATE (open-ring) structures (FIGS. 1E-1F). While this occurrence potentially decreases cross-link spectral abundance, in some embodiments, it was shown that SATE formation can be pushed near completion during the experimental process—minimizing cross-linked peptide ion heterogeneity during MS$^n$ analysis. More importantly, the ring states of BMSO cross-linked cysteines do not interfere with their identification by MS$^n$ analysis, permitting the identification of cross-links in regions not covered by and complementing the structural data afforded by lysine- and acidic residue-targeting cross-linkers.

Without being limited by any particular theory, and to the best of the inventors' knowledge, BMSO represents the first MS-cleavable cysteine-reactive cross-linking reagent. Without being limited by any particular theory, BMSO is expected to advance cross-linking studies targeting cysteine residues, which are currently underrepresented in XL-MS analysis. Without being limited by any particular theory, the comparison showing the complementary nature of BMSO, DSSO and DHSO cross-linking data further signifies the necessity and usefulness of multiple cross-linking chemistries to obtain high-density interaction maps with improved confidence, in order to expand the capacity and capability of mapping PPIs at the systems-level in the future.

Development of a Novel Sulfoxide-Containing MS-Cleavable Cysteine-Reactive Cross-Linker In order to improve the identification of cysteine cross-linked peptides, a novel MS-cleavable cysteine-reactive homobifunctional cross-linking reagent by integrating the MS-cleavability of sulfoxide-containing cross-linkers[9,17,19,20] with maleimide chemistry was developed. This resulted in the development of BMSO (bismaleimide sulfoxide or 3,3'-sulfinylbis(N-(2-(2,5-dioxo-2,5-dihydro-1H-pyrrol-1-yl) ethyl)propanamide) (FIG. 1C). This cross-linker consists of two maleimide functional groups for cross-linking cysteines connected by a spacer arm containing a central sulfoxide group with two symmetric MS-cleavable C—S bonds. As shown, BMSO contains the same type of MS-cleavable bonds as DSSO and DHSO (FIGS. 1A-1B)[9,17]. The synthesis of BMSO only requires one additional amide bond forming step using DSSO as the starting material (FIG. 1D). The core of DSSO is elaborated through the addition of the trifluoroacetate salt of 1-(2-aminoethyl) maleimide to install the cysteine-reactive moiety[32]. BMSO has a spacer arm of 24.2 Å, well within the distance range among cross-linking reagents that have been successfully applied for studying PPIs[3].

Predicted MS² Fragmentation of BMSO Cross-Linked Peptides

Similar to other residue-specific cross-linkers, BMSO cross-linking is expected to result in three types of cross-linked peptides: dead-end (type 0), intra-link (type 1), and inter-link (type 2) modified peptides[33]. As inter-links (type 2) provide the most useful information pertaining to the relative spatial orientation of cross-linked cysteine residues, the inventors focused on the characterization of BMSO inter-linked peptides here. FIG. 1E illustrates the thiol-maleimide coupling reaction between cysteine sulfhydryl (—SH) groups and the maleimide functional groups of BMSO, resulting in a closed-ring succinimidyl thioether (SITE) bond by way of Michael addition[34]. The succinimidyl moiety of a SITE can then undergo irreversible hydrolysis in aqueous buffer, opening the ring to produce a stable succinamic acid thioether (SATE). These two forms were distinguished by designating the closed-ring SITE inter-linked peptide as $(\alpha_c\text{-}\beta_c)$—in which 'c' represents 'closed-ring SITE'—and the open-ring form of the same BMSO inter-linked peptide as $(\alpha_o\text{-}\beta_o)$, where 'o' represents 'open-ring SITE' (FIG. 1E). The mass difference between the fully closed and opened forms of BMSO cross-linked peptides is equivalent to the mass of $2H_2O$ (+32 Da).

Regardless of the thioester structures (SITE or SATE) covalently linked to the cysteine residues, BMSO cross-linked peptides share the same MS-cleavable bonds as previously reported sulfoxide-containing cross-linked peptides and are thus expected to yield the same characteristic fragmentation patterns that enable cross-link identification by MS$^n$ analysis[9,17,19,20]. To illustrate, FIG. 1F displays the predicted MS² fragmentation of a BMSO inter-linked heterodimer (α-β), with either SITE or SATE structures on cross-linked cysteines. Cleavage of either one of the two symmetric C—S bonds results in physical separation of the two cross-linked peptide constituents, resulting in the detection of peptide fragment ion pairs (i.e. $\alpha_A/\beta_S$ or $\alpha_S/\beta_A$). These fragment peptides are modified either with alkene (A) or sulfenic acid (S) moieties, remnants of BMSO following collision-induced dissociation. As previously noted for other sulfoxide-containing cross-linkers[9,17,19,20], the sulfenic moiety typically undergoes dehydration to become a more stable and dominant unsaturated thiol (T) moiety (FIG. 6). Therefore, the fragmentation pairs for a BMSO cross-linked peptide α-β are expected to be $\alpha_A/\beta_T$ and $\alpha_T/\beta_A$ (FIG. 1F). Such characteristic CID-triggered cross-link fragmentation has been proven unique and robust to sulfoxide-containing cross-linkers, independent of cross-linking chemistry, peptide sequence and charge[9,17,19,20]. The resulting MS² fragment ions represent single peptide chains that can be subjected to individual MS³ analyses, permitting unambiguous identification of both cross-linked peptide sequences and cross-linking sites.

Characterization of BMSO Cross-Linked Model Peptides by MS$^n$ Analysis

To evaluate BMSO cross-linking and establish an analytical workflow for the identification of BMSO cross-linked peptides, BMSO cross-linking was first performed using a synthetic cysteine-containing peptide Ac-LR9 (Ac-LADVCAHER (SEQ ID NO: 96)). Due to this reaction being performed in DMSO, the major inter-linked product detected in MS¹ was an Ac-LR9 homodimer with closed-ring SITE, i.e. $(\alpha_c\text{-}\alpha_c)$ (m/z 637.7849$^{4+}$) (FIG. 2A). MS² analysis of this BMSO inter-linked homodimer generated a pair of dominant fragment ions $\alpha_{Ac}/\alpha_{Tc}$ (m/z 625.29$^{2+}$/641.27$^{2+}$) as expected for BMSO inter-linked homodimers (FIG. 2B). Subsequent MS³ analyses of $\alpha_{Ac}$ (m/z 625.29$^{2+}$) and $\alpha_{Tc}$ (m/z 641.27$^{2+}$) fragment ions yielded series' of b and y sequencing ions identifying them as Ac-LADVC$_{Ac}$AHER (SEQ ID NO: 85) and Ac-LADVC$_{Tc}$AHER (SEQ ID NO: 98), respectively (FIGS. 7A-7B), verifying a cysteine-cysteine BMSO linkage between two separate Ac-LR9 peptides.

During LC-MS$^n$ analysis, the fully open-ring Ac-LR9 homodimer cross-linked with BMSO was also detected, i.e. $(\alpha_o\text{-}\alpha_o)$ (m/z 646.7885$^{4+}$) (FIG. 2C). MS² analysis yielded the characteristic fragment ion pair $\alpha_{Ao}/\alpha_{To}$ (m/z 634.30$^{2+}$/650.28$^{2+}$). MS³ analyses of these two MS² fragments allowed unambiguous peptide identification as Ac-LADVC$_{Ao}$AHER (SEQ ID NO: 92) and Ac-LADVC$_{To}$AHER (SEQ ID NO: 86), respectively (FIGS. 8A-8B). These results demonstrate that the state of the ring structures attached to cross-linked cysteines do not interfere with the characteristic MS² fragmentation of BMSO cross-linked peptides and their subsequent identification by MS$^n$ analysis.

Apart from the fully closed and open-ring forms of BMSO inter-linked Ac-LR9 homodimers, an additional ion $(\alpha_c\text{-}\alpha_o)$ (m/z 642.2861$^{4+}$) was detected, representing a half-hydrolyzed product containing two cross-linked peptides, one with closed-ring and the other with open-ring structures attached to cysteines. Its MS$^n$ analysis further confirms that BMSO cross-linked peptides can be readily identified independent of the ring structures on cross-linked cysteines (FIGS. 9A-9D). Nonetheless, the existence of different forms of the same BMSO cross-linked peptide not only increases sample complexity, but also decreases the abundance of each particular cross-link. Therefore, it would be advantageous, as provided for herein, to obtain a single form of BMSO cross-linked peptides for MS$^n$ analysis. To this end, several experimental conditions were examined to favor complete SITE hydrolysis and thus generate the most stable form of BMSO cross-linked products—open-ring SATE structures. Incubation of BMSO inter-linked Ac-LR9 in 25 mM ammonium bicarbonate buffer overnight at 37° C. led to a nearly complete (98.7%) conversion of the fully closed-ring form $(\alpha_c\text{-}\alpha_c)$ to the fully open-ring form $(\alpha_o\text{-}\alpha_o)$ (FIGS. 10A-10B). This indicates that SITE hydrolysis can be induced in order to minimize the heterogeneity of resulting cross-linked peptides. While BMSO cross-linking of standard peptides was carried out in DMSO, protein cross-linking and digestion are typically performed in physiological buffers. Therefore, it is suspect that the majority of BMSO cross-linked products for protein samples may be in open-ring states. However, similar procedures were carried out in following experiments to ensure homogenous cross-linked products for MS$^n$ analysis.

Identification of BMSO Cross-linked Peptides of BSA

Figure 3C:
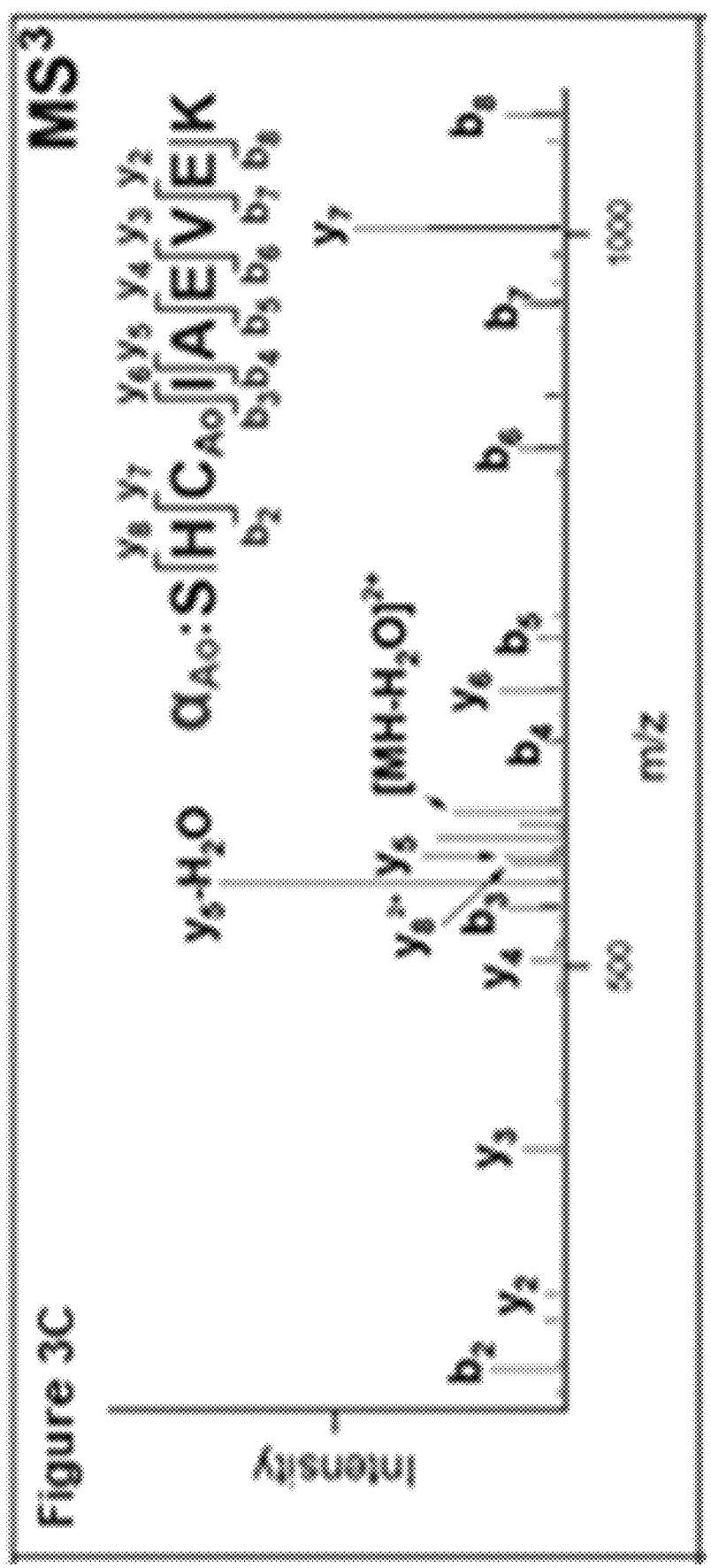
Figure 30:
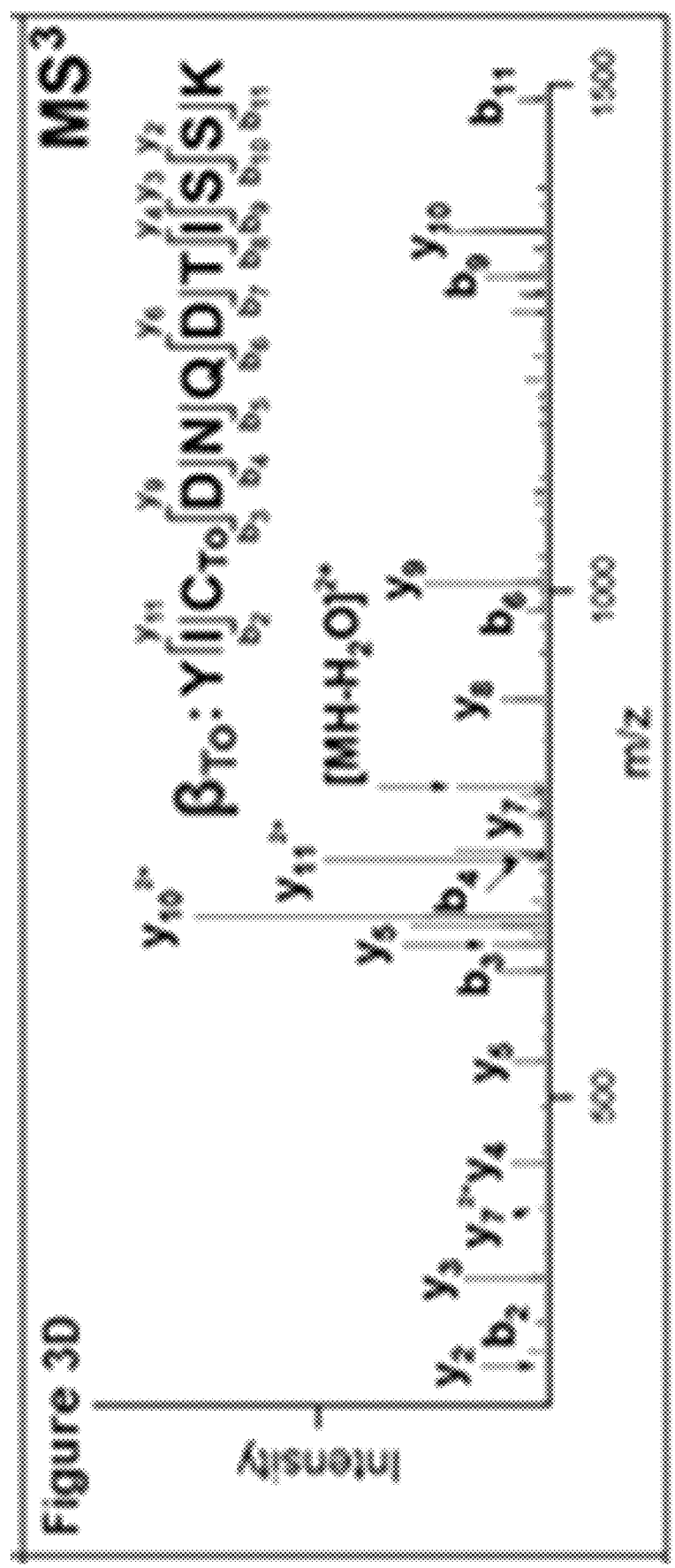

To evaluate BMSO cross-linking of proteins, bovine serum albumin (BSA) was used as a model protein since it has been previously used for characterizing cross-linking studies[9]. Importantly, BSA contains 35 cysteines out of a total of 607 amino acid residues (5.76%), well above the average cysteine content in the proteome (~1.2%) (uniprot.org). The general procedures for optimizing BMSO cross-linking and MS$^n$ analysis of BMSO cross-linked proteins are very similar to those described for other sulfoxide-containing cross-linkers[9,17,19,20]. Briefly, BMSO cross-linking of BSA was optimized by titrating various ratios of protein to cross-linker concentrations, temperature and reaction time. The resulting cross-linked proteins were separated by SDS-PAGE, digested and subjected to LC-MS$^n$ analysis. FIGS. 3A-3D displays an exemplary MS$^n$ analysis of a BMSO inter-linked peptide of BSA ($\alpha_o$-$\beta_o$) (m/z 719.5689$^{4+}$). MS$^2$ fragmentation of this inter-linked peptide resulted in the production of two characteristic peptide fragment pairs: $\alpha_{Ao}/\beta_{To}$ (m/z 614.29$^{2+}$/815.84$^{2+}$) and $\alpha_{To}/\beta_{Ao}$ (m/z 630.28$^{2+}$/799.86$^{2+}$) as predicted for BMSO inter-linked heterodimers (FIG. 3B). Subsequent MS$^3$ analysis of $\alpha_{Ao}$ (m/z 614.29$^{2+}$) (FIG. 3C) determined its sequence as SHCAJAEVEK (SEQ ID NO: 83), in which the cysteine in the 3$^{rd}$ position from the N-terminus was modified with an open-ring alkene moiety. MS$^3$ analysis of $\beta_{To}$ (m/z 815.84$^{2+}$) identified its sequence as YIC$_{To}$DNQDTISSK (SEQ ID NO: 84), with the cysteine in the 3$^{rd}$ position from the N-terminus carrying an open-ring unsaturated thiol moiety (FIG. 3D). Collectively, the inter-linked peptide was identified as [$^{286}$YICDNQDTISSK$^{298}$ (SEQ ID NO: 93) cross-linked to $^{310}$SHCIAEVEK$^{318}$ (SEQ ID NO: 94)], describing a fully open-ring inter-link formed between C289 and C312 of BSA.

Similarly, a total of 41 unique BMSO inter-linked peptides of BSA were identified by LC-MS$^n$ analysis, representing 38 unique C-C linkages (TABLE 1).

TABLE 1

Detailed Summary of BMSO Inter-Linked BSA Peptides Identified by LC-MSn

| XL A | XL B | XL Distance (Å) | XL m/z | XL Charge | Corr. XL PPM | Corr. XL Isotope | m/z A | zA | Sequence A | SEQ ID NO: | Protein Mods A | PPM A | Score A | EV A |
|---|---|---|---|---|---|---|---|---|---|---|---|---|---|---|
| C99 | C200 | 43.896 | 635.0602 | 4 | 4.216 | 0 | 803.867 | 2 | SLHTLFGDELCK | 1 | XL:P2-Thiol@99 | -1.451 | 36.9 | 4.3E-6 |
| C99 | C223 | 25.459 | 617.5406 | 4 | 4.191 | 0 | 803.867 | 2 | SLHTLFGDELCK | 2 | XL:P2-Thiol@99 | -2.197 | 39.9 | 2.3E-6 |
| C99 | C312 | 38.506 | 713.8325 | 4 | 3.492 | 1 | 803.866 | 2 | SLHTLFGDELCK | 3 | XL:P2-Thiol@99 | -.704 | 41.2 | 1.3E-6 |
| C125 | C312 | 35.134 | 617.2736 | 4 | -.306 | 0 | 611.255 | 2 | NECFLSHK | 4 | XL:P2-Thiol@125 | .149 | 22.4 | 1.5E-2 |
| C147 | C200 | 11.452 | 674.8275 | 4 | -.304 | 2 | 882.404 | 2 | LKPDPNTLCDEFK | 5 | XL:P2-Thiol@147 | -1.156 | 29.5 | 4.5E-4 |
| C147 | C223 | 35.403 | 657.0580 | 4 | 1.109 | 1 | 866.419 | 2 | LKPDPNTLCDEFK | 6 | XL:P2-Alkene@147 | -2.949 | 31.6 | 1.1E-4 |
| C147 | C288 | 36.989 | 845.6324 | 4 | 1.853 | 0 | 866.416 | 2 | LKPDPNTLCDEFK | 7 | XL:P2-Alkene@147 | .167 | 18.0 | 1.2E-2 |
| C147 | C312 | 28.096 | 753.1003 | 4 | 2.444 | 1 | 882.404 | 2 | LKPDPNTLCDEFK | 8 | XL:P2-Thiol@147 | -1.722 | 27.8 | 4.0E-4 |
| C147 | C471 | 36.578 | 919.9325 | 4 | 5.228 | 0 | 866.419 | 2 | LKPDPNTLCDEFK | 9 | XL:P2-Alkene@147 | -2.256 | 24.2 | 6.0E-4 |
| C147 | C484 | 38.611 | 709.0851 | 4 | -6.643 | -1 | 866.419 | 2 | LKPDPNTLCDEFK | 10 | XL:P2-Alkene@147 | -2.256 | 13.6 | 7.1E-2 |
| C200 | C223 | 35.862 | 602.6262 | 3 | 2.59 | 0 | 457.245 | 2 | GACLLPK | 11 | XL:P2-Alkene@200 | -1.704 | 23.3 | 4.0E-2 |
| C200 | C288 | 34.847 | 641.0454 | 4 | 1.175 | 0 | 457.245 | 2 | GACLLPK | 12 | XL:P2-Alkene@200 | -1.267 | 23.9 | 4.0E-2 |
| C200 | C312 | 24.707 | 548.2633 | 4 | 3.406 | 0 | 457.245 | 2 | GACLLPK | 13 | XL:P2-Alkene@200 | -2.142 | 27.5 | 2.9E-2 |
| C200 | C392 | 62.869 | 669.3016 | 4 | 3.762 | 2 | 457.246 | 2 | GACLLPK | 14 | XL:P2-Alkene@200 | -2.798 | 24.3 | 4.4E-2 |
| C200 | C415 | 33.208 | 723.65 | 3 | 2.852 | 0 | 457.245 | 2 | GACLLPK | 15 | XL:P2-Alkene@200 | -1.267 | 21.0 | 8.3E-2 |
| C200 | C471 | 30.273 | 715.8453 | 4 | 2.98 | 2 | 457.245 | 2 | GACLLPK | 16 | XL:P2-Alkene@200 | -1.267 | 22.2 | 9.3E-2 |
| C200 | C471 | 30.273 | 711.3536 | 4 | 15.257 | 0 | 457.245 | 2 | GACLLPK | 17 | XL:P2-Alkene@200 | -1.267 | 20.1 | 1.3E-1 |
| C200 | C484 | 37.979 | 504.7543 | 4 | -.378 | 0 | 457.245 | 2 | GACLLPK | 18 | XL:P2-Alkene@200 | -1.048 | 22.1 | 1.6E-1 |
| C200 | C510 | 44.161 | 750.8682 | 4 | 2.828 | 2 | 457.246 | 2 | GACLLPK | 19 | XL:P2-Alkene@200 | -3.454 | 21.7 | 1.0E-1 |
| C223 | C288 | 26.379 | 628.0292 | 4 | 2.391 | 0 | 422.207 | 2 | CASIQK | 20 | XL:P2-Alkene-H2O@223 | -3.563 | 16.8 | 1.3E-1 |
| C223 | C312 | 21.895 | 535.2468 | 4 | 4.316 | 0 | 422.206 | 2 | CASIQK | 21 | XL:P2-Alkene-H2O@223 | -1.432 | 24.8 | 5.4E-2 |

TABLE 1-continued

Detailed Summary of BMSO Inter-Linked BSA Peptides Identified by LC-MSn

| XL A | XL B | XL Distance (Å) | XL m/z | XL Charge | Corr. XL PPM | Corr. XL Isotope | m/zB | zB | Sequence B | SEQ ID NO: | Protein Mods B | PPM B | Score B | EV B |
|---|---|---|---|---|---|---|---|---|---|---|---|---|---|---|
| C223 | C415 | 30.57 | 705.9674 | 3 | 4.573 | 0 | 422.207 | 2 | CASIQK | 22 | XL:P1-Alkene@223 | −3.8 | 22.6 | 4.1 E−2 |
| C223 | C415 | 30.57 | 700.6239 | 3 | 1.119 | 1 | 422.205 | 2 | CASIQK | 23 | XL:P1-Alkene@223 | −.011 | 20.1 | 1.2E−1 |
| C288 | C312 | 11.205 | 959.4242 | 3 | 4.042 | 1 | 815.842 | 2 | YICDNQDTISSK | 24 | XL:P2-Thiol@288 | −2.436 | 37.0 | 7.4E−7 |
| C288 | C392 | 44.019 | 840.3563 | 4 | 3.887 | 1 | 799.855 | 2 | YICDNQDTISSK | 25 | XL:P2-Alkene@288 | −1.403 | 24.0 | 4.8E−5 |
| C288 | C471 | 28.634 | 886.9031 | 4 | 6.763 | 1 | 815.842 | 2 | YICDNQDTISSK | 26 | XL:P2-Thiol@288 | −2.313 | 39.6 | 1.5E−6 |
| C288 | C471 | 28.634 | 882.6517 | 4 | 4.643 | 0 | 799.855 | 2 | YICDNQDTISSK | 27 | XL:P2-Alkene@288 | −1.028 | 34.6 | 1.3E−6 |
| C288 | C484 | 37.129 | 901.0787 | 3 | 2.255 | 0 | 799.857 | 2 | YICDNQDTISSK | 28 | XL:P2-Alkene@288 | −3.654 | 39.5 | 5.5E−7 |
| C288 | C510 | 40.426 | 922.1707 | 4 | −.182 | 2 | 799.854 | 2 | YICDNQDTISSK | 29 | XL:P2-Alkene@288 | −.403 | 36.2 | 2.9E−6 |
| C312 | C415 | 31.513 | 621.5107 | 4 | 2.09 | 0 | 630.274 | 2 | SHCIAEVEK | 30 | XL:P2-Thiol@312 | −.983 | 30.1 | 1.8E−4 |
| C312 | C471 | 20.567 | 793.8638 | 4 | .933 | 0 | 614.287 | 2 | SHCIAEVEK | 31 | XL:P2-Alkene@312 | .236 | 33.9 | 3.3E−5 |
| C312 | C471 | 20.567 | 789.8665 | 4 | 2.653 | 0 | 614.289 | 2 | SHCIAEVEK | 32 | XL:P2-Alkene@312 | −1.88 | 32.0 | 5.4E−5 |
| C312 | C484 | 30.371 | 583.2780 | 4 | 3.313 | 0 | 614.288 | 2 | SHCIAEVEK | 33 | XL:P2-Alkene@312 | −.903 | 29.6 | 4.9E−5 |
| C312 | C510 | 34.466 | 828.8864 | 4 | .513 | 0 | 614.288 | 2 | SHCIAEVEK | 34 | XL:P2-Alkene@312 | −1.066 | 29.7 | 9.2E−5 |
| C383\|C384 | C392 | 5.526\|8.389 | 840.8470 | 4 | 7.64 | 1 | 800.835 | 2 | EYEATLEECCAK | 35 | XL:P2-Alkene@383\|XL:P2-Alkene@384 | −7.725 | 12.3 | 3.1 E−2 |
| C392 | C471 | 33.488 | 914.3992 | 4 | .218 | 0 | 855.362 | 2 | DDPHACYSTVFDK | 36 | XL:P2-Alkene@0392 | −2.891 | 12.6 | 8.9E−2 |
| C392 | C484 | 35.979 | 703.8121 | 4 | .152 | 0 | 871.347 | 2 | DDPHACYSTVFDK | 37 | XL:P2-Thiol@392 | −1.994 | 29.2 | 9.9E−6 |
| C392 | C510 | 26.708 | 949.6774 | 4 | 4.848 | 1 | 855.36 | 2 | DDPHACYSTVFDK | 38 | XL:P2-Alkene@392 | −.787 | 30.6 | 8.1E−6 |
| C415 | C510 | 20.063 | 823.6093 | 4 | −3.863 | 0 | 603.741 | 2 | QNCDQFEK | 39 | Gln->pyro-Glu@413; XL:P2-Alkene@415 | −1.942 | 22.7 | 2.4E−3 |
| C471 | C510 | 18.369 | 996.2224 | 4 | 5.524 | 1 | 948.448 | 2 | MPCTEDYLSLILNR | 40 | Oxidation@469;XL:P2-Alkene@471 | −.507 | 36.1 | 1.9E−6 |
| C484 | C510 | 12.514 | 785.6321 | 4 | 2.843 | 1 | 543.26 | 2 | LCVLHEK | 41 | XL:P2-Thiol@484 | −1.022 | 20.7 | 8.7E−3 |
| C99 | C200 | 43.896 | 635.0602 | 4 | 4.216 | 0 | 457.245 | 2 | GACLLPK | 42 | XL:P2-Alkene@200 | −1.267 | 22.5 | 1.0E−1 |
| C99 | C223 | 25.459 | 617.5406 | 4 | 4.191 | 0 | 422.206 | 2 | CASIQK | 43 | XL:P1-Alkene@223 | −1.905 | 19.7 | 1.5E−1 |
| C99 | C312 | 38.506 | 713.8325 | 4 | 3.492 | 1 | 614.288 | 2 | SHCIAEVEK | 44 | XL:P2-Alkene@312 | −.903 | 30.6 | 3.0E−4 |
| C125 | C312 | 35.134 | 617.2736 | 4 | −.306 | 0 | 630.275 | 2 | SHCIAEVEK | 45 | XL:P2-Thiol@312 | −2.57 | 30.3 | 1.0E−4 |
| C147 | C200 | 11.452 | 674.8275 | 4 | −.304 | 2 | 457.245 | 2 | GACLLPK | 46 | XL:P2-Alkene@200 | −1.048 | 22.2 | 6.8E−2 |
| C147 | C223 | 35.403 | 657.0580 | 4 | 1.109 | 1 | 422.207 | 2 | CASIQK | 47 | XL:P1-Alkene@223 | −3.326 | 19.2 | 9.4E−2 |
| C147 | C288 | 36.989 | 845.6324 | 4 | 1.853 | 0 | 799.855 | 2 | YICDNQDTISSK | 48 | XL:P2-Alkene@288 | −1.653 | 31.5 | 6.6E−6 |
| C147 | C312 | 28.096 | 753.1003 | 4 | 2.444 | 1 | 614.288 | 2 | SHCIAEVEK | 49 | XL:P2-Alkene@312 | −1.229 | 30.8 | 1.3E−4 |
| C147 | C471 | 36.578 | 919.9325 | 4 | 5.228 | 0 | 964.435 | 2 | MPCTEDYLSLILNR | 50 | Oxidation@469;XL:P2-Thiol@471 | −1.706 | 34.7 | 2.0E−6 |
| C147 | C484 | 38.611 | 709.0851 | 4 | −6.643 | −1 | 527.275 | 2 | LCVLHEK | 51 | XL:P2-Alkene@484 | −2.448 | 15.4 | 8.4E−2 |

TABLE 1-continued

Detailed Summary of BMSO Inter-Linked BSA Peptides Identified by LC-MSn

| | | | | | | | | | | | | | |
|---|---|---|---|---|---|---|---|---|---|---|---|---|---|
| C200 | C223 | 35.862 | 602.6262 | 3 | 2.59 | 0 | 422.206 | 2 | CASIQK | 52 | XL:P1-Alkene@223 | −1.668 | 23.0 | 3.4E−2 |
| C200 | C288 | 34.847 | 641.0454 | 4 | 1.175 | 0 | 815.841 | 2 | YICDNQDTISSK | 53 | XL:P2-Thiol@288 | −1.333 | 37.9 | 1.7E−7 |
| C200 | C312 | 24.707 | 548.2633 | 4 | 3.406 | 0 | 630.275 | 2 | SHCIAEVEK | 54 | XL:P2-Thiol@312 | −2.252 | 27.6 | 2.6E−4 |
| C200 | C392 | 62.869 | 669.3016 | 4 | 3.762 | 2 | 871.349 | 2 | DDPHACYSTVFDK | 55 | XL:P2-Thiol@392 | −3.716 | 27.5 | 1.8E−5 |
| C200 | C415 | 33.208 | 723.65 | 3 | 2.852 | 0 | 603.741 | 2 | QNCDQFEK | 56 | Gln->pyro-Glu@413; XL:P2-Alkene@415 | −1.445 | 18.9 | 3.1E−3 |
| C200 | C471 | 30.273 | 715.8453 | 4 | 2.98 | 2 | 964.435 | 2 | MPCTEDYLSLILNR | 57 | Oxidation@469;XL:P2-Thiol@471 | −1.603 | 30.7 | 4.1E−5 |
| C200 | C471 | 30.273 | 711.3536 | 4 | 15.257 | 0 | 940.448 | 2 | MPCTEDYLSLILNR | 58 | XL:P2-Alkene@471 | 2.086 | 38.8 | 1.4E−5 |
| C200 | C484 | 37.979 | 504.7543 | 4 | −.378 | 0 | 543.26 | 2 | LCVLHEK | 59 | XL:P2-Thiol@484 | −.838 | 23.1 | 1.0E−2 |
| C200 | C510 | 44.161 | 750.8682 | 4 | 2.828 | 2 | 673.333 | 3 | RPCFSALTPDETYVPK | 60 | XL:P2-Alkene-H2O@510 | −8.197 | 23.2 | 3.1E−3 |
| C223 | C288 | 26.379 | 628.0292 | 4 | 2.391 | 0 | 815.843 | 2 | YICDNQDTISSK | 61 | XL:P2-Thiol@288 | −3.294 | 37.8 | 4.4E−6 |
| C223 | C312 | 21.895 | 535.2468 | 4 | 4.316 | 0 | 630.274 | 2 | SHCIAVEK | 62 | XL:P2-Thiol@312 | −1.459 | 30.5 | 1.5E−4 |
| C223 | C415 | 30.57 | 705.9674 | 3 | 4.573 | 0 | 612.255 | 2 | QNCDQFEK | 63 | XL:P2-Alkene@415 | −3.099 | 18.1 | 1.2E−2 |
| C223 | C415 | 30.57 | 700.6239 | 3 | 1.119 | 1 | 603.741 | 2 | QNCDQFEK | 64 | Gln->pyro-Glu@413; XL:P2-Alkene@415 | −1.279 | 23.7 | 3.1E−3 |
| C288 | C312 | 11.205 | 959.4242 | 3 | 4.042 | 1 | 630.275 | 2 | SHCIAVEK | 65 | XL:P2-Thiol@312 | −3.045 | 33.9 | 9.9E−5 |
| C288 | C392 | 44.019 | 840.3563 | 4 | 3.887 | 1 | 871.346 | 2 | DDPHACYSTVFDK | 66 | XL:P2-Thiol@312 | −.847 | 27.1 | 1.1E−6 |
| C288 | C471 | 28.634 | 886.9031 | 4 | 6.763 | 1 | 948.451 | 2 | MPCTEDYLSLILNR | 67 | Oxidation@469;XL:P2-Alkene@471 | −3.354 | 42.8 | 6.5E−7 |
| C288 | C471 | 28.634 | 882.6517 | 4 | 4.643 | 0 | 940.453 | 2 | MPCTEDYLSLILNR | 68 | XL:P2-Alkene@471 | −3.55 | 42.1 | 4.9E−6 |
| C288 | C484 | 37.129 | 901.0787 | 3 | 2.255 | 0 | 543.262 | 2 | LCVLHEK | 69 | XL:P2-Thiol@484 | −4.151 | 14.8 | 1.5E−1 |
| C288 | C510 | 40.426 | 922.1707 | 4 | −.182 | 2 | 1034.478 | 2 | RPCFSALTPDETYVPK | 70 | XL:P2-Thiol@510 | 1.499 | 22.1 | 8.3E−4 |
| C312 | C415 | 31.513 | 621.5107 | 4 | 2.09 | 0 | 594.736 | 2 | QNCDQFEK | 71 | Gln->pyro-Glu@413;XL:P2-Alkene-H2O@415 | −2.446 | 22.7 | 8.6E−4 |
| C312 | C471 | 20.567 | 793.8638 | 4 | .933 | 0 | 964.434 | 2 | MPCTEDYLSLILNR | 72 | Oxidation@469;XL:P2-Thiol@471 | −.669 | 40.2 | 4.0E−6 |
| C312 | C471 | 20.567 | 789.8665 | 4 | 2.653 | 0 | 940.452 | 2 | MPCTEDYLSLILNR | 73 | XL:P2-Alkene@471 | −1.848 | 43.5 | 5.7E−7 |
| C312 | C484 | 30.371 | 583.2780 | 4 | 3.313 | 0 | 543.26 | 2 | LCVLHEK | 74 | XL:P2-Thiol@484 | −1.206 | 23.7 | 8.5E−3 |
| C312 | C510 | 34.466 | 828.8864 | 4 | .513 | 0 | 1034.481 | 2 | RPCFSALTPDETYVPK | 75 | XL:P2-Thiol@510 | −1.594 | 24.7 | 4.1E−4 |
| C383\|C384 | C392 | 5.526\|8.389 | 840.8470 | 4 | 7.64 | 1 | 871.344 | 2 | DDPHACYSTVFDK | 76 | XL:P2-Thiol@392 | 1.793 | 21.3 | 9.0E−5 |
| C392 | C471 | 33.488 | 914.3992 | 4 | .218 | 0 | 964.437 | 2 | MPCTEDYLSLILNR | 77 | Oxidation@469;XL:P2-Thiol@471 | −3.158 | 25.2 | 2.1 E−4 |
| C392 | C484 | 35.979 | 703.8121 | 4 | .152 | 0 | 543.261 | 2 | LCVLHEK | 78 | XL:P2-Thiol@484 | −1.942 | 19.4 | 1.6E−2 |
| C392 | C510 | 26.708 | 949.6774 | 4 | 4.848 | 1 | 1018.493 | 2 | RPCFSALTPDETYVPK | 79 | XL:P2-Alkene@510 | .113 | 23.5 | 1.8E−4 |

TABLE 1-continued

Detailed Summary of BMSO Inter-Linked BSA Peptides Identified by LC-MSn

| | | | | | | | | | | | | | |
|---|---|---|---|---|---|---|---|---|---|---|---|---|---|
| C415 | C510 | 20.063 | 823.6093 | 4 | −3.863 | 0 | 1034.479 | 2 | RPCFSALTPDETYVPK | 80 | XL:P2-Thiol@510 | .242 | 19.3 | 5.4E−3 |
| C471 | C510 | 18.369 | 996.2224 | 4 | 5.524 | 1 | 1034.484 | 2 | RPCFSALTPDETYVPK | 81 | XL:P2-Thiol@510 | −4.108 | 25.8 | 1.5E−4 |
| C484 | C510 | 12.514 | 785.6321 | 4 | 2.843 | 1 | 1034.481 | 2 | RPCFSALTPDETYVPK | 82 | XL:P2-Thiol@510 | −1.691 | 25.0 | 1.1E−3 |

Note: P1--cross-linked cysteine linked to closed-ring SITE; P2-- cross-linked cysteine linked to open-ring SATE.

It is noted that nearly all modified peptides comprising BMSO cross-links were identified in the open-ring SATE state—with the exception of CASIQK (SEQ ID NO: 95), which was identified frequently with a closed-ring SITE. Without being limited by any particular theory, it is believed that that the free amine group of the N-terminal cysteine may react with the 5-member SITE ring to form a more stable 6-member ring without any mass change, thereby preventing SITE hydrolysis. These results demonstrate that BMSO cross-linking is effective and that the heterogeneity of cross-linked products can be controlled (in other words, SITE hydrolysis can be stabilized by conversion to SATE products). More importantly, these results prove that BMSO cross-linked peptides exhibit the characteristic $MS^n$ fragmentation patterns as expected for all sulfoxide-containing MS-cleavable cross-linked peptides[9,17,19,20], thus enabling their simplified and accurate identification using the same $MS^n$ workflow as previously established for sulfoxide-containing cross-linkers.

BMSO Cross-Linking Maps of BSA

In some embodiments, BMSO, the results herein indicate that BMSO cross-linking is effective for mapping protein-protein interactions. To examine the efficacy and interaction coverage of BMSO cross-linking on the model protein, a 2-D cross-linking map was first derived using the unique C-C linkages identified (FIG. 4A). Considering the spacer arm length of BMSO (24.2 Å) and the distances contributed by cysteine side chains (2.8 Å), as well as backbone flexibility and structural dynamics, it was estimated that the theoretical upper limit for the $C\alpha$-$C\alpha$ distances between BMSO cross-linked cysteine residues is ~45 Å. To determine whether the identified BMSO cross-links correlate to residues with distances below the theoretical limit, they were mapped onto a published BSA crystal structure (PDB: 4F5S). All identified cross-links were able to be mapped to the crystal structure (FIG. 4B), with 97.4% (37 out of 38) having measurable $C\alpha$-$C\alpha$ distances below 45 Å (FIG. 4C, TABLE 1). This indicates that nearly all cross-links satisfy the expected distance constraints permitted by the molecular structure of BMSO and that the captured cross-links correlate well with known BSA structure. In summary, the results herein suggest that BMSO cross-linking is effective for mapping protein-protein interactions.

Comparison of BMSO with DSSO and DHSO Cross-Linking

To determine the complementarity of cysteine-reactive cross-linking with the previously developed amine-reactive and acidic residue-reactive cross-linkers, the cross-links identified using BMSO in this study were compared to those previously reported using DSSO and DHSO[9]. As aspartic/glutamic acid residues are most abundant in BSA, it is not surprising that acidic-residue cross-linking yielded the highest number of cross-links overall (69). Interestingly, although BSA has more lysines (9.8%) than cysteines (5.7%), more C-C linkages were identified than K-K linkages (i.e. 43 vs. 33, respectively). Compared to XL-MS maps derived from DSSO and DHSO cross-linking data[9], BMSO cross-linking improves the overall coverage by identifying proximal regions unfavored by amine- and acidic residue-targeting cross-linkers, thereby complementing previous results. This observation is most evident when examining the spatial relationships of the centrally located helices (H4, H13, H17, and H22) relative to more peripheral helices in the 3-D structure of BSA (PDB: 4F5S). These regions poorly covered by DSSO and DHSO are better characterized by BMSO, which has identified a total of 17 C-C-linkages describing clusters of physical contacts between: 1) H4 with H10 (C99-C200, C99-C223) and H17 (C99-C312); 2) H13 with H7 (C288-C147), H10 (C288-C200, C288-C223), H22 (C288-C392), H26 (C288-C471, C288-C484), and H28 (C288-0510); 3) H17 with H6 (C312-C125); and 4) H22 with H10 (C392-C200), H21 (C392-C383, C392-C384), H26 (C392-C471; C392-C484), and H28 (C392-0510). The number of cysteines and their positions within the core as well as the length of BMSO are likely contributing factors that enable the detection of cross-links within these regions. A large portion of identified cysteine cross-links within these clusters correspond to residues with $C\alpha$-$C\alpha$ distances over 30 Å (11/17, 64.7%), which are more likely to be missed with cross-linkers containing shorter spacer arms (i.e. DSSO and DHSO). While BMSO appears to obtain more contacts in the center regions of BSA, DSSO and DHSO cross-linking have provided broader coverage of various regions, including both termini. This observation may also be correlated to the relative distribution of cysteines within the primary sequence and their roles in stabilizing the structure of BSA. While BSA is a single protein, the data herein suggests that the three distinct cross-linking chemistries can indeed facilitate a more comprehensive mapping of intramolecular BSA contacts. Therefore, such a combinatory XL-MS approach would be even more beneficial for detailed PPI profiling when applied to more complex samples such as large multiprotein assemblies and cell lysates.

Additional Embodiments

In some embodiments, an MS-cleavable cross-linker for mapping intra-protein interactions is provided.

In some embodiments, an MS-cleavable cross-linker for mapping intra-protein interactions in a protein, inter-protein interactions in a protein complex or a combination thereof is provided.

In some embodiments, an MS-cleavable cross-linker for mapping intra-protein interactions in a protein, inter-protein interactions in a protein complex or a combination thereof, the MS-cleavable cross-linker comprises at least one maleimide functional group.

In some embodiments, an MS-cleavable cross-linker for mapping intra-protein interactions in a protein, inter-protein interactions in a protein complex or a combination thereof, the MS-cleavable cross-linker comprises at least one maleimide functional group, and at least one spacer arm with at least one central sulfoxide group.

In some embodiments, an MS-cleavable cross-linker for mapping intra-protein interactions in a protein, inter-protein interactions in a protein complex or a combination thereof, the MS-cleavable cross-linker comprises at least one maleimide functional group, and at least one spacer arm with at least one central sulfoxide group, wherein the at least one central sulfoxide group is linked to the at least one maleimide functional group.

In some embodiments, an MS-cleavable cross-linker for mapping intra-protein interactions in a protein, inter-protein interactions in a protein complex or a combination thereof, the MS-cleavable cross-linker comprises at least one maleimide functional group, and at least one spacer arm with at least one central sulfoxide group, wherein the at least one central sulfoxide group is linked to the at least one maleimide functional group, and at least one collision-induced dissociation (CID) cleavable bond on the spacer arm.

In some embodiments, an MS-cleavable cross-linker for mapping intra-protein interactions in a protein, inter-protein interactions in a protein complex or a combination thereof, the MS-cleavable cross-linker comprises at least one maleimide functional group, and at least one spacer arm with at least one central sulfoxide group, wherein the at least one central sulfoxide group is linked to the at least one maleimide functional group, and at least one collision-induced dissociation (CID) cleavable bond on the spacer arm, and wherein the at least one CID cleavable bond is a C—S bond adjacent to the at least one central sulfoxide.

In some embodiments, an MS-cleavable cross-linker for mapping intra-protein interactions in a protein, inter-protein interactions in a protein complex or a combination thereof, the MS-cleavable cross-linker comprises two maleimide functional groups.

In some embodiments, an MS-cleavable cross-linker for mapping intra-protein interactions in a protein, inter-protein interactions in a protein complex or a combination thereof, the MS-cleavable cross-linker comprises two maleimide functional groups, and a spacer arm with at least one central sulfoxide group.

In some embodiments, an MS-cleavable cross-linker for mapping intra-protein interactions in a protein, inter-protein interactions in a protein complex or a combination thereof, the MS-cleavable cross-linker comprises two maleimide functional groups, and a spacer arm with at least one central sulfoxide group, wherein the at least one central sulfoxide group is linked to each of the two maleimide functional groups.

In some embodiments, an MS-cleavable cross-linker for mapping intra-protein interactions in a protein, inter-protein interactions in a protein complex or a combination thereof, the MS-cleavable cross-linker comprises two maleimide functional groups, and a spacer arm with at least one central sulfoxide group, wherein the at least one central sulfoxide group is linked to each of the two maleimide functional groups, and two symmetric collision-induced dissociation (CID) cleavable bonds on the spacer arm.

In some embodiments, an MS-cleavable cross-linker for mapping intra-protein interactions in a protein, inter-protein interactions in a protein complex or a combination thereof, the MS-cleavable cross-linker comprises two maleimide functional groups, and a spacer arm with at least one central sulfoxide group, wherein the at least one central sulfoxide group is linked to each of the two maleimide functional groups, and two symmetric collision-induced dissociation (CID) cleavable bonds on the spacer arm, and wherein each of the two CID cleavable bond is a C—S bond adjacent to the at least one central sulfoxide.

In some embodiments of the MS-cleavable cross-linker, each maleimide functional group is designed to react with a cysteine in a peptide or a protein.

In some embodiments of the MS-cleavable cross-linker, the MS-cleavable cross-linker is homobifunctional.

In some embodiments of the MS-cleavable cross-linker, the two maleimide functional groups are separated by a 24.2 Å long spacer arm comprising the two symmetric CID cleavable C—S bonds flanking the at least one central sulfoxide group.

In some embodiments of the MS-cleavable cross-linker, the MS-cleavable cross-linker is BMSO, comprising the structure:

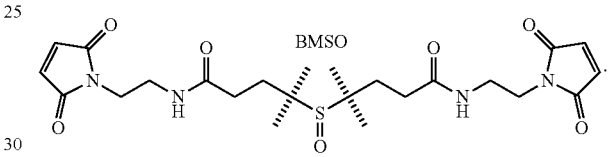

In some embodiments of the MS-cleavable cross-linker, the MS-cleavable cross-linker is BMSO, consisting of the structure:

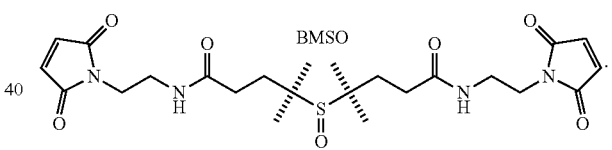

In some embodiments, a method for synthesis of an MS-cleavable cross-linker for mapping intra-protein interactions in a protein, inter-protein interactions in a protein complex or a combination thereof, the method comprises the steps of:

(i) providing a solution comprising DSSO and a trifluoroacetate salt of 1-(2-aminoethyl) maleimide;

(ii) adding $NaHCO_3$ to the solution of step (i) to obtain a mixture;

(iii) concentrating the mixture of step (ii) in vacuo to obtain a crude material; and (iv) purifying the MS-cleavable cross-linker from the crude material of step (iii) using column chromatography.

In some embodiments of the method for synthesis of an MS-cleavable cross-linker, step (ii) is performed at room temperature.

In some embodiments of the method for synthesis of an MS-cleavable cross-linker, step (ii) is performed for about 12 h.

In some embodiments of a method for mapping, the MS-cleavable cross-linking agent is BMSO, comprising the structure:

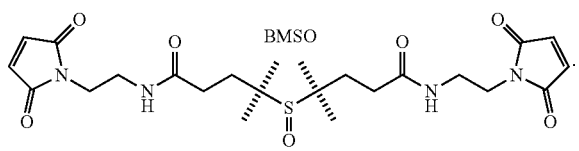

In some embodiments, other methods of synthesis of the MS-cleavable cross-linker BMSO that are within the ordinary skill in the art are also contemplated and within the scope of this disclosure.

In some embodiments, a method for mapping intra-protein interactions in a protein, inter-protein interactions in a protein complex or a combination thereof, the method comprises providing the MS-cleavable cross-linker BMSO.

In some embodiments, a method for mapping intra-protein interactions in a protein, inter-protein interactions in a protein complex or a combination thereof, the method comprises providing the MS-cleavable cross-linker BMSO, and forming a cross-linked protein or protein complex by cross-linking the protein or the protein complex with the MS-cleavable cross-linker.

In some embodiments, a method for mapping intra-protein interactions in a protein, inter-protein interactions in a protein complex or a combination thereof, the method comprises providing the MS-cleavable cross-linker BMSO, and forming a cross-linked protein or protein complex by cross-linking the protein or the protein complex with the MS-cleavable cross-linker, and forming one or more peptide fragments that are chemically bound to the MS-cleavable cross-linker by digesting the cross-linked protein or protein complex with an enzyme.

In some embodiments, a method for mapping intra-protein interactions in a protein, inter-protein interactions in a protein complex or a combination thereof, the method comprises providing the MS-cleavable cross-linker BMSO, and forming a cross-linked protein or protein complex by cross-linking the protein or the protein complex with the MS-cleavable cross-linker, and forming one or more peptide fragments that are chemically bound to the MS-cleavable cross-linker by digesting the cross-linked protein or protein complex with an enzyme, and identifying the one or more peptide fragments using tandem mass spectrometry ($MS^n$).

In some embodiments, a method for mapping intra-protein interactions in a protein, inter-protein interactions in a protein complex or a combination thereof, the method comprises providing the MS-cleavable cross-linker BMSO, forming a cross-linked protein or protein complex by cross-linking the protein or the protein complex with the MS-cleavable cross-linker, forming one or more peptide fragments that are chemically bound to the MS-cleavable cross-linker by digesting the cross-linked protein or protein complex with an enzyme, and identifying the one or more peptide fragments using tandem mass spectrometry ($MS^n$), thereby mapping intra-protein interactions in a protein and inter-protein interactions in a protein complex.

In some embodiments of method for mapping intra-protein interactions in a protein, inter-protein interactions in a protein complex or a combination thereof, the cross-linking the protein or the protein complex with the MS-cleavable cross-linker occurs by conjugation of cysteines.

In some embodiments of method for mapping intra-protein interactions in a protein, inter-protein interactions in a protein complex or a combination thereof, the conjugation of cysteines occurs via maleimide chemistry.

In some embodiments of method for mapping intra-protein interactions in a protein, inter-protein interactions in a protein complex or a combination thereof, wherein the maleimide chemistry yields two different forms of cross-linked cysteines.

In some embodiments of method for mapping intra-protein interactions in a protein, inter-protein interactions in a protein complex or a combination thereof, the two different forms of cross-linked cysteines comprise a closed-ring structure and a hydrolyzed open-ring structure.

In some embodiments of a method for mapping, the MS-cleavable cross-linking agent is BMSO, comprising the structure:

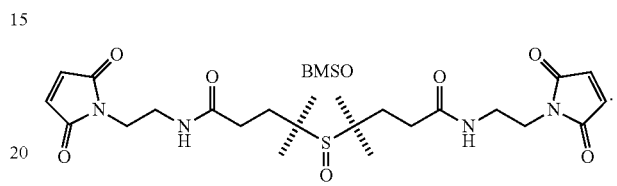

In some embodiments of a method for mapping, the MS-cleavable cross-linking agent is BMSO, consisting of the structure:

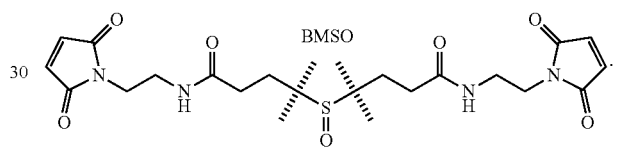

In some embodiments, a method for cross-linking mass spectrometry (XL-MS) for identifying one or more cross-linked peptides, the method comprises performing cross-linking with the MS-cleavable cross-linker BMSO.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, and digesting the one or more cross-linked proteins with trypsin to obtain one or more cross-linked peptides.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, digesting the one or more cross-linked proteins with trypsin to obtain one or more cross-linked peptides, and performing a liquid chromatography-tandem mass spectrometry ($LC-MS^n$) analysis on the one or more cross-linked peptides.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, digesting the one or more cross-linked proteins with trypsin to obtain one or more cross-linked peptides, and performing a liquid chromatography-tandem mass spectrometry ($LC-MS^n$) analysis on the one or more cross-linked peptides, wherein the LC-MS″ analysis comprises detecting the one or more cross-linked peptides by MS¹ analysis.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, digesting the one or more cross-linked proteins with trypsin to obtain one or more cross-linked peptides, performing a liquid chromatography-tandem mass spectrometry (LC-MS″) analysis on the one or more cross-linked peptides, wherein the LC-MS″ analysis comprises detecting the one or more cross-linked peptides by MS¹ analysis, selecting the one or more cross-linked peptides detected by MS¹ for MS² analysis.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, digesting the one or more cross-linked proteins with trypsin to obtain one or more cross-linked peptides, performing a liquid chromatography-tandem mass spectrometry (LC-MS″) analysis on the one or more cross-linked peptides, wherein the LC-MS″ analysis comprises detecting the one or more cross-linked peptides by MS¹ analysis, selecting the one or more cross-linked peptides detected by MS¹ for MS² analysis, and selectively fragmenting the at least one CID cleavable bond and separating the one or more cross-linked peptides during MS² analysis.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, digesting the one or more cross-linked proteins with trypsin to obtain one or more cross-linked peptides, performing a liquid chromatography-tandem mass spectrometry (LC-MS″) analysis on the one or more cross-linked peptides, wherein the LC-MS″ analysis comprises detecting the one or more cross-linked peptides by MS¹ analysis, selecting the one or more cross-linked peptides detected by MS¹ for MS² analysis, selectively fragmenting the at least one CID cleavable bond and separating the one or more cross-linked peptides during MS² analysis, and sequencing the one or more cross-linked peptides separated during MS² analysis by MS³ analysis.

In some embodiments, a method for cross-linking mass spectrometry (XL-MS) for identifying one or more cross-linked peptides, the method comprises performing cross-linking with the MS-cleavable cross-linker BMSO to obtain one or more cross-linked proteins, digesting the one or more cross-linked proteins with trypsin to obtain one or more cross-linked peptides, performing a liquid chromatography-tandem mass spectrometry (LC-MS″) analysis on the one or more cross-linked peptides, wherein the LC-MS″ analysis comprises detecting the one or more cross-linked peptides by MS¹ analysis, selecting the one or more cross-linked peptides detected by MS¹ for MS² analysis, selectively fragmenting the at least one CID cleavable bond and separating the one or more cross-linked peptides during MS² analysis, sequencing the one or more cross-linked peptides separated during MS² analysis by MS³ analysis, and integrating data obtained during MS¹, MS² and MS³ analyses.

In some embodiments, a method for cross-linking mass spectrometry (XL-MS) for identifying one or more cross-linked peptides is provided, the method comprises performing cross-linking with the MS-cleavable cross-linker BMSO to obtain one or more cross-linked proteins, digesting the one or more cross-linked proteins with trypsin to obtain one or more cross-linked peptides, performing a liquid chromatography-tandem mass spectrometry (LC-MS″) analysis on the one or more cross-linked peptides, wherein the LC-MS″ analysis comprises detecting the one or more cross-linked peptides by MS¹ analysis, selecting the one or more cross-linked peptides detected by MS¹ for MS² analysis, selectively fragmenting the at least one CID cleavable bond and separating the one or more cross-linked peptides during MS² analysis, sequencing the one or more cross-linked peptides separated during MS² analysis by MS³ analysis, and integrating data obtained during MS¹, MS² and MS³ analyses to identify the one or more cross-linked peptides.

In some embodiments of the method for cross-linking mass spectrometry (XL-MS) for identifying one or more cross-linked peptides, the cross-linking with the MS-cleavable cross-linker occurs by conjugation of cysteines.

In some embodiments of the method for cross-linking mass spectrometry (XL-MS) for identifying one or more cross-linked peptides, the conjugation of cysteines occurs via maleimide chemistry.

In some embodiments of the method for cross-linking mass spectrometry (XL-MS) for identifying one or more cross-linked peptides, the maleimide chemistry yields two different forms of cross-linked cysteines, wherein the two different forms of cross-linked cysteines comprise a closed-ring structure and a hydrolyzed open-ring structure.

In some embodiments of a method for XL-MS, the MS-cleavable cross-linking agent is BMSO, comprising the structure:

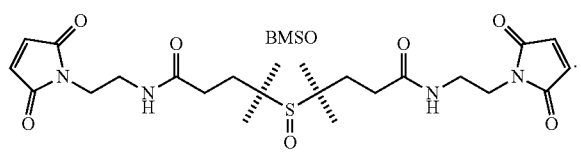

In some embodiments of a method for XL-MS, the MS-cleavable cross-linking agent is BMSO, consisting essentially of, or consisting of the structure:

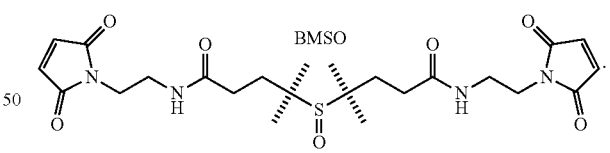

EXAMPLES

The following examples are non-limiting and other variants within the scope of the art are also contemplated and within the scope of this disclosure.

Example 1—Materials and Reagents

General chemicals were purchased from Fisher Scientific or VWR International. Bovine serum albumin (≥96% purity) was purchased from Sigma-Aldrich. Ac-LR9 peptide (Ac-LADVCAHER (SEQ ID NO: 96), 98% purity) was custom ordered from Biomatik (Wilmington, Del.).

Example 2—Synthesis and Characterization of BMSO

BMSO was synthesized as described in FIG. 1D. Disuccinimidyl sulfoxide (DSSO) and the trifluoroacetate salt of 1-(2-aminoethyl) maleimide were synthesized as previously published[17,32] To a cooled (0° C.) solution of disuccinimidyl sulfoxide (468 mg, 1.21 mmol) and the maleimide salt (674 mg, 2.65 mmol) in $H_2O$ (12 mL) was added 1M aq. $NaHCO_3$ (3.6 mL). After stirring for 12 h while allowing the reaction vessel to reach room temperature, the mixture was concentrated in vacuo. The crude material was then purified with column chromatography (30% MeOH in $CH_2Cl_2$) to afford BMSO as a colorless solid (251 mg, 47%): mp 90-98° C.; $^1$H-NMR (600 MHz, $CDCl_3$) δ 6.76 (t, J=5.5 Hz), 6.73 (s, 4H), 3.66-3.70 (app t, J=5.7 Hz, 4H), 3.39-3.49 (m, 4H), 3.05-3.10 (m, 2H), 2.87-2.91 (m, 2H), 2.61 (app t, J=7.1 Hz, 4H); $^{13}$C-NMR (150 MHz, $CDCl_3$) δ170.92, 170.35, 134.2, 46.9, 38.7, 37.5, 28.8; IR: 3307, 3086, 1693, 1645, 1543, 1173, 1024 $cm^{-1}$; HRMS (ESI) m/z $[M+Na]^+$ Calcd for $C_{18}H_{22}N_4O_7SNa$ 461.1107; Found 461.1119.

Example 3—BMSO Cross-linking of Synthetic Peptides

Synthetic peptide Ac-LR9 was dissolved in DMSO to 1 mM and cross-linked with BMSO in a 1:1 molar ratio of peptide to cross-linker. The resulting samples were diluted to 10 pmol/μL in 3% ACN/2% formic acid prior to $MS^n$ analysis.

Example 4—Preparation of BMSO Cross-Linked Bovine Serum Albumin

50 μL of 50 μM BSA in PBS buffer (pH 7.4) was reacted with BMSO in molar ratios of 1:50 and 1:100. The cross-linking reaction was initiated by adding BMSO to protein solutions, reacted for 2 h at 37° C. Cross-linked protein samples were subjected to SDS-PAGE followed by in-gel digestion prior to $MS^n$ analysis[17] (Examples 7-8).

Example 5—Liquid Chromatography-Multistage Tandem Mass Spectrometry (LC-$MS^n$) Analysis BMSO cross-linked Ac-LR9 was analyzed by LC-$MS^n$ utilizing an Easy-nLC 1000 (Thermo Fisher, San Jose, Calif.) coupled on-line to an LTQ-Orbitrap XL mass spectrometer (Thermo Fisher, San Jose, Calif.)[17]. BMSO cross-linked peptides of BSA were analyzed by LC-$MS^n$ utilizing a Dionex UltiMate™ 3000 (Thermo Fisher, San Jose, Calif.) coupled on-line to an Orbitrap Fusion™ Lumos™ mass spectrometer (Thermo Fisher, San Jose, Calif.). LC-$MS^n$ data extraction and database searching for the identification of BMSO cross-linked peptides were performed similarly as previously described[17,30] (and Examples 6-8).

Example 6—Digestion of BMSO Cross-Linked Proteins

Cross-linked BSA was separated by SDS-PAGE and visualized by Coomassie blue staining. Selected cross-linked gel bands were excised and then digested with trypsin at 37° C. overnight. Peptide digests were extracted and concentrated and reconstituted in 25 mM ammonium bicarbonate and incubated at 37° C. overnight. The ammonium bicarbonate was then evaporated, and the peptides were reconstituted in 3% ACN/2% formic acid for $MS^n$ analysis.

Example 7—Liquid Chromatography-Multistage Tandem Mass Spectrometry (LC $MS^n$) Analysis LC $MS^n$ analysis was performed using a Thermo Scientific™ Dionex UltiMate 3000 system coupled with an Orbitrap Fusion Lumos™ MS. A 15 cm×75 μm Acclaim™ PepMap™ C18 Column was used to separate peptides over acetonitrile gradients of 1% to 25% at a flow rate of 300 nL/min. Two different types of acquisition methods were utilized to maximize the identification of BMSO cross-linked peptides: 1) top 4 data-dependent $MS^3$ and 2) targeted $MS^3$ acquisition optimized for capturing DSSO cross-linked peptides by utilizing the mass difference between alkene- and thiol-modified ion pairs (31.9721 Da)[35].

Example 8—Data Analysis and Identification of BMSO Cross-Linked Peptides $MS^n$ data extraction and analysis were performed in the same way as previously described[36]. $MS^3$ data was subjected to a developmental version of Protein Prospector (v.5.19.1) for database searching, using Batch-Tag against SwissProt.2016.5.9.random.concat database limited to *Bos taurus* taxonomy (5998 entries) with mass tolerances for parent ions and fragment ions set as ±20 ppm and 0.6 Da, respectively. Trypsin was set as the enzyme with three maximum missed cleavages allowed. A maximum of four variable modifications were also allowed, including protein N-terminal acetylation, cysteine carbamidomethylation, methionine oxidation, and N-terminal conversion of glutamine to pyroglutamic acid. In addition, five defined modifications representing cross-linker fragment moieties on cysteine residues were selected: alkene closed-ring (Ac, C9H10N2O3, +194.0691 Da), alkene open-ring (Ao, C9H12N2O4, +212.0797 Da), sulfenic acid closed-ring/unsaturated thiol open-ring (Sc/To, C9H12N2O4S1, +244.0518 Da), sulfenic acid open-ring (So, C9H14N2O5S1, +262.0623 Da), and unsaturated thiol closed-ring (Tc, C9H10N2O3S1, +226.0412 Da) modifications. Initial acceptance criteria for peptide identification at the $MS^3$ level required a reported expectation value≤0.15, which yielded a false discovery rate of 0.5%. The in-house program XL-Discoverer, a revised version of previously developed Xl-discoverer, was used to validate and summarize cross-linked peptides based on $MS^n$ data and database searching[35,37]. Integration of $MS^1$, $MS^2$, and $MS^3$ spectral data identified 41 unique BMSO inter-linked BSA peptides (TABLE 1). Following integration of $MS^n$ data, no cross-links were identified involving decoy proteins.

Abbreviations

XL-MS: cross-linking mass spectrometry
BMSO: Bismaleimide Sulfoxide, a.k.a. 3,3'-sulfinylbis (N-(2-(2,5-dioxo-2,5-dihydro-1H-pyrrol-1-yl)ethyl)propanamide
DSSO: Disuccinimidyl Sulfoxide
DHSO: Dihydrazide Sulfoxide
DMDSSO: Dimethyl Disuccinimidyl Sulfoxide
Azide/Alkyne-A-DSBSO: Azide/Alkene-tagged, Acid-cleavable Disuccinimidyl Bis-sulfoxide
MS: mass spectrometry
$MS^n$: multi-stage tandem mass spectrometry
CID: collisional induced dissociation LC-MS$^n$: liquid chromatography multistage tandem mass spectrometry SITE: succinimidyl thioether SATE: succinamic acid thioether

REFERENCES

All references cited in this disclosure are incorporated herein by reference in their entireties.
(1) Wells, J. A.; McClendon, C. L. *Nature* 2007, 450, 1001-1009.
(2) Arkin, M. R.; Tang, Y.; Wells, J. A. *Chem Biol* 2014, 21, 1102-1114.
(3) Yu, C.; Huang, L. *Anal Chem* 2018, 90, 144-165.
(4) Fernandez-Martinez, J.; Kim, S. J.; Shi, Y.; Upla, P.; Pellarin, R.; Gagnon, M.; Chemmama, I. E.; Wang, J.; Nudelman, I.; Zhang, W.; Williams, R.; Rice, W. J.; Stokes, D. L.; Zenklusen, D.; Chait, B. T.; Sali, A.; Rout, M. P. *Cell* 2016, 167, 1215-1228 e1225.
(5) Leitner, A.; Faini, M.; Stengel, F.; Aebersold, R. *Trends Biochem Sci* 2016, 41, 20-32.
(6) Sinz, A. *Anal Bioanal Chem* 2010, January 15. [Epub ahead of print].
(7) Bruce, J. E. *Proteomics* 2012, 12, 1565-1575.
(8) Leitner, A.; Joachimiak, L. A.; Unverdorben, P.; Walzthoeni, T.; Frydman, J.; Forster, F.; Aebersold, R. *Proc Natl Acad Sci USA* 2014, 111, 9455-9460.
(9) Gutierrez, C. B.; Yu, C.; Novitsky, E. J.; Huszagh, A. S.; Rychnovsky, S. D.; Huang, L. *Anal Chem* 2016.
(10) Gunnoo, S. B.; Madder, A. *Chembiochem* 2016, 17, 529-553.
(11) Geula, S.; Naveed, H.; Liang, J.; Shoshan-Barmatz, V. *J Biol Chem* 2012, 287, 2179-2190.
(12) Knepp, A. M.; Periole, X.; Marrink, S. J.; Sakmar, T. P.; Huber, T. *Biochemistry* 2012, 51, 1819-1821.
(13) Tang, X.; Munske, G. R.; Siems, W. F.; Bruce, J. E. *Anal Chem* 2005, 77, 311-318.
(14) Lu, Y.; Tanasova, M.; Borhan, B.; Reid, G. E. *Anal Chem* 2008, 80, 9279-9287.
(15) Muller, M. Q.; Dreiocker, F.; Ihling, C. H.; Schafer, M.; Sinz, A. *Anal Chem* 2010, 82, 6958-6968.
(16) Petrotchenko, E. V.; Serpa, J. J.; Borchers, C. H. *Mol Cell Proteomics* 2011, 10, M110.001420.
(17) Kao, A.; Chiu, C. L.; Vellucci, D.; Yang, Y.; Patel, V. R.; Guan, S.; Randall, A.; Baldi, P.; Rychnovsky, S. D.; Huang, L. *Mol Cell Proteomics* 2011, 10, M110.002212.
(18) Luo, J.; Fishburn, J.; Hahn, S.; Ranish, *J. Mol Cell Proteomics* 2012,11, M111 008318.
(19) Yu, C.; Kandur, W.; Kao, A.; Rychnovsky, S.; Huang, L. *Anal Chem* 2014, 86, 2099-2106.
(20) Kaake, R. M.; Wang, X.; Burke, A.; Yu, C.; Kandur, W.; Yang, Y.; Novtisky, E. J.; Second, T.; Duan, J.; Kao, A.; Guan, S.; Vellucci, D.; Rychnovsky, S. D.; Huang, L. *Mol Cell Proteomics* 2014, 13, 3533-3543.
(21) Chakrabarty, J. K.; Naik, A. G.; Fessler, M. B.; Munske, G. R.; Chowdhury, S. M. *Anal Chem* 2016, 88, 10215-10222.
(22) Sinz, A. *Anal Bioanal Chem* 2017, 409, 33-44.
(23) Burke, A. M.; Kandur, W.; Novitsky, E. J.; Kaake, R. M.; Yu, C.; Kao, A.; Vellucci, D.; Huang, L.; Rychnovsky, S. D. *Org Biomol Chem* 2015, 13, 5030-5037.
(24) Kao, A.; Randall, A.; Yang, Y.; Patel, V. R.; Kandur, W.; Guan, S.; Rychnovsky, S. D.; Baldi, P.; Huang, L. *Mol Cell Proteomics* 2012, 11, 1566-1577.
(25) Liu, J.; Yu, C.; Hu, X.; Kim, J. K.; Bierma, J. C.; Jun, H. I.; Rychnovsky, S. D.; Huang, L.; Qiao, F. *Cell Rep* 2015,12, 2169-2180.
(26) Scott, H.; Kim, J. K.; Yu, C.; Huang, L.; Qiao, F.; Taylor, D. J. *J Mol Biol* 2017, 429, 2863-2872.
(27) Wang, X.; Cimermancic, P.; Yu, C.; Schweitzer, A.; Chopra, N.; Engel, J. L.; Greenberg, C.; Huszagh, A. S.; Beck, F.; Sakata, E.; Yang, Y.; Novitsky, E. J.; Leitner, A.; Nanni, P.; Kahraman, A.; Guo, X.; Dixon, J. E.; Rychnovsky, S. D.; Aebersold, R.; Baumeister, W., et al. *Mol Cell Proteomics* 2017, 16, 840-854.
(28) Liu, F.; Rijkers, D. T.; Post, H.; Heck, A. *J. Nat Methods* 2015, 12, 1179-1184.
(29) Liu, F.; Lossl, P.; Scheltema, R.; Viner, R.; Heck, A. J. R. *Nat Commun* 2017, 8, 15473.
(30) Wang, X.; Chemmama, I. E.; Yu, C.; Huszagh, A.; Xu, Y.; Viner, R.; Block, S. A.; Cimermancic, P.; Rychnovsky, S. D.; Ye, Y.; Sali, A.; Huang, L. *J Biol Chem* 2017, 292, 16310-16320.
(31) Yu, C.; Mao, H.; Novitsky, E. J.; Tang, X.; Rychnovsky, S. D.; Zheng, N.; Huang, L. *Nat Commun* 2015, 6, 10053.
(32) Tang, F.; Yang, Y.; Tang, Y.; Tang, S.; Yang, L.; Sun, B.; Jiang, B.; Dong, J.; Liu, H.; Huang, M.; Geng, M. Y.; Huang, W. *Org Biomol Chem* 2016, 14, 9501-9518.
(33) Schilling, B.; Row, R. H.; Gibson, B. W.; Guo, X.; Young, M. M. *J Am Soc Mass Spectrom.* 2003, 14, 834-850.
(34) Fontaine, S. D.; Reid, R.; Robinson, L.; Ashley, G. W.; Santi, D. V. *Bioconjug Chem* 2015, 26, 145-152.
(35) Yu, C.; Huszagh, A.; Viner, R.; Novitsky, E. J.; Rychnovsky, S. D.; Huang, L. *Anal Chem* 2016, 88, 10301-10308.
(36) Kao, A.; Chiu, C. L.; Vellucci, D.; Yang, Y.; Patel, V. R.; Guan, S.; Randall, A.; Baldi, P.; Rychnovsky, S. D.; Huang, L. *Mol Cell Proteomics* 2011, 10, M110.002212.
(37) Wang, X.; Cimermancic, P.; Yu, C.; Schweitzer, A.; Chopra, N.; Engel, J. L.; Greenberg, C.; Huszagh, A. S.; Beck, F.; Sakata, E.; Yang, Y.; Novitsky, E. J.; Leitner, A.; Nanni, P.; Kahraman, A.; Guo, X.; Dixon, J. E.; Rychnovsky, S. D.; Aebersold, R.; Baumeister, W., et al. *Mol Cell Proteomics* 2017, 16, 840-854.

Structural Dynamics of the Human COP9 Signalosome Revealed by Cross-Linking Mass Spectrometry and Integrative Modeling In some embodiments, disclosed herein is application of BMSO in elucidating structures of protein complexes. In some embodiments, BMSO is employed to elucidate structural dynamics of COP9 signalosome complex. In some embodiments, DSSO, DHSO and BMSO are employed to elucidate structural dynamics of COP9 signalosome complex.

Structural plasticity is a critical property of many protein complexes that has been challenging to study using conventional structural biology tools. Cross-linking mass spectrometry (XL-MS) has become an emergent technology for elucidating architectures of large protein complexes. While effective, current XL-MS methods mostly rely on lysine reactive cross-linking chemistry and have limited capacity in fully defining dynamic structures of protein complexes. In some embodiments, an integrated structural approach is disclosed based on three MS-cleavable cross-linkers with distinct chemistries. In some embodiments, this approach enabled to obtain highly reliable and comprehensive cross-link data that significantly facilitate integrative structural modeling of dynamic protein complexes. In addition, in some embodiments, this approach was successfully applied to the COP9 signalosome to determine its structural dynamics associated with its function.

The COP9 signalosome (CSN) is an evolutionarily conserved 8-subunit (CSN1-8) protein complex that controls protein ubiquitination by deneddylating Cullin-RING E3 ligases (CRLs). The activation and function of CSN hinges on its structural dynamics, which has been challenging to decipher by conventional tools. Here, a multi-chemistry cross-linking mass spectrometry approach enabled by three MS-cleavable cross-linkers was developed to generate highly reliable cross-link data. This approach was applied with integrative structure modeling to determine the interaction and structural dynamics of CSN with a newly discovered 9$^{th}$ subunit, CSN9, in solution. The results determined the localization of CSN9 binding sites and revealed CSN9-dependent structural changes of CSN. Together with biochemical analysis, a structural model is proposed in which CSN9 binding triggers CSN to adopt a configuration that facilitates CSN-CRL interactions, thereby augmenting CSN deneddylase activity. The integrative structure analysis workflow can be generalized to define in-solution architectures of dynamic protein complexes that remain inaccessible to other approaches.

The COP9 signalosome (CSN) is an evolutionarily conserved and essential multi-subunit protein complex involved in diverse cellular and developmental processes in animals and plants (1-3). CSN functions as a deneddylase, specific for cleaving Nedd8 modification from cullin proteins, the key components of Cullin-RING ubiquitin E3 ligases (CRLs)(4-8). CRLs represent the largest evolutionarily conserved superfamily of multi-subunit E3s (5, 6) which embody ~30% of all human E3 proteins and coordinate degradation of ~20% of the proteins processed by the proteasome. The dynamic cycle of neddylation and deneddylation of cullins is a critical step in regulating the assembly and activity of CRLs (6, 9, 10). In addition to enzymatic regulation of CRLs, CSN can inactivate CRLs non-catalytically by direct binding, preventing their association with E2 enzymes and ubiquitination substrates (11-14). While abnormal CRL activity is frequently associated with various human diseases, multiple studies have also identified CSN as a positive regulator of oncogenes and negative regulator of tumor suppressors (15-19). Moreover, elevated expression of CSN subunits has been found in a number of human tumors, often with poor prognosis. Therefore, better understanding of CSN structure would provide new insights on their function and the regulation of CRLs associated with human pathology.

The canonical CSN complex (hereafter referred to as CSN) typically consists of eight subunits (CSN1-8) (1, 3), including six different PCI (Proteasome lid-CSN-Initiation factor 3) domain-containing subunits (CSN1-CSN4, CSN7 and CSN8) and two MPN (MPR1/PAD1 amino-terminal) domain-containing proteins (CSN5 and CSN6). Among them, CSN5 is the catalytic subunit directly responsible for CSN deneddylase activity (4). The CSN complex shares sequence similarities to the 19S proteasome lid subcomplex and the eukaryotic translation initiation complex eIF3, which also contain PCI and MPN domains (1, 3). The X-ray structure of recombinant human CSN has revealed that CSN5 and CSN6 MPN domains form a heterodimer, while the six remaining PCI subunits assemble into a horseshoe-shaped ring from which their arm-like α-helical domains project (22). The PCI subunits provide a scaffold, primarily through CSN2 and CSN4, which facilitates the recruitment of neddylated CRLs. Meanwhile, the two MPN subunits are slightly juxtaposed, exposing the active MPN catalytic core in CSN5 (12, 23-25). All eight subunits are united in a helical bundle formed by their C-terminal carboxyl α-helices, which are stacked between the CSN5-CSN6 dimer and PCI ring. Interestingly, substrate-free CSN exists in an inactive, auto-inhibited state (23). Structural and biochemical characterization of CSN-CRL complexes have revealed substrate-induced structural dynamics associated with CSN activation (12, 23-26). Binding of neddylated CRLs to CSN triggers substantial remodeling and extensive conformational changes of the complex, activating the isopeptidase activity of CSN5. Although the structural plasticity of CSN is important for CSN activation and function in regulating CRL activities in cells, it has not been well characterized due to limitations in existing technologies.

Recently, the 9$^{th}$ CSN subunit, CSN9 (a.k.a. CSNAP (CSN acidic protein)), has been discovered to complex with CSN1-8 stoichiometrically to form a 9-membered non-canonical CSN complex (a.k.a. CSN9-bound CSN, hereafter referred to as CSNn)(27). As canonical CSN subunits (CSN1-8) have a one-to-one correspondence to the subunits of the 19S proteasome lid subcomplex (3, 28), CSN9 is homologous to DSS1, the smallest component of the 19S lid. While CSN9 is not essential for the assembly and catalytic activity of CSN (27), a recent study has suggested that CSN9 reduces the affinity of CSN-CRL interactions, contributing to steric regulation of CRLs (14). The depletion of CSN9 appears to have a global impact on CRL-associated activities, leading to altered reproductive capacity, suppressed DNA damage response, decreased viability and delayed cell cycle progression (14). It has also been suggested that the C-terminus of CSN9 is important in its incorporation within the CSN complex, likely through interactions with CSN3, CSN5 and CSN6(27). However, due to its small size and highly disordered structure, it remains challenging to accurately determine interaction interfaces between CSN9 and CSN. As a result, no high-resolution structures are available for the CSN9-bound CSN complex. Thus, alternative strategies to dissect the architecture of the non-canonical CSN complex and determine how CSN9 interacts with CSN1-8 are needed to help us uncover structural details underlying the functional importance of CSN9 in cells.

In recent years, cross-linking mass spectrometry (XL-MS) has become a powerful strategy for probing protein-protein interactions (PPIs)(29-31). While effective, XL-MS possesses several inherent challenges including unambiguous identification of cross-linked peptides due to their complex fragmentation when conventional (i.e. non-cleavable) cross-linkers are used. To facilitate MS identification, a suite of sulfoxide-containing MS-cleavable cross-linkers was developed (e.g. disuccinimidyl sulfoxide (DSSO))(32-36). These MS-cleavable reagents contain symmetric MS-labile C—S bonds (adjacent to the sulfoxide group) that are selectively and preferentially fragmented prior to peptide backbone cleavage during collision induced dissociation (CID)(31-36). Such fragmentation has proven robust, thus enabling simplified and accurate identification of sulfoxide-containing cross-linked peptides by MS$^n$ analysis. Among them, DSSO is an amine-reactive sulfoxide-containing MS-cleavable cross-linker that has been successfully applied for in vitro studies of purified protein complexes (32, 37, 38) and cell lysates (39, 40). Although lysine-reactive reagents are most popular, they alone cannot provide a full PPI mapping as some interaction interfaces do not contain proximal lysines for cross-linking (31). Therefore, DHSO (dihydrazide sulfoxide) was developed for acidic residues (35) and BMSO (bismaleimide sulfoxide) for cysteine cross-linking (36), complementing the lysine-reactive DSSO and expanding PPI coverage on residue-specific protein inter-connectivity. In addition to PPI mapping, XL-MS data has been successfully used for integrative structure modeling of protein complexes as observed cross-links impose upper distance bounds on pairs of cross-linked residues (41-44). Coupling cross-link data with other biophysical data (43, 44) and/or utilizing cross-linkers with different reactive chemistries (43) can significantly increase the accuracy of the resulting structures by integrative modeling. In comparison to conventional structural tools, XL-MS approaches can uniquely characterize large, heterogeneous, and dynamic protein assemblies in solution (31).

In some embodiments, developed and employed herein is a multi-chemistry cross-linking mass spectrometry approach enabled by three MS-cleavable cross-linkers to obtain comprehensive PPI maps of the CSN (CSN9-free) and CSNn (CSN9-bound) complexes to significantly improve precision and accuracy of their models. Based on the cross-link data, X-ray structures and comparative models of CSN subunits, the complete integrative structures of CSN and CSNn at 16 Å and 22 Å precisions was computed, respectively. The integrative structures have maintained the core architecture of the known X-ray structure of CSN (PDB 4D10), but importantly revealed additional conformations and configurations of CSN in solution that were absent in the static structure. The integrative structure of CSNn has defined the CSN9 binding site in a cleft formed among CSN1, CSN3 and CSN8, resulting in local subunit reorientations that more likely contribute to CSN9-dependent increase of CSN deneddylase activity in vitro. Collectively, this work not only provides new molecular features for us to better determine the structure dynamics of the CSN complex, but also reveals the structural basis underlying the role of CSN9 in CSN-mediated activities. Moreover, the integrated structural approach presented here is effective and can be generalized to define in-solution structures of dynamic protein complexes that remain inaccessible to other approaches.

In some embodiments, a multi-chemistry XL-MS approach was developed based on three distinct MS-cleavable cross-linkers (i.e. DSSO, DHSO and BMSO) to comprehensively map PPIs and facilitate integrative structure modeling of CSN complexes. The large number of cross-links identified in this work is highly complementary, allowing expanding PPI coverage and cross-validating results. This approach enables us to obtain the most extensive intra-subunit and inter-subunit interaction maps of CSN (CSN9-free) and CSNn (CSN9-bound) complexes. It is noted that CSN9-containing interactions were only identified through DHSO cross-linking, not by DSSO and BMSO, signifying the need of multi-chemistry XL-MS to fully characterize PPIs of CSN complexes. Importantly, the combinatory XL-MS data enabled structural characterization of the CSN complexes with complete sequences and significantly enhanced the precision of integrative structure modeling, resulting in the precisions of 16 Å and 22 Å for CSN and CSNn, respectively. These are considerably higher than the precision of models from single and dual cross-linking chemistries (24 Å-37 Å). While lysine-to-lysine and acidic-to-acidic residue cross-links have been successfully applied for structural mapping and/or modeling (31, 35, 38, 46 2014, 54, 55), it is demonstrated here that cysteine-to-cysteine cross-links are as effective for structure determination of protein complexes. This is illustrated by the fact that a single integrative structure (i.e., a single cluster of models) satisfies most of the BMSO cross-links, similarly to DSSO and DHSO cross-links (FIGS. 13A-13C and FIGS. 24A-24H). In addition, highly overlapping model ensembles based on 7 different combinations of the three types of cross-link data, i.e. DSSO, DHSO and BMSO cross-links (FIG. 13c and FIGS. 25A-25F) was obtained, confirming the validity and coherence of the cross-link data. Therefore, coupling combinatory XL-MS based on multiple cross-linking chemistries with integrative structure modeling facilitates the determination of the interaction and structure dynamics of CSN complexes. The same strategy can be directly adopted for characterizing architectures of other dynamic protein complexes in solution.

In some embodiments, during XL-MS analyses, it was found that although the majority of intra-subunit cross-links of CSN from all three linkers were satisfied by the known X-ray structure (PDB 4D10), most of inter-subunit cross-links were classified as violating. This implies that CSN has much more flexible inter-subunit than intra-subunit interactions. Since X-ray crystallography only reveals static structures with single conformation, distance violation of cross-links suggests the presence of multiple conformations and configurations of CSN in solution. Similar results have been obtained for the CSNn complex, further confirming the interaction and structural plasticity of CSN complexes. While CSN is known to carry structural flexibility to allow its interaction with a diverse array of CRLs to regulate their activities (12, 23-25), the XL-MS results provide additional evidence to support CSN structural heterogeneity in solution. Because of this, the cross-link dataset generated here is comprised of a wide range of possible conformations of CSN complexes. Therefore, to minimize complexity, only highly reproducible cross-link data was used to derive structural ensembles that represent major conformations of CSN complexes in solution. The integrative structures of CSN complexes have satisfied 98% of all of the cross-links obtained in this work, considerably better than the X-ray structure. This result further indicates that CSN contains additional accessible states other than the one determined by X-ray crystallography. In contrast to the observed conformational and configurational differences in inter-subunit interactions, the core structure of CSN is preserved. Indeed, in some embodiments, it was found that the CSN model maintains overall configuration with the presence of the PCI ring and the positioning of CSN5-CSN6 dimer, apart from a rearrangement of CSN2 with respect to CSN1 and CSN3 and CSN4 positioning in the complex. The core structure of CSN has also been detected in the CSNn model, which was derived from a completely different set of cross-link data used for CSN modeling. As these core modules are crucial for the CSN assembly, structure and function (12, 23-25, 45, 51), their determination by integrative modeling based primarily on cross-links further demonstrates the effectiveness of the approach and the validity of the determined integrative structures.

In some embodiments, it was determined that CSN9 predominantly interacts with CSN3 and CSN1, and is localized in a cavity formed by CSN1-3-8 in the CSNn structure. Although CSN3-CSN9 interaction has previously been shown biochemically (27), the results have identified interaction contacts between the two interactors. In some embodiments, CSN1 was identified as an additional CSN9 interactor and determined CSN9 binding sites within the CSN complex. While it has been suggested that CSN9 may bind to CSN5 and CSN6(27), no cross-links between CSN9 and CSN5 or CSN6 were identified and the integrative structure of CSNn shows that both subunits are much farther away from CSN9 than CSN1 and CSN3. Interestingly, CSN1, CSN3 and CSN8 form a connected submodule in the integrative and X-ray structures of CSN (23), and the assembled CSN1-3-8 subcomplex can be isolated in mammalian cells (56). It is known that each CSN subunit has a corresponding homolog in the 9-subunit 19S lid complex (27, 59). Recently, the proteasome subunit DSS1/Rpn15, the homolog of CSN9, has been determined to interact with Rpn3 (homolog of CSN3) and Rpn7 (homolog of CSN1), which forms a subcomplex prior to the 19S lid assembly (60), corroborating well with the close interactions of CSN9 with CSN3 and CSN1. These results further indicate interaction similarities between the CSN and the 19S lid complexes.

In some embodiments, apart from similarities in organizational architectures in the CSN integrative and X-ray structures, structural differences were observed between the integrative structures of CSN and CSNn that may contribute to CSN dynamics. One notable difference is the CSN2-CSN3 interaction and its relative location to CSN1 subunit. Specifically, in the CSN integrative structure, the CSN2 N-terminus wraps around CSN1 towards CSN3 and away from CSN4, whereby CSN2 is not readily available to interact with Cullin and Rbx1. This is of importance because CSN2 plays a major role along with CSN4 in stabilizing the CSN-CRL interaction when CSN binds to CRLs (12, 23-25). CSN1 has been shown to bind to the CRL4A adaptor DDB1, which is important in stabilizing Cul4A and required for efficient deneddylation (24). However, CSN1 involvement appears to be specific for CRL4 and not CRL2 and CRL3 complexes (24, 26). While CSN3 has not been shown to directly contact CRL components, overexpression of CSN3 leads to increased amounts of CSN in cells and downregulation of CSN3 causes the destruction of CSN and cell death (61). Without being limited by any particular theory, it is speculated that the observed changes of interactions among CSN1, CSN2 and CSN3 may represent one of the major conformations of CSN that is needed to interact with specific subsets of CRLs in cells.

Without being limited by any particular theory, while the integrative structures of CSN and CSNn have both maintained the core structure of CSN, CSN9 binding causes a major shift in CSN2 and its interactions with neighboring subunits that have been confirmed by quantitative XL-MS analysis. Without being limited by any particular theory, given the critical importance of CSN2 in CSN-CRL interactions (12, 24, 25), it is speculated that CSN9-induced structural changes may be associated with the augmented CSN in vitro deneddylase activity observed in this work. Comparative analysis has revealed that the major differences between canonical CSN (CSN9-free) and CRL-bound CSN lie in the relative position of CSN2 and its interaction with CSN5 (FIGS. 26C and 26E), indicating that CSN2 has to undergo conformational changes to fulfill its role in facilitating CSN binding to CRLs (24, 25). Therefore, the observed structural alterations at CSN2 would be important for the formation of CSN-CRL complex, the prerequisite for subsequent deneddylation. The structure similarity between CSN9-bound CSN and CRL-bound CSN (FIG. 26D) strongly supports the biological relevance of CSN9-induced structural changes. Thus, these results prompt us to propose a structural model in which CSN9 causes the canonical CSN to adopt a configuration favorable for interacting with CRLs (FIG. 17). In the absence of CSN9, binding of neddylated CRL to CSN results in a series of conformational changes, among which the initial important steps involve the movement of N-terminal domains of CSN2 and CSN4 towards cullin (12, 24, 25). These rearrangements occur prior to the release and activation of CSN5. In contrast, the addition of CSN9 triggers CSN to undergo conformational changes by repositioning the N-terminus of CSN2 away from CSN3 but closer to CSN4 (FIG. 17). As the resulting conformation and configuration of CSN9-bound CSN are highly similar to those of CRL-bound CSN, without being limited by any particular theory, it is believed that CSN9 may enhance the affinity (or recognition) between CSN and its substrate, neddylated CRLs, thus facilitating the assembly of CSN-neddylated CRL complex to enhance CSN activation and deneddylation of CRLs. In addition, the conformation of CSNn may also enable its faster release from deneddylated CRLs as reported (14). In the absence of CSN9, the assembly/disassembly of CSN-CRL complex would more likely be much slower due to substantial conformational changes required for the activation of CSN upon binding to CRLs, thus leading to slower deneddylation rate. Therefore, the differences in the assembly/disassembly of CSN-CRL complexes more likely contribute to their interaction affinity, and slower disassembly of CSN-CRL complex could imply tighter interaction. In summary, CSN9-induced conformational changes related to CSN2, are biologically relevant, especially in preparing CSN for associating with neddylated CRLs, thereby contributing to augmenting deneddylation activity of CSN. The integrative structures of CSN complexes determined in this work have established a structural basis for us to further dissect condition-induced structural dynamics of CSN, including insights into its activation, function and regulation under different physiological and pathological conditions.

Multi-Chemistry XL-MS Strategy for CSN Complexes

In order to define the architectures of CSN and CSNn complexes, a comprehensive XL-MS analysis was performed to maximize PPI mapping and to facilitate integrative structure modeling. To this end, a combinatory XL-MS approach was developed based on multiple MS-cleavable cross-linkers that carry specific but complementary cross-linking chemistries. Specifically, in some embodiments, three sulfoxide-containing MS-cleavable cross-linkers were selected that target lysines (DSSO)(32), acidic residues (DHSO)(35), and cysteines (BMSO)(36), respectively. This combination is based on the critical roles of the selected reactive residues in protein structures, and the complementarity of the resulting cross-links for mapping PPIs. Both lysines and acidic residues are highly prevalent and often enriched at protein interaction interfaces, whereas cysteines are less abundant but can be more selective for targeting specific regions. In addition, no disulfide bonds have been reported for CSN subunits, indicating that cysteine cross-linking would be suited for structural analysis of CSN. Importantly, the usage of these reagents has shown to significantly improve the coverage of PPI mapping even for simple proteins (35, 36). The general workflow of the multi-chemistry XL-MS strategy is illustrated in FIG. 18. CSN complexes were purified under reducing condition after co-expression in *E. Coli* (embodiments of Expressed CSN Sequences are available in Dataset 51 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), which were catalytically active and used for all XL-MS experiments. It is noted that CSN7 exists as two functionally redundant homologs in mammalian cells, CSN7a and CSN7b (45). Here, CSN7b was expressed and incorporated into CSN complexes for structural analysis. Each purified complex was first subjected to DSSO, DHSO and BMSO cross-linking separately (FIG. 18). The resulting cross-linked complexes were then enzymatically digested and separated to enrich cross-linked peptides by peptide size exclusion chromatography (SEC)(46). The cross-links identified by LC MS$^n$ analysis were then used for generating 2-D XL-maps to describe inter-subunit interactions and for integrative structure modeling. Embodiments of the Interactome of the CSN Complex and Interactome of the CSNn Complex are available as Datasets S16 and S17, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety.

Identification of CSN Cross-Linked Peptides

To illustrate cross-link identification, representative $MS^n$ spectra of DSSO, DHSO, and BMSO cross-linked peptides of CSN are displayed in FIGS. 19A-19I. As DSSO, DHSO, and BMSO cross-linked peptides all carry two symmetric MS-cleavable bonds adjacent to the central sulfoxide in linker regions, cleavage of either one during $MS^2$ analysis physically separates cross-linked peptide constituents ($\alpha$ and $\beta$), resulting in the detection of two characteristic fragment ion pairs modified with complementary cross-linker remnants ($\alpha_A/\beta_T$ & $\alpha_T/\beta_A$), regardless of linker chemistries (FIGS. 19A-19C). $MS^3$ analyses of these characteristic $MS^2$ fragment ion pairs enabled accurate identification of their sequences (FIGS. 19D-19I). In combination with $MS^1$ and $MS^2$ data, DSSO, DHSO, and BMSO cross-linked peptides were identified unambiguously. In some embodiments, at least 4 biological replicates for each XL-MS experiment as performed. As a result, from all of XL-MS experiments, a total of 682 DSSO, 275 DHSO, and 456 BMSO unique cross-linked peptides of CSN (embodiments of Sequence Lengths of CSN Subunits used herein and in the CSN Crystal Structure (PDB 4D10) are available in Dataset S2 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), and a total of 856 DSSO, 723 DHSO, and 576 BMSO unique cross-linked peptides of CSNn (embodiments of the identified DSSO cross-linked peptides of CSN are available as Dataset S3 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety) were identified, respectively. Based on the identified cross-linked peptides, residue-to-residue linkages were determined (FIG. 20). In order to ensure the validity of subsequent analyses, only highly reproducible residue-to-residue linkages that have ≥60% occurrence among all biological replicates of each experiment were used. Thus, in some embodiments, a total of 452 highly reproducible cross-links were obtained for CSN, including 214 K-K, 169 D/E-D/E and 69 C-C linkages, describing 205 inter-subunit (74 DSSO, 91 DHSO, and 40 BMSO) and 247 intra-subunit interactions (140 DSSO, 78 DHSO, 29 BMSO) (embodiments of the identified DHSO cross-linked peptides of CSN are available as Dataset S4 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). For CSNn, a total of 544 highly reproducible cross-links were acquired with 269 K-K, 167 D/E-D/E and 108 C-C linkages, representing 244 inter-subunit (86 DSSO, 83 DHSO, and 75 BMSO) and 300 intra-subunit interactions (183 DSSO, 84 DHSO, 33 BMSO) (embodiments of the identified BMSO cross-linked peptides of CSN are available as Dataset S5 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). These high confidence cross-links were used for subsequent analyses (FIG. 20).

The CSN Interaction Topology

In order to define inter-subunit physical contacts, experimentally-derived interaction topology maps of CSN complexes were generated based on the highly reproducible cross-link data (FIG. 12; embodiments of the identified DHSO cross-linked peptides of CSN and identified BMSO cross-linked peptides of CSN are available as Datasets S4 and S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). As a result, extensive interaction networks were formulated comprising a total of 26 and 24 unique pairwise interactions for CSN and CSNn, respectively (embodiments of the identified DHSO cross-linked peptides of CSN and identified BMSO cross-linked peptides of CSN are available as Datasets S4 and S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Among the three linkers, DSSO yielded the most connectivity within CSN, indicating lysine reactive reagents best-suited for general assessment of PPIs within CSN. While DHSO and BMSO identified less overall, they did yield additional subunit contacts. Specifically, DSSO alone identified five unique PPIs; in comparison, DHSO and BMSO yielded a total of seven unique PPIs (embodiments of the identified DHSO cross-linked peptides of CSN are available as Dataset S4 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). In order to better assess linker-dependent interactions, DSSO, DHSO and BMSO PPI maps were constructed separately for each CSN complex (FIGS. 21A-21F). Since the majority of CSN subunits possess similar % of K, D/E and C residues in their primary sequences, the number of cross-links representing each inter-subunit interaction is more likely dependent on the number of cross-linkable residues at their interaction interfaces as well as the detectability of resulting cross-linked peptides. This is further illustrated by 2-D XL-maps (FIGS. 21G-21L). For example, for the two smallest subunits of CSN, CSN7b has a relatively high percentage of acidic residues and its interactions were mostly revealed by DHSO, whereas CSN8 interactions were better described by DSSO due to its relatively high percentage of lysines (FIG. 12A and FIGS. 21A-21C).

Similar to the CSN complex, all three linkers have yielded extensive and complementary cross-links to represent subunit interconnectivities of CSNn (embodiments of the identified BMSO cross-linked peptides of CSN are available as Dataset S5 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Importantly, 16 CSN9-containing cross-links have been identified (embodiments of the identified BMSO cross-linked peptides of CSN are available as Dataset S5 in the Supporting Information of Gutierrez, C., et al., Proc Natl Acad Sci USA., 117(8):4088-

4098, 2020, accessible on the World Wide Web at pnas.org/content/117/8/4088/tab-figures-data, the contents of which are hereby incorporated by reference in its entirety), demonstrating its physical interactions within CSN at the residue level. Specifically, the C-terminal tail of CSN1 and several regions across CSN3 have been found to interact with CSN9. Since CSN9 is highly acidic with few lysine and no cysteine residues, only DHSO was able to capture CSN9 interactions within the CSNn complex. With the addition of CSN9, it appears that CSNn presented unique characteristics in its XL-maps in comparison to those of CSN (FIG. 12B and FIGS. 21D-21F). This suggests that CSN9 may induce local changes in the CSNn complex that impact cross-link formation. Collectively, the results have demonstrated the effectiveness and complementarity of the combinatory XL-MS strategy in mapping PPIs within CSN complexes. Integration of multi-chemistry cross-linking enabled not only cross-validation of inter-subunit interactions, but also expanded interaction coverage due to their distinct capabilities of uncovering interactions at specific protein regions.

Mapping of CSN Cross-Links to the X-Ray Structure

Figure 22C:
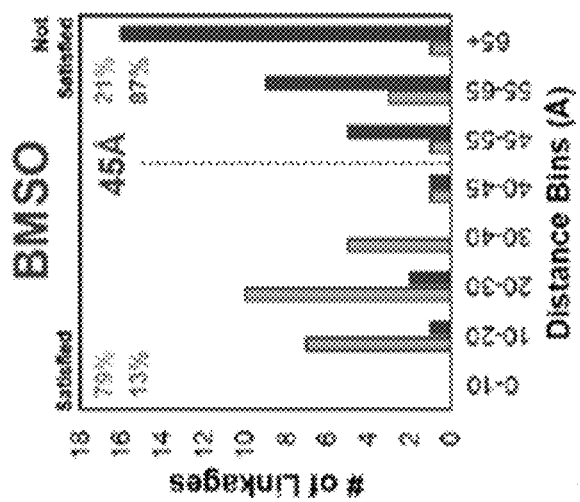
Figure 22B:
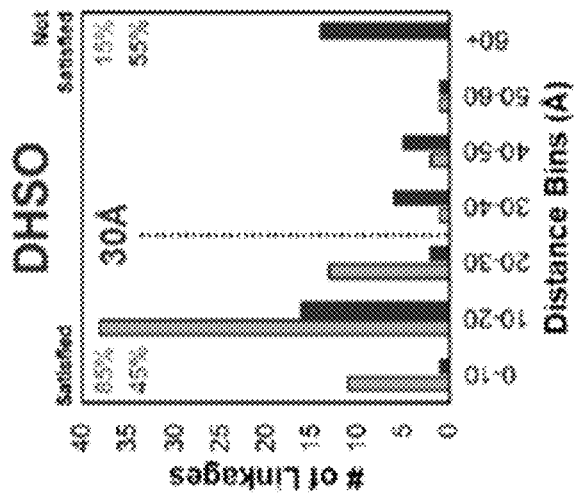
Figure 22A:
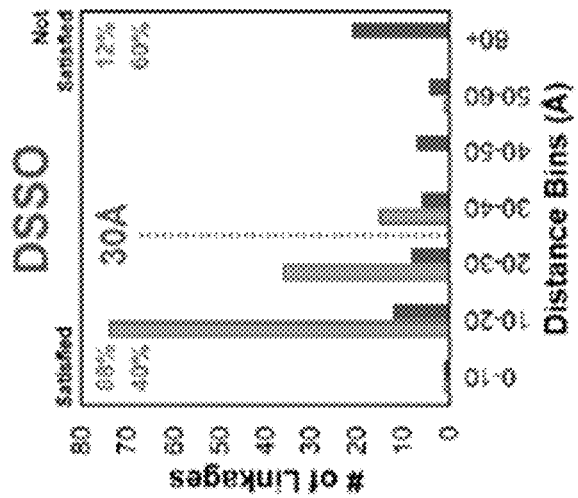
Figure 22F:
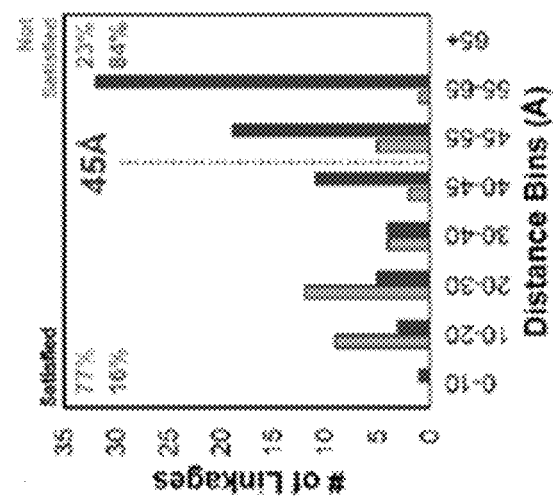
Figure 22E:
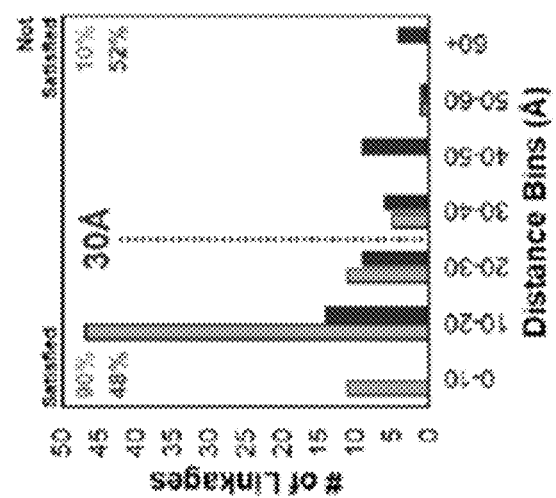
Figure 22D:
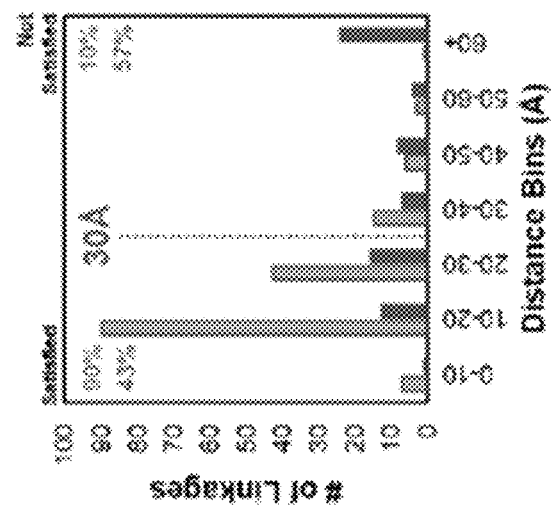

In order to assess whether the cross-links agreed with the X-ray structure, the identified K-K, D/E-D/E and C-C linkages of CSN complexes were first mapped to the existing CSN X-ray structure (3.8 Å, PDB 4D10) by determining their Cα-Cα spatial distances (embodiments of the identified DHSO cross-linked peptides of CSN and identified BMSO cross-linked peptides of CSN are available as Datasets S4 and S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Considering linker spacer arm lengths (i.e. DSSO (10.1 Å), DHSO (14.3 Å) and BMSO (24.2 Å)), side chain lengths of targeted amino acids (i.e. K (5.4 Å), D/E (2.5/3.7 Å) and C (2.8 Å)), as well as side chain flexibility and dynamics, the maximum Cα-Cα distances spanned by each linker was estimated: DSSO at 30 Å, DHSO at 30 Å, and BMSO at 45 Å. Thus, cross-links with distances above these thresholds were considered non-satisfying or violating. For inter-subunit interactions, 60% of DSSO cross-links of CSN were considered violating (FIG. 22A). This is surprising as usually less than 20% of lysine-reactive cross-links are violated when mapped onto existing high-resolution structures (30, 38, 40). Similar discrepancies with the X-ray structure were observed for DHSO and BMSO data as 55% DHSO and 87% of BMSO inter-subunit cross-links were beyond the expected thresholds (FIGS. 22B-22C). In contrast, most of intra-subunit cross-links of CSN were satisfied in the X-ray structure, with only 12% of DSSO, 15% of DHSO and 21% BMSO violating intra-subunit cross-links (FIGS. 22A-22C). Since the high-resolution structure of CSNn has not been resolved, in some embodiments, CSNn cross-links were also mapped onto the same CSN structure. Similarly, a significant portion of inter-subunit cross-links of CSNn from all three linkers, i.e. 57% of DSSO, 52% of DHSO and 84% BMSO, were non-satisfying (FIGS. 22D-22F), whereas for the intra-subunit cross-links, only 10% of DSSO, 10% of DHSO and 23% BMSO were non-satisfying (FIGS. 22D-22F). The high proportion of violating inter-subunit cross-links is more likely due to the additional conformations that CSN complexes may adopt in solution beyond the one observed in the X-ray structure.

Integrative Structure Modeling of the CSN Complex

In order to determine CSN structure in solution, an integrative structure modeling was performed using the previously described four-stage workflow (FIG. 23 and Examples 9-14 (embodiments of the identified BMSO cross-linked peptides of CSNn are available as Dataset S9 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety)(38, 43, 44, 47-50). The input information included the highly reproducible cross-link datasets (embodiments of the identified DHSO cross-linked peptides of CSN and identified BMSO cross-linked peptides of CSN are available as Datasets S4 and S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), the X-ray structure of CSN (PDB 4D10), and two comparative models of CSN7b subunit domains based on the structure of the CSN7a subunit in the X-ray structure of CSN. The representation of the system used for modeling of CSN was chosen as follows. First, the helical bundle comprising segments from each of the eight subunits was constrained based on the X-ray structure. Second, the remaining structures of subunits CSN1-8 were represented by 15 rigid bodies, corresponding to different domains of the proteins (Examples 15-17 and FIG. 24H) (embodiments of the identified BMSO cross-linked peptides of CSNn are available as Dataset S9 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Finally, short (4-13 residues) segments linking rigid bodies and regions missing in the X-ray structure (2-52 residues long) were modeled as flexible strings of 2-10 residue beads each. Next, in some embodiments, configurations of the 16 rigid bodies were exhaustively sampled (i.e., the helical bundle and the 15 rigid bodies) that satisfy the cross-links as well as sequence connectivity and excluded volume restraints, using a Monte Carlo method that started with a random initial structure. The modeling did not rely on any knowledge of the X-ray structure except for the shapes of the 16 rigid bodies. The sampling yielded 71,350 representative models that sufficiently satisfied the input restraints. The clustering of the ensemble identified a single distinct cluster containing the majority (76%) of the individual models (FIGS. 24A-24I)), corresponding to the complete integrative structure of CSN in solution. The precision of the cluster corresponds to the variability among the clustered ensemble and defines the overall precision (uncertainty) of the integrative CSN structure (FIG. 13A and FIGS. 24A-24H), which was quantified by the average root-mean-square deviation (RMSD) with respect to the centroid of 16 Å (Examples 15-17). The centroid structure is the most similar structure to all the other structures in the cluster.

Validation of the Integrative Structure of the CSN Complex

In order to validate the integrative structure of CSN, an assessment was first made on how well it satisfied the input cross-links used to compute it. The integrative structure of CSN satisfied 98% of the cross-links. The remaining 2% of the cross-links would be satisfied if the threshold was increased by 10 Å (FIG. 24F). These violations can be rationalized by experimental uncertainty, coarse-grained representation of the complex, and/or finite structural sampling.

Next, the integrative structure of CSN was evaluated by cross-validation against different input cross-link datasets. In some embodiments, the integrative modeling described above was independently repeated with six different subsets of CSN cross-links (embodiments of the identified DHSO cross-linked peptides of CSN are available as Dataset S4 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), including (i) DSSO only, (ii) DHSO only, (iii) BMSO only, (iv) DSSO and DHSO, (v) DSSO and BMSO, and (vi) DHSO and BMSO. The results were examined in three ways as follows. First, in some embodiments, it was gauged how well each of the six CSN model ensembles satisfied different subsets of the cross-links. All six models satisfied more than 95% of all cross-links, whether or not they were used for modeling, thus increasing the confidence in modeling. Second, in some embodiments, it was shown that increasing the amount of input information improved the precision of the output model when sampling was exhaustive. This result is expected when the choice of model representation (here, the 16 rigid bodies) is appropriate for input information (here, mainly the cross-links) as encoded in the scoring function. In addition to validating the model and the data, the improved precision of the model resulting from increasing the number of cross-linking chemistries demonstrate the complementarity of the three cross-linking datasets (FIGS. 13B-13C). Specifically, the model precision increased from 37 Å for BMSO cross-links only to 16 Å for all three types of cross-links (i.e. DSSO+DHSO+BMSO). Third, in some embodiments, overlaps between the integrative structure ensemble using all cross-links and each of the six model ensembles based on a subset of cross-links were calculated. The overlap was quantified by the ratio of the distance between ensemble centroids to three times the sum of the ensemble precisions (Examples 15-17). The distance between two ensemble centroids is defined by their RMSD. The ensemble precision is defined by the RMSD from the centroid averaged over all models in the ensemble. In particular, two structural aspects were evaluated, including the tertiary structure of each individual subunit (a total of 8 subunits) as described by the intramolecular distances as well as the relative positions and orientations of all pairs of subunits (a total of 28 pairs) in the complex as described by the intermolecular distances. For each of the eight subunits and each of the 28 pairs of subunits, the integrative structure based on all cross-links overlapped with the integrative structures based on each of the six cross-link subsets (FIGS. 25A-25F). Therefore, these cross-validations further increased the confidence in the integrative structure of CSN.

Comparison of Integrative and X-ray Structures of CSN

In order to compare the integrative and X-ray structures of CSN, it was first examined how well both structures satisfied the cross-link datasets and determined that the integrative structure did much better than the X-ray structure, for both intra-subunit (98% vs. 85%) and inter-subunit (99% vs. 39%) cross-links (FIG. 24F) (embodiments of the identified DSSO cross-linked peptides of CSNn are available in Dataset S6 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). These results indicate that the integrative structure ensemble is a better representation of CSN conformations in solution than the X-ray structure.

Next, it was inspected whether or not the integrative model preserved the core of the previously determined CSN structures, which contains three main features: 1) the PCI ring (in the order of CSN7-CSN4-CSN2-CSN1-CSN3-CSN8); 2) the CSN5-CSN6 dimer; and 3) a helical bundle consisting of a helix from each of the 8 subunits (23, 45, 51). During the modeling, while the helical bundle was constrained as a rigid body (FIGS. 13A, 14A, and 14D), the order of the PCI ring and CSN5-CSN6 dimer were not enforced. However, the latter two features emerged from the simulation and resemble those in the X-ray structure (FIGS. 13A and 14B, and FIG. 24G). This preservation is important especially for the CSN5-CSN6 dimer as it is crucial for keeping CSN5 inactive in the absence of a substrate, and releasing CSN5 for activation upon substrate binding (12, 23, 24, 52). The CSN5-CSN6 dimer was well-represented by the cross-link data, resulting in the highest precisions among the 28 pairs of subunits in the integrative structure of CSN (16 Å) (FIGS. 13A, 14B, 14D, and FIGS. 24A-24G). Moreover, subunits CSN3 and CSN8 also adopted similar positions and orientations relative to other subunits in both the integrative and X-ray structures (FIGS. 13A and 14A, and FIG. 24G), albeit the precision of the CSN3-CSN8 pair in the integrative structure was relatively low (25 Å). In summary, the core of CSN integrative structure in solution is similar to previous X-ray and EM structures (23, 45, 51).

Finally, in some embodiments, the RMSD between the CSN X-ray and integrative structure centroids was computed to assess whether the RMSD was larger than three times the precision of the integrative structure, as the resolution of the X-ray structure is much higher than that of the integrative structure. The crystallographic structures of 3 subunits (i.e. CSN2, CSN4, and CSN5) and 4 pairs of subunits (i.e., CSN2-CSN4, CSN2-CSN5, CSN4-CSN5, and CSN4-CSN6) were found to lie further than three times the integrative structure precision from the ensemble centroid (FIG. 14D), indicating significant differences in these regions between the two compared structures. The observed differences were further supported by the largest RMSDs measured in these regions between the X-ray and integrative structure centroid of CSN (FIG. 26A). The detected discrepancies are unlikely the result of integrative modeling uncertainty; instead, they likely reflect different functional states in solution and/or differences between the solution and X-ray structures. Specifically, the C-terminus of CSN4 interacts tightly with the C-terminus of CSN6 (precision of 20 Å; FIG. 14D and FIG. 24G), opposite from CSN5 in the integrative structure (FIGS. 13A and 14A). In contrast, CSN4 does not interact with CSN6 in the X-ray structure (FIG. 14D). The relative positions and orientations of CSN2, CSN4, CSN5, and CSN6 in the integrative structure were determined by satisfying all but one of the 47 inter-subunit cross-links. In contrast, the X-ray structure only satisfied 30 of these cross-links.

Although the arrangement order of CSN1, CSN2 and CSN3 remained unchanged, the N-terminus of CSN2 was found to wrap around CSN1 toward CSN3 in the integrative structure (FIGS. 13A, 14A, and 14C), whereas it projected outwards without contacting neither CSN1 nor CSN3 in the X-ray structure. The relative positions and orientations of CSN1, CSN2, CSN3, and CSN4 in the integrative structure were determined by satisfying all but one of the 98 inter-subunit cross-links. In contrast, the X-ray structure only satisfied 28 of these cross-links and none of the 16 cross-links between CSN2 and CSN3. Taken together, the results demonstrate that integrative structure modeling of CSN based on the comprehensive cross-link data was able to not only recapitulate the core architecture common to all known CSN structures, but also uncover significant quaternary differences relative to the X-ray structure.

Integrative Structure Modeling of the CSNn Complex

In order to localize the CSN9 subunit and map its interactions with the CSN complex, integrative structure modeling of CSNn (CSN9-bound CSN) was performed, based primarily on 619 highly reproducible cross-links for CSNn from all three cross-linkers (FIGS. 27A-27H and Examples 9-14 (embodiments of the Highly Reproducible DSSO Cross-links of CSN and Their Distance Mapping to the Known CSN Crystal Structure (PDB 4D10) are available in Dataset S10 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Integrative structure modeling of CSNn was performed the same way as described above for CSN. The structure of CSN9, a 57 amino acid-long acidic protein, is unknown and cannot be modeled. Therefore, it was represented as a string of flexible beads corresponding to two residues each. The sampling of the CSNn complex yielded 125,750 representative models that sufficiently satisfied the input restraints. The clustering of the ensemble identified a single distinct cluster containing the majority (79%) of the individual models (FIG. 27A-27H), corresponding to the complete integrative structure of CSNn in solution. The precision of the cluster is 22 Å (FIGS. 27A-27D), which is sufficient to map all positions and relative orientations of CSN1-9 subunits (FIGS. 14A, 15A, and FIG. 27E). Moreover, the integrative structure of CSNn satisfied 99% of the input cross-links (inter-subunit and intra-subunit). Importantly, the resulting structure of CSNn has precisely localized CSN9 at a cavity formed by the C-terminus of CSN1, all of CSN3 and CSN8 (FIG. 15A). The position of amino acid residues 20-57 of CSN9 was specified by satisfying all of the 16 CSN9-containing inter-subunit cross-links (FIGS. 15A-15B). It is noted that the exact position of the first 19 amino acid residues of CSN9 could not be accurately determined since cross-linked peptides involving this region were not identified. Regardless, in some embodiments, the interactions of CSN9 with CSN1-8 in the integrative structure were determined. In some embodiments, it is considered a contact between CSN9 and any of the CSN1-8 subunit if the two subunits are within 12 Å from each other; a contact is defined as an interaction if the contact frequency across the ensemble is at least 75% (FIG. 27G). As a result, CSN1 and CSN3 were found in the closest proximity to CSN9 across the ensemble and thus were identified as CSN9 interactors, corroborating well with the cross-link data. Therefore, the CSN9-CSN interactions have been precisely determined by integrative structure modeling (FIG. 15A-15B and FIG. 27G), providing CSN9's binding cavity and its interactors.

Comparison of Integrative Structures of the Canonical and Non-Canonical CSNs

In order to compare the two CSN complexes in light of their precisions, their structural differences were examined among the conformations of single subunits and configurations of pairs of subunits by assessing whether the differences are larger than the sum of their precisions (FIG. 14D) and by computing the RMSD between their respective centroid (FIG. 26B). While a large portion of the two compared structures was similar, the conformation of 3 out of the 8 subunits (i.e. CSN2, CSN5, and CSN7) and 3 out of the 28 pairs of subunits (i.e., CSN2-CSN3, CSN2-CSN5, and CSN2-CSN7) had notable differences in these regions (FIG. 14D and FIG. 26B). Both the integrative structures of CSN and CSNn maintained similar core structures (i.e., ordering of the PCI ring, the CSN5-CSN6 dimer, and the helical bundle) (FIG. 14B). However, CSN2 changed its conformation and position relative to its neighbors (i.e., CSN3, CSN5, and CSN7) (FIGS. 14A, 14C-14D and FIG. 26B). Specifically, in the integrative structure of CSNn, CSN2 and CSN4 localize adjacent to one another, allowing the formation of the CSN9-binding cavity (FIGS. 14D, 15A, and 15B). The conformation and relative position of the CSN2 subunit in the integrative structure of CSNn were determined by satisfying all 74 inter-subunit cross-links obtained for CSNn. Therefore, the results suggest that CSN2 possesses structural plasticity, enabling its interaction with CSN1 and CSN3 to yield a more open configuration in CSN9-bound CSN than in CSN9-free CSN.

In order to explore the potential role of CSN9-mediated structural changes, the integrative structures of CSN and CSNn were compared to the cryo-EM structure of the CRL4A-bound CSN complex (at resolution of 6.4 Å)(24). Specifically, in some embodiments, it was assessed whether the structure of the CSN complexed with neddylated CRL4A overlapped with the two integrative structures. The structure of CRL4A-bound CSN differs from the integrative structure of CSN for one subunit (i.e., CSN2) and 2 pairs of subunits (i.e., CSN2-CSN4 and CSN2-CSN5) (FIG. 26C). In contrast, the structure of CRL4A-bound CSN has no significant differences with the integrative structure of CSNn (FIG. 26D). Similar comparisons were performed with the structure of CRL1-bound CSN (at resolution of 7.2 Å)(25). While the structure of CSN bound to neddylated CRL1 differs from the integrative structure of CSN for two subunits (i.e., CSN2 and CSN5) and three pairs of subunits (i.e., CSN2-CSN4, CSN2-CSN5, and CSN2-CSN6) (FIG. 26E), it has no significant differences with the integrative structure of CSNn (FIG. 26D). Collectively, these assessments suggest that CSN9-bound CSN is structurally similar to CRL-bound CSN (24, 25). Upon CSN9 binding, the integrative structure of CSNn displays local structural changes, mainly on the conformation and position of CSN2. Specifically, CSN2 moves closer to CSN4, causing CSN9-bound CSN to adopt a configuration resembling CRL-bound CSN (24, 25).

Biochemical Validation of CSN9 Binding

In order to validate the interactions of CSN9 with the CSN complex revealed by XL-MS and structural modeling, in vitro binding assays using purified CSN subunits were performed. CSN9 only interacts with CSN1-2-3 and CSN1-2-3-8 subcomplexes, whereas no binding was detected with CSN4-6-7, CSN4-6-7-5, or CSN4-6-7-5-8 subcomplexes (FIG. 28). These results confirm that CSN1 and CSN3 are present in the subcomplex required for CSN9 binding onto CSN. In order to understand the importance of CSN9, in vitro deneddylase activities of CSN and CSNn was compared with neddylated Cullin 1 as the substrate. Similar results were obtained for the same assay performed at different time scales (FIGS. 29A-29D), demonstrating that CSNn displayed markedly increased activity over CSN and CSN9 can enhance CSN activity in vitro.

Quantitative Validation of the Structural Dynamics of the CSN Complexes

In order to validate the observed structural differences between CSN models with and without CSN9, parallel reaction monitoring (PRM)-based targeted quantitation of CSN cross-links was utilized (53). Since DHSO crosslinking yielded the most inter-subunit linkages best describing CSN9-induced structural changes, in some embodiments, CSN and CSNn were individually cross-linked with DHSO for PRM experiments. In order to perform unbiased quantitative analysis, a total of 341 PRM targets were generated based on highly reproducible DHSO cross-linked peptides previously obtained from CSN and CSNn complexes (embodiments of the identified DHSO cross-linked peptides of CSN and identified BMSO cross-linked peptides of CSN are available as Datasets S4 and S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Peptide quantitation was derived from the summation of peak areas of all transitions through Skyline software. As exemplified in FIG. 16A, an intra-CSN4 cross-link (E306-E345) from both CSN and CSNn samples displayed similar abundance, indicating that this interaction is independent of CSN9. In contrast, a CSN2-CSN3 cross-link (CSN2:E63-CSN3:E333) was only observed in CSNn and not in CSN, suggesting a CSN9-induced conformational change. In total, 229 DHSO cross-linked peptides were quantified which represent 18 inter-subunit interactions (embodiments of the identified DHSO cross-linked peptides of CSNn (Chymotrypsin Digest) and PRM Targeted Quantitation of the 229 DHSO Cross-links are available in Datasets S8 and S26, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). As shown in FIG. 16B, the vast majority of quantified cross-links remained unchanged between CSN and CSNn, confirming that CSN9 does not trigger major organizational changes within the CSN complex during its binding. This corroborates well with the modeling results as both of the CSN models satisfied 99% of DHSO cross-links from both complexes. Apart from unchanged interactions, a total of 22 cross-linked peptides were found with significant changes (>2.5-fold, greater than 3σ) between the two compared complexes (FIG. 16B). Besides cross-links involving CSN9, 2 additional cross-linked peptides corresponding to 2 inter-subunit interactions (i.e. CSN4-CSN6 and CSN6-CSN7) have decreased CSN/CSNn ratios, suggesting that these cross-links are favored in CSNn. In contrast, 18 cross-linked peptides describing 7 inter-subunit interactions (CSN1-CSN2, CSN1-CSN3, CSN1-CSN5, CSN2-CSN3, CSN2-CSN7, CSN4-CSN5, and CSN6-CSN7) and 1 intra-CSN1 interaction have increased CSN/CSNn ratios, implying that these cross-links are preferably formed in CSN. Apart from CSN9-containing interactions, 5 quantifiable CSN2-CSN3 cross-links exhibited the most significant changes between the two compared complexes with CSN/CSNn ratios all greater than 10.2 (FIG. 16C), indicating that CSN2-CSN3 interactions were severely disrupted upon CSN9 binding. This is consistent with the structural differences between CSN and CSNn revealed by integrative modeling as these linkages were only satisfied by the CSN models (FIG. 16D). Since CSN1 closely interacts with CSN2, CSN3 and CSN9, the decreased abundance of CSN1-CSN2 and CSN1-CSN3 cross-links in CSNn supports the CSNn model, suggesting that the main body of CSN2 swings away CSN1 and CSN3 into a more open state. Collectively, PRM-based targeted quantitation of CSN cross-links strongly supports structural similarities and differences between the integrative models of the two CSN complexes.

EXAMPLES

The following examples are non-limiting and other variants within the scope of the art are also contemplated and within the scope of this disclosure.

Example 9—Expression and Purification of CSN Complexes

Eight of total nine subunits of human COP9 signalosome (CSN) complex, except CSN5, were over-expressed and purified from *E. coli*. Two three-subunit subcomplexes, CSN1-2-3 and CSN4-6-7, were prepared through co-expression. Briefly, CSN2 was subcloned into a modified pGEX4T1 (Amersham Biosciences) vector containing a glutathione S-transferase (GST) tag followed by a Tobacco etch virus (TEV) protease cleavage site, while both CSN1 and CSN3 were subcloned into a modified pET15b (Novagen) vector containing a chloramphenicol resistance cassette. After co-expression in BL21(DE3) (Novagen), the CSN1-2-3 formed a complex and was purified by glutathione-affinity chromatography. Following TEV cleavage, the CSN1-2-3 subcomplex was further purified by anion exchange and gel filtration chromatography. CSN4-6-7 was prepared in the same way. CSN8 and CSN9 were subcloned into the pGEX4T1 vector individually and subjected to the same purification procedure. Recombinant full length CSN5 inserted into a modified GTE vector (Invitrogen). It has a GST tag which was removed during purification and was prepared from insect cells using baculovirus expression system. Two CSN complexes, with or without CSN9, were reconstituted by incubating the purified subcomplexes and individual subunits in equimolar ratio and polished by size exclusion chromatography. Neddylated Cul1-Rbx1 complex was prepared as described previously (62).

Example 10—XL-MS Analysis of CSN Complexes

Affinity purified human CSN complex with or without CSN9 were cross-linked with DSSO, DHSO, or BMSO, respectively. Each CSN complex was reacted with a selected cross-linker at their optimized molar ratios (protein to linker) respectively: DSSO (1:250), BMSO (1:400) and DHSO (1:30) (32, 35, 36). DMTMM was used to activate acidic residues for DHSO cross-linking (35). All reactions were performed for 1 h at room temperature. The resulting cross-linked proteins were digested by lys-C and trypsin. Cross-linked peptides were enriched by peptide SEC, analyzed by LC MS$^n$ and identified through database searching as previously described (Examples 15-17) (35, 36).

Example 11—PRM Targeted Quantitation of Cross-Linked Peptides

341 PRM targets were obtained based on highly reproducible DHSO cross-linked peptides of CSN and CSNn complexes (embodiments of the identified DHSO cross-linked peptides of CSN and identified BMSO cross-linked peptides of CSN are available as Datasets S4 and S5, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). For targeted analysis, the mass spectrometer was operated with the following settings: No survey scan collected, tMS2 resolving power 30,000, AGC target 5e4, maximum injection time 54 ms, isolation window 1 m/z, and CID normalized collision energy of 23%. A total of 341 cross-links were monitored over 3 separate targeted analyses for each sample, along with a set of 16 heavy-labeled AQUA peptides. Targeted analysis of AQUA peptides used the same settings as cross-link ions except were subjected to HCD with NCE of 30%. Transition lists based on expected cross-link fragmentation ions were generated and quantified using Skyline v.4.2.0.19072. Once exported, extracted intensities were normalized within sample sets using relative intensities of AQUA peptides based on quantified b and y ions.

Example 12—In Vitro Deneddylation Assay

A mixture containing 5 μM Nedd8-Cull-Rbx1 and 20 nM CSN was incubated in reaction buffer of 50 mM HEPES (pH 7.5), 150 mM NaCl and 1 mM TCEP. The reactions were carried out at room temperature and stopped by adding SDS-PAGE sample buffer at indicated time points, then analyzed by 9% SDS-PAGE and stained with Coomassie Blue.

Example 13—Biochemical Validation of the CSN9 Interactors

Purified components of CSN, including CSN5, CSN8, subcomplex CSN1-2-3 and CSN4-6-7, were used for pull-down assay. His-GB1 fused CSN9 served as the bait protein. The prey samples (different combinations of CSN subunits) were mixed with His-GB1-CSN9 at molar ratio 2:1. After 10-minute incubation, His Mag Sepharose Ni beads (GE Healthcare) were added into the samples and suspended by gently tapping the sample tubes for 5 minutes to immobilize His-GB1-CSN9 and its binding partners. Then the beads were washed with 20 mM Tris-HCl (pH 8.0), 300 mM NaCl, 20 mM imidazole for 5 times. The beads were further eluted with 200 mM imidazole and the elution was analyzed on a 4-15% Mini-PROTEAN TGX Gel (Bio-RAD). To identify the binding partners of CSN9, all the purified CSN components were loaded on the same gel (lane 8 and 9).

Example 14—Integrative Structure Modeling

Integrative structure modeling was carried out to determine the structures of the human canonical and non-canonical Cop9 signalosome complexes (Examples 15-17) (embodiments of the identified BMSO cross-linked peptides of CSNn and the Highly Reproducible DSSO Cross-links of CSN and Their Distance Mapping to the Known CSN Crystal Structure (PDB 4D10) are available as Datasets S9 and S10, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). All the relevant scripts, data, and results are available at salilab.org/CSN2019. The integrative structures of CSN and CSNn are deposited at PDB-dev (pdb-dev.wwpdb.org/) with accession code PDBDEV_00000037 and PDBDEV_00000038 respectively.

REFERENCES

All references cited in this disclosure are incorporated herein by reference in their entireties.

1. Wei N & Deng X W (2003) The COP9 signalosome. *Annu Rev Cell Dev Biol* 19:261-286.
2. Wolf D A, Zhou C, & Wee S (2003) The COP9 signalosome: an assembly and maintenance platform for cullin ubiquitin ligases? *Nat Cell Biol* 5(12):1029-1033.
3. Wei N, Serino G, & Deng X W (2008) The COP9 signalosome: more than a protease. *Trends Biochem Sci* 33(12):592-600.
4. Cope G A, et al. (2002) Role of predicted metalloprotease motif of Jab1/Csn5 in cleavage of Nedd8 from Cul1. *Science* 298(5593):608-611.
5. Deshaies R J & Joazeiro C A (2009) RING domain E3 ubiquitin ligases. *Annu Rev Biochem* 78:399-434.
6. Petroski M D & Deshaies R J (2005) Function and regulation of cullin-RING ubiquitin ligases. *Nat Rev Mol Cell Biol* 6(1):9-20.
7. Cope G A & Deshaies R J (2003) COP9 signalosome: a multifunctional regulator of SCF and other cullin-based ubiquitin ligases. *Cell* 114(6):663-671.
8. Lee J E, et al. (2011) The steady-state repertoire of human SCF ubiquitin ligase complexes does not require ongoing Nedd8 conjugation. *Mol Cell Proteomics* 10(5):M110 006460.
9. Skaar J R, Pagan J K, & Pagano M (2013) Mechanisms and function of substrate recruitment by F-box proteins. *Nat Rev Mol Cell Biol* 14(6):369-381.
10. Jia L & Sun Y (2011) SCF E3 ubiquitin ligases as anticancer targets. *Curr Cancer Drug Targets* 11(3):347-356.
11. Emberley E D, Mosadeghi R, & Deshaies R J (2012) Deconjugation of Nedd8 from Cul1 is directly regulated by Skp1-F-box and substrate, and the COP9 signalosome inhibits deneddylated SCF by a noncatalytic mechanism. *J Biol Chem* 287(35):29679-29689.
12. Enchev R I, et al. (2012) Structural basis for a reciprocal regulation between SCF and CSN. *Cell Rep* 2(3):616-627.
13. Fischer E S, et al. (2011) The molecular basis of CRL4DDB2/CSA ubiquitin ligase architecture, targeting, and activation. *Cell* 147(5):1024-1039.
14. Füzesi-Levi M G, et al. (2019) CSNAP, the smallest CSN subunit, modulates proteostasis through cullin-RING ubiquitin ligases. *Cell Death & Differentiation*.
15. Cope G A & Deshaies R J (2006) Targeted silencing of Jab1/Csn5 in human cells downregulates SCF activity through reduction of F-box protein levels. *BMC Biochem* 7:1.
16. Lee Y H, et al. (2011) Molecular targeting of CSN5 in human hepatocellular carcinoma: a mechanism of therapeutic response. *Oncogene* 30(40):4175-4184.
17. Pan Y & Claret F X (2012) Targeting Jab1/CSN5 in nasopharyngeal carcinoma. *Cancer Lett* 326(2): 155-160.
18. Zhong G, Li H, Shan T, & Zhang N (2015) CSN5 silencing inhibits invasion and arrests cell cycle progression in human colorectal cancer SW480 and LS174T cells in vitro. *Int J Clin Exp Pathol* 8(3):2809-2815.
19. Zhang H, et al. (2017) COPS5 inhibition arrests the proliferation and growth of serous ovarian cancer cells via the elevation of p27 level. *Biochem Biophys Res Commun* 493(1):85-93.
20. Lee M H, Zhao R, Phan L, & Yeung S C (2011) Roles of COP9 signalosome in cancer. *Cell Cycle* 10(18):3057-3066.
21. Richardson K S & Zundel W (2005) The emerging role of the COP9 signalosome in cancer. *Mol Cancer Res* 3(12):645-653.

22. Fischer E S, et al. (2014) Structure of the DDB1-CRBN E3 ubiquitin ligase in complex with thalidomide. *Nature* 512(7512):49-53.
23. Lingaraju G M, et al. (2014) Crystal structure of the human COP9 signalosome. *Nature* 512(7513): 161-165.
24. Cavadini S, et al. (2016) Cullin-RING ubiquitin E3 ligase regulation by the COP9 signalosome. *Nature* 531 (7596):598-603.
25. Mosadeghi R, et al. (2016) Structural and kinetic analysis of the COP9-Signalosome activation and the cullin-RING ubiquitin ligase deneddylation cycle. *Elife* 5.
26. Faull S V, et al. (2018) Structural basis of Cullin-2 RING E3 ligase regulation by the COP9 signalosome. *bioRxiv*: 483024.
27. Rozen S, et al. (2015) CSNAP Is a Stoichiometric Subunit of the COP9 Signalosome. *Cell Rep* 13(3):585-598.
28. Sharon M, et al. (2009) Symmetrical modularity of the COP9 signalosome complex suggests its multifunctionality. *Structure* 17(1):31-40.
29. Sinz A, Arlt C, Chorev D, & Sharon M (2015) Chemical cross-linking and native mass spectrometry: A fruitful combination for structural biology. *Protein Science* 24(8): 1193-1209.
30. Leitner A, Faini M, Stengel F, & Aebersold R (2016) Crosslinking and Mass Spectrometry: An Integrated Technology to Understand the Structure and Function of Molecular Machines. *Trends Biochem Sci* 41(1):20-32.
31. Yu C & Huang L (2018) Cross-Linking Mass Spectrometry: An Emerging Technology for Interactomics and Structural Biology. *Anal Chem* 90(1):144-165.
32. Kao A, et al. (2011) Development of a novel cross-linking strategy for fast and accurate identification of cross-linked peptides of protein complexes. *Mol Cell Proteomics* 10(1):M110.002212.
33. Yu C, Kandur W, Kao A, Rychnovsky S, & Huang L (2014) Developing new isotope-coded mass spectrometry-cleavable cross-linkers for elucidating protein structures. *Anal Chem* 86(4):2099-2106.
34. Kaake R M, et al. (2014) A new in vivo cross-linking mass spectrometry platform to define protein-protein interactions in living cells. *Mol Cell Proteomics* 13(12): 3533-3543.
35. Gutierrez C B, et al. (2016) Developing an Acidic Residue Reactive and Sulfoxide-Containing M S-Cleavable Homobifunctional Cross-Linker for Probing Protein-Protein Interactions. *Anal Chem*.
36. Gutierrez C B, et al. (2018) Development of a Novel Sulfoxide-Containing M S-Cleavable Homobifunctional Cysteine-Reactive Cross-Linker for Studying Protein-Protein Interactions. *Anal Chem* 90(12):7600-7607.
37. Kao A, et al. (2012) Mapping the structural topology of the yeast 19S proteasomal regulatory particle using chemical cross-linking and probabilistic modeling. *Mol Cell Proteomics* 11(12): 1566-1577.
38. Wang X, et al. (2017) Molecular Details Underlying Dynamic Structures and Regulation of the Human 26S Proteasome. *Mol Cell Proteomics* 16(5):840-854.
39. Liu F, Rijkers D T, Post H, & Heck A J (2015) Proteome-wide profiling of protein assemblies by cross-linking mass spectrometry. *Nat Methods* 12(12):1179-1184.
40. Liu F, Lossl P, Rabbitts B M, Balaban R S, & Heck A J R (2018) The interactome of intact mitochondria by cross-linking mass spectrometry provides evidence for coexisting respiratory supercomplexes. *Mol Cell Proteomics* 17(2):216-232.
41. Herzog F, et al. (2012) Structural probing of a protein phosphatase 2A network by chemical cross-linking and mass spectrometry. *Science* 337(6100):1348-1352.
42. Erzberger J P, et al. (2014) Molecular architecture of the 40SeIF1eIF3 translation initiation complex. *Cell* 158(5): 1123-1135.
43. Kim S J, et al. (2018) Integrative structure and functional anatomy of a nuclear pore complex. *Nature* 555(7697): 475-482.
44. Rout M P & Sali A (2019) Principles for Integrative Structural Biology Studies. *Cell* 177(6): 1384-1403.
45. Dubiel D, Rockel B, Naumann M, & Dubiel W (2015) Diversity of COP9 signalosome structures and functional consequences. *FEBS Lett* 589(19 Pt A):2507-2513.
46. Leitner A, Walzthoeni T, & Aebersold R (2014) Lysine-specific chemical cross-linking of protein complexes and identification of cross-linking sites using LC-MS/MS and the xQuest/xProphet software pipeline. *Nat Protoc* 9(1): 120-137.
47. Alber F, et al. (2007) Determining the architectures of macromolecular assemblies. *Nature* 450(7170):683-694.
48. Russel D, et al. (2012) Putting the pieces together: integrative modeling platform software for structure determination of macromolecular assemblies. *PLoS Biol* 10(1):e1001244.
49. Sali A, et al. (2015) Outcome of the First wwPDB Hybrid/Integrative Methods Task Force Workshop. *Structure* 23(7):1156-1167.
50. Schneidman-Duhovny D, Pellarin R, & Sali A (2014) Uncertainty in integrative structural modeling. *Curr Opin Struct Biol* 28:96-104.
51. Rockel B, Schmaler T, Huang X, & Dubiel W (2014) Electron microscopy and in vitro deneddylation reveal similar architectures and biochemistry of isolated human and Flag-mouse COP9 signalosome complexes. *Biochem Biophys Res Commun* 450(2):991-997.
52. Birol M, et al. (2014) Structural and biochemical characterization of the Cop9 signalosome CSN5/CSN6 heterodimer. *PLoS One* 9(8):e105688.
53. Chavez J D, et al. (2016) A General Method for Targeted Quantitative Cross-Linking Mass Spectrometry. *PLoS One* 11(12):e0167547.
54. Zhang X, et al. (2018) Carboxylate-Selective Chemical Cross-Linkers for Mass Spectrometric Analysis of Protein Structures. *Anal Chem* 90(2):1195-1201.
55. Leitner A, et al. (2014) Chemical cross-linking/mass spectrometry targeting acidic residues in proteins and protein complexes. *Proc Natl Acad Sci USA* 111(26): 9455-9460.
56. Heusel M, et al. (2019) Complex-centric proteome profiling by SEC-SWATH-MS. *Molecular Systems Biology* 15(1):e8438.
57. Seeger M, et al. (1998) A novel protein complex involved in signal transduction possessing similarities to 26S proteasome subunits. *Faseb J* 12(6):469-478.
58. Wei N & Deng X W (1999) Making sense of the COP9 signalosome. A regulatory protein complex conserved from *Arabidopsis* to human. *Trends Genet* 15(3):98-103.
59. Sharon M, Taverner T, Ambroggio X I, Deshaies R J, & Robinson C V (2006) Structural organization of the 19S proteasome lid: insights from M S of intact complexes. *PLoS Biol* 4(8):e267.
60. Bal M, et al. (2019) In-depth Analysis of the Lid Subunits Assembly Mechanism in Mammals. *Biomolecules* 9(6):213.

61. Peth A, Berndt C, Henke W, & Dubiel W (2007) Downregulation of COP9 signalosome subunits differentially affects the CSN complex and target protein stability. *BMC Biochem* 8:27.
62. Yu C, et al. (2016) Characterization of Dynamic UbR-Proteasome Subcomplexes by In vivo Cross-linking (X) Assisted Bimolecular Tandem Affinity Purification (XBAP) and Label-free Quantitation. *Mol Cell Proteomics*.

EXAMPLES

The following examples are non-limiting and other variants within the scope of the art are also contemplated and within the scope of this disclosure.

Example 15—LC MS$^n$ Analysis of Cross-Linked Peptides

LC MS$^n$ analysis was performed using a Thermo Scientific™ Dionex UltiMate 3000 system online coupled with an Orbitrap Fusion Lumos™ mass spectrometer. A 50 cm×75 µm Acclaim™ PepMap™ C18 column was used to separate peptides over a gradient of 1% to 25% ACN in 114 mins at a flow rate of 300 nL/min. Two different types of acquisition methods were utilized to maximize the identification of DSSO, DHSO and BMSO cross-linked peptides: (1) top 4 data-dependent MS$^3$ and (2) targeted MS$^3$ acquisition optimized for capturing DSSO, DHSO and BMSO cross-linked peptides by utilizing the mass difference between characteristic MS$^2$ fragment ions of DSSO cross-linked peptides (α–β) (i.e. $\Delta=\alpha_T-\alpha_A=\beta_T-\beta_A=31.9721$ Da)(1).

Example 16—Database Searching and Identification of Cross-Linked Peptides

MS$^n$ data extraction and analysis were performed in the same way as previously described (2). MS$^3$ data was subjected to a developmental version of Protein Prospector (v.5.19.1) for database searching, using Batch-Tag against limited to custom random concatenated database consisting of CSN 1-9 (18 entries) with mass tolerances for parent ions and fragment ions set as ±20 ppm and 0.6 Da, respectively. Trypsin or Chymotrypsin was set as the enzyme with three or four maximum missed cleavages allowed, respectively. A maximum of four variable modifications were also allowed, including protein N-terminal acetylation, methionine oxidation, and N-terminal conversion of glutamine to pyroglutamic acid. Cysteine carbamidomethylation was selected as a constant modification except when using BMSO. In addition, the previously defined modifications for either DSSO (2), DHSO (3) or BMSO (4) were also input into the search. For DSSO cross-links, three defined modification on uncleaved lysines were chosen, which included alkene ($C_3H_2O$; +54 Da), sulfenic acid ($C_3H_4O_2S$; +104 Da), and thiol ($C_3H_2SO$; +86 Da), representing cross-linker fragment moieties on lysine residues (2). For DHSO cross-links, three defined modification were chosen, which included alkene ($C_3H_4N_2$; +68 Da), sulfenic acid ($C_3H_6N_2SO$; +118 Da), and thiol ($C_3H_4N_2S$; +100 Da), representing cross-linker fragment moieties on aspartic or glutamic acid residues (3). For BMSO cross-links, five defined modifications representing cross-linker fragment moieties on cysteine residues were selected: alkene closed-ring ($C_9H_{10}N_2O_3$, +194.0691 Da), alkene open-ring ($C_9H_{12}N_2O_4$, +212.0797 Da), sulfenic acid closed-ring/unsaturated thiol open-ring ($C_9H_{12}N_2O_4S$, +244.0518 Da), sulfenic acid open-ring ($C_9H_{14}N_2O_5S$, +262.0623 Da), and unsaturated thiol closed-ring ($C_9H_{10}N_2O_3S$, +226.0412 Da) modifications on cysteine residues (4). Initial acceptance criteria for peptide identification at the MS$^3$ level required a reported expectation value≤0.18, which yielded a false discovery rate of 0.34%. The in-house program xl-Tools, a revised version of the previously developed Xl-Discoverer, was used to validate and summarize cross-linked peptides based on MS$^n$ data and database searching (1, 5). Following integration of MS$^n$ data, no cross-links were identified involving decoy proteins. Only cross-linked peptides that were identified in more than 60% biological replicates were reported (embodiments of the Highly Reproducible DSSO Cross-links of CSN and Their Distance Mapping to the Known CSN Crystal Structure (PDB 4D10), Highly Reproducible DHSO Cross-links of CSN and Their Distance Mapping to the Known CSN Crystal Structure (PDB 4D10), Highly Reproducible BMSO Cross-links of CSN and Their Distance Mapping to the Known CSN Crystal Structure (PDB 4D10), Highly Reproducible DSSO Cross-links of CSNn and Their Distance Mapping to the Known CSN Crystal Structure (PDB 4D10), Highly Reproducible DHSO Cross-links of CSNn and Their Distance Mapping to the Known CSN Crystal Structure (PDB 4D10), and Highly Reproducible BMSO Cross-links of CSNn and Their Distance Mapping to the Known CSN Crystal Structure (PDB 4D10) are available as Datasets S10-S15, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). Raw data has been deposited at the PRIDE Archive proteomics data repository site: ebi.ac.uk/pride/archive/ (Data are available via ProteomeXchange with identifier PXDO14673).

Example 17—Integrative Structure Determination of the Human CSN Complexes

Example 17.1—Integrative Structure Determination of the Human Canonical CSN Complex Integrative structure determination of the human canonical CSN complex proceeded through four stages (FIG. 23) (6-11): (1) gathering, data, (2) representing subunits and translating data into spatial restraints, (3) configurational sampling to produce an ensemble of structures that satisfies the restraints, and (4) analyzing and validating the ensemble structures and data. The integrative structure modeling protocol (stage 2, 3, and 4) was scripted using the Python Modeling Interface (PMI) package, which is a library for modeling macromolecular assemblies based on the open-source Integrative Modeling Platform (IMP) package (9) version 2.8 (integrativemodeling.org). The current procedure is an updated version of previously described protocols (7, 12-18). Files containing the input data, scripts, and output results are available at salilab.org/CSN2O19 as well as the nascent Protein Data Bank archive for integrative structures (pdb-dev.rcsb.rutgers.edu) accession code PDB-DEV_00000037 (CSN) (pdb-dev.wwpdb.org/static/cif/PDBEV_00000037.eif) and accession code PDB-DEV_00000038 (CSNn) (pdb-dev.wwpdb.org/static/cif/PDBDEV_00000038.cif).

Example 17.2—Integrative Structure Determination of the Human Canonical CSN Complex Stage 1: Gathering Data.

In total, 452 highly reproducible intra- and intermolecular DSSO, DHSO, and BMSO cross-links were identified using mass spectrometry (embodiments of the Highly Reproducible DSSO Cross-links of CSN and Their Distance Mapping to the Known CSN Crystal Structure (PDB 4D10), Highly Reproducible DHSO Cross-links of CSN and Their Distance Mapping to the Known CSN Crystal Structure (PDB 4D10), and Highly Reproducible BMSO Cross-links of CSN and Their Distance Mapping to the Known CSN Crystal Structure (PDB 4D10) are available as Datasets S10-S12, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), which informed the spatial proximities among the 8 subunits of the CSN and their conformations.

Representations of individual subunits relied on (1) atomic structures of the CSN1-6 and CSN8 subunits determined by X-ray crystallography (PDB code 4D10)(19), and (2) comparative models of 2 domains of CSN7b built with MODELLER 9.17(20) based on the known related structures of CSN7a (19).

Stage 2: Representing Subunits and Translating Data into Spatial Restraints

Information about the modeled system (above) can in general be used for defining the system's representation, defining the scoring function that guides sampling of alternative structural models, limiting sampling, filtering of representative structures obtained by sampling and final validation of the structures. Here, the CSN representation relies primarily on the atomic structure of CSN (PDB code 4D10). The CSN7b representation relies on comparative models for the following regions: (1) CSN7b$^{8-158}$ and CSN7b$^{163-212}$ (PDB code 4D10, sequence identity 60%, Z-DOPE score −0.90). The helical bundle comprising segments from each of the eight subunits was extracted and constrained based on the crystallographic structure. The scoring function relies on chemical cross-links, excluded volume, and sequence connectivity.

An optimal representation facilitates accurate formulation of spatial restraints as well as efficient and complete sampling representative solutions, while retaining sufficient detail without overfitting, so that the resulting models are maximally useful for subsequent biological analysis.

In order to maximize computational efficiency while avoiding using too coarse a representation, the system was represented in a multi-scale fashion. 16 rigid bodies consisting of multiple beads were defined for the comparative models of CSN7b and CSN (FIG. 24H). In a rigid body, the beads have their relative distances constrained during conformational sampling, whereas in a flexible string the beads are restrained by the sequence connectivity, excluded volume, and chemical cross-links (15, 21, 22).

Rigid bodies were coarse-grained using two resolutions, where beads represented either individual residues or segments of up to 10 residues. The coordinates of a 1-residue bead were those of the corresponding Cα atoms. The coordinates of a 10-residue bead were the center of mass of the 10 constituent 1-residue beads. Finally, the remaining regions without an atomic model were represented by a flexible string of beads encompassing up to 10 residues each.

With this representation in hand, next the spatial restraints were encoded into a scoring function based on the information gathered in Stage 1, as follows (embodiments of the Highly Reproducible DSSO Cross-links of CSN and Their Distance Mapping to the Known CSN Crystal Structure (PDB 4D10), Highly Reproducible DHSO Cross-links of CSN and Their Distance Mapping to the Known CSN Crystal Structure (PDB 4D10), and Highly Reproducible BMSO Cross-links of CSN and Their Distance Mapping to the Known CSN Crystal Structure (PDB 4D10) are available as Datasets S10-S12, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety).

(1) Cross-link restraints: The 214 DSSO, 169 DHSO, and 69 BMSO cross-links (embodiments of the Highly Reproducible DSSO Cross-links of CSN and Their Distance Mapping to the Known CSN Crystal Structure (PDB 4D10), Highly Reproducible DHSO Cross-links of CSN and Their Distance Mapping to the Known CSN Crystal Structure (PDB 4D10), and Highly Reproducible BMSO Cross-links of CSN and Their Distance Mapping to the Known CSN Crystal Structure (PDB 4D10) are available as Datasets S10-S12, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety) were used to construct the Bayesian scoring function (23) that restrained the distances spanned by the cross-linked residues (15).

(2) Excluded volume restraints: The excluded volume restraints were applied to each 10-residue bead, using the statistical relationship between the volume and the number of residues that it covered (6, 22, 24).

(3) Sequence connectivity restraints: The sequence connectivity restraints were applied, using a harmonic upper distance bound on the distance between consecutive beads in a subunit, with a threshold distance equal to twice the sum of the radii of the two connected beads. The bead radius was calculated from the excluded volume of the corresponding bead, assuming standard protein density (7, 15, 21, 22).

Stage 3: Conformational Sampling to Produce an Ensemble of Structures that Satisfies the Restraints It was aimed to maximize the precision at which the sampling of solutions was exhaustive (Stage 4). Positions of the 16 rigid bodies of CSN were sampled. The search for representative models relied on Gibbs sampling, based on the Metropolis Monte Carlo algorithm. The initial positions of CSN were randomized. The Monte Carlo moves included random translation and rotation of rigid bodies (up to 1 Å and 0.01 radians, respectively), and random translation of individual beads in the flexible segments (up to 2 Å). A model was saved every 10 Gibbs sampling steps, each consisting of a cycle of Monte Carlo steps that moved every rigid body and flexible bead once. This sampling produced a total of 5,250,000 models from 70 independent runs, each starting from a different initial conformation of CSN, requiring ~1 day on 560 computational cores. For the most detailed specification of the sampling procedure, see the IMP modeling script (salilab.org/CSN2019). Only the sampling yielded 71,349 representative models that sufficiently satisfy the input restraints were consider for further analysis.

Stage 4: Analyzing and Validating the Ensemble Structures and Data

Input information and output structures need to be analyzed to estimate structure precision and accuracy, detect inconsistent and missing information, and to suggest more informative future experiments. The analysis and validation protocol published earlier (25) was used. Assessment began with a test of the thoroughness of structural sampling, followed by structural clustering of the models and estimating their precision based on the variability in the ensemble of representative structures, and quantification of the structure fit to the input information. These validations are based on the nascent wwPDB effort on archival, validation, and dissemination of integrative structure models (10). Each one of these points is discussed below.

(1) Convergence of Sampling

Whether or not sampling found all representative solutions must be first assessed; this assessment is needed in particular for estimating the precision of the model ensemble consistent with the input data. The four tests were performed, as follows.

The first convergence test confirmed that the scores of refined models do not continue to improve as more models are computed essentially independently (FIG. 24A).

The second convergence test confirmed that the representative models in independent sampling runs 1-35 (model sample 1) and 36-70 (model sample 2) satisfied the data equally well. While the non-parametric Mann-Whitney test indicates that the difference between the two score distributions is significant (p-value is less than 0.05), the magnitude of the difference is small, as demonstrated by the Cliffs d of 0.04 (FIG. 24B); thus, the two score distributions are effectively equal.

Next, the representative structures themselves were considered, not their scores as in the two tests described above. For stochastic sampling methods, thoroughness of sampling can be assessed by showing that multiple independent runs (e.g., using random starting configurations and different random number generator seeds, as is the case for model samples 1 and 2) do not result in significantly different models. The similarity between model samples 1 and 2 was tested in the following two ways.

The third convergence test relied on the $\chi^2$-test for homogeneity of proportions between model samples 1 and 2 (FIGS. 24C-24D). The test involves clustering models from both samples, followed by comparing the proportions of models from each sample in each cluster. A comparison of two CSN structures considered all the beads representing subunits in the complex. The sampling precision is defined as the average bead RMSD between the models within the cluster and its corresponding centroid in the finest clustering for which each sample contributes models proportionally to its size (considering both significance and magnitude of the difference) and for which a sufficient proportion of all models occur in sufficiently large clusters. The sampling precision for the CSN modeling is 16 Å (FIGS. 23C-23D). In particular, a model was computed at a precision of 16 Å.

The fourth convergence test relied on a comparison of two localization probability density maps for CSN, obtained for models in samples 1 and 2 (FIG. 24E). A localization probability density map defines the probability of any voxel (here, 5×5×5 Å$^3$) being occupied by a specific protein in a set of model densities, which in turn are obtained by convolving superposed models with a Gaussian kernel (here, with a standard deviation of 3.4 Å, corresponding to a resolution equal to the cluster precision). The average cross-correlation coefficient between the two maps of CSN is 0.99, indicating that the position of CSN in the two samples is nearly identical at the model precision of 16 Å.

In conclusion, all four sampling tests indicate that the sampling was exhaustive at 16 Å precision. The caveat is that passing these tests is only necessary but not sufficient as evidence of thorough sampling; a positive outcome of the tests may be misleading if, for example, the landscape contains only a narrow, and thus difficult to find, pathway to the pronounced minimum corresponding to the correct structure.

(2) Clustering and Structure Precision

An ensemble of good-scoring structures needs to be analyzed in terms of the precision of its structural features (6-8, 17). The precision of a component position can be quantified by its variation in an ensemble of superposed good-scoring structures. It can also be visualized by the localization probability density for each of the components of the model. As described above, integrative structure determination of the CSN resulted in effectively a single solution, at the precision of 16 Å (FIG. 24D). This precision is sufficient to determine the structure of CSN. Embodiments of the Summary of Integrative Structure Determination of the CSN complex are available as Dataset S18 in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety.

(3) Fit to Input Information

An accurate structure needs to satisfy the input information used to compute it. Because the sampling was exhaustive at 16 Å precision, overfitting is not a problem at this precision; all structures at this precision that are consistent with the data are provided in the ensemble.

Here, it is consider that a cluster satisfies a cross-link if the cross-linked distance in any individual model in the cluster is less than the maximum threshold (i.e., the maximum length of the assessed cross-linkers). In particular, the threshold is 30 Å, 30 Å, and 45 Å for the DSSO, DHSO, and BMSO cross-linkers, respectively. The integrative CSN structure satisfied 98% of the input cross-links of the inter-subunit and intra-subunit cross-links; the remaining 2% of the cross-links are satisfied if the threshold is increased by 10 Å (FIG. 24F). These violations can be rationalized by possible false positive cross-links, coarse-grained representation of the complex, and/or finite structural sampling.

The remainder of the restraints are harmonic, with a specified standard deviation. The dominant cluster generally satisfied at least 95% of restraints of each type (embodiments of Distance Mapping and Satisfaction of Highly Reproducible DSSO Cross-links of CSN on the CSN Integrative Structure, Distance Mapping and Satisfaction of Highly Reproducible DHSO Cross-links of CSN on the CSN Integrative Structure, and Distance Mapping and Satisfaction of Highly Reproducible BMSO Cross-links of CSN on the CSN Integrative Structure are available as Datasets S19-S21, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety); a restraint is satisfied by a cluster of structures if the restrained distance in any structure in the cluster (considering restraint ambiguity) is violated by less than 3 standard deviations, specified for the restraint. Most of the violations are small, and can be rationalized by local structural fluctuations, coarse-grained representations of some CSN domains and/or finite structural sampling.

(4) Cross-Validation Against the Input Cross-Links

The integrative modeling described above were independently repeated with six different subsets of cross-links of CSN (embodiments of the Highly Reproducible DSSO Cross-links of CSN and Their Distance Mapping to the Known CSN Crystal Structure (PDB 4D10), Highly Reproducible DHSO Cross-links of CSN and Their Distance Mapping to the Known CSN Crystal Structure (PDB 4D10), and Highly Reproducible BMSO Cross-links of CSN and Their Distance Mapping to the Known CSN Crystal Structure (PDB 4D10) are available as Datasets S10-S12, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), including (i) DSSO only, (ii) DHSO only, (iii) BMSO only, (iv) DSSO and DHSO, (v) DSSO and BMSO, and (vi) DHSO and BMSO (FIGS. 25A-25F). See Validation of the Integrative CSN Structure in main text.

In conclusion, sampling is exhaustive, representation is appropriate for modeling, and both the tertiary and quaternary organization of the integrative structure are cross-validated, thus validating the integrative structure of CSN.

(5) Structural Ensemble Comparison

To compare two structures (i.e., ensemble) taking into considerations their precisions, the overlap between the two structures was calculated. The overlap was quantified by the ratio of the distance between ensemble centroids to three times the sum of the ensemble precisions. For two normal distributions with the same standard deviation, an overlap of 1 corresponds to 0.13% of one distribution being overlapped by the other. Thus, an overlap greater than 1 indicates that the two model ensembles are different, given their precisions. The distance between two ensemble centroids is defined by their RMSD. The ensemble precision is defined by the RMSD from the centroid averaged over all models in the ensemble.

Example 17.3—Integrative Structure Determination of the Human Non-Canonical CSN Complex Stage 1: Gathering Data.

In total, 544 highly reproducible intra- and intermolecular DSSO, DHSO, and BMSO cross-links were identified using mass spectrometry (embodiments of Highly Reproducible DSSO Cross-links of CSNn and Their Distance Mapping to the Known CSN Crystal Structure (PDB 4D10), Highly Reproducible DHSO Cross-links of CSNn and Their Distance Mapping to the Known CSN Crystal Structure (PDB 4D10), and Highly Reproducible BMSO Cross-links of CSNn and Their Distance Mapping to the Known CSN Crystal Structure (PDB 4D10) are available as Datasets S13-S15, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety), which informed the spatial proximities among the 9 subunits of the CSNn and their conformations.

Representations of CSN1-8 subunits were identical to the representation used to determine the CSN structure above. Representation of CSN9 relied on secondary structure and disordered regions predicted by PSIPRED based on the CSN9 sequence (26).

Stage 2: Representing Subunits and Translating Data into Spatial Restraints

The CSN1-8 representation for CSNn structure was identical to the one used for CSN structure (FIG. 27H). Because the structure of CSN9 has not been previously determined nor can it be modeled based on its sequence, it was represented as a string of flexible beads corresponding to two residues each.

With this representation in hand, next the spatial restraints were encoded into a scoring function based on the information gathered in Stage 1, as follows (embodiments of Highly Reproducible DSSO Cross-links of CSNn and Their Distance Mapping to the Known CSN Crystal Structure (PDB 4D10), Highly Reproducible DHSO Cross-links of CSNn and Their Distance Mapping to the Known CSN Crystal Structure (PDB 4D10), and Highly Reproducible BMSO Cross-links of CSNn and Their Distance Mapping to the Known CSN Crystal Structure (PDB 4D10) are available as Datasets S13-S15, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety).

(1) Cross-link restraints: The 269 DSSO, 83 DHSO, and 75 BMSO cross-links (embodiments of Highly Reproducible DSSO Cross-links of CSNn and Their Distance Mapping to the Known CSN Crystal Structure (PDB 4D10), Highly Reproducible DHSO Cross-links of CSNn and Their Distance Mapping to the Known CSN Crystal Structure (PDB 4D10), and Highly Reproducible BMSO Cross-links of CSNn and Their Distance Mapping to the Known CSN Crystal Structure (PDB 4D10) are available as Datasets S13-S15, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety) were used to construct the Bayesian scoring function (23) that restrained the distances spanned by the cross-linked residues (15).

(2) Excluded volume restraints: The excluded volume restraints were applied to each 10-residue bead, using the statistical relationship between the volume and the number of residues that it covered (6, 22, 24).

(3) Sequence connectivity restraints: The sequence connectivity restraints were applied, using a harmonic upper distance bound on the distance between consecutive beads in a subunit, with a threshold distance equal to twice the sum of the radii of the two connected beads. The bead radius was calculated from the excluded volume of the corresponding bead, assuming standard protein density (6, 22 2014).

This sampling produced a total of 7,500,000 models from 100 independent runs, each starting from a different initial conformation of CSNn, requiring ~1 day on 800 computational cores. For the most detailed specification of the sampling procedure, see the IMP modeling script (salilab.org/CSN2019). Only the sampling yielded 125,750 representative models that sufficiently satisfy the input restraints were considered for further analysis.

Stage 4: Analyzing and Validating the Ensemble Structures and Data

CSNn structures were assessed with identical tests for thoroughness of sampling, its fit to input information, and to data not used for modeling.

(1) Convergence of Sampling

The first convergence test confirmed that the scores of refined models do not continue to improve as more models are computed essentially independently (FIG. 27A). The second convergence test confirmed that representative models in independent sampling runs 1-50 (model sample 1) and 51-100 (model sample 2) satisfied the data equally well (p-value is less than 0.05 and Cliff's d of 0.10) (FIG. 27B). The third convergence test validated that the CSNn structure is exhaustive at 22 Å and a structure of CSNn was computed at a precision of 22 Å (FIGS. 27C-27D). The fourth test confirmed that the CSNn structures in sample 1 and 2 are identical. In particular, the cross-correlation of the localization probability density maps for the two samples of CSNn is 0.91 (FIG. 27E). In conclusion, all four sampling tests indicate that the sampling was exhaustive at 22 Å precision.

(2) Clustering and Structure Precision

As described above, integrative structure determination of the CSNn resulted in effectively a single solution, at the precision of 22 Å (FIG. 27D). This precision is sufficient to determine the structure of CSNn and the binding mode of CSN9 on the CSNn (embodiments of the Summary of Integrative Structure Determination of the CSNn Complex are available as Dataset S22 in the Supporting Information of Gutierrez, C., et al., Proc Natl Acad Sci USA., 117(8): 4088-4098, 2020, accessible on the World Wide Web at pnas.org/content/117/8/4088/tab-figures-data, the contents of which are hereby incorporated by reference in its entirety).

(3) Fit to Input Information

The structure of the integrative CSNn satisfied 99% of the input cross-links (inter-subunit and intra-subunit) (FIG. 27F) (embodiments of Distance Mapping and Satisfaction of Highly Reproducible DSSO Cross-links of CSNn on the CSNn Integrative Structure, Distance Mapping and Satisfaction of Highly Reproducible DHSO Cross-links of CSNn on the CSNn Integrative Structure, and Distance Mapping and Satisfaction of Highly Reproducible BMSO Cross-links of CSNn on the CSNn Integrative Structure are available as Datasets S23-S25, respectively, in the Supporting Information of Gutierrez, C., et al., Proc Natl Acad Sci USA., 117(8):4088-4098, 2020, accessible on the World Wide Web at pnas.org/content/117/8/4088/tab-figures-data, the contents of which are hereby incorporated by reference in its entirety). In conclusion, sampling is exhaustive, representation is appropriate for modeling, and the structure of CSNn satisfies data not used for modeling, thus validating the integrative structure of CSNn.

REFERENCES

All references cited in this disclosure are incorporated herein by reference in their entireties.

1. Yu C, et al. (2016) Characterization of Dynamic UbR-Proteasome Subcomplexes by In vivo Cross-linking (X) Assisted Bimolecular Tandem Affinity Purification (XBAP) and Label-free Quantitation. *Molecular &cellular proteomics: MCP.*
2. Kao A, et al. (2011) Development of a novel cross-linking strategy for fast and accurate identification of cross-linked peptides of protein complexes. *Molecular & cellular proteomics: MCP* 10(1):M110.002212.
3. Gutierrez C B, et al. (2016) Developing an Acidic Residue Reactive and Sulfoxide-Containing M S-Cleavable Homobifunctional Cross-Linker for Probing Protein-Protein Interactions. *Analytical chemistry.*
4. Gutierrez C B, et al. (2018) Development of a Novel Sulfoxide-Containing M S-Cleavable Homobifunctional Cysteine-Reactive Cross-Linker for Studying Protein-Protein Interactions. *Analytical chemistry* 90(12):7600-7607.
5. Wang X, et al. (2017) Molecular Details Underlying Dynamic Structures and Regulation of the Human 26S Proteasome. *Molecular & cellular proteomics: MCP* 16(5): 840-854.
6. Alber F, et al. (2007) The molecular architecture of the nuclear pore complex. *Nature* 450(7170):695-701.
7. Kim S J, et al. (2018) Integrative structure and functional anatomy of a nuclear pore complex. *Nature* 555(7697): 475-482.
8. Rout M P & Sali A (2019) Principles for Integrative Structural Biology Studies. *Cell* 177(6): 1384-1403.
9. Russel D, et al. (2012) Putting the pieces together: integrative modeling platform software for structure determination of macromolecular assemblies. *PLoS biology* 10(1):e1001244.
10. Sali A, et al. (2015) Outcome of the First wwPDB Hybrid/Integrative Methods Task Force Workshop. *Structure* 23(7):1156-1167.
11. Schneidman-Duhovny D, Pellarin R, & Sali A (2014) Uncertainty in integrative structural modeling. *Current opinion in structural biology* 28:96-104.
12. Fernandez-Martinez J, et al. (2016) Structure and Function of the Nuclear Pore Complex Cytoplasmic mRNA Export Platform. *Cell* 167(5):1215-1228 e1225.
13. Luo J, et al. (2015) Architecture of the Human and Yeast General Transcription and DNA Repair Factor TFIIH. *Mol Cell* 59(5):794-806.
14. Robinson P J, et al. (2015) Molecular architecture of the yeast Mediator complex. *Elife* 4.
15. Shi Y, et al. (2014) Structural characterization by cross-linking reveals the detailed architecture of a coatomer-related heptameric module from the nuclear pore complex. *Molecular & cellular proteomics: MCP* 13(11): 2927-2943.
16. Upla P, et al. (2017) Molecular Architecture of the Major Membrane Ring Component of the Nuclear Pore Complex. *Structure* 25(3):434-445.
17. Wang X, et al. (2017) The proteasome-interacting Ecm29 protein disassembles the 26S proteasome in response to oxidative stress. *J Biol Chem* 292(39): 16310-16320.
18. Webb B, et al. (2014) Modeling of proteins and their assemblies with the Integrative Modeling Platform. *Methods Mol Biol* 1091:277-295.
19. Lingaraju G M, et al. (2014) Crystal structure of the human COP9 signalosome. *Nature* 512(7513): 161-165.
20. Sali A & Blundell T L (1993) Comparative protein modelling by satisfaction of spatial restraints. *J Mol Biol* 234(3):779-815.
21. Algret R, et al. (2014) Molecular architecture and function of the SEA complex, a modulator of the TORC1 pathway. *Mol Cell Proteomics* 13(11):2855-2870.
22. LoPiccolo J, et al. (2015) Assembly and Molecular Architecture of the Phosphoinositide 3-Kinase p85alpha Homodimer. *The Journal of biological chemistry* 290(51): 30390-30405.
23. Rieping W, Habeck M, & Nilges M (2005) Inferential structure determination. *Science* 309(5732):303-306.

24. Shen M Y & Sali A (2006) Statistical potential for assessment and prediction of protein structures. *Protein Sci* 15(11):2507-2524.
25. Viswanath S, Chemmama I E, Cimermancic P, & Sali A (2017) Assessing Exhaustiveness of Stochastic Sampling for Integrative Modeling of Macromolecular Structures. *Biophys J* 113(11):2344-2353.
26. Buchan D W, Minneci F, Nugent T C, Bryson K, & Jones D T (2013) Scalable web services for the PSIPRED Protein Analysis Workbench. *Nucleic Acids Res* 41 (Web Server issue):W349-357.
27. Cavadini S, et al. (2016) Culling RING ubiquitin E3 ligase regulation by the COP9 signalosome. *Nature* 531: 598.
28. Mosadeghi R, et al. (2016) Structural and kinetic analysis of the COP9-Signalosome activation and the cullin-RING ubiquitin ligase deneddylation cycle. *eLife* 5:e12102.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

What is claimed is:

1. An MS-cleavable cross-linker for mapping intra-protein interactions in a protein, inter-protein interactions in a protein complex or a combination thereof, wherein the MS-cleavable cross-linker is BMSO, comprising the structure:

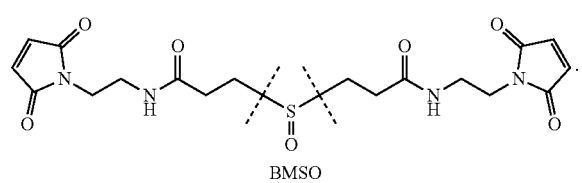

BMSO

2. A method for synthesis of the MS-cleavable cross-linker of claim 1 for mapping intra-protein interactions in a protein, inter-protein interactions in a protein complex or a combination thereof, the method comprising the steps of:

(i) providing a solution comprising DSSO and a trifluoroacetate salt of 1-(2-aminoethyl) maleimide;

(ii) adding $NaHCO_3$ to the solution of step (i) to obtain a mixture;

(iii) concentrating the mixture of step (ii) in vacuo to obtain a crude material; and (iv) purifying the MS-cleavable cross-linker from the crude material of step (iii) using column chromatography.

3. The method of claim 2, wherein step (ii) is performed at room temperature.

4. The method of claim 2, wherein step (ii) is performed for about 12 h.

5. A method for mapping intra-protein interactions in a protein, inter-protein interactions in a protein complex or a combination thereof, the method comprising:

providing the MS-cleavable cross-linker of claim 1, forming a cross-linked protein or protein complex by cross-linking the protein or the protein complex with the MS-cleavable cross-linker;

forming one or more peptide fragments that are chemically bound to the MS-cleavable cross-linker by digesting the cross-linked protein or protein complex with an enzyme; and identifying the one or more peptide fragments using tandem mass spectrometry ($MS^n$), thereby mapping intra-protein interactions in a protein and inter-protein interactions in a protein complex.

6. The method of claim 5, wherein the cross-linking the protein or the protein complex with the MS-cleavable cross-linker occurs by conjugation of cysteines.

7. The method of claim 6, wherein the conjugation of cysteines occurs via maleimide chemistry.

8. The method of claim 7, wherein the maleimide chemistry yields two different forms of cross-linked cysteines.

9. The method of claim 8, wherein the two different forms of cross-linked cysteines comprise a closed-ring structure and a hydrolyzed open-ring structure.

10. A method for cross-linking mass spectrometry (XL-MS) for identifying one or more cross-linked peptides, the method comprising:

performing cross-linking with the MS-cleavable cross-linker of claim 1 to obtain one or more cross-linked proteins, digesting the one or more cross-linked proteins with trypsin to obtain one or more cross-linked peptides;

performing a liquid chromatography-tandem mass spectrometry (LC-$MS^n$) analysis on the one or more cross-linked peptides, wherein the LC-$MS^n$ analysis comprises: detecting the one or more cross-linked peptides by $MS^1$ analysis;

selecting the one or more cross-linked peptides detected by $MS^1$ for $MS^2$ analysis;

selectively fragmenting the at least one CID cleavable bond and separating the one or more cross-linked peptides during $MS^2$ analysis;

sequencing the one or more cross-linked peptides separated during $MS^2$ analysis by $MS^3$ analysis; and integrating data obtained during $MS^1$, $MS^2$ and $MS^3$ analyses to identify the one or more cross-linked peptides.

11. The method of claim 10, wherein the cross-linking with the MS-cleavable cross-linker occurs by conjugation of cysteines.

12. The method of claim 11, wherein the conjugation of cysteines occurs via maleimide chemistry.

13. The method of claim 12, wherein the maleimide chemistry yields two different forms of cross-linked cysteines, wherein the two different forms of cross-linked cysteines comprise a closed-ring structure and a hydrolyzed open-ring structure.

* * * * *

SEQUENCE LISTING

```
<160> NUMBER OF SEQ ID NOS: 98

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Ser Leu His Thr Leu Phe Gly Asp Glu Leu Cys Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Ser Leu His Thr Leu Phe Gly Asp Glu Leu Cys Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3
```

Ser Leu His Thr Leu Phe Gly Asp Glu Leu Cys Lys
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Asn Glu Cys Phe Leu Ser His Lys
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Leu Lys Pro Asp Pro Asn Thr Leu Cys Asp Glu Phe Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Leu Lys Pro Asp Pro Asn Thr Leu Cys Asp Glu Phe Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic

<400> SEQUENCE: 7

Leu Lys Pro Asp Pro Asn Thr Leu Cys Asp Glu Phe Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Leu Lys Pro Asp Pro Asn Thr Leu Cys Asp Glu Phe Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic

<400> SEQUENCE: 9

```
Leu Lys Pro Asp Pro Asn Thr Leu Cys Asp Glu Phe Lys
1               5                   10
```

<210> SEQ ID NO 10
<211> LENGTH: 13
<212> TYPE: PRT
<213> ORGANISM: Artificial Sequence
<220> FEATURE:
<223> OTHER INFORMATION: Synthetic

<400> SEQUENCE: 10

```
Leu Lys Pro Asp Pro Asn Thr Leu Cys Asp Glu Phe Lys
1               5                   10
```

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

```
Gly Ala Cys Leu Leu Pro Lys
1               5
```

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

```
Gly Ala Cys Leu Leu Pro Lys
1               5
```

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

```
Gly Ala Cys Leu Leu Pro Lys
1               5
```

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

```
Gly Ala Cys Leu Leu Pro Lys
1               5
```

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

```
Gly Ala Cys Leu Leu Pro Lys
```

```
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Gly Ala Cys Leu Leu Pro Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Gly Ala Cys Leu Leu Pro Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Gly Ala Cys Leu Leu Pro Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Gly Ala Cys Leu Leu Pro Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Cys Ala Ser Ile Gln Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Cys Ala Ser Ile Gln Lys
1               5
```

```
<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Cys Ala Ser Ile Gln Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Cys Ala Ser Ile Gln Lys
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Tyr Ile Cys Asp Asn Gln Asp Thr Ile Ser Ser Lys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic

<400> SEQUENCE: 25

Tyr Ile Cys Asp Asn Gln Asp Thr Ile Ser Ser Lys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic

<400> SEQUENCE: 26

Tyr Ile Cys Asp Asn Gln Asp Thr Ile Ser Ser Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Tyr Ile Cys Asp Asn Gln Asp Thr Ile Ser Ser Lys
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Tyr Ile Cys Asp Asn Gln Asp Thr Ile Ser Ser Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Tyr Ile Cys Asp Asn Gln Asp Thr Ile Ser Ser Lys
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Ser His Cys Ile Ala Glu Val Glu Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Ser His Cys Ile Ala Glu Val Glu Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Ser His Cys Ile Ala Glu Val Glu Lys
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Ser His Cys Ile Ala Glu Val Glu Lys
1               5

```
<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Ser His Cys Ile Ala Glu Val Glu Lys
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Glu Tyr Glu Ala Thr Leu Glu Glu Cys Cys Ala Lys
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthetic

<400> SEQUENCE: 36

Asp Asp Pro His Ala Cys Tyr Ser Thr Val Phe Asp Lys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic

<400> SEQUENCE: 37

Asp Asp Pro His Ala Cys Tyr Ser Thr Val Phe Asp Lys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic

<400> SEQUENCE: 38

Asp Asp Pro His Ala Cys Tyr Ser Thr Val Phe Asp Lys
1               5                   10

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Gln Asn Cys Asp Gln Phe Glu Lys
1               5

<210> SEQ ID NO 40
```

-continued

```
<211> LENGTH: 14
<212> TYPE: PRT
<213> ORGANISM: Artificial Sequence
<220> FEATURE:
<223> OTHER INFORMATION: Synthetic

<400> SEQUENCE: 40

Met Pro Cys Thr Glu Asp Tyr Leu Ser Leu Ile Leu Asn Arg
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Leu Cys Val Leu His Glu Lys
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic

<400> SEQUENCE: 42

Gly Ala Cys Leu Leu Pro Lys
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic

<400> SEQUENCE: 43

Cys Ala Ser Ile Gln Lys
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Ser His Cys Ile Ala Glu Val Glu Lys
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Ser His Cys Ile Ala Glu Val Glu Lys
1               5

<210> SEQ ID NO 46
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 46

Gly Ala Cys Leu Leu Pro Lys
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic

<400> SEQUENCE: 47

Cys Ala Ser Ile Gln Lys
1               5

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Tyr Ile Cys Asp Asn Gln Asp Thr Ile Ser Ser Lys
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Ser His Cys Ile Ala Glu Val Glu Lys
1               5

<210> SEQ ID NO 50
<211> LENGTH: 14
<212> TYPE: PRT
<213> ORGANISM: Artificial Sequence
<220> FEATURE:
<223> OTHER INFORMATION: Synthetic

<400> SEQUENCE: 50

Met Pro Cys Thr Glu Asp Tyr Leu Ser Leu Ile Leu Asn Arg
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic

<400> SEQUENCE: 51

Leu Cys Val Leu His Glu Lys
1               5

<210> SEQ ID NO 52
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 52

Cys Ala Ser Ile Gln Lys
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Tyr Ile Cys Asp Asn Gln Asp Thr Ile Ser Ser Lys
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Ser His Cys Ile Ala Glu Val Glu Lys
1               5

<210> SEQ ID NO 55
<211> LENGTH: 13
<212> TYPE: PRT
<213> ORGANISM: Artificial Sequence
<220> FEATURE:
<223> OTHER INFORMATION: Synthetic

<400> SEQUENCE: 55

Asp Asp Pro His Ala Cys Tyr Ser Thr Val Phe Asp Lys
1               5                   10

<210> SEQ ID NO 56
<211> LENGTH: 8
<212> TYPE: PRT
<213> ORGANISM: Artificial Sequence
<220> FEATURE:
<223> OTHER INFORMATION: Synthetic

<400> SEQUENCE: 56

Gln Asn Cys Asp Gln Phe Glu Lys
1               5

<210> SEQ ID NO 57
<211> LENGTH: 14
<212> TYPE: PRT
<213> ORGANISM: Artificial Sequence
<220> FEATURE:
<223> OTHER INFORMATION: Synthetic

<400> SEQUENCE: 57

Met Pro Cys Thr Glu Asp Tyr Leu Ser Leu Ile Leu Asn Arg
1               5                   10

<210> SEQ ID NO 58
<211> LENGTH: 14
<212> TYPE: PRT
<213> ORGANISM: Artificial Sequence
```

```
<220> FEATURE:
<223> OTHER INFORMATION: Synthetic

<400> SEQUENCE: 58

Met Pro Cys Thr Glu Asp Tyr Leu Ser Leu Ile Leu Asn Arg
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic

<400> SEQUENCE: 59

Leu Cys Val Leu His Glu Lys
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

Arg Pro Cys Phe Ser Ala Leu Thr Pro Asp Glu Thr Tyr Val Pro Lys
1               5                   10                  15

<210> SEQ ID NO 61
<211> LENGTH: 12
<212> TYPE: PRT
<213> ORGANISM: Artificial Sequence
<220> FEATURE:
<223> OTHER INFORMATION: Synthetic

<400> SEQUENCE: 61

Tyr Ile Cys Asp Asn Gln Asp Thr Ile Ser Ser Lys
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Ser His Cys Ile Ala Glu Val Glu Lys
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Gln Asn Cys Asp Gln Phe Glu Lys
1               5

<210> SEQ ID NO 64
<211> LENGTH: 8
<212> TYPE: PRT
<213> ORGANISM: Artificial Sequence
<220> FEATURE:
```

```
<223> OTHER INFORMATION: Synthetic

<400> SEQUENCE: 64

Gln Asn Cys Asp Gln Phe Glu Lys
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Ser His Cys Ile Ala Glu Val Glu Lys
1               5

<210> SEQ ID NO 66
<211> LENGTH: 13
<212> TYPE: PRT
<213> ORGANISM: Artificial Sequence
<220> FEATURE:
<223> OTHER INFORMATION: Synthetic

<400> SEQUENCE: 66

Asp Asp Pro His Ala Cys Tyr Ser Thr Val Phe Asp Lys
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic

<400> SEQUENCE: 67

Met Pro Cys Thr Glu Asp Tyr Leu Ser Leu Ile Leu Asn Arg
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic

<400> SEQUENCE: 68

Met Pro Cys Thr Glu Asp Tyr Leu Ser Leu Ile Leu Asn Arg
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic

<400> SEQUENCE: 69

Leu Cys Val Leu His Glu Lys
1               5

<210> SEQ ID NO 70
<211> LENGTH: 16
<212> TYPE: PRT
<213> ORGANISM: Artificial Sequence
<220> FEATURE:
<223> OTHER INFORMATION: Synthetic
```

<400> SEQUENCE: 70

Arg Pro Cys Phe Ser Ala Leu Thr Pro Asp Glu Thr Tyr Val Pro Lys
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Gln Asn Cys Asp Gln Phe Glu Lys
1               5

<210> SEQ ID NO 72
<211> LENGTH: 14
<212> TYPE: PRT
<213> ORGANISM: Artificial Sequence
<220> FEATURE:
<223> OTHER INFORMATION: Synthetic

<400> SEQUENCE: 72

Met Pro Cys Thr Glu Asp Tyr Leu Ser Leu Ile Leu Asn Arg
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic

<400> SEQUENCE: 73

Met Pro Cys Thr Glu Asp Tyr Leu Ser Leu Ile Leu Asn Arg
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetic

<400> SEQUENCE: 74

Leu Cys Val Leu His Glu Lys
1               5

<210> SEQ ID NO 75
<211> LENGTH: 16
<212> TYPE: PRT
<213> ORGANISM: Artificial Sequence
<220> FEATURE:
<223> OTHER INFORMATION: Synthetic

<400> SEQUENCE: 75

Arg Pro Cys Phe Ser Ala Leu Thr Pro Asp Glu Thr Tyr Val Pro Lys
1               5                   10                  15

<210> SEQ ID NO 76
<211> LENGTH: 13
<212> TYPE: PRT
<213> ORGANISM: Artificial Sequence
<220> FEATURE:
<223> OTHER INFORMATION: Synthetic

```
<400> SEQUENCE: 76

Asp Asp Pro His Ala Cys Tyr Ser Thr Val Phe Asp Lys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic

<400> SEQUENCE: 77

Met Pro Cys Thr Glu Asp Tyr Leu Ser Leu Ile Leu Asn Arg
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Synthetic

<400> SEQUENCE: 78

Leu Cys Val Leu His Glu Lys
1               5

<210> SEQ ID NO 79
<211> LENGTH: 16
<212> TYPE: PRT
<213> ORGANISM: Artificial Sequence
<220> FEATURE:
<223> OTHER INFORMATION: Synthetic

<400> SEQUENCE: 79

Arg Pro Cys Phe Ser Ala Leu Thr Pro Asp Glu Thr Tyr Val Pro Lys
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Synthetic

<400> SEQUENCE: 80

Arg Pro Cys Phe Ser Ala Leu Thr Pro Asp Glu Thr Tyr Val Pro Lys
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Synthetic

<400> SEQUENCE: 81

Arg Pro Cys Phe Ser Ala Leu Thr Pro Asp Glu Thr Tyr Val Pro Lys
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic

<400> SEQUENCE: 82
```

```
Arg Pro Cys Phe Ser Ala Leu Thr Pro Asp Glu Thr Tyr Val Pro Lys
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Ser His Cys Ile Ala Glu Val Glu Lys
1               5

<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

Tyr Ile Cys Asp Asn Gln Asp Thr Ile Ser Ser Lys
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Synthetic

<400> SEQUENCE: 85

Leu Ala Asp Val Cys Ala His Glu Arg
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

Leu Ala Asp Val Cys Ala His Glu Arg
1               5

<210> SEQ ID NO 87
<211> LENGTH: 13
<212> TYPE: PRT
<213> ORGANISM: Artificial Sequence
<220> FEATURE:
<223> OTHER INFORMATION: Synthetic

<400> SEQUENCE: 87

Thr Ile Ser Ala Gly Lys Val Asn Leu Gly Ala Phe Arg
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthetic

<400> SEQUENCE: 88
```

```
Glu Tyr Tyr Tyr Thr Lys Glu Glu Gln Phe Lys
1               5                   10
```

<210> SEQ ID NO 89
<211> LENGTH: 15
<212> TYPE: PRT
<213> ORGANISM: Artificial Sequence
<220> FEATURE:
<223> OTHER INFORMATION: Synthetic

<400> SEQUENCE: 89

```
Thr Thr Ile Glu Ala Ile His Gly Leu Met Ser Gln Val Ile Lys
1               5                   10                  15
```

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

```
Ile Glu Asp Phe Gly Val His Cys Lys
1               5
```

<210> SEQ ID NO 91
<211> LENGTH: 11
<212> TYPE: PRT
<213> ORGANISM: Artificial Sequence
<220> FEATURE:
<223> OTHER INFORMATION: Synthetic

<400> SEQUENCE: 91

```
Thr Cys Asn Thr Met Asn Gln Phe Val Asn Lys
1               5                   10
```

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

```
Leu Ala Asp Val Cys Ala His Glu Arg
1               5
```

<210> SEQ ID NO 93
<211> LENGTH: 12
<212> TYPE: PRT
<213> ORGANISM: Artificial Sequence
<220> FEATURE:
<223> OTHER INFORMATION: Synthetic

<400> SEQUENCE: 93

```
Tyr Ile Cys Asp Asn Gln Asp Thr Ile Ser Ser Lys
1               5                   10
```

<210> SEQ ID NO 94
<211> LENGTH: 9
<212> TYPE: PRT
<213> ORGANISM: Artificial Sequence
<220> FEATURE:
<223> OTHER INFORMATION: Synthetic

<400> SEQUENCE: 94

Ser His Cys Ile Ala Glu Val Glu Lys

```
<210> SEQ ID NO 95
<211> LENGTH: 6
<212> TYPE: PRT
<213> ORGANISM: Artificial Sequence
<220> FEATURE:
<223> OTHER INFORMATION: Synthetic

<400> SEQUENCE: 95

Cys Ala Ser Ile Gln Lys
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Leu Ala Asp Val Cys Ala His Glu Arg
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Ile Gly Val Asp His Val Ala Arg
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Leu Ala Asp Val Cys Ala His Glu Arg
1               5
```